US007799764B2

(12) United States Patent
Marcusson et al.

(10) Patent No.: US 7,799,764 B2

(45) Date of Patent: Sep. 21, 2010

(54) MODULATION OF HIF1-BETA EXPRESSION

(75) Inventors: Eric G. Marcusson, San Diego, CA (US); Scott W. Henry, Cardiff, CA (US); Youngsoo Kim, San Diego, CA (US); Kenneth Dobie, Del Mar, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 12/578,468

(22) Filed: Oct. 13, 2009

(65) Prior Publication Data

US 2010/0113573 A1 May 6, 2010

Related U.S. Application Data

(63) Continuation of application No. 11/213,593, filed on Aug. 25, 2005, now Pat. No. 7,618,947.

(60) Provisional application No. 60/604,190, filed on Aug. 25, 2004, provisional application No. 60/649,586, filed on Feb. 2, 2005.

(51) Int. Cl.

| | |
|---|---|
| ***A61K 31/70*** | (2006.01) |
| ***C07H 21/02*** | (2006.01) |
| ***C07H 21/04*** | (2006.01) |
| *C12Q 1/68* | (2006.01) |
| *C12N 5/00* | (2006.01) |

(52) U.S. Cl. ......................... 514/44 A; 435/6; 435/375; 435/377; 536/23.1; 536/24.1; 536/24.5

(58) Field of Classification Search ....................... None
See application file for complete search history.

(56) References Cited

U.S. PATENT DOCUMENTS

| | | | |
|---|---|---|---|
| 5,801,154 | A | 9/1998 | Baracchini et al. |
| 5,998,148 | A | 12/1999 | Bennett et al. |
| 6,352,829 | B1 | 3/2002 | Chenchik et al. |
| 6,582,908 | B2 | 6/2003 | Fodor et al. |
| 6,627,619 | B2 | 9/2003 | Cech et al. |
| 7,030,236 | B2 | 4/2006 | Jhaveri et al. |
| 2001/0053519 | A1 | 12/2001 | Fodor et al. |
| 2003/0228597 | A1 | 12/2003 | Cowsert et al. |
| 2004/0086498 | A9 | 5/2004 | Krissansen et al. |
| 2004/0096848 | A1 | 5/2004 | Thrue et al. |
| 2004/0101858 | A1 | 5/2004 | Ward et al. |
| 2004/0152655 | A1 | 8/2004 | Yoon et al. |
| 2004/0180357 | A1 | 9/2004 | Reich et al. |
| 2004/0220393 | A1 | 11/2004 | Ward et al. |
| 2005/0070474 | A1 | 3/2005 | Krissansen et al. |
| 2005/0148496 | A1 | 7/2005 | Defranoux et al. |
| 2005/0163781 | A1 | 7/2005 | Konickx et al. |

FOREIGN PATENT DOCUMENTS

| | | |
|---|---|---|
| WO | WO 99/48916 | 9/1999 |
| WO | WO 99/50403 | 10/1999 |
| WO | WO 02/053735 | 7/2002 |
| WO | WO 2004/048526 | 6/2004 |

OTHER PUBLICATIONS

Aplin, "Hypoxia and human placental development" J. Clin. Investig. (2000) 105(5):559-560.

Branch, "A good antisense molecule is hard to find" TIBS (1998) 23:45-50.

Carmeliet et al., "Apgiogenesis in cancer and other diseases" Nature (2000) 407:249-257.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Ebert et al., "Hypoxia and Mitochondrial Inhibitors Regulate Expression of Glucose Transporter-1 via Distinct Cis-acting Sequences" J. Biol. Chem. (1995) 270(49):29083-29089.

Ema et al., "A novel bHLH-PAS factor with close sequence similarity to hypoxia-inducible factor 1alpha regulates VEGF expression and is potentially involved in lung and vascular development" PNAS USA (1997) 94:4273-4278.

Furuta et al., "Hypoxia-Induced Factor Dependent Induction of Intestinal Trefoil Factor Protects Barrier Function During Hypoxia" J. Exp. Med. (2001) 193(9):1027-1034.

Golach et al., "Efficient translation of mouse hypoxia-inducible factor-1alpha under normoxic and hypoxic conditions" Biochim, Biophys. Acta (2000) 1493:125-134.

Gunton et al., "Loss or ARNT/HIF1.beta Mediated Altered Gene Expression and Pancreatic-Islet Dysfunction in Human Type 2 Diabetes" Cell (2005) 122:337-349.

Harris, "Hypoxia—A Key Regulatory Factor in Tumour Growth" Nature Rev. Cancer (2002) 2:38-47.

Henry et al., "Setting sights on the treatment of ocular angiogenesis using antisense oligonucleotides" Trends Pharm. Sci. (2004) 25(10):523-527.

Hoffman et al., "Cloning of a Factor Required for Activity of the Ah (Dioxin) Receptor" Science (1991) 252:954-958.

Hogenesch et al., "Characterization of a Subset of the Basic-Helix-Loop-Helix-PAS Superfamily that Interacts with Components of the Dioxin Signaling Pathway" J. Biol. Chem. (1997) 272(13):8581-8593.

Jewell et al., "Induction of HIF-1alpha in response to hypoxia is instantaneous" FASEB J. (2001) 15:1312-1314.

Kallio et al., "Signal transduction in hypoxic cells: inducible nuclear translocation and recruitment of the CBP/p300 coactivator by the hypoxia-inducible factor-1alpha" EMBO J. (1998) 17(22):6573-6586.

(Continued)

*Primary Examiner*—Sean R McGarry

(74) *Attorney, Agent, or Firm*—Knobbe Martens Olson & Bear LLP

(57) ABSTRACT

Compounds, compositions and methods are provided for modulating the expression of HIF1-beta. The compositions comprise oligonucleotides, targeted to nucleic acid encoding HIF1-beta. Methods of using these compounds for modulation of HIF1-beta expression and for diagnosis and treatment of diseases and conditions associated with expression of HIF1-beta are provided.

31 Claims, No Drawings

OTHER PUBLICATIONS

Lee et al., "Early Expression of Angiogenesis Factors in Acute Myocardial Ischemia and Infarction" N. Eng. J. Med. (2000) 342:626-633.

Levy et al., "Transcriptional Regulation of the Rat Vascular Endothelial Growth Factor Gene by Hypoxia" J. Biol. Chem. (1995) 270(22):13333-13340.

Maxwell et al., "Inducible operation of the erythropoietin 3' enhancer in multiple cell lines: Evidence for a widespread oxygen-sensing mechanism" PNAS USA (1993) 90:2423-2427.

Moore et al., "A genomewide survey of basic helix-loop-helix factors in Drosophila" PNAS (2000) 97(19):10436-10441.

New England Biolabs 1998/99 Catalog (cover page and pp. 121 and 284).

Ohtake et al., "Modulation of oestrogen receptor signaling by association with the activated dioxin receptor" Nature (2003) 423:545-550.

Poland et al., "Evidence that the Binding Species is Receptor for Induction of Aryl Hydrocarbon Hydroxylase" J. Biol. Chem. (1976) 251(16):4936-4946.

Reisz-Porszasz et al., "Identification of Functional Domains of the Aryl Hydrocarbon Receptor Nuclear Translocator Protein (ARNT)" Mol. Cell. Biol. (1994) 14(9):6075-6086.

Reynolds et al., "Rational siRNA design for RNA interference" Nature Biotechnology (2004) 22(3):326-330.

Rolfs et al., "Oxygen-regulated Transferrin Expression is Mediated by Hypoxia-inducible Factor-1" J. Biol. Chem. (1997) 272(32):20055-20062.

Safe, "Molecular biology of the Ah receptor and its role in carcinogenesis" Toxicol. Lett. (2001) 120:1-7.

Safran et al., "HIF hydroxylation and the mammalian oxygen-sensing pathway" J. Clin. Investig. (2003) 111(6):779-783.

Sanghvi et al., "Heterocyclic Base Modifications in Nucleic Acids and Their Applications in Antisense Oligonucleotides" Antisense Research and Applications (1993) pp. 273-288.

Semenza, "Hypoxia-inducible factor 1: oxygen homeostasis and disease pathophysiology" Trends. Mol. Med. (2001) 7(8):345-350.

Semenza et al., "Transcriptional Regulation of Genes Encoding Glycolytic Enzymes by Hypoxia-inducible Factor 1" J. Biol. Chem. (1994) 269(38):23757-23763.

Sun et al., "Gene transfer of antisense hypoxia inducible factor-1 alpha enhances the therapeutic efficacy of cancer immunotherapy" Gene Therapy (2001) 8:638-645.

Wang et al., "General involvement of hypoxia-inducible factor 1 in transcriptional response to hypoxia" PNAS USA (1993) 90:4304-4308.

Wang et al., "Effect of Protein Kinase and Phosphatase Inhibitors on Expression of Hypoxia-Inducibile Factor 1" Biochem. Biophys. Res. Commun. (1995) 216(2):669-675.

Wang et al. "Purification and Characterization of Hypoxia-inducible Factor 1" J. Biol. Chem. (1995) 270(3):1230-1237.

Wang et al., "Characterization of Hypoxia-inducible Factor 1 and Regulation of DNA Binding Activity by Hypoxia" J. Biol. Chem. (1993) 268(29):21513-21518.

Weintraub, "Antisense RNA and DNA: Molecules that bind with specific messenger RNA's can selectively turn off genes. Eventually certain diseases may be treated with them; today antisense molecules are valuable research tools" Scientific American (1990) 40-46.

Wiesener et al., "Induction of Endothelial PAS Domain Protein-1 by Hypoxia: Characterization and Comparison with Hypoxia-Inducibile Factor-1alpha" Blood (1998) 92(1):2260-2268.

Wood et al., "The Role of the Aryl Hydrocarbon Receptor Nuclear Translocator (ARNT) in Hypoxic Induction of Gene Expression" J. Biol. Chem. (1996) 271(25):15117-15123.

Zhang et al., "Conbined Anti-Fetal Liver Kinase 1 Monoclonal Antibody and Continuous Low-Dose Doxorubicin Inhibits Angiogenesis and Growth of Human Soft Tissue Sarcoma Xenografts by Induction of Endothelial Cell Apoptosis" Cancer Res. (2002) 62:2034-2042.

International Search Report for application PCT/US2005/030513 dated Apr. 19, 2006.

MODULATION OF HIF1-BETA EXPRESSION

CROSS-REFERENCE TO RELATED APPLICATIONS

This application is a continuation of U.S. patent application Ser. No. 11/213,593, filed Aug. 25, 2005, which claims the benefit of priority to U.S. provisional patent application Ser. No. 60/604,190, filed Aug. 25, 2004, and U.S. provisional patent application Ser. No. 60/649,586, filed Feb. 2, 2005, each of which are incorporated herein by reference in their entirety.

FIELD OF THE INVENTION

The present invention provides compositions and methods for modulating the expression of HIF1-beta. In particular, this invention relates to antisense compounds, particularly oligonucleotide compounds, which, in preferred embodiments, hybridize with nucleic acid molecules encoding HIF1-beta. Such compounds are shown herein to modulate the expression of HIF1-beta.

BACKGROUND OF THE INVENTION

Oxygen homeostasis in mammals is tightly regulated, necessitated by the need to maintain sufficient levels for critical oxygen-dependent processes while minimizing the production of oxygen reactive species that are capable of causing oxidative damage to DNA, lipids, and proteins. In a state of hypoxia, where oxygen demand exceeds supply, a physiological response is mounted that increases the capacity of blood to carry oxygen to tissues and alters cellular metabolism, such as facilitating ATP production by anaerobic glycolysis. The hypoxia-inducible factors (HIFs) are key transcriptional regulators of this hypoxic response. These factors have also been implicated in the pathology of many major human diseases, including cancer, myocardial infarction, ischemia and preeclampsia (Harris, *Nat. Rev. Cancer,* 2002, 2, 38-47); (Lee et al., *N Engl J Med,* 2000, 342, 626-633); (Aplin, *J Clin Invest,* 2000, 105, 559-560)). Cells are typically cultured in the laboratory at an ambient oxygen concentration of 21%, but cells in the human body are exposed to much lower oxygen concentrations ranging from 16% in the lungs to less than 6% in most other organs of the body and often significantly less in tumors (Semenza, *Trends Mol Med,* 2001, 7, 345-350).

The HIF proteins are heterodimers consisting of HIF1-beta and one of three alpha subunits, HIF1-alpha, HIF2-alpha and HIF3-alpha (Safran and Kaelin, *J. Clin. Invest.,* 2003, 111, 779-783). The discovery of the HIF proteins was enabled by the identification of a minimal hypoxia-responsive element (HRE) in the 3' enhancer of the erythropoietin gene (Wang and Semenza, *Proc Natl Acad Sci USA,* 1993, 90, 4304-4308). Subsequent analysis identified the HIF protein as a phosphorylation-dependent protein that binds DNA under hypoxic conditions (Wang and Semenza, *J Biol Chem,* 1993, 268, 21513-21518). Purification of this DNA-binding factor revealed HIF was a heterodimeric complex consisting of a novel protein, HIF1-alpha, and the aryl hydrocarbon nuclear translocator (ARNT, also termed HIF1-beta), previously identified as a binding partner of the dioxin/aryl hydrocarbon receptor (Wang and Semenza, *J. Biol. Chem.,* 1995, 270, 1230-1237.); (Hoffman et al., *Science,* 1991, 252, 954-958). HIF proteins belong to a class of transcription factors termed basic helix-loop-helix proteins, grouped by two conserved domains. The basic region consists of approximately 15 predominantly basic amino acids responsible for direct DNA binding. This region is adjacent to two amphipathic alpha helices, separated by a loop of variable length, which forms the primary dimerization interface between family members (Moore et al., *Proc Natl Acad Sci USA,* 2000, 97, 10436-10441).

HIF1-beta is a key player in two major signaling pathways, the hypoxic-response pathway and the aryl hydrocarbon receptor (AHR) pathway. Since the discovery of HIF1-alpha/HIF1-beta involvement in erythropoietin transcription, HIF activity has been detected in various non-erythropoietin-producing cell lines cultured under hypoxic conditions (Wang and Semenza, *Proc Natl Acad Sci USA,* 1993, 90, 4304-4308); (Maxwell et al., *Proc Natl Acad Sci USA,* 1993, 90, 2423-2427), providing the first evidence that the HIF1 dimer not only activates the erythropoietin gene, but is part of a widespread oxygen-sensing and signal transduction mechanism. Under normoxic conditions, HIF1-alpha is rapidly degraded due to the oxygen-dependent hydroxylation of specific proline residues that mark the protein for proteasomal degradation (Jewell et al., *Faseb J,* 2001, 15, 1312-1314); (Gorlach et al., *Biochim Biophys Acta,* 2000, 1493, 125-134). Under hypoxic conditions, this hydroxylation is reversed, and the protein is further stabilized by phosphorylation (Wang et al., *Biochem Biophys Res Commun,* 1995, 216, 669-675). Subsequently, the protein is translocated to the nucleus, where it interacts with HIF1-beta to form a heterodimeric transcription factor (Kallio et al., *Embo J,* 1998, 17, 6573-6586). Studies in HIF1-beta deficient cells revealed an absolute requirement for this dimerization step for the transcriptional activation of hypoxia response element genes (Wood et al., *J Biol Chem,* 1996, 271, 15117-15123). Categories of genes that are activated by the HIF1 dimer include oxygen transport genes, such as erythropoietin (Semenza et al., *J Biol Chem,* 1994, 269, 23757-23763) and transferrin (Rolfs et al., *J Biol Chem,* 1997, 272, 20055-20062); genes involved in angiogenesis, such as VEGF (Levy et al., *J Biol Chem,* 1995, 270, 13333-13340); and genes involved in anaerobic metabolism, such as glucose transporter 1 (Ebert et al., *J Biol Chem,* 1995, 270, 29083-29089). Hypoxia-induced genes such as VEGF are thought to play a role in promoting angiogenesis and subsequent tumor growth (Harris, *Nat. Rev. Cancer,* 2002, 2, 38-47).

HIF transcriptional activity is precisely regulated by cellular oxygen concentration. Whereas changes in oxygen levels do no affect HIF1-beta protein levels, the abundance of the HIF-alpha subunits is markedly increased upon exposure of cells to hypoxia, primarily due to stabilization of the alpha subunits (Safran and Kaelin, *J. Clin. Invest.,* 2003, 111, 779-783). HIF2-alpha mRNA and protein is expressed at low levels in tissue culture cells, but protein expression is markedly induced by exposure to 1% oxygen, a hypoxic state (Wiesener et al., *Blood,* 1998, 92, 2260-2268). The HIF2-alpha/HIF1-beta heterodimer protein binds to the hypoxic response element, which contains the core recognition sequence 5'-TACGTG-3' and is found in the cis-regulatory regions of hypoxia-regulated genes (Ema et al., *Proc. Natl. Acad. Sci. U.S.A.,* 1997, 94, 4273-4278); (Hogenesch et al., *J. Biol. Chem.,* 1997, 272, 8581-8593). Binding of the heterodimer to the HRE induces gene expression (Wiesener et al., *Blood,* 1998, 92, 2260-2268).

In contrast to the HIF-alpha subunits, HIF1-beta is stable under both hypoxic and normoxic conditions, and also participates in the aryl hydrocarbon receptor (AHR) signaling pathway. AHR is a cytoplasmic receptor protein that translocates to the nucleus after ligand binding. Ligands of AHR include 2,3,7,8-tetrachlorodibenzo-p-dioxin (TCDD), an environmental toxin that is a by-product of industrial processes (Poland et al., *J Biol Chem,* 1976, 251, 4936-4946); polycylic aromatic hydrocarbons, found in cigarette smoke and smog (Reisz-Porszasz et al., *Mol Cell Biol,* 1994, 14, 6075-6086); and heterocyclic amines, found in some cooked meats (Reisz-Porszasz et al., *Mol Cell Biol,* 1994, 14, 6075-6086). After ligand-binding and nuclear translocation, AHR forms a dimer with HIF1-beta, resulting in the activation of a number of genes involved in drug metabolism, such as the cytochromes P450, CYP1A1, CYP1A2, and CYP1B1. AHR/HIF1-beta dimers are capable of activating a range of other genes regulated by the dioxin response element (DRE), resulting in some of the toxic and carcinogenic effects associated with many of the AHR ligands, such as immunotoxicity, developmental and reproductive toxicity, disruption of endocrine pathways, a wasting syndrome, and tumor promotion (Safe, *Toxicol Lett,* 2001, 120, 1-7). Ohtake and colleagues (Ohtake et al., *Nature,* 2003, 423, 545-550) demonstrated that the AHR/HIF1-beta heterodimer directly associates with the estrogen receptors ER-alpha and ER-beta. They showed that this association results in the recruitment of unliganded estrogen receptor and coactivator p300 to estrogen-responsive gene promoters, leading to activation of transcription and estrogenic effects and giving rise to the adverse estrogen-related actions of dioxin-type environmental contaminants.

The role of HIF1-beta in both hypoxia-induced and AHR signaling pathways makes it an attractive therapeutic candidate, as both of these pathways have been linked to various forms of malignancies (Harris, *Nat. Rev. Cancer,* 2002, 2, 38-47); (Safe, *Toxicol Lett,* 2001, 120, 1-7). The angiogenic promoting capabilities of HIF1-beta also mark this gene as a potential therapeutic target for a variety of angiogenic disorders, such as arthritis, cardiovascular diseases, skin conditions, aberrant wound healing and ocular conditions (e.g., macular degeneration, diabetic retinopathy, diabetic macular edema and retinopathy of prematurity).

PCT publication WO 02/053735 discloses the use of an oligonucleotide 35 nucleotides in length as a PCR primer for amplification of the HIF1-beta sequence.

U.S. Pat. No. 6,352,829 discloses the use of an oligonucleotide 26 nucleotides in length as a PCR primer for amplification of the HIF1-beta sequence.

U.S. pre-grant publication 2004-0152655 discloses antisense oligonucleotide compounds for inhibiting HIF1-alpha.

U.S. pre-grant publication 2004-0096848 discloses oligomeric compounds directed against HIF1-alpha.

U.S. pre-grant publication 2005-0163781 discloses compounds for use as inhibitors of hypoxia-induced genes, such as HIF1-alpha and HIF2-alpha, to treat adhesion formation.

U.S. pre-grant publication 2004-0180357 discloses HIF1-alpha siRNA compounds for downregulating expression of HIF1-alpha and VEGF and inhibiting angiogenesis.

U.S. pre-grant publication 2005-0148496 discloses methods of treating inflammatory disorders such as rheumatoid arthritis using compounds that inhibit HIF1-alpha activity.

U.S. pre-grant publication 2004-0086498 discloses methods for treating animals with advanced or large tumor burdens by administration of an immunotherapeutic agent and a tumor growth restricting agent, such as an expression vector encoding an antisense version of HIF1-alpha.

U.S. pre-grant publication 2005-0070474 discloses methods of treating tumors using an agent to increase B7-H3 in combination with an agent to inhibit HIF1-alpha, HIF2-alpha or HIF3-alpha.

Currently, there are no known therapeutic agents which effectively inhibit the synthesis of HIF1-beta and to date, investigative strategies aimed at modulating the function of HIF1-beta have involved the use of antibodies and inactive mutants. Consequently, there remains a long felt need for additional agents capable of effectively inhibiting HIF1-beta function.

Antisense technology is an effective means for reducing the expression of specific gene products and may therefore prove to be uniquely useful in a number of therapeutic, diagnostic, and research applications for the modulation of HIF1-beta expression. Provided herein are antisense compounds for inhibition of HIF1-beta expression. The disclosed compounds can used for treating or preventing conditions associated with HIF1-beta, such as cancer and angiogenic disorders.

SUMMARY OF THE INVENTION

The present invention is directed to antisense compounds, especially nucleic acid and nucleic acid-like oligomers, which are targeted to a nucleic acid encoding HIF1-beta, and which modulate the expression of HIF1-beta. Pharmaceutical and other compositions comprising the compounds of the invention and methods of treating an animal, particularly a human, suspected of having or being prone to a disease or condition associated with expression of HIF1-beta are also set forth herein.

Provided herein are antisense oligonucleotides which are specifically hybridizable with a nucleic acid molecule encoding human HIF1-beta. The HIF1-beta antisense oligonucleotides comprise at least one internucleoside, sugar or nucleobase modification. Contemplated are oligonucleotides 13 to 80, 13 to 50, 13 to 30, 20 to 30, 15 to 25 or 20 nucleobases in length. In one embodiment, the internucleoside modification is a phosphorothioate. In one embodiment, the modified sugar moiety is a 2'-O-(2-methoxyethyl). In one embodiment, the modified nucleobase in a 5-methyl cytosine. In some embodiments, the HIF1-beta antisense oligonucleotides further comprise a complementary strand. Also provided are antisense oligonucleotides which specifically hybridize to a splice variant of human HIF1-beta.

In one embodiment, the antisense oligonucleotides comprise at least an 8-nucleobase portion of one of the illustrative antisense oligonucleotides provided herein. In one embodiment, the antisense oligonucleotide is specifically hybridizable with at least a portion of a start codon region of human HIF1-beta. In another embodiment, the antisense oligonucleotide comprises at least an 8-nucleobase portion of SEQ ID NO: 30. In one embodiment, the antisense oligonucleotide is, specifically hybridizable with at least of portion of nucleotides 1876-1895 of a coding region of human HIF1-beta. In another embodiment, the antisense oligonucleotide comprises at least an 8-nucleobase portion of SEQ ID NO: 77.

Further provided are chimeric antisense oligonucleotides which are specifically hybridizable with a nucleic acid molecule encoding human HIF1-beta. In one embodiment, the chimeric antisense oligonucleotides have a first region comprising deoxynucleotides and second and third regions flanking the first region comprising at least one 2'-O-(2-methoxyethyl) nucleotide. In some embodiments, the first region is 10 deoxynucleotides in length and the second and third regions are each 5 nucleotides in length. The chimeric antisense oligonucleotides provided herein may further comprise a phosphorothioate linkage at each position.

Also provided are pharmaceutical compositions comprising the antisense oligonucleotides of the invention and a pharmaceutically acceptable carrier or diluent. Pharmaceutical compositions further comprising a colloidal dispersion system are also provided.

The present invention also provides methods of inhibiting expression of human HIF1-beta in cells or tissues by contacting the cells or tissues with one or more of the compounds provided herein such that expression is inhibited. In one embodiment, HIF1-beta expression is inhibited by 20%. In another embodiment, HIF1-beta expression is inhibited by 40%. In another embodiment, HIF1-beta expression is inhibited by 50%. In another embodiment, HIF1-beta expression is inhibited by 60%. In another embodiment, HIF1-beta expression is inhibited by 70%. In another embodiment, HIF1-beta expression is inhibited by 80%. In one embodiment, the compounds used to inhibit expression of human HIF1-beta comprise at least an 8-nucleobase portion of SEQ ID NO: 30. In another embodiment, the compounds used to inhibit expression of human HIF1-beta comprise at least an 8-nucleobase portion of SEQ ID NO: 77.

Also provided are methods of inhibiting expression of HIF1-beta regulated genes in cells or tissues by contacting the cells or tissues with one or more of the compounds provided herein. In one embodiment, the HIF1-beta regulated gene is VEGF. In another embodiment, the HIF1-beta regulated gene is GLUT-1. In another embodiment, the HIF1-beta regulated gene is PGK-1. In another embodiment, the HIF1-beta regulated gene is PAI-1. In yet another embodiment, the HIF1-beta regulated gene is Epo.

Further provided are methods of treating an animal having a disease or condition associated with HIF1-beta comprising administrating to the animal a therapeutically or prophylactically effective amount of a composition comprising one of more of the antisense oligonucleotides provided herein. In one embodiment, the disease or condition associated with HIF1-beta is a hyperproliferative disorder. In one aspect, the hyperproliferative disorder is cancer. In another aspect, the hyperproliferative disorder is an angiogenic disorder. In further embodiments, the angiogenic disorder is an ocular disorder. Ocular disorders contemplated herein, include, but are not limited to macular degeneration, diabetic retinopathy, macular edema and retinopathy of prematurity. In one embodiment, the compounds used to treat the disease or disorder comprise at least an 8-nucleobase portion of SEQ ID NO: 30. In another embodiment, the compounds used to treat the disease or disorder comprise at least an 8-nucleobase portion of SEQ ID NO: 77.

Also provided are methods of treating an animal having a disease or condition associated with a HIF1-beta regulated gene by administrating to the animal a therapeutically or prophylactically effective amount of a composition comprising one or more of the HIF1-beta antisense oligonucleotides provided herein. In one embodiment, the disease or condition is a hyperproliferative disorder. In a further embodiment, the hyperproliferative disorder is an angiogenic disorder.

The present invention also provides methods of preventing or inhibiting aberrant angiogenesis in an animal, methods of inhibiting tumor growth in an animal and methods of preventing or inhibiting ocular neovascularization in an animal, comprising administering to said animal one or more of the antisense oligonucleotides provided herein.

In one embodiment of the methods, the antisense oligonucleotides comprise at least an 8-nucleobase portion of one of the illustrative antisense oligonucleotides provided herein.

DETAILED DESCRIPTION OF ILLUSTRATIVE EMBODIMENTS

HIF1-beta is known to play an important role in cellular signaling pathways that can contribute to a number of medically-important pathologic conditions such as cancer and disorders arising from aberrant angiogenesis. To date, there are no effective means for inhibition of HIF1-beta expression. Thus, disclosed herein are antisense compounds for modulation of HIF1-beta expression. The compounds of the invention can be used, for example, to inhibit or prevent aberrant angiogenesis, inhibit tumor growth, or inhibit expression of HIF1-beta regulated genes.

As used herein, "aberrant angiogenesis" refers to unwanted or uncontrolled angiogenesis.

As used herein, "targeting" or "targeted to" refer to the process of designing an oligomeric compound such that the compound hybridizes with a selected nucleic acid molecule or region of a nucleic acid molecule.

As used herein, "hybridization" means the pairing of complementary strands of oligomeric compounds. In the context of the present invention, an oligomeric compound is "specifically hybridizable" when there is a sufficient degree of complementarity to avoid non-specific binding of the oligomeric compound to non-target nucleic acid sequences. One of skill in the art will be able to determine when an oligomeric compound is specifically hybridizable.

As used herein, a "HIF1-beta regulated gene" is a gene whose expression is modulated by HIF1-beta gene products.

The present invention employs antisense compounds, preferably oligonucleotides and similar species for use in modulating the function or effect of nucleic acid molecules encoding HIF1-beta. This is accomplished by providing oligonucleotides which specifically hybridize with one or more nucleic acid molecules encoding HIF1-beta. As used herein, the terms "target nucleic acid" and "nucleic acid molecule encoding HIF1-beta" have been used for convenience to encompass DNA encoding HIF1-beta, RNA (including pre-mRNA and mRNA or portions thereof) transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of HIF1-beta. In the context of the present invention, “modulation” and “modulation of expression” mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, “hybridization” means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention, the phrase “stringent hybridization conditions” or “stringent conditions” refers to conditions under which a compound of the invention will hybridize to its target sequence, but to a minimal number of other sequences. Stringent conditions are sequence-dependent and will be different in different circumstances and in the context of this invention, “stringent conditions” under which oligomeric compounds hybridize to a target sequence are determined by the nature and composition of the oligomeric compounds and the assays in which they are being investigated.

“Complementary,” as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the DNA, RNA, or oligonucleotide molecule are complementary to each other when a sufficient number of complementary positions in each molecule are occupied by nucleobases which can hydrogen bond with each other. Thus, “specifically hybridizable” and “complementary” are terms which are used to indicate a sufficient degree of precise pairing or complementarity over a sufficient number of nucleobases such that stable and specific binding occurs between the oligonucleotide and a target nucleic acid.

B. Compounds of the Invention

According to the present invention, antisense compounds include antisense oligomeric compounds, antisense oligonucleotides, siRNAs, ribozymes, external guide sequence (EGS) oligonucleotides, alternate splicers and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are “DNA-like” elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the one form of antisense compound is a single-stranded antisense oligonucleotide, in many species the introduction of double-stranded structures, such as double-stranded RNA (dsRNA) molecules; has been shown to induce potent and specific antisense-mediated reduction of the function of a gene or its associated gene products. This phenomenon occurs in both plants and animals and is believed to have an evolutionary connection to viral defense and transposon silencing.

The term “oligomeric compound” refers to a polymeric structure capable of hybridizing to a region of a nucleic acid molecule. This term includes oligonucleotides, oligonucleosides, oligonucleotide analogs, oligonucleotide mimetics and chimeric combinations of these. Oligomeric compounds are routinely prepared linearly but can be joined or otherwise prepared to be circular. Moreover, branched structures are known in the art. An “antisense compound” or “antisense oligomeric compound” refers to an oligomeric compound that is at least partially complementary to the region of a nucleic acid molecule to which it hybridizes and which modulates (increases or decreases) its expression. Consequently, while all antisense compounds can be said to be oligomeric compounds, not all oligomeric compounds are antisense compounds. An “antisense oligonucleotide” is an antisense compound that is a nucleic acid-based oligomer. An antisense oligonucleotide can be chemically modified. Non-limiting examples of oligomeric compounds include primers, probes, antisense compounds, antisense oligonucleotides, external guide sequence (EGS) oligonucleotides and alternate splicers. In one embodiment, the oligomeric compound comprises an antisense strand hybridized to a sense strand. Oligomeric compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound.

The oligomeric compounds in accordance with this invention comprise compounds from about 8 to about 80 nucleobases (i.e. from about 8 to about 80 linked nucleosides). One of ordinary skill in the art will appreciate that this comprehends antisense compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the antisense compounds of the invention comprise 13 to 80 nucleobases. One having ordinary skill in the art will appreciate that this embodies antisense compounds of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the antisense compounds of the invention comprise 13 to 50 nucleobases. One having ordinary skill in the art will appreciate that this embodies antisense compounds of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, or 50 nucleobases.

In one embodiment, the antisense compounds of the invention comprise 13 to 30 nucleobases. One having ordinary skill in the art will appreciate that this embodies antisense compounds of 13, 14, 15, 16, 17, 18, 19, 20, 21, 22, 23, 24, 25, 26, 27, 28, 29 or 30 nucleobases.

In one embodiment, the antisense compounds of the invention comprise 20 to 30 nucleobases. One having ordinary skill in the art will appreciate that this embodies antisense compounds of 20, 21, 22, 23, 24, 25, 26, 27, 28, 29, or 30 nucleobases.

In one embodiment, the antisense compounds of the invention comprise 15 to 25 nucleobases. One having ordinary skill in the art will appreciate that this embodies antisense compounds of 15, 16, 17, 18, 19, 20, 21, 22, 23, 24 or 25.

In one embodiment, the antisense compounds of the invention comprise 20 nucleobases.

In one embodiment, the antisense compounds of the invention comprise 19 nucleobases.

In one embodiment, the antisense compounds of the invention comprise 18 nucleobases.

In one embodiment, the antisense compounds of the invention comprise 17 nucleobases.

In one embodiment, the antisense compounds of the invention comprise 16 nucleobases.

In one embodiment, the antisense compounds of the invention comprise 15 nucleobases.

In one embodiment, the antisense compounds of the invention comprise 14 nucleobases.

In one embodiment, the antisense compounds of the invention comprise 13 nucleobases.

Antisense compounds 13-80 nucleobases in length comprising a stretch of at least eight (8) consecutive nucleobases selected from within the illustrative antisense compounds are considered to be suitable antisense compounds. Antisense compounds 13-80 nucleobases in length comprising a stretch of at least eight (8) consecutive nucleobases selected from within the illustrative antisense compounds are considered to be suitable antisense compounds as well.

Compounds of the invention include oligonucleotide sequences that comprise at least the 8 consecutive nucleobases from the 5'-terminus of one of the illustrative antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 13 to about 80 nucleobases). Other compounds are represented by oligonucleotide sequences that comprise at least the 8 consecutive nucleobases from the 3'-terminus of one of the illustrative antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 13 to about 80 nucleobases). It is also understood that compounds may be represented by oligonucleotide sequences that comprise at least 8 consecutive nucleobases from an internal portion of the sequence of an illustrative compound, and may extend in either or both directions until the oligonucleotide contains about 13 to about 80 nucleobases.

One having skill in the art armed with the antisense compounds illustrated herein will be able, without undue experimentation, to identify further antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes HIF1-beta.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Suitable target regions include, for example, 3' untranslated region (3'UTR), start codon region, coding region, stop codon region, 5' untranslated region (5' UTR), 5' cap region, exons, introns, intron-exon junctions and exon-exon junctions.

In the context of the invention, "start codon" and "translation initiation codon" refer to the codon or codons that are used in vivo to initiate translation of an mRNA transcribed from a gene, regardless of the sequence(s) of such codons. The terms "start codon region" and "translation initiation codon region" refer to a portion of an mRNA or gene that, encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. The open reading frame (ORF) or "coding region" is known in the art to refer to the region between the translation initiation codon and the translation termination codon. The 5'UTR refers to the portion of an mRNA in the 5' direction from the translation initiation codon, and thus including nucleotides between the 5' cap site and the translation initiation codon of an mRNA (or corresponding nucleotides on the gene), and the 3'UTR refers to the portion of an mRNA in the 3' direction from the translation termination codon, and thus including nucleotides between the translation termination codon and 3' end of an mRNA (or corresponding nucleotides on the gene). The 5' cap site of an in RNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence, resulting in exon-exon junctions at the sites where exons are joined. Targeting exon-exon junctions can be useful in situations where the overproduction of a normal splice product is implicated in disease, or where the overproduction of an aberrant splice product is implicated in disease. Targeting splice sites, i.e., intron-exon junctions or exon-intron junctions, may also be particularly useful in situations where aberrant splicing is implicated in disease, or where an overproduction of a particular splice product is implicated in disease. It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as “variants”. More specifically, “pre-mRNA variants” are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller “mRNA variants”. Consequently, mRNA variants are processed pre-mRNA variants and each unique pre-mRNA variant must always produce a unique mRNA variant as a result of splicing. These mRNA variants are also known as “alternative splice variants”. If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as “alternative start variants” of that pre-mRNA or mRNA. Those transcripts that use an alternative stop codon are known as “alternative stop variants” of that pre-mRNA or mRNA. One specific type of alternative stop variant is the “polyA variant” in which the multiple transcripts produced result from the alternative selection of one of the “polyA stop signals” by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are referred to as “preferred target segments.” As used herein the term “preferred target segment” is defined as at least an 8-nucleobase portion of a target region to which an active antisense compound is targeted. While not wishing to be bound by theory, it is presently believed that these target segments represent portions of the target nucleic acid which are accessible for hybridization.

Target segments 13-80 nucleobases in length comprising a stretch of at least eight (8) consecutive nucleobases selected from within a preferred target segment are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 13 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 13 to about 80 nucleobases). It is also understood that preferred antisense target segments may be represented by DNA or RNA sequences that comprise at least 8 consecutive nucleobases from an internal portion of the sequence of an illustrative preferred target segment, and may extend in either or both directions until the oligonucleotide contains about 13 to about 80 nucleobases. One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

The oligomeric antisense compounds can also be targeted to regions of a target nucleobase sequence, such as those disclosed herein.

D. Kits, Research Reagents, Diagnostics, and Therapeutics

The antisense compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.,* 2000, 480, 17-24; Celis, et al., *FEBS Lett.,* 2000, 480, 2-16), SAGE (serial analysis of gene expression) (Madden, et al., *Drug Discov. Today,* 2000, 5, 415-425), READS (restriction enzyme amplification of digested cDNAs) (Prashar and Weissman, *Methods Enzymol.,* 1999, 303, 258-72), TOGA (total gene expression analysis) (Sutcliffe, et al., *Proc. Natl. Acad. Sci. U.S.A.,* 2000, 97, 1976-81), protein arrays and proteomics (Celis, et al., *FEBS Lett.,* 2000, 480, 2-16; Jungblut, et al., *Electrophoresis,* 1999, 20, 2100-10), expressed sequence tag (EST) sequencing (Celis, et al., *FEBS Lett.,* 2000, 480, 2-16; Larsson, et al., *J. Biotechnol.,* 2000, 80, 143-57), subtractive RNA fingerprinting (SuRF) (Fuchs, et al., *Anal. Biochem.,* 2000, 286, 91-98; Larson, et al., *Cytometry,* 2000, 41, 203-208), subtractive cloning, differential display (DD) (Jurecic and Belmont, *Curr. Opin. Microbiol.,* 2000, 3, 316-21), comparative genomic hybridization (Carulli, et al., *J. Cell Biochem. Suppl.,* 1998, 31, 286-96), FISH (fluorescent in situ hybridization) techniques (Going and Gusterson, *Eur. J. Cancer,* 1999, 35, 1895-904)

and mass spectrometry methods (To, *Comb. Chem. High Throughput Screen,* 2000, 3, 235-41).

The antisense compounds of the invention are useful for research and diagnostics, because these compounds hybridize to nucleic acids encoding HIF1-beta and inhibit their function. The primers and probes disclosed herein are useful in methods requiring the specific detection of nucleic acid molecules encoding HIF1-beta and in the amplification of said nucleic acid molecules for detection or for use in further studies of HIF1-beta. Hybridization of the primers and probes with a nucleic acid encoding HIF1-beta can be detected by means known in the art. Such means may include conjugation of an enzyme to the primer or probe, radiolabeling of the primer or probe or any other suitable detection means. Kits using such detection means for detecting the level of HIF1-beta in a sample may also be prepared.

The specificity and sensitivity of antisense is also harnessed by those of skill in the art for therapeutic uses. Antisense compounds are employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds are useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of HIF1-beta is treated by administering antisense compounds in accordance with this invention. For example, in one non-limiting embodiment, the methods comprise the step of administering to the animal in need of treatment, a therapeutically effective amount of a HIF1-beta inhibitor. The HIF1-beta inhibitors of the present invention effectively inhibit the activity of the HIF1-beta protein or inhibit the expression of the HIF1-beta protein. In one embodiment, the activity or expression of HIF1-beta in an animal is inhibited by about 10%. Preferably, the activity or expression of HIF1-beta in an animal is inhibited by about 25%. More preferably, the activity or expression of HIF1-beta in an animal is inhibited by 40% or more. Thus, the oligomeric antisense compounds modulate expression of HIF1-beta mRNA by at least 10%, by at least 20%, by at least 25%, by at least %, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of HIF1-beta may be measured in serum, adipose tissue, liver or any other body fluid, tissue or organ of the animal. Preferably, the cells contained within said fluids, tissues or organs being analyzed contain a nucleic acid molecule encoding HIF1-beta protein and/or the HIF1-beta protein itself.

The antisense compounds of the invention can be utilized in pharmaceutical compositions by adding an effective amount of a compound to a suitable pharmaceutically acceptable diluent or carrier. Use of the compounds and methods of the invention may also be useful prophylactically.

E. Modifications

As is known in the art, a nucleoside is a base-sugar combination. The base portion of the nucleoside is normally a heterocyclic base sometimes referred to as a "nucleobase" or simply a "base". The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of oligomeric antisense compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

Oligomeric compounds of the invention can have one or more modified internucleoside linkages. One phosphorus-containing modified internucleoside linkage is the phosphorothioate internucleoside linkage. Other modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, phosphonoacetate and thiophosphonoacetate (see Sheehan et al., *Nucleic Acids Research,* 2003, 31(14), 4109-4118 and Dellinger et al., *J. Am. Chem. Soc.,* 2003, 125, 940-950), selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

N3'-P5'-phosphoramidates have been reported to exhibit both a high affinity towards a complementary RNA strand and nuclease resistance (Gryaznov et al., *J. Am. Chem. Soc.,* 1994, 116, 3143-3144). N3'-P5'-phosphoramidates have been studied with some success in vivo to specifically down regulate the expression of the c-myc gene (Skorski et al., *Proc. Natl. Acad. Sci.,* 1997, 94, 3966-3971; and Faira et al., *Nat. Biotechnol.,* 2001, 19, 40-44).

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676;

5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

In some embodiments of the invention, oligomeric compounds may have one or more phosphorothioate and/or heteroatom internucleoside linkages, in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). The MMI type internucleoside linkages are disclosed in the above referenced U.S. Pat. No. 5,489,677. Amide internucleoside linkages are disclosed in the above referenced U.S. Pat. No. 5,602,240.

Some oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Modified Sugar and Internucleoside Linkages (Mimetics)

Another group of oligomeric compounds amenable to the present invention includes oligonucleotide mimetics. The term mimetic as it is applied to oligonucleotides is intended to include oligomeric compounds wherein the furanose ring or the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid.

One such oligomeric compound, an oligonucleotide mimetic that has been shown to have excellent hybridization properties, is referred to as a peptide nucleic acid (PNA). Nielsen et al., *Science,* 1991, 254, 1497-1500. PNAs have favorable hybridization properties, high biological stability and are electrostatically neutral molecules. In one recent study PNA compounds were used to correct aberrant splicing in a transgenic mouse model (Sazani et al., *Nat. Biotechnol.,* 2002, 20, 1228-1233). In PNA oligomeric compounds, the sugar-backbone of an oligonucleotide is replaced with an amide containing backbone, in particular an aminoethylglycine backbone. The nucleobases are bound directly or indirectly (—C(=O)—$CH_2$— as shown below) to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262, each of which is herein incorporated by reference. PNA compounds can be obtained commercially from Applied Biosystems (Foster City, Calif., USA). Numerous modifications to the basic PNA backbone are known in the art; particularly useful are PNA compounds with one or more amino acids conjugated to one or both termini. In particular, 1-8 lysine or arginine residues are useful when conjugated to the end of a PNA molecule.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups have been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides which are less likely to form undesired interactions with cellular proteins (Dwaine A. Braasch and David R. Corey, *Biochemistry,* 2002, 41(14), 4503-4510). Morpholino-based oligomeric compounds have been studied in zebrafish embryos (see: *Genesis*, volume 30, issue 3, 2001 and Heasman, J., *Dev. Biol.,* 2002, 243, 209-214). Further studies of morpholino-based oligomeric compounds have also been reported (see: Nasevicius et al., *Nat. Genet.,* 2000, 26, 216-220; and Lacerra et al., *Proc. Natl. Acad. Sci.,* 2000, 97, 9591-9596). Morpholino-based oligomeric compounds are disclosed in U.S. Pat. No. 5,034,506, issued Jul. 23, 1991. The morpholino class of oligomeric compounds have been prepared having a variety of different linking groups joining the monomeric subunits. Linking groups can be varied from chiral to achiral, and from charged to neutral. U.S. Pat. No. 5,166,315 discloses linkages including —O—P(=O)(N($CH_3$)$_2$)—O—; U.S. Pat. No. 5,034,506 discloses achiral intermorpholino linkages; and U.S. Pat. No. 5,185,444 discloses phosphorus containing chiral intermorpholino linkages.

A further class of oligonucleotide mimetic is referred to as cyclohexenyl nucleic acids (CeNA). The furanose ring normally present in a DNA or RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.,* 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. coli* RNase resulting in cleavage of the target RNA strand.

A further modification includes bicyclic sugar moieties such as "Locked Nucleic Acids" (LNAs) in which the 2'-hydroxyl group of the ribosyl sugar ring is linked to the 4' carbon atom of the sugar ring thereby forming a 2'-C,4'-C-oxymethylene linkage to form the bicyclic sugar moiety (reviewed in Elayadi et al., *Curr. Opinion Invens. Drugs,* 2001, 2, 558-561; Braasch et al., *Chem. Biol.,* 2001, 8 1-7; and Orum et al., *Curr.*

*Opinion Mol. Ther.,* 2001, 3, 239-243; see also U.S. Pat. Nos. 6,268,490 and 6,670,461). The linkage can be a methylene ($—CH_2—$) group bridging the 2' oxygen atom and the 4' carbon atom, for which the term LNA is used for the bicyclic moiety; in the case of an ethylene group in this position, the term ENA™ is used (Singh et al., Chem. Commun., 1998, 4, 455-456; ENA™: Morita et al., *Bioorganic Medicinal Chemistry,* 2003, 11, 2211-2226). LNA and other bicyclic sugar analogs display very high duplex thermal stabilities with complementary DNA and RNA (Tm=+3 to +10 C), stability towards 3'-exonucleolytic degradation and good solubility properties. LNAs are commercially available from ProLigo (Paris, France and Boulder, Colo., USA).

An isomer of LNA that has also been studied is α-L-LNA which has been shown to have superior stability against a 3'-exonuclease (Frieden et al., *Nucleic Acids Research,* 2003, 21, 6365-6372). The α-L-LNA's were incorporated into antisense gapmers and chimeras that showed potent antisense activity.

Another similar bicyclic sugar moiety that has been prepared and studied has the bridge going from the 3'-hydroxyl group via a single methylene group to the 4' carbon atom of the sugar ring thereby forming a 3'-C,4'-C-oxymethylene linkage (see U.S. Pat. No. 6,043,060).

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., *J. Mol. Recognit.,* 2000, 13, 44-53). These conformations are associated with improved stacking of the nucleobases (Wengel et al., Nucleosides Nucleotides, 1999, 18, 1365-1370).

LNA has been shown to form exceedingly stable LNA:LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands. DNA LNA chimeras have been shown to efficiently inhibit gene expression when targeted to a variety of regions (5'-untranslated region, region of the start codon or coding region) within the luciferase mRNA (Braasch et al., *Nucleic Acids Research,* 2002, 30, 5160-5167).

Potent and nontoxic antisense oligonucleotides containing LNAs have been described (Wahlestedt et al., Proc. Natl. Acad. Sci. U.S.A., 2000, 97, 5633-5638.) The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli.* Lipofectin-mediated efficient delivery of LNA into living human breast cancer cells has also been accomplished. Further successful in vivo studies involving LNA's have shown knock-down of the rat delta opioid receptor without toxicity (Wahlestedt et al., *Proc. Natl. Acad. Sci.,* 2000, 97, 5633-5638) and in another study showed a blockage of the translation of the large subunit of RNA polymerase II (Fluiter et al., *Nucleic Acids Res.,* 2003, 31, 953-962).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., WO 99/14226). Furthermore, synthesis of 2'-amino-LNA, a novel conformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Another oligonucleotide mimetic amenable to the present invention that has been prepared and studied is threose nucleic acid. This oligonucleotide mimetic is based on threose nucleosides instead of ribose nucleosides. Initial interest in (3',2')-α-L-threose nucleic acid (TNA) was directed to the question of whether a DNA polymerase existed that would copy the TNA. It was found that certain DNA polymerases are able to copy limited stretches of a TNA template (reported in C&EN/Jan. 13, 2003). In another study it was determined that TNA is capable of antiparallel Watson-Crick base pairing with complementary DNA, RNA and TNA oligonucleotides (Chaput et al., *J. Am. Chem. Soc.,* 2003, 125, 856-857).

In one study (3',2')-α-L-threose nucleic acid was prepared and compared to the 2' and 3' amidate analogs (Wu et al., *Organic Letters,* 2002, 4(8), 1279-1282). The amidate analogs were shown to bind to RNA and DNA with comparable strength to that of RNA/DNA.

Further oligonucleotide mimetics have been prepared to include bicyclic and tricyclic nucleoside analogs (see Steffens et al., *Helv. Chim. Acta,* 1997, 80, 2426-2439; Steffens et al., *J. Am. Chem. Soc.,* 1999, 121, 3249-3255; Renneberg et al., *J. Am. Chem. Soc.,* 2002, 124, 5993-6002; and Renneberg et al., *Nucleic acids res.,* 2002, 30, 2751-2757). These modified nucleoside analogs have been oligomerized using the phosphoramidite approach and the resulting oligomeric compounds containing tricyclic nucleoside analogs have shown increased thermal stabilities (Tms) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids which incorporate a phosphorus group in the backbone. This class of oligonucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology. Further oligonucleotide mimetics amenable to the present invention have been prepared wherein a cyclobutyl ring replaces the naturally occurring furanosyl ring.

Modified Sugars

Oligomeric compounds may also contain one or more substituted sugar moieties. Suitable compounds can comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486-504) i.e., an alkoxyalkoxy group. A further modification includes 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$, also described in examples herein below.

Other modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. One 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the *C. elegans* system. Properties that are enhanced by using more stable 3'-endo nucleosides include but are not limited to: modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric triggers of RNAi having one or more nucleosides modified in such a way as to favor a C3'-endo type conformation.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as illustrated in FIG. 2, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2' deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry. Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, oligomeric triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA, Morita et al, Bioorganic & Medicinal Chemistry Letters (2002), 12, 73-76.)

One conformation of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in the modified oligonucleotides of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press., and the examples section below.)

The terms used to describe the conformational geometry of homoduplex nucleic acids are “A Form” for RNA and “B Form” for DNA. The respective conformational geometry for RNA and DNA duplexes was determined from X-ray diffraction analysis of nucleic acid fibers (Arnott and Hukins, *Biochem. Biophys. Res. Comm.,* 1970, 47, 1504.) In general, RNA:RNA duplexes are more stable and have higher melting temperatures (Tms) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., *Nucleic Acids Research,* 1998, 26, 2473-2480, who pointed out that in considering the furanose conformations which give rise to B-form duplexes consideration should also be given to a O4'-endo pucker contribution. DNA:RNA hybrid duplexes, however, are usually less stable than pure RNA:RNA duplexes, and depending on their sequence may be either more or less stable than DNA:DNA duplexes (Searle et al., *Nucleic Acids Res.,* 1993, 21, 2051-2056). The structure of a hybrid duplex is intermediate between A- and B-form geometries, which may result in poor stacking interactions (Lane et al., *Eur. J. Biochem.,* 1993, 215, 297-306; Fedoroff et al., *J. Mol. Biol.,* 1993, 233, 509-523; Gonzalez et al., *Biochemistry,* 1995, 34, 4969-4982; Horton et al., *J. Mol. Biol.,* 1996, 264, 521-533). The stability of the duplex formed between a target RNA and a synthetic sequence is central to therapies such as but not limited to antisense and RNA interference as these mechanisms require the binding of a synthetic oligomer strand to an RNA target strand. In the case of antisense, effective inhibition of the mRNA requires that the antisense DNA have a very high binding affinity with the mRNA. Otherwise the desired interaction between the synthetic oligomer strand and target mRNA strand will occur infrequently, resulting in decreased efficacy.

One routinely used method of modifying the sugar puckering is the substitution of the sugar at the 2'-position with a substituent group that influences the sugar geometry. The influence on ring conformation is dependant on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

Increasing the percentage of C3'-endo sugars in a modified oligonucleotide targeted to an RNA target strand should preorganize this strand for binding to RNA. Of the several sugar modifications that have been reported and studied in the literature, the incorporation of electronegative substituents such as 2'-fluoro or 2'-alkoxy shift the sugar conformation towards the 3' endo (northern) pucker conformation. This preorganizes an oligonucleotide that incorporates such modifications to have an A-form conformational geometry. This A-form conformation results in increased binding affinity of the oligonucleotide to a target RNA strand.

Representative 2'-substituent groups amenable to the present invention that give A-form conformational properties (3'-endo) to the resultant duplexes include 2'-O-alkyl, 2'-O-substituted alkyl and 2'-fluoro substituent groups. Suitable for the substituent groups are various alkyl and aryl ethers and thioethers, amines and monoalkyl and dialkyl substituted amines. It is further intended that multiple modifications can be made to one or more of the oligomeric compounds of the invention at multiple sites of one or more monomeric subunits (nucleosides are suitable) and or internucleoside linkages to enhance properties such as but not limited to activity in a selected application.

Natural and Modified Nucleobases

Antisense compounds may also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C{\equiv}C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido

[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750, 692, which is commonly owned with the instant application and also herein incorporated by reference.

Conjugates

Another modification of the antisense compounds of the invention involves chemically linking to the antisense compound one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Antisense compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270, incorporated by reference herein). These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated by reference herein).

Particularly preferred 3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925; incorporated by reference herein).

Further 3' and 5'-stabilizing groups that can be used to cap one or both ends of an oligomeric compound to impart nuclease stability include those disclosed in WO 03/004602 published on Jan. 16, 2003.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. Chimeric antisense oligonucleotides are thus a form of antisense compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Chimeric antisense compounds can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers". Such compounds have also been referred to in the art as hybrids. In a gapmer that is 20 nucleotides in length, a gap or wing can be 1, 2, 3, 4, 5, 6, 7, 8, 9, 10, 11, 12, 13, 14, 15, 16, 17 or 18 nucleotides in length. In one embodiment, a 20-nucleotide gapmer is comprised of a gap 8 nucleotides in length, flanked on both the 5' and 3' sides by wings 6 nucleotides in length. In another embodiment, a 20-nucleotide gapmer is comprised of a gap 10 nucleotides in length, flanked on both the 5' and 3' sides by wings 5 nucleotides in length. In another embodiment, a 20-nucleotide gapmer is comprised of a gap 12 nucleotides in length flanked on both the 5' and 3' sides by wings 4 nucleotides in length. In a further embodiment, a 20-nucleotide gapmer is comprised of a gap 14 nucleotides in length flanked on both the 5' and 3' sides by wings 3 nucleotides in length. In another embodiment, a 20-nucleotide gapmer is comprised of a gap 16 nucleotides in length flanked on both the 5' and 3' sides by wings 2 nucleotides in length. In a further embodiment, a 20-nucleotide gapmer is comprised of a gap 18 nucleotides in length flanked on both the 5' and 3' ends by wings 1 nucleotide in length. Alternatively, the wings are of different lengths, for example, a 20-nucleotide gapmer may be comprised of a gap 10 nucleotides in length, flanked by a 6-nucleotide wing on one side (5' or 3') and a 4-nucleotide wing on the other side (5' or 3').

In a hemimer, an "open end" chimeric antisense compound, 20 nucleotides in length, a gap segment, located at either the 5' or 3' terminus of the oligomeric compound, can be 1, 2, 3, 4, 5, 6, 7, 8, 9, 10, 11, 12, 13, 14, 15, 16, 17, 18 or 19 nucleotides in length. For example, a 20-nucleotide hemimer can have a gap segment of 10 nucleotides at the 5' end and a second segment of 10 nucleotides at the 3' end. Alternatively, a 20-nucleotide hemimer can have a gap segment of 10 nucleotides at the 3' end and a second segment of 10 nucleotides at the 5' end.

Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

F. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

G. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Such considerations are well known to those skilled in the art.

While the present invention has been described with specificity in accordance with certain of its preferred embodiments, the following examples serve only to illustrate the invention and are not intended to limit the same. Each of the references, GenBank accession numbers, and the like recited in the present application is incorporated herein by reference in its entirety.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methylcytidine penultimate intermediate, [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-([2-phthalimidoxy) ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O-[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides

Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.,* 1998, 120, 11820-11821; Matteucci, M. D. and Caruthers, M. H. *J. Am. Chem. Soc.,* 1981, 103, 3185-3191; Beaucage, S. L. and Caruthers, M. H. *Tetrahedron Lett.,* 1981, 22, 1859-1862; Dahl, B. J., et al., *Acta Chem. Scand.,* 1990, 44, 639-641; Reddy, M. P., et al., *Tetrahedrom Lett.,* 1994, 25, 4311-4314; Wincott, F. et al., *Nucleic Acids Res.,* 1995, 23, 2677-2684; Griffin, B. E., et al., *Tetrahedron,* 1967, 23, 2301-2313; Griffin, B. E., et al., *Tetrahedron,* 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 μl of each of the complementary strands of RNA oligonucleotides (50 μM RNA oligonucleotide solution) and 15 μl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid, or for diagnostic or therapeutic purposes.

Example 4

Synthesis of Chimeric Compounds

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligo is then recovered by an appropriate method (precipitation, column chromatography, volume reduced in vacuo and analyzed spectrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting HIF1-Beta

In accordance with the present invention, a series of nucleic acid duplexes comprising the antisense compounds of the present invention and their complements can be designed to target HIF1-beta. The nucleobase sequence of the antisense strand of the duplex comprises at least an 8-nucleobase portion of an oligonucleotide in Table 1 or Table 2. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini. The antisense and sense strands of the duplex comprise from about 17 to 25 nucleotides, or from about 19 to 23 nucleotides. Alternatively, the antisense and sense strands comprise 20, 21 or 22 nucleotides.

For example, a duplex comprising an antisense strand having the sequence CGAGAGGCGGACGGGACCG (SEQ ID NO: 187) and having a two-nucleobase overhang of deoxythymidine(dT) would have the following structure:

```
  cgagaggcggacgggaccgTT Antisense Strand        (SEQ ID NO: 188)
  |||||||||||||||||||||
TTgctctccgcctgccctggc Sense Strand              (SEQ ID NO: 189)
```

Overhangs can range from 2 to 6 nucleobases and these nucleobases may or may not be complementary to the target nucleic acid. In another embodiment, the duplexes may have an overhang on only one terminus.

In another embodiment, a duplex comprising an antisense strand having the same sequence CGAGAGGCGGACGGGACCG may be prepared with blunt ends (no single stranded overhang) as shown:

```
cgagaggcggacgggaccg Antisense Strand            (SEQ ID NO: 187)
|||||||||||||||||||
gctctccgcctgccctggc Sense Strand                (SEQ ID NO: 190)
```

The RNA duplex can be unimolecular or bimolecular; i.e., the two strands can be part of a single molecule or may be separate molecules.

RNA strands of the duplex can be synthesized by methods disclosed herein or purchased from Dharmacon Research Inc., (Lafayette, Colo.). Once synthesized, the complementary strands are annealed. The single strands are aliquotted and diluted to a concentration of 50 μM. Once diluted, 30 μL of each strand is combined with 15 μL of a 5× solution of annealing buffer. The final concentration of said buffer is 100 mM potassium acetate, 30 mM HEPES-KOH pH 7.4, and 2 mM magnesium acetate. The final volume is 75 μL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 μM. This solution can be stored frozen (−20° C.) and freeze-thawed up to 5 times.

Once prepared, the duplexed antisense compounds are evaluated for their ability to modulate HIF1-beta expression.

When cells reach 80% confluency, they are treated with duplexed antisense compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., *J. Biol. Chem.*

1991, 266, 18162-18171. Results obtained with HPLC-purified material were similar to those obtained with non-HPLC purified material.

Example 7

Oligonucleotide Synthesis

96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis

96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal bovine serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal bovine serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

b.END Cells:

The mouse brain endothelial cell line b.END was obtained from Dr. Werner Risau at the Max Plank Institute (Bad Nauheim, Germany). b.END cells were routinely cultured in DMEM, high glucose (Invitrogen Corporation, Carlsbad, Calif.) supplemented with 10% fetal bovine serum (Invitrogen Corporation, Carlsbad, Calif.). Cells were routinely passaged by trypsinization and dilution when they reached 90% confluence. Cells were seeded into 96-well plates (Falcon-Primaria #3872) at a density of 3000 cells/well for use in RT-PCR analysis.

MCF7 Cells:

The human breast carcinoma cell line MCF-7 was obtained from the American Type Culture Collection (Manassas, Va.). MCF-7 cells were routinely cultured in DMEM low glucose supplemented with 10% fetal bovine serum (Invitrogen Life Technologies, Carlsbad, Calif.). Cells were routinely passaged by trypsinization and dilution when they reached 90% confluence. Cells were seeded into poly-D-lysine coated 96-well plates (Falcon-Primaria #3872) at a density of 8000 cells/well for use in antisense oligonucleotide transfection.

PC3 Cells:

The human prostatic carcinoma cell line PC3 was obtained from the American Type Culture Collection (ATCC) (Manassas, Va.). PC3 cells were routinely cultured in Ham's F12K medium with 2 mM L-glutamine adjusted to contain 1.5 g/L sodium bicarbonate supplemented with 10% fetal bovine serum (Invitrogen Life Technologies, Carlsbad, Calif.) and antibiotics (Invitrogen Life Technologies, Carlsbad, Calif.).

Cells were routinely passaged by trypsinization and dilution when they reached approximately 90% confluence. Cells were seeded into 96-well plates (Falcon-Primaria #353872) at a density of approximately 6000 cells/well for use in antisense oligonucleotide transfection.

Hep3B Cells:

The human hepatoma cell line Hep3B (Hep3B2.1-7) was obtained from the American Type Culture Collection (ATCC-ATCC Catalog #HB-8064) (Manassas, Va.). This cell line was initially derived from a hepatocellular carcinoma of an 8-yr-old black male. The cells are epithelial in morphology and are tumorigenic in nude mice. Hep3B cells are routinely cultured in Minimum Essential Medium (MEM) with Earle's Balanced Salt Solution, 2 mM L-glutamine, 1.5 g/L sodium bicarbonate, 0.1 mM nonessential amino acids, 1.0 mM sodium pyruvate (ATCC #20-2003, Manassas, Va.) and with 10% heat-inactivated fetal bovine serum (Invitrogen Life Technologies, Carlsbad, Calif.). Cells are routinely passaged by trypsinization and dilution when they reach 90% confluence.

HeLa Cells:

The human epithelioid carcinoma cell line HeLa was obtained from the American Tissue Type Culture Collection (Manassas, Va.). HeLa cells were routinely cultured in DMEM, high glucose (Invitrogen Corporation, Carlsbad, Calif.) supplemented with 10% fetal bovine serum (Invitrogen Corporation, Carlsbad, Calif.). Cells were routinely passaged by trypsinization and dilution when they reached 90% confluence. Cells were seeded into 24-well plates (Falcon-Primaria #3846) at a density of 50,000 cells/well or in 96-well plates at a density of 5,000 cells/well for use in RT-PCR analysis. For Northern blotting or other analyses, cells were harvested when they reached 90% confluence.

HuVEC Cells:

The human umbilical vein endothelial cell line HuVEC is obtained from Cascade Biologics (Portland, Oreg.). HuVEC cells are routinely cultured in EBM (Clonetics Corporation Walkersville, Md.) supplemented with SingleQuots supplements (Clonetics Corporation, Walkersville, Md.). Cells are routinely passaged by trypsinization and dilution when they reach 90% confluence and are maintained for up to 15 passages.

Treatment with Antisense Compounds:

When cells reached 65-75% confluency, they were treated with oligonucleotide. For cells grown in 96-well plates, wells were washed once with 100 µL OPTI-MEM™-1 reduced-serum medium (Invitrogen Corporation, Carlsbad, Calif.) and then treated with 130 µL of OPTI-MEM™-1 containing 3.75 µg/mL LIPOFECTIN™ (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCTCAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770 (ATGCATTCTGCCCCCAAGGA, SEQ ID NO: 3), a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

For Northern blotting or other analyses, cells may be seeded onto 100 mm or other standard tissue culture plates and treated similarly, using appropriate volumes of medium and oligonucleotide.

Example 10

Analysis of Oligonucleotide Inhibition of HIF1-Beta Expression

Antisense modulation of HIF1-beta expression can be assayed in a variety of ways known in the art. For example, HIF1-beta mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of HIF1-beta can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to HIF1-beta can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays for the Use of HIF1-Beta Inhibitors

Phenotypic Assays

Once HIF1-beta inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of HIF1-beta in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with HIF1-beta inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the HIF1-beta inhibitors. Hallmark genes, or those genes suspected to be associated with a specific disease state, condition, or phenotype, are measured in both treated and untreated cells.

Example 12

RNA Isolation

Poly(A)+ mRNA Isolation

Poly(A)+ mRNA was isolated according to Miura et al., (*Clin. Chem.*, 1996, 42, 1758-1764). Other methods for poly (A)+ mRNA isolation are routine in the art. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 μL cold PBS. 150 μL Buffer RW1 was added to each well and the plate vigorously agitated for 20 seconds. 150 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 μL of Buffer RNAse was added to each well of the RNEASY 96™ plate and incubated for 15 minutes and the vacuum was again applied for 1 minute. An additional 500 μL of Buffer RNAse was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 μL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of HIF1-beta mRNA Levels

Quantitation of HIF1-beta mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

Gene target quantities are obtained by real-time PCR. Prior to the real-time PCR, isolated RNA is subjected to a reverse transcriptase (RT) reaction, for the purpose of generating complementary DNA (cDNA). Reverse transcriptase and PCR reagents were obtained from Invitrogen Corporation, (Carlsbad, Calif.). RT, real-time PCR reactions were carried out by adding 20 μL PCR cocktail (2.5×PCR buffer minus $MgCl_2$, 6.6 mM $MgCl_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension). The method of obtaining gene target quantities by RT, real-time PCR is herein referred to as real-time PCR.

Gene target quantities obtained by real-time PCR were normalized using either the expression level of GAPDH, a gene whose expression is constant, or by quantifying total RNA using RiboGreen™ (Molecular Probes, Inc. Eugene, Oreg.). GAPDH expression is quantified by real-time PCR by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 μL of RiboGreen™ working reagent (RiboGreen™ reagent diluted 1:350 in 10 mM Tris-HCl, 1 mM EDTA, pH 7.5) was pipetted into a 96-well plate containing 30 μL purified, cellular RNA. The plate was read in a CytoFluor 4000 (PE Applied Biosystems) with excitation at 485 nm and emission at 530 nm.

Probes and primers to human HIF1-beta were designed to hybridize to a human HIF1-beta sequence, using published sequence information (Genbank accession number BC028362.1, incorporated herein as SEQ ID NO: 4). For human HIF1-beta the PCR primers were:

forward primer: AGCAGAGGGTGTGGGTGTCT (SEQ ID NO: 5)

reverse primer: TGGCGGTTGTTGAACATGTT (SEQ ID NO: 6) and the PCR probe was: FAM-CCAGCAGCCTCATCATCGTTCA-TAMRA (SEQ ID NO: 7) where FAM is the fluorescent dye and TAMRA is the quencher dye. For human GAPDH the PCR primers were:

forward primer: GAAGGTGAAGGTCGGAGTC(SEQ ID NO: 8)

reverse primer: GAAGATGGTGATGGGATTTC (SEQ ID NO: 9) and the PCR probe was: 5' JOE-CAAGCTTCCCGTTCTCAGCC-TAMRA 3' (SEQ ID NO: 10) where JOE is the fluorescent reporter dye and TAMRA is the quencher dye.

Probes and primers to mouse HIF1-beta were designed to hybridize to a mouse HIF1-beta sequence, using published sequence information (GenBank accession number BC012870.1, incorporated herein as SEQ ID NO: 11). For mouse HIF1-beta the PCR primers were:

forward primer: GGCATCTCCTCCAGCACTGT (SEQ ID NO: 12)

reverse primer: GGTAAGACCACTATTCCTGAAATTCTCT (SEQ ID NO: 13) and the PCR probe was: FAM-TCCCTCCTAACCCCCGGCCG-TAMRA (SEQ ID NO: 14) where FAM is the fluorescent reporter dye and TAMRA is the quencher dye. For mouse GAPDH the PCR primers were:

forward primer: GGCAAATTCAACGGCACAGT (SEQ ID NO: 15)

reverse primer: GGGTCTCGCTCCTGGAAGAT (SEQ ID NO: 16) and the PCR probe was: 5' JOE-AAGGCCGAGAATGGGAAGCTTGTCATC-TAMRA 3' (SEQ ID NO: 17) where JOE is the fluorescent reporter dye and TAMRA is the quencher dye.

Example 14

Northern Blot Analysis of HIF1-beta mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBONDT™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human HIF1-beta, a human HIF1-beta specific probe was prepared by PCR using the forward primer AGCAGAGGGTGTGGGTGTCT (SEQ ID NO: 5) and the reverse primer TGGCGGTTGTTGAACATGTT (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

To detect mouse HIF1-beta, a mouse HIF1-beta specific probe was prepared by PCR using the forward primer GGCATCTCCTCCAGCACTGT (SEQ ID NO: 12) and the reverse primer GGTAAGACCACTATTCCTGAAATTCTCT (SEQ ID NO: 13). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human HIF1-Beta Expression by Chimeric Phosphorothioate Oligonucleotides Having 2'-MOE Wings and a Deoxy Gap In accordance with the present invention, a series of antisense compounds was designed to target different regions of the human HIF1-beta RNA, using published sequences (GenBank accession number BC028362.1, incorporated herein as SEQ ID NO: 4, nucleotides 336578 to 404364 of Genbank accession number NT_021907.12, the complement of which is incorporated herein as SEQ ID NO: 18, GenBank accession number N72808.1, incorporated herein as SEQ ID NO: 19, and GenBank accession number AL834279.1, incorporated herein as SEQ ID NO: 20). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl nucleotides, also known as 2'-MOE nucleotides. The internucleoside (backbone) linkages are phosphorothioate (P═S) throughout the oligonucleotide. All cytidine residues are 5-methylcytidines. The compounds were analyzed for their effect on human HIF1-beta mRNA levels by quantitative real-time PCR as described in other examples herein. Data are averages from two experiments in which T-24 cells were treated with 100 nM of antisense oligonucleotides of the present invention. The positive control for each datapoint is identified in the table by sequence ID number. If present, "N.D." indicates "no data".

TABLE 1

Inhibition of human HIF1-beta mRNA levels by chimeric phosphorothioate oligonucleotides having 2'-MOE wings and a deoxy gap

| ISIS # | REGION | TARGET SEQ ID NO | TARGET SITE | SEQUENCE (5' to 3') | % INHIB | SEQ ID NO | CONTROL SEQ ID NO |
|---|---|---|---|---|---|---|---|
| 311073 | Intron 1 | 18 | 1578 | acacacatatctcaaggccc | 65 | 21 | 2 |
| 311074 | Intron 1 | 18 | 10523 | aagggagcagaggactccct | 6 | 22 | 2 |
| 311075 | Intron 1 | 18 | 15791 | caagatcaggctgggaaaca | 25 | 23 | 2 |
| 311076 | Intron 2 | 18 | 23071 | cccctaatctggtcacctgt | 71 | 24 | 2 |
| 311077 | Intron 8: Exon 9 junction | 18 | 44694 | actgccacacctgtttcaag | 51 | 25 | 2 |
| 311078 | Intron 13 | 18 | 52827 | taggaataataacttatttc | 0 | 26 | 2 |
| 311079 | Exon 21: Intron 21 junction | 18 | 63922 | actctcttacctggaagacc | 4 | 27 | 2 |
| 311080 | 5'UTR | 4 | 19 | caagatggcggcttcagcag | 3 | 28 | 2 |
| 311081 | 5'UTR | 4 | 80 | ggaaaagaaaggccactccc | 0 | 29 | 2 |
| 311082 | Start Codon | 4 | 163 | gccgccatggccgcagatgc | 87 | 30 | 2 |
| 311083 | Coding | 4 | 199 | ggtacatctgatgtcatttc | 38 | 31 | 2 |
| 311084 | Coding | 4 | 281 | cttaatagccctctggacaa | 29 | 32 | 2 |
| 311085 | Coding | 4 | 308 | atcatcaaaatccagccctg | 42 | 33 | 2 |
| 311086 | Coding | 4 | 388 | tccgacctggcaaaccgctc | 52 | 34 | 2 |
| 311087 | Coding | 4 | 393 | catcatccgacctggcaaac | 17 | 35 | 2 |
| 311088 | Coding | 4 | 432 | attttccctggcaagtctct | 55 | 36 | 2 |
| 311089 | Coding | 4 | 472 | ctgtcatcttgttccgtcgc | 69 | 37 | 2 |
| 311090 | Coding | 4 | 494 | tctgacagttctgtgatgta | 82 | 38 | 2 |

TABLE 1-continued

Inhibition of human HIF1-beta mRNA levels by chimeric phosphorothioate oligonucleotides having 2'-MOE wings and a deoxy gap

| ISIS # | REGION | TARGET SEQ ID NO | TARGET SITE | SEQUENCE (5' to 3') | % INHIB | SEQ ID NO | CONTROL SEQ ID NO |
|---|---|---|---|---|---|---|---|
| 311091 | Coding | 4 | 527 | tttcgagccagggcactaca | 83 | 39 | 2 |
| 311092 | Coding | 4 | 532 | ctggttttcgagccagggca | 76 | 40 | 2 |
| 311093 | Coding | 4 | 652 | aatgtttcagttcctgatca | 56 | 41 | 2 |
| 311094 | Coding | 4 | 658 | agatcaaatgtttcagttcc | 66 | 42 | 2 |
| 311095 | Coding | 4 | 663 | ctccaagatcaaatgtttca | 43 | 43 | 2 |
| 311096 | Coding | 4 | 668 | gctgcctccaagatcaaatg | 55 | 44 | 2 |
| 311097 | Coding | 4 | 673 | catctgctgcctccaagatc | 73 | 45 | 2 |
| 311098 | Coding | 4 | 678 | aaagccatctgctgcctcca | 80 | 46 | 2 |
| 311099 | Coding | 4 | 804 | atcatctgggtgcacctgat | 76 | 47 | 2 |
| 311100 | Coding | 4 | 810 | atccacatcatctgggtgca | 80 | 48 | 2 |
| 311101 | Coding | 4 | 815 | agtttatccacatcatctgg | 43 | 49 | 2 |
| 311102 | Coding | 4 | 892 | cctttttcactgttccagtc | 81 | 50 | 2 |
| 311103 | Coding | 4 | 900 | ctgaccttcctttttcactg | 68 | 51 | 2 |
| 311104 | Coding | 4 | 906 | agactgctgaccttcctttt | 63 | 52 | 2 |
| 311105 | Coding | 4 | 1029 | tccattcctgcatctgttcc | 53 | 53 | 2 |
| 311106 | Coding | 4 | 1036 | agccaagtccattcctgcat | 84 | 54 | 2 |
| 311107 | Coding | 4 | 1139 | gcctctgggtcatcatctgg | 79 | 55 | 2 |
| 311108 | Coding | 4 | 1200 | gggagaactagttacctgca | 48 | 56 | 2 |
| 311109 | Coding | 4 | 1205 | cagttgggagaactagttac | 43 | 57 | 2 |
| 311110 | Coding | 4 | 1210 | ctgtacagttgggagaacta | 74 | 58 | 2 |
| 311111 | Coding | 4 | 1215 | catgtctgtacagttgggag | 34 | 59 | 2 |
| 311112 | Coding | 4 | 1220 | ttactcatgtctgtacagtt | 84 | 60 | 2 |
| 311113 | Coding | 4 | 1251 | tcgggagatgaactctgttg | 65 | 61 | 2 |
| 311114 | Coding | 4 | 1256 | ttgtgtcgggagatgaactc | 49 | 62 | 2 |
| 311115 | Coding | 4 | 1261 | caatgttgtgtcgggagatg | 57 | 63 | 2 |
| 311116 | Coding | 4 | 1310 | tagccaacagtagccacaca | 48 | 64 | 2 |
| 311117 | Coding | 4 | 1315 | gctggtagccaacagtagcc | 51 | 65 | 2 |
| 311118 | Coding | 4 | 1320 | ctgtggctggtagccaacag | 52 | 66 | 2 |
| 311119 | Coding | 4 | 1343 | acaatattctttcctaagag | 27 | 67 | 2 |
| 311120 | Coding | 4 | 1405 | atttcactacctgttggaag | 67 | 68 | 2 |
| 311121 | Coding | 4 | 1418 | acttggccttttaatttcac | 55 | 69 | 2 |
| 311122 | Coding | 4 | 1423 | acagcacttggccttttaat | 63 | 70 | 2 |
| 311123 | Coding | 4 | 1434 | gaacatgacagacagcactt | 62 | 71 | 2 |
| 311124 | Coding | 4 | 1551 | gttcttcacattggtgttgg | 68 | 72 | 2 |
| 311125 | Coding | 4 | 1556 | ctagagttcttcacattggt | 56 | 73 | 2 |
| 311126 | Coding | 4 | 1706 | ccatctcttcctggtaccat | 77 | 74 | 2 |

TABLE 1-continued

Inhibition of human HIF1-beta mRNA levels by chimeric phosphorothioate oligonucleotides having 2'-MOE wings and a deoxy gap

| ISIS # | REGION | TARGET SEQ ID NO | TARGET SITE | SEQUENCE (5' to 3') | % INHIB | SEQ ID NO | CONTROL SEQ ID NO |
|---|---|---|---|---|---|---|---|
| 311127 | Coding | 4 | 1862 | ttactctgatccgcattgat | 49 | 75 | 2 |
| 311128 | Coding | 4 | 1871 | gagatgcctttactctgatc | 67 | 76 | 2 |
| 311129 | Coding | 4 | 1876 | tggaggagatgcctttactc | 84 | 77 | 2 |
| 311130 | Coding | 4 | 1881 | agtgctggaggagatgcctt | 75 | 78 | 2 |
| 311131 | Coding | 4 | 1953 | gaaattctctgccggccggg | 70 | 79 | 2 |
| 311132 | Coding | 4 | 1958 | ttcctgaaattctctgccgg | 67 | 80 | 2 |
| 311133 | Coding | 4 | 1967 | agaccactattcctgaaatt | 15 | 81 | 2 |
| 311134 | Coding | 4 | 1990 | ggacaatggttacaggaggg | 68 | 82 | 2 |
| 311135 | Coding | 4 | 1995 | tggctggacaatggttacag | 80 | 83 | 2 |
| 311136 | Coding | 4 | 2276 | gtctcaggagcaaagttaga | 48 | 84 | 2 |
| 311137 | Coding | 4 | 2339 | cactgtggccagacacccac | 65 | 85 | 2 |
| 311138 | Coding | 4 | 2349 | ctggccctgccactgtggcc | 42 | 86 | 2 |
| 311139 | Coding | 4 | 2354 | ggctgctggccctgccactg | 85 | 87 | 2 |
| 311140 | Coding | 4 | 2507 | ggaaacatagttagatcagg | 66 | 88 | 2 |
| 311141 | Stop Codon | 4 | 2531 | caatagttctattctgaaaa | 21 | 89 | 2 |
| 311142 | Stop Codon | 4 | 2537 | tcaccccaatagttctattc | 27 | 90 | 2 |
| 311143 | Stop Codon | 4 | 2542 | tatcctcaccccaatagttc | 24 | 91 | 2 |
| 311144 | 3'UTR | 4 | 2616 | agaggaactttattctgtt | 51 | 92 | 2 |
| 311145 | 3'UTR | 4 | 2621 | aagggagaggaactttatt | 0 | 93 | 2 |
| 311146 | 3'UTR | 4 | 2873 | atccaaggcaaacagtggat | 66 | 94 | 2 |
| 311147 | 3'UTR | 4 | 3791 | gtccaggccccatctatcat | 57 | 95 | 2 |
| 311148 | 3'UTR | 4 | 4429 | tgaaaatctttgctacatgt | 72 | 96 | 2 |
| 311149 | 5'UTR | 19 | 231 | ccaggtggtcacatctggtc | 33 | 97 | 2 |
| 311150 | Exon1: Exon1A junction | 20 | 162 | tgagtccaagatcaggcggg | 18 | 98 | 2 |

As shown in Table 1, the majority of antisense compounds targeting human HIF1-beta resulted in inhibition of HIF1-beta mRNA levels. Treatment of cells with antisense compounds represented by SEQ ID NOs: 21, 23-25, 30-34, 36-80, 82-92 and 94-97 resulted in at least 20% inhibition of HIF1-beta mRNA; SEQ ID NOs: 21, 24, 25, 30, 33, 34, 36-58, 60-66, 68-80, 82-88, 92 and 94-96 resulted in at least 40% inhibition of HIF1-beta mRNA; SEQ ID NOs: 21, 24, 25, 30, 34, 36-42, 44-48, 50-55, 58, 60, 61, 63, 65, 66, 68-74, 76-80, 82, 83, 85, 87, 88, 92 and 94-96 resulted in at least 50% inhibition of HIF1-beta mRNA; SEQ ID NOs: 21, 24, 30, 37-40, 42, 45-48, 50-52, 54, 55, 58, 60, 61, 68, 70-72, 74, 76-80, 82, 83, 85, 87, 88, 94 and 96 resulted in at least 60% inhibition of HIF1-beta mRNA; SEQ ID NOs: 24, 30, 38-40, 45-48, 50, 54, 55, 58, 60, 74, 77-79, 83, 87 and 96 resulted in at least 70% inhibition of HIF1-beta mRNA; and SEQ ID NOs: 30, 38, 39, 46, 48, 50, 54, 60, 77, 83 and 87 resulted in at least 80% inhibition of HIF1-beta mRNA.

Example 16

Antisense Inhibition of Mouse HIF1-Beta Expression by Chimeric Phosphorothioate Oligonucleotides Having 2'-MOE Wings and a Deoxy Gap In accordance with the present invention, a second series of antisense compounds was designed to target different regions of the mouse HIF1-beta RNA, using published sequences (GenBank accession number BC012870.1, incorporated herein as SEQ ID NO: 11, nucleotides 1145000 to 1210000 of GenBank accession number NW_000199.1, incorporated herein as SEQ ID NO: 99, GenBank accession number AK040475.1, incorporated herein as SEQ ID NO: 100, Gen- Bank accession number AK028546.1, incorporated herein as SEQ ID NO: 101, GenBank accession number BG083773.1, incorporated herein as SEQ ID NO: 102, and GenBank accession number AK049738.1, incorporated herein as SEQ ID NO: 103). The compounds are shown in Table 2. "Target site" indicates the first (5'-most) nucleotide number on the particular target nucleic acid to which the compound binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl nucleotides, also known as 2'-MOE nucleotides. The internucleoside (backbone) linkages are phosphorothioate (P=S) throughout the oligonucleotide. All cytidine residues are 5-methylcytidines. The compounds were analyzed for their effect on mouse HIF1-beta mRNA levels by quantitative real-time PCR as described in other examples herein. Data are averages from two experiments in which b.END cells were treated with 40 nM of antisense oligonucleotides of the present invention. The positive control for each datapoint is identified in the table by sequence ID number. If present, "N.D." indicates "no data".

TABLE 2

Inhibition of mouse HIF1-beta mRNA levels by chimeric phosphorothioate oligonucleotides having 2'-MOE wings and a deoxy gap

| ISIS # | REGION | TARGET SEQ ID NO | TARGET SITE | SEQUENCE (5' to 3') | % INHIB | SEQ ID NO | CONTROL SEQ ID NO |
|---|---|---|---|---|---|---|---|
| 347985 | Intron 1 | 99 | 12686 | gattccagcagaaacaagat | 76 | 104 | 2 |
| 347986 | Intron 2 | 99 | 20208 | agtaccataaccaggaagag | 82 | 105 | 2 |
| 347987 | Intron 3: Exon 4 junction | 99 | 28425 | atcatcgcatctgaaaagaa | 51 | 106 | 2 |
| 347988 | Exon 11: Intron 11 junction | 99 | 51989 | tcatacttgcctgcagcctg | 59 | 107 | 2 |
| 347989 | 5'UTR | 11 | 3 | agattaggcaccttaccgcc | 80 | 108 | 2 |
| 347990 | Start Codon | 11 | 98 | gccgccatggtcgagatggc | 73 | 109 | 2 |
| 347991 | Start Codon | 11 | 111 | gttagctgtagtcgccgcca | 88 | 110 | 2 |
| 347992 | Coding | 11 | 121 | tcatttctgggttagctgta | 75 | 111 | 2 |
| 347993 | Coding | 11 | 131 | acatctgatgtcatttctgg | 79 | 112 | 2 |
| 347994 | Coding | 11 | 163 | ttccagaagcaatggtggga | 69 | 113 | 2 |
| 347995 | Coding | 11 | 195 | agctcctccaccttgaatcc | 41 | 114 | 2 |
| 347996 | Coding | 11 | 221 | cgtcgcttaatagccctctg | 81 | 115 | 2 |
| 347997 | Coding | 11 | 231 | cagccctgaccgtcgcttaa | 83 | 116 | 2 |
| 347998 | Coding | 11 | 241 | catcaaaatccagccctgac | 29 | 117 | 2 |
| 347999 | Coding | 11 | 317 | ctggcaaaccgctctttgtc | 47 | 118 | 2 |
| 348000 | Coding | 11 | 327 | atcatccgacctggcaaacc | 85 | 119 | 2 |
| 348001 | Coding | 11 | 337 | agctctgctcatcatccgac | 41 | 120 | 2 |
| 348002 | Coding | 11 | 355 | gtctctctttatccgcagag | 89 | 121 | 2 |
| 348003 | Coding | 11 | 362 | ctggcaagtctctctttatc | 66 | 122 | 2 |
| 348004 | Coding | 11 | 367 | tttccctggcaagtctctct | 56 | 123 | 2 |
| 348005 | Coding | 11 | 372 | atgattttccctggcaagtc | 75 | 124 | 2 |
| 348006 | Coding | 11 | 414 | gtaagctgtcatcttgttcc | 73 | 125 | 2 |
| 348007 | Coding | 11 | 424 | gttctgtgatgtaagctgtc | 49 | 126 | 2 |
| 348008 | Coding | 11 | 477 | tagcttgtctggttttcgag | 63 | 127 | 2 |
| 348009 | Coding | 11 | 591 | caaatgtttcagttcctgat | 82 | 128 | 2 |
| 348010 | Coding | 11 | 622 | taaacagaaagccatctgct | 83 | 129 | 2 |
| 348011 | Coding | 11 | 686 | tggttcaaaacgggagtcac | 39 | 130 | 2 |

TABLE 2-continued

Inhibition of mouse HIF1-beta mRNA levels by chimeric phosphorothioate oligonucleotides having 2'-MOE wings and a deoxy gap

| ISIS # | REGION | TARGET SEQ ID NO | TARGET SITE | SEQUENCE (5' to 3') | % INHIB | SEQ ID NO | CONTROL SEQ ID NO |
|---|---|---|---|---|---|---|---|
| 348012 | Coding | 11 | 763 | gctgctctcgaagtttatcc | 58 | 131 | 2 |
| 348013 | Coding | 11 | 858 | gcacatcctcatggaagact | 90 | 132 | 2 |
| 348014 | Coding | 11 | 929 | ttcatggaaacagggtccac | 84 | 133 | 2 |
| 348015 | Coding | 11 | 939 | gctcagtctattcatggaaa | 76 | 134 | 2 |
| 348016 | Coding | 11 | 949 | tcctcaaaaagctcagtcta | 56 | 135 | 2 |
| 348017 | Coding | 11 | 959 | ctgcatctgttcctcaaaaa | 86 | 136 | 2 |
| 348018 | Coding | 11 | 1015 | tgcagtggactaccacaaag | 68 | 137 | 2 |
| 348019 | Coding | 11 | 1081 | ggccagcctctgggtcatca | 89 | 138 | 2 |
| 348020 | Coding | 11 | 1097 | cagaatttgctcccctggcc | 73 | 139 | 2 |
| 348021 | Coding | 11 | 1107 | ggccactaggcagaatttgc | 79 | 140 | 2 |
| 348022 | Coding | 11 | 1119 | cagcctgccaatggccacta | 70 | 141 | 2 |
| 348023 | Coding | 11 | 1211 | gtgaatatcccttcaatgtt | 74 | 142 | 2 |
| 348024 | Coding | 11 | 1241 | acagtagccacacaacgatg | 79 | 143 | 2 |
| 348025 | Coding | 11 | 1291 | gacaaaattctacaatattc | 53 | 144 | 2 |
| 348026 | Coding | 11 | 1302 | gtcttcaggatgacaaaatt | 79 | 145 | 2 |
| 348027 | Coding | 11 | 1312 | gaagttgttggtcttcagga | 65 | 146 | 2 |
| 348028 | Coding | 11 | 1323 | gctgtctcttagaagttgtt | 25 | 147 | 2 |
| 348029 | Coding | 11 | 1333 | cctgctgaaagctgtctctt | 76 | 148 | 2 |
| 348030 | Coding | 11 | 1343 | aatttcaccacctgctgaaa | 56 | 149 | 2 |
| 348031 | Coding | 11 | 1408 | tcatccacagccattctcgg | 75 | 150 | 2 |
| 348032 | Coding | 11 | 1504 | gtggttcctggctagagttc | 58 | 151 | 2 |
| 348033 | Coding | 11 | 1550 | gtcggacctagctgtgacct | 80 | 152 | 2 |
| 348034 | Coding | 11 | 1579 | ctgtacccatctctagggat | 79 | 153 | 2 |
| 348035 | Coding | 11 | 1651 | ccagcccatctcttcctggt | 23 | 154 | 2 |
| 348036 | Coding | 11 | 1681 | ggacagaaacctgggaatga | 76 | 155 | 2 |
| 348037 | Coding | 11 | 1719 | gggcttgctgtgttctgatc | 70 | 156 | 2 |
| 348038 | Coding | 11 | 1742 | aagagaccttctgacttctc | 57 | 157 | 2 |
| 348039 | Coding | 11 | 1855 | cctgggagaacagctgttgg | 84 | 158 | 2 |
| 348040 | Coding | 11 | 1865 | aatgagctgccctgggagaa | 83 | 159 | 2 |
| 348041 | Coding | 11 | 1875 | gttaggagggaatgagctgc | 69 | 160 | 2 |
| 348042 | Coding | 11 | 1906 | cactattcctgaaattctct | 65 | 161 | 2 |
| 348043 | Coding | 11 | 1958 | atctgccctgcagaagatga | 58 | 162 | 2 |
| 348044 | Coding | 11 | 2083 | aagaacgagtcttggctgta | 70 | 163 | 2 |
| 348045 | Coding | 11 | 2110 | tctgaaagttgttcacacca | 51 | 164 | 2 |
| 348046 | Coding | 11 | 2219 | gtctcaggaggaaagttgga | 88 | 165 | 2 |
| 348047 | Coding | 11 | 2287 | cctgccactgtggccagaca | 77 | 166 | 2 |

TABLE 2-continued

Inhibition of mouse HIF1-beta mRNA levels by chimeric phosphorothioate oligonucleotides having 2'-MOE wings and a deoxy gap

| ISIS # | REGION | TARGET SEQ ID NO | TARGET SITE | SEQUENCE (5' to 3') | % INHIB | SEQ ID NO | CONTROL SEQ ID NO |
|---|---|---|---|---|---|---|---|
| 348048 | Coding | 11 | 2379 | ttcttgaaagacctcaggct | 52 | 167 | 2 |
| 348049 | Coding | 11 | 2399 | tctcccagcatggacagcat | 68 | 168 | 2 |
| 348050 | Stop Codon | 11 | 2475 | ccaatagttctattcggaaa | 87 | 169 | 2 |
| 348051 | 3'UTR | 11 | 2538 | tctgtttacaaaagatttgc | 78 | 170 | 2 |
| 348052 | 5'UTR | 100 | 10 | cggaatccaagatggcggac | 88 | 171 | 2 |
| 348053 | 3'UTR | 100 | 2358 | ctccaaacaagcctgagacc | 87 | 172 | 2 |
| 348054 | Coding | 101 | 352 | atgattttccctggcaaacc | 79 | 173 | 2 |
| 348055 | Coding | 101 | 2031 | ggcacctgggcggcaaagcc | 60 | 174 | 2 |
| 348056 | Coding | 102 | 608 | agacttttcccccacatatc | 67 | 175 | 2 |
| 348057 | 5'UTR | 103 | 50 | taacctatgtattcagtgat | 34 | 176 | 2 |
| 311090 | Coding | 11 | 431 | tctgacagttctgtgatgta | 75 | 38 | 2 |
| 311091 | Coding | 11 | 464 | tttcgagccagggcactaca | 82 | 39 | 2 |
| 311112 | Coding | 11 | 1157 | ttactcatgtctgtacagtt | 82 | 60 | 2 |
| 311129 | Coding | 11 | 2819 | tggaggagatgcctttactc | 75 | 77 | 2 |
| 311130 | Coding | 11 | 1824 | agtgctggaggagatgcctt | 78 | 78 | 2 |

As shown in Table 1, the majority of antisense compounds targeting mouse HIF1-beta resulted in inhibition of HIF1-beta mRNA levels. Treatment of cells with antisense compounds represented by SEQ ID NOs: 38, 39, 60, 77, 78, 104-153 and 155-176 resulted in at least 25% inhibition of HIF1-beta mRNA; SEQ ID NOs: 38, 39, 60, 77, 78, 104-113, 115, 116, 119, 121-125, 127-129, 131-146, 148-153 and 155-175 resulted in at least 50% inhibition of HIF1-beta mRNA; 38, 39, 60, 77, 78, 104, 105, 108-113, 115, 116, 119, 121, 122, 124, 125, 127-129, 132-134, 136-143, 145, 146, 148, 150, 152, 153, 155, 156, 158-161, 163, 165, 166 and 168-175 resulted in at least 60% inhibition of HIF1-beta mRNA; SEQ ID NOs: 38, 39, 60, 77, 78, 104, 105, 108-112, 115, 116, 119, 121, 124, 125, 128, 129, 132-134, 136, 138-143, 145, 148, 150, 152, 153, 155, 156, 158, 159, 163, 165, 166 and 169-173 resulted in at least 70% inhibition of HIF1-beta mRNA; and SEQ ID NOs: 39, 60, 105, 108, 110, 115, 116, 119, 121, 128, 129, 132, 133, 136, 138, 152, 158, 159, 165, 169, 171 and 172 resulted in at least 80% inhibition of HIF1-beta mRNA.

Example 17

Targeting of Individual Oligonucleotides to Specific Variants of Human HIF1-Beta A search of the National Center for Biotechnology Information database revealed alternative mRNA variants of human HIF1-beta which are the result of alternative splicing. The sequence identified as Genbank accession number N72808.1 represents a variant of HIF1-beta designated herein as HIF1-beta-1 (incorporated herein as SEQ ID NO: 19). The sequence identified as Genbank accession number AL834279.1 represents a variant of HIF1-beta designated herein as HIF1-beta-2 (incorporated herein as SEQ ID NO: 20).

It is advantageous to selectively inhibit the expression of one or more variants of HIF1-beta. Consequently, in one embodiment of the present invention are oligonucleotides that selectively target, hybridize to, and specifically inhibit one or more, but fewer than all the variants of HIF1-beta. The oligonucleotides of the present invention that selectively target human HIF1-beta variants are presented in Table 4.

TABLE 4

Targeting of individual oligonucleotides to specific variants of human HIF1-beta

| ISIS # | SEQ ID NO | Target Site | Target Variant | Target SEQ ID NO |
|---|---|---|---|---|
| 311149 | 97 | 231 | HIF1-beta-1 | 19 |
| 331150 | 98 | 162 | HIF1-beta-2 | 20 |

Example 18

Targeting of Individual Oligonucleotides to Specific Variants of Mouse HIF1-Beta A search of the National Center for Biotechnology Information database revealed alternative mRNA variants of mouse HIF1-beta which are the result of alternative splicing. The sequence identified as Genbank accession number AK040475.1 represents a variant of HIF1-beta designated herein as HIF1-beta-3 (incorporated herein as SEQ ID NO:

100). The sequence identified as Genbank accession number AK028546.1 represents a variant of HIF1-beta designated herein as HIF1-beta-4 (incorporated herein as SEQ ID NO: 101). The sequence identified as Genbank accession number BG083773.1 represents a variant of HIF1-beta designated herein as HIF1-beta-5 (incorporated herein as SEQ ID NO: 102). The sequence identified as Genbank accession number AK049738.1 represents a variant of HIF1-beta designated herein as HIF1-beta-6 (incorporated herein as SEQ ID NO: 103).

It is advantageous to selectively inhibit the expression of one or more variants of HIF1-beta. Consequently, in one embodiment of the present invention are oligonucleotides that selectively target, hybridize to, and specifically inhibit one or more, but fewer than all the variants of mouse HIF1-beta. The oligonucleotides of the present invention that selectively target mouse HIF1-beta variants are presented in Table 5.

TABLE 5

Targeting of individual oligonucleotides to specific variants of mouse HIF1-beta

| ISIS # | SEQ ID NO | Target Site | Target Variant | Target SEQ ID NO |
|---|---|---|---|---|
| 348052 | 171 | 10 | HIF1-beta-3 | 100 |
| 348053 | 172 | 2358 | HIF1-beta-3 | 100 |
| 348053 | 172 | 1543 | HIF1-beta-6 | 103 |
| 348054 | 173 | 352 | HIF1-beta-4 | 101 |
| 348054 | 173 | 149 | HIF1-beta-5 | 102 |
| 348055 | 174 | 2031 | HIF1-beta-4 | 101 |
| 348056 | 175 | 608 | HIF1-beta-5 | 102 |
| 348057 | 176 | 50 | HIF1-beta-6 | 103 |

Example 19

Expression of HIF1-Beta in Various Human Cell Lines

U87-MG human glioblastoma, PC-3 human prostate cancer, JEG-3 human choriocarcinoma, HeLa human cervical cancer, SK-N-BE(2) neuroblastoma, MCF-7 human breast cancer, 786-O human clear-cell renal cell carcinoma, Calu-1 human lung cancer, and Hep3B human hepatocellular carcinoma cells were purchased from American Type Culture Collection (ATCC; Manassas, Va.) and cultured according to ATCC directions. Human umbilical endothelial cells (HUVEC) were obtained from Cascade Biologics (Portland, Oreg.). Hypoxic treatments of cells (0.5-0.8×$10^6$/60 mm dish or 1-2×$10^6$/100 mm dish) were performed at 1% $O_2$ in a chamber controlled by ProOx oxygen sensor (BioSpherix, Redfield, N.Y.) for 18 h. To achieve the optimal hypoxic induction, 2 or 5 ml of medium was used for 60 mm and 100 mm culture dishes, respectively, during incubation. $CoCl_2$ (150 μM) was added to the cells to mimic hypoxic condition in some experiments.

After 18 h of culture at normoxia, hypoxia, or with $CoCl_2$, cells were harvested and whole cell lysates prepared with RIPA buffer containing protease inhibitor cocktails (Roche), 0.5 mM sodium orthovanadate, 10 mM β-glycerophophate, 250 ng/ml ubiquitin aldehyde (Sigma-Aldrich), and 400 nM epoxomicin (Alexis). Lysates were separated on 10% SDS-PAGE and transferred to PVDF membranes (Amersham Biosciences). Immunoblotting was performed with the following antibodies and dilutions: anti-HIF1-beta (BD Transduction Laboratories) at 1:1000; anti-VHL (BD Transduction Laboratories) at 1:500; anti-GLUT-1 (Alpha Diagnostic International) at 1:600, and anti-α-tubulin (Sigma) at 1:2000. Antibodies were diluted in 0.05% Tween-20/Tris-buffered saline (T-TBS) blocking buffer containing 5% nonfat skim milk and incubated with the PVDF membranes at 4° C. overnight, followed by washing with T-TBS for 30 min. Goat anti-mouse or rabbit IgGs coupled with HRP (BioRad) were used as secondary antibodies at 1:3000. Immunospecific bands were detected by enhanced chemiluminescence plus (ECL-Plus) detection kit (Amersham Biosciences).

Expression of HIF1-beta was detected under both normoxic and hypoxic conditions; however, levels of expression of HIF1-beta varied among cell lines. HIF1-beta expression was induced under hypoxic conditions and in the presence of $CoCl_2$ (which mimics hypoxia) in U87-MG human glioblastoma cells and MCF-7 human breast cancer cells. However, expression of HIF1-beta in JEG-3, PC-3, Hep3B, HeLa, 786-O, SK-N-BE(2), Calu-1 and HUVECs was not significantly altered by culturing under hypoxic conditions or in the presence of $CoCl_2$.

Example 20

Antisense Modulation of HIF1-Beta mRNA Expression in Cancer Cells (Dose Response)

Hep3B or U87-MG cells were plated in 96-well plates (8-10,000/well) 16 h prior to transfection. Control oligonucleotide ISIS 129688 (SEQ ID NO: 177) or HIF1-beta antisense oligonucleotides ISIS 311082 (SEQ ID NO: 30) and ISIS 311129 (SEQ ID NO: 77) at a concentration of 0, 6.25 or 25 nM were delivered into cells by lipofectin (3 μg/ml per 100 nM oligonucleotide) in Opti-Mem media (Invitrogen). Both control and HIF1-beta antisense oligonucleotides are chimeric oligonucleotides (“gapmers”) 20 nucleotides in length, composed of a central “gap” region consisting of ten 2'-deoxynucleotides, which is flanked on both sides (5' and 3' directions) by five-nucleotide “wings”. The wings are composed of 2'-O-methoxyethyl nucleotides, also known as 2'-MOE nucleotides. The internucleoside (backbone) linkages are phosphorothioate (P═S) throughout the oligonucleotide. All cytidine residues are 5-methylcytidines.

The transfection medium (120 μl/well) was switched to low-serum medium (0.1% FBS) 4 h after transfection. Sixty microliters of medium was removed from the well 3 h after media switch and the cells were further incubated at normoxia or hypoxia for 16-20 h.

Total RNAs were isolated using RNeasy 96 BioRobot 9604 kit (Qiagen) according to the manufacturer’s instructions. Quantitative real-time RT-PCR for detection of HIF1-beta mRNA was performed as described in other Examples herein by ABI Prism 7700 Sequence Detector (Applied Biosystems) in 25 or 50 μl reaction volumes. The level of mRNA for each gene was normalized to the amount of total RNA determined by Ribogreen™ (Molecular Probes).

TABLE 6

HIF1-beta mRNA expression in hypoxic Hep3B cells treated with antisense oligonucleotide to HIF1-beta (shown as percent of untreated control cells at normoxia)

| Oligonucleotide | Percent expression of HIF1-beta mRNA after treatment with oligonucleotide at the concentrations shown: 0 nM | 6.25 nM | 25 nM |
|---|---|---|---|
| 129688 | 78 | 78 | 77 |
| 311082 | 79 | 50 | 20 |
| 311129 | 77 | 70 | 30 |

TABLE 7

HIF1-beta mRNA expression in hypoxic U87-MG cells treated with antisense oligonucleotide to HIF1-beta (shown as percent of untreated control cells at normoxia)

| Oligonucleotide | Percent expression of HIF1-beta mRNA after treatment with oligonucleotide at the concentrations shown: 0 nM | 6.25 nM | 25 nM |
|---|---|---|---|
| 129688 | 78 | 78 | 77 |
| 311082 | 79 | 50 | 20 |
| 311129 | 77 | 70 | 20 |

HIF1-beta antisense oligonucleotides ISIS 311082 and ISIS 311129 specifically inhibited mRNA expression of HIF1-beta in both Hep3B and U87-MG cells in a dose-dependent manner.

Example 21

Antisense Modulation of HIF1-Beta Protein Expression

U87-MG cells were plated in 10 cm dishes (1-2×$10^6$ cells/dish) 16 h prior to transfection. 100 nM control oligonucleotide (ISIS 129688, SEQ ID NO: 177) or HIF1-beta antisense oligonucleotide (ISIS 311082, SEQ ID NO: 30) were delivered into cells by lipofectin (3 μg/ml per 100 nM oligonucleotide) in Opti-Mem media (Invitrogen).

The transfection medium (10 ml/dish) was switched to low-serum medium (0.1% FBS) 4 h after transfection. Five ml of medium was removed from the well 3 h after media switch and the cells were further incubated at normoxia or hypoxia for 16-20 h.

Following incubation at normoxia or hypoxia, transfected cells were harvested and whole cell lysates prepared with RIPA buffer containing protease inhibitor cocktails (Roche), 0.5 mM sodium orthovanadate, 10 mM β-glycerophophate, 250 ng/ml ubiquitin aldehyde (Sigma-Aldrich), and 400 nM epoxomicin (Alexis). Lysates were separated on 10% SDS-PAGE and transferred to PVDF membranes (Amersham Biosciences). Immunoblotting was performed with the following antibodies and dilutions: anti-HIF1-BETA (BD Transduction Laboratories) at 1:1000; anti-GLUT-1 (Alpha Diagnostic International) at 1:600, and anti-α-tubulin (Sigma) at 1:2000. Antibodies were diluted in 0.05% Tween-20/Tris-buffered saline (T-TBS) blocking buffer containing 5% nonfat skim milk and incubated with the PVDF membranes at 4° C. overnight, followed by washing with T-TBS for 30 min. Goat anti-mouse or rabbit IgGs coupled with HRP (BioRad) were used as secondary antibodies at 1:3000. Immunospecific bands were detected by enhanced chemiluminescence plus (ECL-Plus) detection kit (Amersham Biosciences).

The results demonstrated that transfection with HIF1-beta antisense oligonucleotide inhibited HIF1-beta protein expression. Furthermore, protein expression of GLUT-1, a HIF1-beta-responsive gene, was induced under hypoxia in the absence of HIF1-beta antisense oligonucleotide, but was nearly eliminated in hypoxic cells transfected with HIF1-beta antisense oligonucleotide.

Example 22

Expression HIF1-Beta-Regulated Genes in Cells Cultured Under Hypoxic Conditions Genes whose products are significantly induced by hypoxia (or $CoCl_2$, a mimic of hypoxia) include erythropoietin (Epo), glucose transporter-1 (GLUT-1), vascular endothelial growth factor (VEGF), phosphoglycerate kinase-1 (PGK-1) and plasminogen activator inhibitor-1 (PAI-1). These genes are regulated by HIF1-beta and are induced under hypoxic conditions to varying extents in different cell lines. To determine mRNA expression levels of Epo, GLUT-1, VEGF, PGK-1 and PAI-1 at normoxia (21% $O_2$), hypoxia (1% $O_2$) and in the presence of 150 μM $CoCl_2$, in HeLa, Hep3B, U87-MG, PC-3 and 786-0 cells, RT-PCR was performed. Total RNA was isolated after 18 h of culture using the RNeasy 96 BioRobot 9604 (Qiagen) according to the manufacturer's protocol. Quantitative real-time RT-PCR was performed as described in other Examples herein by ABI Prism 7700 Sequence Detector (Applied Biosystems) in 25 or 50 μl reaction volumes. The level of mRNA for each gene was normalized to the amount of total RNA determined by Ribogreen™ (Molecular Probes).

TABLE 8

VEGF, GLUT-1, PGK-1, PAI-1 and Epo mRNA expression levels at normoxia, hypoxia and 150 μM $CoCl_2$ (shown as fold-induction relative to HeLa cells at normoxia)

| Gene | Cell Type | Normoxia | Hypoxia | $CoCl_2$ |
|---|---|---|---|---|
| VEGF | HeLa | 1 | 3 | 2 |
| | Hep3B | 4 | 24 | 11 |
| | U87-MG | 17 | 46 | 28 |
| | PC-3 | 1 | 2 | 2 |
| | 786-O | 6 | 6 | 10 |
| GLUT-1 | HeLa | 1 | 2.1 | 1.5 |
| | Hep3B | 0.2 | 1 | 1 |
| | U87-MG | 2.5 | 3.1 | 5.3 |
| | PC-3 | 1 | 4.1 | 3.7 |
| | 786-O | 2.9 | 3.4 | 5.7 |
| PGK-1 | HeLa | 1 | 3 | 2 |
| | Hep3B | 4 | 24 | 10 |
| | U87-MG | 16 | 46 | 28 |
| | PC-3 | 1 | 2 | 2 |
| | 786-O | 6 | 6 | 9 |
| PAI-1 | HeLa | 1 | 1.5 | 1 |
| | Hep3B | 1.5 | 28 | 2 |
| | U87-MG | 9 | 24 | 32 |
| | PC-3 | 3 | 4 | 3 |
| | 786-O | 2 | 3 | 16 |
| Epo | HeLa | 1 | 1 | 1 |
| | Hep3B | 7 | 260 | 15 |
| | U87-MG | 1 | 1 | 1 |
| | PC-3 | 1 | 1 | 1 |
| | 786-O | 1 | 1 | 1 |

Although expression levels of the five genes under each condition varied widely among cell lines, VEGF, GLUT-1, PGK-1, PAI-1 and Epo exhibited a trend of increased expression when cells were cultured under hypoxia or in the presence of 150 μM $CoCl_2$. As previously reported, hypoxia-induced Epo expression occurred only in Hep3B cells.

Example 23

Antisense Inhibition of HIF1-Beta Target Genes

Hep3B or U87-MG cells were plated in 96-well plates (8-10,000/well) 16 h prior to transfection. Control oligonucleotide ISIS 129688 (SEQ ID NO: 177) or HIF1-beta antisense oligonucleotides ISIS 311082 (SEQ ID NO: 30) and ISIS 311129 (SEQ ID NO: 77) at a concentration of 0, 6.25 or 25 nM were delivered into cells by lipofectin (3 μg/ml per 100 nM oligonucleotide) in Opti-Mem media (Invitrogen).

The transfection medium (120 μl/well) was switched to low-serum medium (0.1% FBS) 4 h after transfection. Sixty microliters of medium was removed from the well 3 h after media switch and the cells were further incubated at normoxia or hypoxia for 16-20 h.

Total RNAs were isolated using RNeasy 96 BioRobot 9604 kit (Qiagen) according to the manufacturer's instructions. Quantitative real-time RT-PCR for detection of GLUT-1, VEGF or Epo mRNA was performed as described in other Examples herein by ABI Prism 7700 Sequence Detector (Applied Biosystems) in 25 or 50 μl reaction volumes. The level of mRNA for each gene was normalized to the amount of total RNA determined by Ribogreen™ (Molecular Probes).

TABLE 9

GLUT-1 mRNA expression in hypoxic Hep3B cells treated with antisense oligonucleotide to HIF1-beta (shown as percent of untreated control cells)

| | Percent expression of GLUT-1 mRNA after treatment with oligonucleotide at the concentrations shown: | | |
|---|---|---|---|
| Oligonucleotide | 0 nM | 6.25 nM | 25 nM |
| 129688 | 100 | 85 | 83 |
| 311082 | 100 | 72 | 34 |
| 311129 | 100 | 74 | 79 |

TABLE 10

GLUT-1 mRNA expression in hypoxic U87-MG cells treated with antisense oligonucleotide to HIF1-beta (shown as percent of untreated control cells)

| | Percent expression of GLUT-1 mRNA after treatment with oligonucleotide at the concentrations shown: | | |
|---|---|---|---|
| Oligonucleotide | 0 nM | 6.25 nM | 25 nM |
| 129688 | 100 | 100 | 102 |
| 311082 | 100 | 76 | 28 |
| 311129 | 100 | 83 | 40 |

TABLE 11

VEGF mRNA expression in hypoxic U87-MG cells treated with antisense oligonucleotide to HIF1-beta (shown as percent of untreated control cells)

| | Percent expression of VEGF mRNA after treatment with oligonucleotide at the concentrations shown: | | |
|---|---|---|---|
| Oligonucleotide | 0 nM | 6.25 nM | 25 nM |
| 129688 | 100 | 101 | 82 |
| 311082 | 100 | 62 | 26 |
| 311129 | 100 | 71 | 28 |

TABLE 12

Epo mRNA expression in hypoxic Hep3B cells treated with antisense oligonucleotide to HIF1-beta (shown as percent of untreated control cells)

| | Percent expression of Epo mRNA after treatment with oligonucleotide at the concentrations shown: | | |
|---|---|---|---|
| Oligonucleotide | 0 nM | 6.25 nM | 25 nM |
| 129688 | 100 | 107 | 114 |
| 311082 | 100 | 95 | 38 |
| 311129 | 100 | 100 | 74 |

As shown in other Examples herein, GLUT-1, Epo and VEGF mRNA expression was induced under hypoxic conditions. HIF1-beta antisense oligonucleotides ISIS 311082 and ISIS 311129 specifically inhibited mRNA expression of GLUT-1, Epo and VEGF in both Hep3B cells (GLUT-1 and Epo) and U87-MG cells (GLUT-1 and VEGF).

Example 24

Antisense Inhibition of Protein Expression of HIF1-Beta Downstream Targets

U87-MG, HeLa or Hep3B cells were plated in 10 cm dishes (1-2×$10^6$ cells/dish) 16 h prior to transfection. 100 nM control oligonucleotide (ISIS 129688, SEQ ID NO: 177) or HIF1-beta antisense oligonucleotide (ISIS 311082, SEQ ID NO: 30) were delivered into cells by lipofectin (3 μg/ml per 100 nM oligonucleotide) in Opti-Mem media (Invitrogen).

The transfection medium (10 ml/well) was switched to low-serum medium (0.1% FBS) 4 h after transfection. Five ml of medium was removed from the well 3 h after media switch and the cells were further incubated at normoxia or hypoxia.

After incubation at normoxia or hypoxia for 16 h, the media was removed and stored at −80° C. prior to use. Levels of VEGF protein in either U87-MG or HeLa cells was determined by Quantikine ELISA kit (R&D Systems) according to the manufacturer's protocol. To determine levels of Epo protein in Hep3B cells, cell culture media was concentrated up to 10% of the original volume by Amicon Ultra (Millipore) and Epo protein was quantitated by Quantikine IVD human Epo ELISA kit (R&D Systems). The obtained values were normalized to the number of cells (VEGF) or the amount of total protein (Epo) used for the assay.

Under hypoxic conditions, VEGF protein production in U87-MG cells treated with HIF1-beta antisense oligonucleotide was significantly reduced (approximately 4-fold) relative to cells treated with control oligonucleotide. In HeLa cells, VEGF protein levels were slightly reduced by treatment with HIF1-beta antisense oligonucleotide. In Hep3B cells treated with HIF1-beta antisense oligonucleotide, Epo protein levels were significantly reduced (approximately 15-fold) relative to cells treated with control oligonucleotide. Thus, treatment with HIF1-beta antisense oligonucleotides not only inhibits expression of HIF1-beta, but also results in downregulation of HIF1-beta target genes.

Example 25

Hypoxia-Induced Binding of HIF1-Beta to Hypoxia Response Element (HRE) In Vivo

To demonstrate binding of HIF1-beta to the hypoxia response element (HRE) on the promoter region of the VEGF gene under hypoxic conditions, chromatin immunoprecipitation (ChIP) assays were performed. U87-MG cells were plated in 10 cm dishes in complete growth media containing 10% FBS at a density of $1\times10^6$ cells/dish. After 24 h, the media was replaced with low serum media (0.1% FBS) and the cells were incubated at either normoxia or hypoxia for 16 h. After incubation, cells were cross-linked with a 1% formaldehyde solution for 10 min at 37° C. After two washes with cold PBS, cells were processed following the ChIP assay kit protocol (Upstate). For immunoprecipitation, protein extracts were incubated with antibodies to HIF1-beta (10 μg) and mouse IgG (10 μg) at 4° C. for 40 h, followed by 2 h incubation with salmon sperm DNA/Protein A agarose slurry. After extensive washing, the immune/DNA complex was eluted in 500 μl of buffer (1% SDS, 0.1 M $NaHCO_3$), reverse-crosslinked at 65° C. for 4 h in the presence of 0.2 M NaCl and subjected to proteinase K (Ambion) digestion at 45° C. for 1 h. Samples were extracted with phenol-chloroform-isoamylalcohol, ethanol-precipitated overnight at −80° C. and the DNA was resuspended in water.

Samples were analyzed by PCR using Accuprime II (Invitrogen) Taq polymerase in the presence of [$^{32}$P-dCTP]. PCR products were separated on 6% Tris-borate-EDTA (TBE)-PAGE, dried and exposed to X-ray film at −80° C. The forward (F) and reverse (R) primers used for PCR are as follows:

```
VEGF I (F):
CCTGGCAACATCTGGGGTTGG          (SEQ ID NO: 178)

VEGF I (R):
CAACAGGCTGGAGTGACTGGGCTCC      (SEQ ID NO: 179)

VEGF II (F):
GTGGAGACAGGACTAGTGCACGAATG     (SEQ ID NO: 180)

VEGF II (R):
CTGTGGAGGCATGGACTGAGAATGG      (SEQ ID NO: 181)

Epo (F):
CTGGGAACCTCCAAATCCCCTGGC       (SEQ ID NO: 182)

Epo (R):
CTGGGCAGGGTTGGCAGCTGCCTTAC     (SEQ ID NO: 183)
```

VEGF I primers amplify a region that includes the HRE. VEGF II primers amplify a promoter region upstream of the HRE, therefore this region serves as a negative control. The Epo gene also is a negative control since it is not expressed in U87-MG cells.

HIF1-beta was not detected on the VEGF HRE at normoxia. However, hypoxia induced the recruitment of HIF1-beta to the VEGF HRE (VEGF I). No binding of HIF1-beta was detected to the regions amplified by the VEGF II or Epo primers.

Example 26

Inhibition of HIF1-Beta Expression In Vivo

C57B1/6 mice are maintained on a standard rodent diet and are used as control animals. Seven-week old male C57B1/6 mice are injected subcutaneously with oligonucleotides at a dose of 25 mg/kg two times per week for 4 weeks. Saline-injected animals serve as a control. After the treatment period, mice are sacrificed and target levels are evaluated in liver, spleen, adipose and other tissues using RNA isolation and target mRNA expression level quantitation (RT-PCR) as described in other examples herein.

Example 27

Tube Formation Assay to Determine Effect of HIF1-Beta Antisense Inhibitors on Angiogenesis Angiogenesis is stimulated by numerous factors that promote interaction of endothelial cells with each other and with extracellular matrix molecules, resulting in the formation of capillary tubes. This process can be reproduced in tissue culture by the formation of tube-like structures by endothelial cells. Loss of tube formation in vitro has been correlated with the inhibition of angiogenesis in vivo (Carmeliet et al., (2000) Nature 407:249-257; and Zhang et al., (2002) Cancer Research 62:2034-42), which supports the use of in vitro tube formation as an endpoint for angiogenesis.

Angiogenesis, or neovascularization, is the formation of new capillaries from existing blood vessels. In adult organisms this process is typically controlled and short-lived, for example in wound repair and regeneration. However, aberrant capillary growth can occur and this uncontrolled growth plays a causal and/or supportive role in many pathologic conditions such as tumor growth and metastasis. In the context of this invention "aberrant angiogenesis" refers to unwanted or uncontrolled angiogenesis. Angiogenesis inhibitors are being evaluated for use as antitumor drugs. Other diseases and conditions associated with angiogenesis include arthritis, cardiovascular diseases, skin conditions (e.g., psoriasis), and aberrant wound healing. Aberrant angiogenesis can also occur in the eye, causing loss of vision. Examples of ocular conditions involving aberrant angiogenesis include macular degeneration, diabetic retinopathy, diabetic macular edema and retinopathy of prematurity.

The tube formation assay is performed using an in vitro Angiogenesis Assay Kit (Chemicon International, Temecula, Calif.), or growth factor reduced Matrigel (BD Biosciences, Bedford, Mass.). HUVECs were plated at 4000 cells/well in 96-well plates. One day later, cells were transfected with antisense and control oligonucleotides according to standard published procedures (Monia et al., (1993) J Biol Chem. 1993 Jul. 5; 268(19):14514-22) using 75 nM oligonucleotide in lipofectin (Gibco, Grand Island, N.Y.). Approximately fifty hours post-transfection, cells were transferred to 96-well plates coated with ECMatrix™ (Chemicon International) or growth factor depleted Matrigel. Under these conditions, untreated HUVECs form tube-like structures. After an overnight incubation at 37° C., treated and untreated cells were inspected by light microscopy. Individual wells were assigned discrete scores from 1 to 5 depending on the extent of tube formation. A score of 1 refers to a well with no tube formation while a score of 5 is given to wells where all cells are forming an extensive tubular network.

ISIS 29848 is a control oligonucleotide containing an equal mixture of the bases A, C, G and T at every position. ISIS 175510 (TGAGCTGTCTGTGATCCAGC; SEQ ID NO: 184) is targeted to HIF1α; ISIS 222035 (GCGCTGCTCCCAAGAACTCT; SEQ ID NO: 185) is targeted to HIF2α. ISIS 298697 (TCCTCATGGTCACATGGATG; SEQ ID NO: 186) is a cross-HIF1α/HIF2α oligonucleotide having perfect complementarity to HIF1α target and imperfect complementarity (and thus less inhibitory effect) for HIF2α; ISIS 311082 (SEQ ID NO: 30) is targeted to HIF1-beta.

TABLE 13

Effect of antisense oligonucleotides on angiogenic tube formation

| ISIS # | Target | Score |
|---|---|---|
| Lipid control | N/A | 4.7 |
| 29848 | Control | 4.7 |
| 175510 | HIF1α | 2.0 |
| 222035 | HIF2α | 1.0 |
| 298697 | HIF1α/2α | 3.0 |
| 311082 | HIF1-beta | 2.0 |

As calculated from the assigned discrete scores, the results demonstrate that HUVEC tube formation is inhibited by treatment with antisense oligonucleotides targeting the Hif family. Thus, a reduction in HIF1-beta expression results in inhibition of angiogenic processes.

Example 28

HIF1-Beta Antisense Compounds in an Animal Model of Ocular Neovascularization

A pig model of ocular neovascularization, the branch retinal vein occlusion (BVO) model, is used to study ocular neovascularization. Male farm pigs (8-10 kg) are subjected to branch retinal vein occlusions (BVO) by laser treatment in both eyes. The extent of BVO is determined by indirect opthalmoscopy after a 2 week period. Intravitreous injections (10 μM) of HIF1-beta antisense oligonucleotides and control oligonucleotides are started on the day of BVO induction and are repeated at weeks 2, 6 and 10 after BVO (Right eye=vehicle, Left eye=antisense oligonucleotide). Stereo fundus photography and fluorescein angiography are performed at baseline BVO and at weeks 1, 6 and 12 following intravitreous injections to measure the neovascular response. In addition, capillary gel electrophoresis analysis of the eye sections containing sclera, choroid, and the retina are performed to determine antisense concentrations, and gross and microscopic evaluations are performed to determine eye histopathology.

Example 29

Matrix Metalloproteinase Activity Assay

During angiogenesis, endothelial cells need to be able to degrade the extracellular matrix (ECM). Endothelial cells secrete matrix metalloproteinases (MMPs) in order to accomplish this degradation. HIF1-beta antisense compounds of the invention are evaluated for their effects on MMP activity in HUVECs. MMP activity is measured using the EnzChek Gelatinase/Collagenase Assay Kit (Molecular Probes, Eugene, Oreg.). In this assay, HUVECs are plated at approximately 4000 cells per well in 96-well plates and transfected one day later. A 20-nucleotide oligomeric compound with a randomized sequence is used a negative control. An oligomeric compound targeted to integrin β3 is known to inhibit MMP activity and is used as a positive control.

Cells are transfected as described herein. Antisense compounds are mixed with LIPOFECTIN™ in Opti-MEM to achieve a final concentration of 75 nM of antisense compound and 2.25 μg/mL LIPOFECTIN™. Antisense compounds of the invention and the positive control are tested in triplicate, and the negative control is tested in up to six replicates. Untreated control cells received LIPOFECTIN™ in Opti-MEM only.

Approximately 50 hours after transfection, a p-aminophenylmercuric acetate (APMA, Sigma-Aldrich, St. Louis, Mo.) solution is added to each well of a Corning-Costar 96-well clear bottom plate (VWR International, Brisbane, Calif.). The APMA solution is used to promote cleavage of inactive MMP precursor proteins. Medium above the HUVECs is then transferred to the wells in the 96-well plate. After approximately 30 minutes, the quenched, fluorogenic MMP cleavage substrate is added, and baseline fluorescence is read immediately at 485 nm excitation/530 nm emission. Following an overnight incubation at 37° C. in the dark, plates are read again to determine the amount of fluorescence, which corresponds to MMP activity. Total protein from HUVEC lysates is used to normalize the readings, and MMP activity from cells treated with antisense compounds is normalized to that of untreated control cells. MMP activities above or below 100% are considered to indicate a stimulation or inhibition of MMP activity, respectively. HIF1-beta antisense compounds resulting in a decrease in MMP activity are candidate therapeutic agents for the inhibition of angiogenesis where such activity is desired, for example, in the treatment of cancer, diabetic retinopathy, cardiovascular disease, rheumatoid arthritis and psoriasis.

Various modifications of the invention, in addition to those described herein, will be apparent to those skilled in the art from the foregoing description. Such modifications are also intended to fall within the scope of the appended claims. Each of the patents, applications, printed publications, and other published documents mentioned or referred to in this specification are herein incorporated by reference in their entirety. Those skilled in the art will appreciate that numerous changes and modifications may be made to the embodiments of the invention and that such changes and modifications may be made without departing from the spirit of the invention. It is therefore intended that the appended claims cover all such equivalent variations as fall within the true spirit and scope of the invention.

What is claimed is:

1. A compound comprising a modified oligonucleotide consisting of 12 to 30 linked nucleosides and having a nucleobase sequence comprising at least 8 contiguous nucleobases of the nucleobase sequence recited in SEQ ID NO:30, wherein the nucleobase sequence of the modified oligonucleotide is at least 90% complementary to SEQ ID NO:4 as measured over the entirety of said modified oligonucleotide, wherein said compound inhibits expression of human HIF-1 beta.

2. The compound of claim 1, consisting of a single-stranded modified oligonucleotide.

3. The compound of claim 2, wherein the nucleobase sequence of the modified oligonucleotide is 100% complementary to SEQ ID NO:4 as measured over the entirety of said modified oligonucleotide.

4. The compound of claim 2, wherein at least one internucleoside linkage is a modified internucleoside linkage.

5. The compound of claim 4, wherein each internucleoside linkage is a phosphorothioate internucleoside linkage.

6. The compound of claim 2, wherein at least one nucleoside comprises a modified sugar.

7. The compound of claim 6, wherein at least one modified sugar is a bicyclic sugar.

8. The compound of claim 6, wherein at least one modified sugar comprises a 2'-O-methoxyethyl or a 4'-$(CH_2)_n$—O-2' bridge, wherein n is 1 or 2.

9. The compound of claim 2, wherein at least one nucleoside comprises a modified nucleobase.

10. The compound of claim 9, wherein the modified nucleobase is a 5-methylcytosine.

11. The compound of claim 1, wherein the modified oligonucleotide comprises:

a gap segment consisting of linked deoxynucleosides;

a 5' wing segment consisting of linked nucleosides;

a 3' wing segment consisting of linked nucleosides;

wherein the gap segment is positioned between the 5' wing segment and the 3' wing segment and wherein each nucleoside of each wing segment comprises a modified sugar.

12. The compound of claim 11, wherein the modified oligonucleotide comprises:

a gap segment consisting of ten linked deoxynucleosides;

a 5' wing segment consisting of five linked nucleosides;

a 3' wing segment consisting of five linked nucleosides;

wherein the gap segment is positioned between the 5' wing segment and the 3' wing segment, wherein each nucleoside of each wing segment comprises a 2'-O-methoxyethyl sugar; wherein each cytosine in said modified oligonucleotide is a 5-methylcytosine, and wherein each internucleoside linkage of said modified oligonucleotide is a phosphorothioate linkage.

13. The compound of claim 2, wherein the modified oligonucleotide consists of 20 linked nucleosides.

14. A composition comprising the compound of claim 1 or a salt thereof and a pharmaceutically acceptable carrier or diluent.

15. The composition of claim 14, wherein said compound consists of a single-stranded oligonucleotide.

16. The composition of claim 14, wherein the modified oligonucleotide consists of 20 linked nucleosides.

17. A method of inhibiting HIF-1 beta comprising administering to an animal an effective amount of the compound of claim 1.

18. The method of claim 17, wherein the animal is a human.

19. The method of claim 18, wherein administering the compound treats a hyperproliferative disorder.

20. The method of claim 19, wherein the hyperproliferative disorder is cancer.

21. The method of claim 19, wherein the hyperproliferative disorder is an angiogenic disorder.

22. The method of claim 21, wherein the angiogenic disorder is an ocular disorder.

23. The method of claim 22, wherein the ocular disorder is selected from the group consisting of macular degeneration, diabetic retinopathy, macular edema and retinopathy of prematurity.

24. The method of claim 17, wherein said administration comprises subcutaneous or intravitreous injection.

25. A method comprising identifying a human with a hyperproliferative disorder and administering to the human a therapeutically effective amount of the compound of claim 1.

26. A method of inhibiting expression of HIF-1 beta in a cell or tissue, comprising contacting said cell or tissue with the compound of claim 1, such that expression of HIF-1 beta is inhibited.

27. A method of inhibiting expression of a HIF-1 beta regulated gene in a cell or tissue comprising contacting said cell or tissue with the compound of claim 1, such that expression of the HIF-1 beta regulated gene is inhibited.

28. The method of claim 27, wherein the HIF-1 beta regulated gene is selected from the group consisting of VEGF, GLUT-1, PGK-1, PAI-1 and Epo.

29. The compound of claim 2, wherein the nucleobase sequence of the modified oligonucleotide is at least 95% complementary to SEQ ID NO:4 as measured over the entirety of said modified oligonucleotide.

30. The compound of claim 12, wherein said nucleobase sequence comprises SEQ ID NO:30.

31. The compound of claim 12, wherein said modified oligonucleotide consists of 20 linked nucleosides having a nucleobase sequence consisting of SEQ ID NO:30.

* * * * *

SEQUENCE LISTING

```
<160> NUMBER OF SEQ ID NOS: 190

<210> SEQ ID NO 1
<211> LENGTH: 20
<212> TYPE: DNA
<213> ORGANISM: Artificial Sequence
<220> FEATURE:
<223> OTHER INFORMATION: Antisense Compound

<400> SEQUENCE: 1
```

-continued

```
tccgtcatcg ctcctcaggg                                                20


<210> SEQ ID NO 2
<211> LENGTH: 20
<212> TYPE: DNA
<213> ORGANISM: Artificial Sequence
<220> FEATURE:
<223> OTHER INFORMATION: Antisense Compound

<400> SEQUENCE: 2

gtgcgcgcga gcccgaaatc                                                20


<210> SEQ ID NO 3
<211> LENGTH: 20
<212> TYPE: DNA
<213> ORGANISM: Artificial Sequence
<220> FEATURE:
<223> OTHER INFORMATION: Antisense Compound

<400> SEQUENCE: 3

atgcattctg cccccaagga                                                20


<210> SEQ ID NO 4
<211> LENGTH: 4504
<212> TYPE: DNA
<213> ORGANISM: H. sapiens
<220> FEATURE:
<221> NAME/KEY: CDS
<222> LOCATION: (175)...(2542)

<400> SEQUENCE: 4

agcgggggat gctgggggct gctgaagccg ccatcttgga ttccgcggta gcggaggcgg     60

cggtcaggcg ccgcttctgg ggagtggcct ttcttttccc ctccctcccg gttcggtggc    120

ggcggctcct cccactgggg ggggggtggc gcggcggcgg tggcatctgc ggcc atg      177
                                                            Met
                                                             1

gcg gcg act act gcc aac ccc gaa atg aca tca gat gta cca tca ctg      225
Ala Ala Thr Thr Ala Asn Pro Glu Met Thr Ser Asp Val Pro Ser Leu
             5                  10                  15

ggt cca gcc att gcc tct gga aac tct gga cct gga att caa ggt gga      273
Gly Pro Ala Ile Ala Ser Gly Asn Ser Gly Pro Gly Ile Gln Gly Gly
         20                  25                  30

gga gcc att gtc cag agg gct att aag cgg cga cca ggg ctg gat ttt      321
Gly Ala Ile Val Gln Arg Ala Ile Lys Arg Arg Pro Gly Leu Asp Phe
     35                  40                  45

gat gat gat gga gaa ggg aac agt aaa ttt ttg agg tgt gat gat gat      369
Asp Asp Asp Gly Glu Gly Asn Ser Lys Phe Leu Arg Cys Asp Asp Asp
 50                  55                  60                  65

cag atg tct aac gat aag gag cgg ttt gcc agg tcg gat gat gag cac      417
Gln Met Ser Asn Asp Lys Glu Arg Phe Ala Arg Ser Asp Asp Glu His
                 70                  75                  80

ctc tgc gga taa aga gag act tgc cag gga aaa tca cag tga aat tga      465
Leu Cys Gly  *  Arg Glu Thr Cys Gln Gly Lys Ser Gln  *  Asn  *
                 85                  90

acg gcg gcg acg gaa caa gat gac agc cta cat cac aga act gtc aga      513
Thr Ala Ala Thr Glu Gln Asp Asp Ser Leu His His Arg Thr Val Arg
 95                 100                 105                 110

tat ggt acc cac ctg tag tgc cct ggc tcg aaa acc aga caa gct aac      561
Tyr Gly Thr His Leu  *  Cys Pro Gly Ser Lys Thr Arg Gln Ala Asn
                115                     120                 125

cat ctt acg cat ggc agt ttc tca cat gaa gtc ctt gcg ggg aac tgg      609
```

-continued

```
His Leu Thr His Gly Ser Phe Ser His Glu Val Leu Ala Gly Asn Trp
                130                 135                 140

caa cac atc cac tga tgg ctc cta taa gcc gtc ttt cct cac tga tca      657
Gln His Ile His  *  Trp Leu Leu  *  Ala Val Phe Pro His  *  Ser
            145                     150

gga act gaa aca ttt gat ctt gga ggc agc aga tgg ctt tct gtt tat      705
Gly Thr Glu Thr Phe Asp Leu Gly Gly Ser Arg Trp Leu Ser Val Tyr
155                 160                 165                 170

tgt ctc atg tga gac agg cag ggt ggt gta tgt gtc tga ctc cgt gac      753
Cys Leu Met  *  Asp Arg Gln Gly Gly Val Cys Val  *  Leu Arg Asp
                175                     180

tcc tgt ttt gaa cca gcc aca gtc tga atg gtt tgg cag cac act cta      801
Ser Cys Phe Glu Pro Ala Thr Val  *  Met Val Trp Gln His Thr Leu
185                 190                     195

tga tca ggt gca ccc aga tga tgt gga taa act tcg tga gca gct ttc      849
*  Ser Gly Ala Pro Arg  *  Cys Gly  *  Thr Ser  *  Ala Ala Phe
   200                    205                          210

cac ttc aga aaa tgc cct gac agg gcg tat cct gga tct aaa gac tgg      897
His Phe Arg Lys Cys Pro Asp Arg Ala Tyr Pro Gly Ser Lys Asp Trp
            215                 220                 225

aac agt gaa aaa gga agg tca gca gtc ttc cat gag aat gtg tat ggg      945
Asn Ser Glu Lys Gly Arg Ser Ala Val Phe His Glu Asn Val Tyr Gly
        230                 235                 240

ctc aag gag atc gtt tat ttg ccg aat gag gtg tgg cag tag ctc tgt      993
Leu Lys Glu Ile Val Tyr Leu Pro Asn Glu Val Trp Gln  *  Leu Cys
    245                 250                 255

gga ccc agt ttc tgt gaa tag gct gag ctt tgt gag gaa cag atg cag     1041
Gly Pro Ser Phe Cys Glu  *  Ala Glu Leu Cys Glu Glu Gln Met Gln
    260                     265                 270

gaa tgg act tgg ctc tgt aaa gga tgg gga acc tca ctt cgt ggt ggt     1089
Glu Trp Thr Trp Leu Cys Lys Gly Trp Gly Thr Ser Leu Arg Gly Gly
    275                 280                 285

cca ctg cac agg cta cat caa ggc ctg gcc ccc agc agg tgt ttc cct     1137
Pro Leu His Arg Leu His Gln Gly Leu Ala Pro Ser Arg Cys Phe Pro
290                 295                 300                 305

ccc aga tga tga ccc aga ggc tgg cca ggg aag caa gtt ttg cct agt     1185
Pro Arg  *   *  Pro Arg Gly Trp Pro Gly Lys Gln Val Leu Pro Ser
                    310                 315

ggc cat tgg cag att gca ggt aac tag ttc tcc caa ctg tac aga cat     1233
Gly His Trp Gln Ile Ala Gly Asn  *  Phe Ser Gln Leu Tyr Arg His
320                 325                     330

gag taa tgt ttg tca acc aac aga gtt cat ctc ccg aca caa cat tga     1281
Glu  *  Cys Leu Ser Thr Asn Arg Val His Leu Pro Thr Gln His  *
335                 340                 345

ggg tat ctt cac ttt tgt gga tca ccg ctg tgt ggc tac tgt tgg cta     1329
Gly Tyr Leu His Phe Cys Gly Ser Pro Leu Cys Gly Tyr Cys Trp Leu
    350                 355                 360

cca gcc aca gga act ctt agg aaa gaa tat tgt aga att ctg tca tcc     1377
Pro Ala Thr Gly Thr Leu Arg Lys Glu Tyr Cys Arg Ile Leu Ser Ser
365                 370                 375                 380

tga aga cca gca gct tct aag aga cag ctt cca aca ggt agt gaa att     1425
*  Arg Pro Ala Ala Ser Lys Arg Gln Leu Pro Thr Gly Ser Glu Ile
               385                 390                 395

aaa agg cca agt gct gtc tgt cat gtt ccg gtt ccg gtc taa gaa cca     1473
Lys Arg Pro Ser Ala Val Cys His Val Pro Val Pro Val  *  Glu Pro
                400                 405                 410

aga atg gct ctg gat gag aac cag ctc ctt tac ttt cca gaa ccc tta     1521
Arg Met Ala Leu Asp Glu Asn Gln Leu Leu Tyr Phe Pro Glu Pro Leu
                415                 420                 425
```

-continued

```
ctc aga tga aat tga gta cat cat ctg tac caa cac caa tgt gaa gaa      1569
Leu Arg  *  Asn  *  Val His His Leu Tyr Gln His Gln Cys Glu Glu
                    430                 435                 440

ctc tag cca aga acc acg gcc tac act ctc caa cac aat cca gag gcc      1617
Leu  *  Pro Arg Thr Thr Ala Tyr Thr Leu Gln His Asn Pro Glu Ala
                    445                 450                 455

aca act agg tcc cac agc taa ttt acc cct gga gat ggg ctc agg aca      1665
Thr Thr Arg Ser His Ser  *  Phe Thr Pro Gly Asp Gly Leu Arg Thr
                460                 465                 470

gct ggc acc cag gca gca gca aca gca aac aga att gga cat ggt acc      1713
Ala Gly Thr Gln Ala Ala Ala Thr Ala Asn Arg Ile Gly His Gly Thr
                475                 480                 485

agg aag aga tgg act ggc cag cta caa tca ttc cca ggt ggt tca gcc      1761
Arg Lys Arg Trp Thr Gly Gln Leu Gln Ser Phe Pro Gly Gly Ser Ala
            490                 495                 500

tgt gac aac cac agg acc aga aca cag caa gcc cct tga gaa gtc aga      1809
Cys Asp Asn His Arg Thr Arg Thr Gln Gln Ala Pro  *  Glu Val Arg
        505                 510                 515

tgg ttt att tgc cca gga tag aga tcc aag att ttc aga aat cta tca      1857
Trp Phe Ile Cys Pro Gly  *  Arg Ser Lys Ile Phe Arg Asn Leu Ser
        520                 525                 530

caa cat caa tgc gga tca gag taa agg cat ctc ctc cag cac tgt ccc      1905
Gln His Gln Cys Gly Ser Glu  *  Arg His Leu Leu Gln His Cys Pro
        535                 540                 545

tgc cac cca aca gct att ctc cca ggg caa cac att ccc tcc tac ccc      1953
Cys His Pro Thr Ala Ile Leu Pro Gly Gln His Ile Pro Ser Tyr Pro
        550                 555                 560

ccg gcc ggc aga gaa ttt cag gaa tag tgg tct agc ccc tcc tgt aac      2001
Pro Ala Gly Arg Glu Phe Gln Glu  *  Trp Ser Ser Pro Ser Cys Asn
    565                 570                 575

cat tgt cca gcc atc agc ttc tgc agg aca gat gtt ggc cca gat ttc      2049
His Cys Pro Ala Ile Ser Phe Cys Arg Thr Asp Val Gly Pro Asp Phe
    580                 585                 590

ccg cca ctc caa ccc cac cca agg agc aac ccc aac ttg gac ccc tac      2097
Pro Pro Leu Gln Pro His Pro Arg Ser Asn Pro Asn Leu Asp Pro Tyr
595                 600                 605                 610

tac ccg ctc agg ctt ttc tgc cca gca ggt ggc tac cca ggc tac tgc      2145
Tyr Pro Leu Arg Leu Phe Cys Pro Ala Gly Gly Tyr Pro Gly Tyr Cys
                615                 620                 625

taa gac tcg tac ttc cca gtt tgg tgt ggg cag ctt tca gac tcc atc      2193
*  Asp Ser Tyr Phe Pro Val Trp Cys Gly Gln Leu Ser Asp Ser Ile
               630                 635                 640

ctc ctt cag ctc cat gtc cct ccc tgg tgc ccc aac tgc atc gcc tgg      2241
Leu Leu Gln Leu His Val Pro Pro Trp Cys Pro Asn Cys Ile Ala Trp
            645                 650                 655

tgc tgc tgc cta ccc tag tct cac caa tcg tgg atc taa ctt tgc tcc      2289
Cys Cys Cys Leu Pro  *  Ser His Gln Ser Trp Ile  *  Leu Cys Ser
        660                 665                 670

tga gac tgg aca gac tgc agg aca att cca gac acg gac agc aga ggg      2337
*  Asp Trp Thr Asp Cys Arg Thr Ile Pro Asp Thr Asp Ser Arg Gly
               675                 680                 685

tgt ggg tgt ctg gcc aca gtg gca ggg cca gca gcc tca tca tcg ttc      2385
Cys Gly Cys Leu Ala Thr Val Ala Gly Pro Ala Ala Ser Ser Ser Phe
            690                 695                 700

aag ttc tag tga gca aca tgt tca aca acc gcc agc aca gca acc tgg      2433
Lys Phe  *   *  Ala Thr Cys Ser Thr Thr Ala Ser Thr Ala Thr Trp
                705                 710                 715

cca gcc tga ggt ctt cca gga gat gct gtc cat gct ggg aga tca gag      2481
Pro Ala  *  Gly Leu Pro Gly Asp Ala Val His Ala Gly Arg Ser Glu
                720                 725                 730
```

-continued

```
caa cag cta caa caa tga aga att ccc tga tct aac tat gtt tcc ccc     2529
Gln Gln Leu Gln Gln  *  Arg Ile Pro  *  Ser Asn Tyr Val Ser Pro
            735                          740                 745

ctt ttc aga ata g aactattggg gtgaggataa ggggtggggg agaaaaaatc       2582
Leu Phe Arg Ile

actgtttgtt tttaaaaagc aaatctttct gtaaacagaa taaaagttcc tctcccttcc   2642

cttccctcac ccctgacatg taccccccttt cccttctggc tgttcccctg ctctgttgcc   2702

tctctaaggt aacatttata gaagaaatgg aatgaatctc caaggctttt aggactgtct   2762

gaaaatttga ggctgggtga agttaaaaca cctttcctta tgtctcctga cctgaaattg   2822

tatagtgttg atttgtgctg agatcaagag gcaggttaga agaacctgac atccactgtt   2882

tgccttggat agtatggctt gtttttggaa aggaattctg aagagagtgg aggagaggag   2942

aaatgtcctc atatttgagg accatgaaac attgtaggta tatatggggc tttagcaagt   3002

ttgagcctag gctcttttttg ctgcctgtga gcagtccctc tggaaagaaa catgtgagta  3062

agtgagagag agtgtgtgtg tatgtgtgtg tgtgtgtgtg tgtgtgtgcg cacacatgct   3122

tctgtatttc actctttctc cctattaggg agttatgcaa aatttgtccc cgattttacc   3182

tttgtctttc tgtgtacttt tcaaagagtc ctaaggagtt aaatcttcca ggtattttcc   3242

acttagtatt gcagccaaag aatatttaaa taaacgtctt tgctgcgctt gcatccatgc   3302

ccagccaata tacaactgta aagcaaatat agaaagtcgg ctgttgatac gattgtctgt   3362

tatcgaacac attcagtgat aaagctgggt tactgctgct tttggtgctc tcaccttatc   3422

tggaagatct gcaaacatta cctaaatagg ctggcaagat aaacactttc tggaacccga   3482

gacttggcca taaagataat gctgcatttt tctgtcagaa tcacatatga tgtgtgttct   3542

gtagaggtta tttctgcatg gaaactcaac ttcttggatt agccgtccca gtgaaaatcc   3602

tcattgttgg agtgtaaacc aaatacgaag ccctcttgca aagtagcctc tttcatccca   3662

tactcaaaat acccagttta gcaagcaact gagatttaag tctctctggc cctaagaggt   3722

ttttcctctt tgctccctcc aatcttgaga ttgggttttg ctttagagtg caagtatcat   3782

aattccgtat gatagatggg gcctggacac ccatctcaac agggtcactt ggtaattaac   3842

aatagccata taaatgcgga tacaggttac taccctcacc ctttaccttc ctcaggtaac   3902

agtcgtagat accagctttt tttttttttt ttttaaattg gctttggcca gtagctaaag   3962

tgcaagactg agttaatgag aagatatatt aaatgtagtc atagggggact gaggagcaag  4022

ggtggccttg aagaggccaa aggaatgtcc atttgctgag tttcccttcc ttatgtctcc   4082

agtctggtgc caggtagtgg agtaaaaaag gagacagttt attttttttat tctatgtgca  4142

cacttacagt atacatatat atttatatca caatttacga aaccaaaaag ttgagtttcc   4202

aatggaaccc ttgtttttta ataatcgact ttttaaatgt gatcaagact ataatattgt   4262

acagttatta tagggctttt ggggaagggg aggatagcga gaagatgctc tgggggtttt   4322

gtttttgctt ttccttcagg gttttatttt tgactgtttt gttttcttgt tggccatttc   4382

tgtattgctg gcatctgtgc taagctttac agtggcaaaa ataatgacat gtagcaaaga   4442

ttttcaaaca aaatattttt tccttttgta aaaaaaaaaa aaaaagaaaa aaaaaaaaaa   4502

aa                                                                  4504
```

<210> SEQ ID NO 5
<211> LENGTH: 20
<212> TYPE: DNA
<213> ORGANISM: Artificial Sequence -continued

```
<220> FEATURE:
<223> OTHER INFORMATION: PCR Primer

<400> SEQUENCE: 5

agcagagggt gtgggtgtct                                                    20


<210> SEQ ID NO 6
<211> LENGTH: 20
<212> TYPE: DNA
<213> ORGANISM: Artificial Sequence
<220> FEATURE:
<223> OTHER INFORMATION: PCR Primer

<400> SEQUENCE: 6

tggcggttgt tgaacatgtt                                                    20


<210> SEQ ID NO 7
<211> LENGTH: 22
<212> TYPE: DNA
<213> ORGANISM: Artificial Sequence
<220> FEATURE:
<223> OTHER INFORMATION: PCR Probe

<400> SEQUENCE: 7

ccagcagcct catcatcgtt ca                                                 22


<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8

gaaggtgaag gtcggagtc                                                     19


<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9

gaagatggtg atgggatttc                                                    20


<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10

caagcttccc gttctcagcc                                                    20


<210> SEQ ID NO 11
<211> LENGTH: 2691
<212> TYPE: DNA
<213> ORGANISM: M. musculus
<220> FEATURE:
<220> FEATURE:
<221> NAME/KEY: CDS
<222> LOCATION: (110)...(2485)

<400> SEQUENCE: 11
```

-continued

```
gcggcggtaa ggtgcctaat ctgcggagtg gctcttccct cccctccccc agctcggtgg      60

cggctgcccc tcccaccgag ggtggcgcag ggacggtgcc atctcgacc atg gcg gcg     118
                                                      Met Ala Ala
                                                        1

act aca gct aac cca gaa atg aca tca gat gta cca tcg ctg ggt ccc      166
Thr Thr Ala Asn Pro Glu Met Thr Ser Asp Val Pro Ser Leu Gly Pro
      5                  10                  15

acc att gct tct gga aac cct gga cct ggg att caa ggt gga gga gct      214
Thr Ile Ala Ser Gly Asn Pro Gly Pro Gly Ile Gln Gly Gly Gly Ala
 20                  25                  30                  35

gtt gta cag agg gct att aag cga cgg tca ggg ctg gat ttt gat gat      262
Val Val Gln Arg Ala Ile Lys Arg Arg Ser Gly Leu Asp Phe Asp Asp
                 40                  45                  50

gaa gta gaa gtg aac act aaa ttt ttg aga tgc gat gat gac cag atg      310
Glu Val Glu Val Asn Thr Lys Phe Leu Arg Cys Asp Asp Asp Gln Met
             55                  60                  65

tgt aat gac aaa gag cgg ttt gcc agg tcg gat gat gag cag agc tct      358
Cys Asn Asp Lys Glu Arg Phe Ala Arg Ser Asp Asp Glu Gln Ser Ser
         70                  75                  80

gcg gat aaa gag aga ctt gcc agg gaa aat cat agt gaa ata gaa cgg      406
Ala Asp Lys Glu Arg Leu Ala Arg Glu Asn His Ser Glu Ile Glu Arg
     85                  90                  95

cgg cga cgg aac aag atg aca gct tac atc aca gaa ctg tca gac atg      454
Arg Arg Arg Asn Lys Met Thr Ala Tyr Ile Thr Glu Leu Ser Asp Met
100                 105                 110                 115

gta cct aca tgt agt gcc ctg gct cga aaa cca gac aag cta acc atc      502
Val Pro Thr Cys Ser Ala Leu Ala Arg Lys Pro Asp Lys Leu Thr Ile
                120                 125                 130

tta cgc atg gcc gtt tct cac atg aag tcc ttg agg gga act ggc aac      550
Leu Arg Met Ala Val Ser His Met Lys Ser Leu Arg Gly Thr Gly Asn
            135                 140                 145

aca tct act gat ggc tcc tac aag cca tct ttc ctc act gat cag gaa      598
Thr Ser Thr Asp Gly Ser Tyr Lys Pro Ser Phe Leu Thr Asp Gln Glu
        150                 155                 160

ctg aaa cat ttg atc ttg gag gca gca gat ggc ttt ctg ttt att gtc      646
Leu Lys His Leu Ile Leu Glu Ala Ala Asp Gly Phe Leu Phe Ile Val
    165                 170                 175

tcc tgt gag act gga cgg gtg gtg tat gtc tct gac tca gtg act ccc      694
Ser Cys Glu Thr Gly Arg Val Val Tyr Val Ser Asp Ser Val Thr Pro
180                 185                 190                 195

gtt ttg aac cag cca cag tct gaa tgg ttc ggg agc aca ctg tat gat      742
Val Leu Asn Gln Pro Gln Ser Glu Trp Phe Gly Ser Thr Leu Tyr Asp
                200                 205                 210

cag gtg cac cca gat gat gtg gat aaa ctt cga gag cag ctc tct aca      790
Gln Val His Pro Asp Asp Val Asp Lys Leu Arg Glu Gln Leu Ser Thr
            215                 220                 225

tca gaa aat gcc cta aca ggg cgg gtc ctg gat ctg aag act gga aca      838
Ser Glu Asn Ala Leu Thr Gly Arg Val Leu Asp Leu Lys Thr Gly Thr
        230                 235                 240

gtg aaa aag gaa ggc cag cag tct tcc atg agg atg tgc atg ggc tca      886
Val Lys Lys Glu Gly Gln Gln Ser Ser Met Arg Met Cys Met Gly Ser
    245                 250                 255

cga agg tcg ttc atc tgc cgc atg agg tgt ggt act agc tcc gtg gac      934
Arg Arg Ser Phe Ile Cys Arg Met Arg Cys Gly Thr Ser Ser Val Asp
260                 265                 270                 275

cct gtt tcc atg aat aga ctg agc ttt ttg agg aac aga tgc agg aat      982
Pro Val Ser Met Asn Arg Leu Ser Phe Leu Arg Asn Arg Cys Arg Asn
                280                 285                 290

ggg ctt ggc tct gtg aag gaa gga gaa cct cac ttt gtg gta gtc cac     1030
```

-continued

```
Gly Leu Gly Ser Val Lys Glu Gly Glu Pro His Phe Val Val Val His
            295                 300                 305

tgc aca ggc tac atc aag gcc tgg cca cca gca ggt gtc tcc ctc cca      1078
Cys Thr Gly Tyr Ile Lys Ala Trp Pro Pro Ala Gly Val Ser Leu Pro
        310                 315                 320

gat gat gac cca gag gct ggc cag ggg agc aaa ttc tgc cta gtg gcc      1126
Asp Asp Asp Pro Glu Ala Gly Gln Gly Ser Lys Phe Cys Leu Val Ala
    325                 330                 335

att ggc agg ctg cag gta act agt tct ccc aac tgt aca gac atg agt      1174
Ile Gly Arg Leu Gln Val Thr Ser Ser Pro Asn Cys Thr Asp Met Ser
340                 345                 350                 355

aac att tgt cag cca aca gag ttc atc tcc cga cac aac att gaa ggg      1222
Asn Ile Cys Gln Pro Thr Glu Phe Ile Ser Arg His Asn Ile Glu Gly
                360                 365                 370

ata ttc act ttt gta gac cat cgt tgt gtg gct act gtt ggc tac cag      1270
Ile Phe Thr Phe Val Asp His Arg Cys Val Ala Thr Val Gly Tyr Gln
            375                 380                 385

cca cag gag ctc tta ggg aag aat att gta gaa ttt tgt cat cct gaa      1318
Pro Gln Glu Leu Leu Gly Lys Asn Ile Val Glu Phe Cys His Pro Glu
        390                 395                 400

gac caa caa ctt cta aga gac agc ttt cag cag gtg gtg aaa tta aaa      1366
Asp Gln Gln Leu Leu Arg Asp Ser Phe Gln Gln Val Val Lys Leu Lys
    405                 410                 415

ggt cag gtg ctg tcc gtc atg ttc cga ttc cga tct aag acc cga gaa      1414
Gly Gln Val Leu Ser Val Met Phe Arg Phe Arg Ser Lys Thr Arg Glu
420                 425                 430                 435

tgg ctg tgg atg aga acg agc tcc ttt acc ttc caa aac cct tat tca      1462
Trp Leu Trp Met Arg Thr Ser Ser Phe Thr Phe Gln Asn Pro Tyr Ser
                440                 445                 450

gat gaa att gag tat att atc tgc acc aac acc aat gtg aag aac tct      1510
Asp Glu Ile Glu Tyr Ile Ile Cys Thr Asn Thr Asn Val Lys Asn Ser
            455                 460                 465

agc cag gaa cca cgg cct aca ctg tcc aac acc atc cca agg tca cag      1558
Ser Gln Glu Pro Arg Pro Thr Leu Ser Asn Thr Ile Pro Arg Ser Gln
        470                 475                 480

cta ggt ccg aca gcc aat tta tcc cta gag atg ggt aca ggg cag ctg      1606
Leu Gly Pro Thr Ala Asn Leu Ser Leu Glu Met Gly Thr Gly Gln Leu
    485                 490                 495

cca tcc agg cag cag cag cag cag cac aca gaa ctg gat atg gta cca      1654
Pro Ser Arg Gln Gln Gln Gln Gln His Thr Glu Leu Asp Met Val Pro
500                 505                 510                 515

gga aga gat ggg ctg gcc agc tat aat cat tcc cag gtt tct gtc cag      1702
Gly Arg Asp Gly Leu Ala Ser Tyr Asn His Ser Gln Val Ser Val Gln
                520                 525                 530

cct gtg gca agt gca gga tca gaa cac agc aag ccc ctt gag aag tca      1750
Pro Val Ala Ser Ala Gly Ser Glu His Ser Lys Pro Leu Glu Lys Ser
            535                 540                 545

gaa ggt ctc ttt gca cag gac aga gat cca agg ttt cca gaa atc tat      1798
Glu Gly Leu Phe Ala Gln Asp Arg Asp Pro Arg Phe Pro Glu Ile Tyr
        550                 555                 560

ccc agc atc act gca gat cag agt aaa ggc atc tcc tcc agc act gtc      1846
Pro Ser Ile Thr Ala Asp Gln Ser Lys Gly Ile Ser Ser Ser Thr Val
    565                 570                 575

cct gcc acc caa cag ctg ttc tcc cag ggc agc tca ttc cct cct aac      1894
Pro Ala Thr Gln Gln Leu Phe Ser Gln Gly Ser Ser Phe Pro Pro Asn
580                 585                 590                 595

ccc cgg ccg gca gag aat ttc agg aat agt ggt ctt acc cct cct gta      1942
Pro Arg Pro Ala Glu Asn Phe Arg Asn Ser Gly Leu Thr Pro Pro Val
                600                 605                 610
```

-continued

```
acc att gtc cag cca tca tct tct gca ggg cag ata ctg gcc cag att     1990
Thr Ile Val Gln Pro Ser Ser Ser Ala Gly Gln Ile Leu Ala Gln Ile
            615                 620                 625

tca cgt cac tcc aac cct gcc cag gga tca gcg ccg acc tgg acc tct     2038
Ser Arg His Ser Asn Pro Ala Gln Gly Ser Ala Pro Thr Trp Thr Ser
        630                 635                 640

agc tcc cgc cca ggc ttt gcc gcc cag cag gtg ccc acc cag gct aca     2086
Ser Ser Arg Pro Gly Phe Ala Ala Gln Gln Val Pro Thr Gln Ala Thr
    645                 650                 655

gcc aag act cgt tct tcc caa ttt ggt gtg aac aac ttt cag act tct     2134
Ala Lys Thr Arg Ser Ser Gln Phe Gly Val Asn Asn Phe Gln Thr Ser
660                 665                 670                 675

tcc tcc ttc agt gct atg tct ctt ccg ggt gct ccc act gcc tca tct     2182
Ser Ser Phe Ser Ala Met Ser Leu Pro Gly Ala Pro Thr Ala Ser Ser
                680                 685                 690

ggt act gct gcc tac cct gct ctc ccc aac cgt ggc tcc aac ttt cct     2230
Gly Thr Ala Ala Tyr Pro Ala Leu Pro Asn Arg Gly Ser Asn Phe Pro
            695                 700                 705

cct gag act gga cag acc aca gga cag ttc cag gcc cgg aca gca gag     2278
Pro Glu Thr Gly Gln Thr Thr Gly Gln Phe Gln Ala Arg Thr Ala Glu
        710                 715                 720

ggc gtg ggt gtc tgg cca cag tgg cag ggc cag cag ccc cat cat cgg     2326
Gly Val Gly Val Trp Pro Gln Trp Gln Gly Gln Gln Pro His His Arg
    725                 730                 735

tct agt tcc agt gag cag cat gtt cag cag aca caa gca caa gca cct     2374
Ser Ser Ser Ser Glu Gln His Val Gln Gln Thr Gln Ala Gln Ala Pro
740                 745                 750                 755

agc cag cct gag gtc ttt caa gaa atg ctg tcc atg ctg gga gac caa     2422
Ser Gln Pro Glu Val Phe Gln Glu Met Leu Ser Met Leu Gly Asp Gln
                760                 765                 770

agc aac acc tac aac aat gaa gaa ttt cct gat cta act atg ttt ccc     2470
Ser Asn Thr Tyr Asn Asn Glu Glu Phe Pro Asp Leu Thr Met Phe Pro
            775                 780                 785

ccc ttt tcc gaa tag aactattggg gtgaggataa gggtgggggg aaatcactgt     2525
Pro Phe Ser Glu
        790

ttgtttttaa aagcaaatct tttgtaaaca gaataaaagt tcctctccct tcccttccct   2585

caccccctgat atgtaccctt tccacccctt gacttgctga agaaacgtta tagaagaaat   2645

taaatgaatt tcccaggcaa aaaaaaaaaa aaaaaaaaaa aaaaaa                  2691


<210> SEQ ID NO 12
<211> LENGTH: 20
<212> TYPE: DNA
<213> ORGANISM: Artificial Sequence
<220> FEATURE:
<223> OTHER INFORMATION: PCR Primer

<400> SEQUENCE: 12

ggcatctcct ccagcactgt                                                 20


<210> SEQ ID NO 13
<211> LENGTH: 28
<212> TYPE: DNA
<213> ORGANISM: Artificial Sequence
<220> FEATURE:
<223> OTHER INFORMATION: PCR Primer

<400> SEQUENCE: 13

ggtaagacca ctattcctga aattctct                                       28
```

-continued

<210> SEQ ID NO 14
<211> LENGTH: 20
<212> TYPE: DNA
<213> ORGANISM: Artificial Sequence
<220> FEATURE:
<223> OTHER INFORMATION: PCR Probe

<400> SEQUENCE: 14
tccctcctaa cccccggccg 20

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
ggcaaattca acggcacagt 20

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16
gggtctcgct cctggaagat 20

<210> SEQ ID NO 17
<211> LENGTH: 27
<212> TYPE: DNA
<213> ORGANISM: Artificial Sequence
<220> FEATURE:
<223> OTHER INFORMATION: PCR Probe

<400> SEQUENCE: 17
aaggccgaga atgggaagct tgtcatc 27

<210> SEQ ID NO 18
<211> LENGTH: 67787
<212> TYPE: DNA
<213> ORGANISM: H. sapiens

<400> SEQUENCE: 18
ttagtagaga cggggtttcg ccatgttggc caggctggtt tcgaacccct ggccacaggt 60
gatccggccg cctcggcctc ccaaagtgct gggattacag acgcgagcca ccgcgcccag 120
cctaaaatac ccattttaat tgcatttcaa tgacgttact cggtcattga cctcttacgc 180
aaggagggcg agattaggga gacagctgga cttcttcctc gccctccctt cactggactg 240
gctggcgcag tgagtagccc tgcccttgga cgatttggca ttttcattgg tcaatttttc 300
ttaggaggct ggccgtgtgt tgactccgcc tactatatag gcggggtctc cccgccgcag 360
gggctgggat gctgggggct gctgaagccg ccatcttgga ttccgcggta gcggaggcgg 420
cggtcaggcg ccgcttctgg ggagtggcct ttcttttccc ctccctcccg gttcggtggc 480
ggcggctcct cccactgggg ggggggtgg cgcggcggcg gtggcatctg cggccatggc 540
ggcgactact gccaaccccg gtgaggagac ggaggactgg ggcgcctcta aaggggaggg 600
gccgaagggg ctgacaacta aggagaccca gggctgaggg gacgcagctg gagctgaagg 660
cgccggggcg gggcgggggc cgcgagagac ggtgggggag cggtgacctg gggaggggcc 720

-continued

```
cgatcccggg gacttgggta gactcgagta tacccaaggg agcgaggggg caggtgggag    780
ttgagggggg ctccctgtcc tgacctccgt tggagcggca gccagtgcgg ggctggcccg    840
ccctcactcc tcggtcggcg tctggtctgt gatgtggtcc tcttttaacc ctctgcccgc    900
tggagccgct tgatgccgaa aactgtaggc agagtgtctc ggtttacttt aagagtagtt    960
tggattcata aaccctggac cacactgctc tttagttgag gcgttgcttc caaacattta   1020
aaggtttaga ttttaattta aaaaataaaa aatggacatt ctttgatata tacgacgttt   1080
ctttaggctg ttacctccca cccgcaaccc ccgtccccgt ctccgtcccc ggactatact   1140
ttgaaactta gatcttgtgt taagagggcc tgtaggtctt tgcctgctga gggcaggggt   1200
ttgtgtaatg gttatggttc cggacaggtc tttagttcca cagccccagg tttaaatctt   1260
gttaggccta cgtcgaggca atttccaaac tctttcagaa aagtttgatt ccacaccatt   1320
tctcaatttc aaaaaataat caaatatcaa aaaggtttgg tctgttttgt ctaagagatg   1380
gagtagggtg tagtgcagtt ctagagagat cagatcttca aattactagt cccagccctc   1440
tttcctctat gttacagtta ttcctcttta gaaggcattt cattttaggg gtctagttta   1500
tcttggagac cttggttatt cttgccaaat aaagtctatc cttttccaaa aaccaatata   1560
tttgatagcc ttaaaaaggg ccttgagata tgtgtgtgtg ttgcgtgggg cggagaattt   1620
cttgaaaata aaacagtagg agtgattacc cccatcccca cgttgaaatt taaattagat   1680
ttttttcat gttactgaaa ggcagtatga ttttgcaata tccagatttt gataggacag   1740
ttgaatcact gaaatttctt ttctaccgtg tttctgggaa tagctatttt aagaaatggt   1800
taatttgtca cgtcattttt ttttaatctt ttaaattttt tttgaaggaa agggaggtaa   1860
aattaatcgc aaaaattaca ttgcaggaag tgctgagtga tagaataaaa ctataaaaca   1920
ggaaaaatgc cgttatgtca aacctgacct tgtagtaata taacctatct gtgaactatg   1980
gaataaataa acaagatttt taactgatca cacattgcaa aatacttata taaccctagt   2040
taaattgcaa agcatttctc ttattaagaa gtggcctggg taaacaagtt ttagttcata   2100
tgtcagaagc ttttttccag ctgtgtgggt ggggttgctt tattttgttt tgttttttga   2160
acaacagcaa ccagaatgac agcctcttga ccatattttc ataagctgat caatatcagc   2220
ttaaatctta gcagaaaata gcatatgtta gtgtgtatgt gtgtgtgcag aatccttgtt   2280
aatgaaacag ctttgtttac tatgctttgg ctgcttgctt ctgcaatttt tagatttcct   2340
ttttcttttt ctttgtttc ctttctcctc tcccctctct cctgtcccct ctcccctctt   2400
tttcttttgc tacagggtct tgctccttgc tctgtcgccc agtctggagt gcagtggcaa   2460
gatcactgct cacggcagcc tccacctcag gggctcaagt gatcctctca cgatcagcct   2520
cccgaatagc tgggactaca ggtgccttgc caccatgcgc ggttaatttt taaatttttt   2580
tgtagagaca gatgccttgc tatgttgccc atgctgatct tgatctcctg gtctcaagca   2640
agccttgcct cagtctctcc aagttgggaa tacagatgtg agacactttg accagatttc   2700
tttttgatg ttgaaaaatt attccatctc ttctgactta ttgatcccat gttcagttca   2760
atcaaatcag aagatatatt ttcttttttc ttttctccct ttgctcttgt atatcatgag   2820
gaagagatca gagatacatt gtggattttt tcagtagcct gttgcttttt gggaaatgag   2880
attaatgaat ggagggacat aggtggaaat gtactgtgct tagtgaaagt aaatgttttc   2940
aggtcagaat tctttgctac actgtcatac cttctttcct tagagccatt ttaaggacta   3000
gggacaccat gcctatttct ttgagttttt tctactttgt atttttgctg gagtactaat   3060
tttttttttt tttttttttt ttttacaatt cttgttagtt ttgtcaagat tttaaaaaat   3120
```

-continued

```
atttcactct ttaaccttca cttcagttaa tcctttttaa aaataatact tatttttatt   3180
tttcagacag gttcttgctc tgtctcccag actgtagtgc aatggtgtaa tcacagctca   3240
ctgtagcctt gaactcctga gctcaagtga tcttcccacc tcagcctcct gagtatctgg   3300
gtctacagac acacaccacc acacctggat acatttttta actttttgta gaaatgggat   3360
cttgctatgt tgcccaggct gatcttgaac tcctgtcctc aagcaatcct cccaccttag   3420
cctcctaaac tgctgggatt ataggtgtga gccactgacc cggccaagtt aatccttagg   3480
gttagtaata gtgcttgaac atgttaattg tgctggtggc cctgcagtgt ttttcaaggg   3540
gaccacgttc ttctgcattt ttcactgtgg tgctgcatta gaagaagagt aaaatatggt   3600
tggtactctc taagagttgt gttgaagtaa tagttctgtg atgatttttt ttctcgaatt   3660
gataattctt catattctat catttttcac tagttctact tatcactggc aagtagaact   3720
cggtgggtag gtggtccatg aaactttagg ctgtttctta tctatggact agacaagttt   3780
tgttttgttt ttttttgtt tgtttgtttg ttttgagaca gagtctcact ctgtcgccca   3840
ggctggagtg cagtggtgct atcttggctc actgcaagct ccgcctccca ggttcacgcc   3900
attctcctgc ctcagcctcc cgagtagctg ggactacagg tacccgccac cacgcccggc   3960
taattttttt ttttgtattt ttagtagaga cagggtttca ccctgttagc cagggtggtc   4020
tcgatctcct gaccttgtga tccgcctgcc tcggcctccc aaagtgctgg gattacaggc   4080
ttgagtcacc gtgcccggcc cggactagac aagttttgag gaacacattt tttttcccca   4140
taggagaggg tcttgctctg tcactgaggc tggagtgcag tgacacaatc atggctcact   4200
gcagccttga ccttctggga gcatgtgatc ctcccacttc agcctcctga gtaggtggga   4260
ccacaggtgt gcaccaccgt ggctggctaa ttttaaattt tttttagaga cagggtcttg   4320
ctatgttgcc caggctggtc tttaactcct ggcctcaagt gatcttcctg cgttgggcac   4380
tccccaagag ctgggattat aggcatgacc accatgccca gccaaggtgg aacacttttt   4440
aaattgaatg tgtcatttgt aatgcattgg ctgagggaac agttgggagg agattaggta   4500
tttgatttac aattccaaat tcaaactaga gatgttgaat gagtttgtag taagtgtagg   4560
tttttatctc tcttgattct ggtattctca ttagcagaga attctttttg tgctattatg   4620
tacaagttac tgtggatgaa gaatgtagaa ggaaaagggt aataccgttt gggtttgtaa   4680
ggctgtcatt taggaagaaa atttttttta gctaattttc acctatataa cttagtttta   4740
actgcgtcaa ttaacacaat tcttacctgt tacctttatt taccttttc agatatggga   4800
aaataggaat tcatgcaatg taaagttaag atgtcaagat attcttttat ggccaggtgt   4860
ggtggctcgt gcctctaatc cctttgggag gccgaggcag gccgattgct tgagcccagg   4920
aatttgagac cagcccggac aacgtgacga aacccctta ctacaaaaaa tacaaaaaat   4980
tttccgggca ctgtggtgca cttctatagt cccagctact tgggaggctg agatgggagt   5040
atcacctgag cctggaaagt tgaagctgca gtgagctgtg atcatgccac tgtactccag   5100
cctgggtgtt ggagtgagac cctgtccccc aacaaaaaaa gagatagtat tttattatat   5160
tgcaaaggcc tttttttttt tttttttttt tttttgagac agggtcttac tgtgtcgccc   5220
aggctggagt gcaatggcgt gatcttggct cactgcaacc tccgcctcct gggttcaagc   5280
tattctcccg cctcagcctc ccgagtagct gggattacag gcacctgcca tcacgccggc   5340
taatttttta tttttaatag agacagggtt tctccatgtt ggccaggctg gtcttgaact   5400
cctcacctca ggtgatccgc ccaccttggc ctcccaaagt gctgggatta caggcgtgag   5460
```

-continued

```
ccgccatgct ccgccgccat ctgtttttaa gaatgctgcc ttggccgggc atggtggctc   5520
atgcctgtaa tcctagcatt ttgggaggcc gaagtgggca gatcacctga ggtcaggagt   5580
tcaagaccag cctggccaac atggagaaac cctgtctcta ctaaaaatac aaaaattagc   5640
caggcatggt ggcaggtgcc tgtaatccca gctactcggg aggctgaggc gggagaatcg   5700
cttgaacctg gaaggtggtg gttgcagtga gctgagatcg taccactgca ctctagcctg   5760
ggcgacagag tgagactccg tctaaaaaaa aaaaaaaaaa aaaaaaaacc acgactgcct   5820
aatatgccat aatgacttta gtaagtagac atcagtgaat cttcaggttg gaaatatgac   5880
aacacctatc attttacact taaggagaca aacccaggga aaggagtgga taattaagtt   5940
ccttctatat gccaggctgc actttcctat tttgttgcta atctttatgt ctagtctgta   6000
gcaactgtct ccaacttttc acataaactc ttcaaattta tgtcactttt cataatttcg   6060
tcaatgtatt ttcttgtttt aaagttttta ttattttaga tagtgaccgg gtctcactat   6120
attgccccgg ctggtctcaa actcctgggc tcaagcaatc ctcctgcctc ggcctcccag   6180
agtgccgggg ttacaggtgt gagccaccct ctgaggccca ttttatattt tccctccacg   6240
ttttcattgt agttgaatgg acaagtaagt ttatggattc aacagtatac ttagggctgg   6300
acatggtggc tcatacctgt aatcctagca ctttgggagg ctgatgtagg tggattgctt   6360
gagcccaaaa gtttgagacc agcctgggca acgtggtgaa accccatctg tacaaaaaaa   6420
tacaaaaaat tagcagggtg tggtagcatt ccctgtagtc ccagctacgt gggagactga   6480
gatgcgagga tgacctgagc ctgggaggtt gaggctgcag tgagccatga ttgtgccact   6540
gcattcctgt ctgggtgact aggagacaga gtgagaccct gtctcaaaaa acacaacaaa   6600
accagcatac ttaggatata agttccatga gagcagaact tttgctttcc ttgtttacca   6660
gagcattgca gtgcttacag tgggtgccta gtatgttgga ttagagttca atgtatgttt   6720
gtggaataaa aatgaatgta aaacccactg ttaatatgaa atacctttga agggataaaa   6780
ctaattaagc cattgacatc atgaatttgt actaactata ataatatcta atatttatta   6840
gtaatactta ccagctgttc tcatttaatt tttataacaa tcgtattagg taagtattat   6900
tattcttgtt ttacagatga ggaaactaag gcacagagag tgaataagta acttgtctga   6960
agtcacatag ctactagaag ttagagacag aattttattg ttggcagtcc atctacacag   7020
tcatcattct taatctccaa gttatgattt tttccattgt gacttagagt caccttccta   7080
ctgaaatata gtacaatgga tatcttttga gaaggaggta ggtggagtat tgtctttttt   7140
gtagatgaaa agggtgaaat accacattag gcagcctggg ggcaaggcat tgcttggttg   7200
gagaaccaag tgcaaggtgc taaaaaaagg agctagaaca gtagtttcca ggctgagtgt   7260
ggtggctcat acctgtaatc tcagcacttt gagaggccag ggtgagagga ttgtttaagc   7320
ccaggagttg gagaccagcc tgagcaatat agggagacct tgtctccaca aaaatatata   7380
taaaaaaatt agctagatgt ggtggtggat gcctatagtc ccaactactt gggaggctga   7440
ggtggtggga ggatctctga gcttgctagg tcagggctgc agtgagccat gatcatgcca   7500
ctggactcta atctggttga cagagtgagc ccctgtctct aggaaaaaaa aaaaaaaagg   7560
agtagtttcc taaaatcttt tctgtaacat tctataattc ttcattttgt tttgttttgt   7620
tttttgaga ctgagtgtcc ttctgtcacc caggctgggg tgcagtggca cgatctcagc   7680
tcactgcaag ctccgcctcc caggttcacg ccattctcct gcctcatcct cgcgagtagc   7740
tgggactaca ggcatccacc accatgccct gctaattttt tgtgttttta gtggagatgg   7800
ggtttcactg tgttagccag gatggcctcg atctcctgac cttgtgatcc gcccacctca   7860
```

-continued

```
gcctcccaaa gtgctgggat tataggcttg agctagcgcg cccagcctaa cattctatat   7920
ttctttctcc tagttctatg tttcaattct ttaaatactt ttaagggttt ttttgagaca   7980
aggtcctgtt gtgtcagcca ggctggagtg cagtagcgtg accatagctt cctgcaacac   8040
ctccaattcc taggctcaag cgattctcac tcctcagttt cctgaatagt tgggaccata   8100
ggtatgcacc atcatgccca gctaattttt taattttgta gagacaggat ctcgctatgt   8160
tgcccaggct ggtccttttt tttttaaatt ttattattat tttttgagac ggagtcttgc   8220
tttgtcaccc aggctggagt gcagtggcgt gatctcggct cactgcaacc tctgcctccc   8280
gggtttaagc gattctcctg cctcagcctc ctgtagctgg gactacaggc acgtgccacc   8340
gcgcctggct aatttttgtg tttttagtag agacggggtt tcaccatgtt ggccaggatg   8400
gtctcgatct cctgacctcg tgatctgccc acctcggcct cccaaagtgc tgggattaca   8460
ggcgtgagcc accgcgcccg gcctgcccag gctggtcttg aactactgtc ctcgagtgat   8520
cctcctgctg ttggcctccc agattgctga gattacaggc atgaatcatg cactgcagct   8580
tttaggattg ttattagaat cctctacaag ttcttgatac tccataattg agcctctcct   8640
agaaacttgg tttcagagac actgttgcta ggtctttatc actgattgtt ccttctttgt   8700
ccttttttgct tatctttctg cttgtttctt tctcttgttc agtatgcttc tacttttctc   8760
ttctcaccct tgaggctagg actcttcttt gagacagggt cttgactctt ttttgagaca   8820
gggtcttgct atgttgccca cgttggtctt ggattcctga gctcaaatga tcctcccacc   8880
tctgcttcct gagtagctgg gattacaagt gtacaccaca gtgcccggct tggggctaga   8940
actaaatagt aaaccaagca gtttccttca tttcttccca tttgcccacc tacctgcctt   9000
tctagctgct tgccttccta cttcaatttg acattcactt ggtacctacc atagtcctct   9060
tccctttgta ttagtccatt ctcacactgc tataaataac tacctgagac tgggtaattt   9120
atgaagaaaa gaggtttaat tgactcatag ttccgcaggc tgtatgggag gcagggctgg   9180
ggaggcctca ggaaacttgg aatcatggcg gaaggcgaag gggaagcaag catgtcttca   9240
catggctggc aggatagagg gagagaaggg gaaggtgcta cacactttca aacaaccaga   9300
tctcttgaga actctatcat gagagagcat taggggaatg gtgctaaacc tttggaaacc   9360
acccctatga tccaataacc tcccaccaga ctgcaccttc aacactgggg attacaattt   9420
gacatgatat ttgggtggag acacacagag ccaaaccata tcacccttta tttatctttt   9480
atgtataaaa gactccaaaa atttcattcc tggcttctca cataaactac tttcctatat   9540
ttttatctat ttaaaagata tctctctctt tttcttttaa agttgagaca gggttttact   9600
atgttgccca ggctggtctt gaaatcctgg gctcaagcat tcctcccact tcagcaacct   9660
gagtagctgg actacaggtg tgtgccattg tgcctggctg catctctgtt tgaatagttt   9720
tttttttttt taatttatag aaatgaggtc tcactgtatt gcccagactg gtcttgaact   9780
gctgagctca agtagtcccc ccatcttggt ctccctagta gctgggatta taggtgtatg   9840
acacgatgcc cagctctatt tgagtaatct gttttttttt gttgttgttg ttttttttaa   9900
agacagagtc tttctgtgtt gcccaggctg gagtgcagtg gtgcgatctt ggctcaccgc   9960
agcctccgcc tcctaggttc aaatgatttt tgtgcctcag cctctcgagt agctgggact  10020
acagtgtgcc accacgcctg gctaattttt tgtatcttta gtagagatgg ggtttcacca  10080
tgttggccag gctggtcttg aactcccgtc ctcaagtgat ccacctgcct tggcctccca  10140
cagtgctggg attacaagtg tgagccattg cgcccagcct ctatttgaat aatctttaac  10200
```

-continued

```
atcctatata tgtatgtact caccagtatt tcctttaaat ctgctgttct tcctaccttt  10260
ctgtatcttt catcactatc acaattcagt ttttcatttc cccaggctaa ggaactataa  10320
gtgtttggat tttatttttt atgtgtttat ctgggttatt aactcttctc aggtcttttg  10380
ccaaatatac gtgtgtgtgt gtgtatatgt atgtgtgtat acatacatat ataaaagtta  10440
tttaaatcaa aactatacat ccatatatta atatttaaag acttagatag ttttataaaa  10500
tgtttgttac aaaaaaatta taagggagtc ctctgctccc tttctctcat ttccttctct  10560
ccagtggcat catttttatt tcttttaaca gaattctttg tttctgttta aataaagtgt  10620
cccagtgaaa gacattagtt tccagatcaa aggggctgtg cacacatcaa ggcccattat  10680
gctgaaattt cagcatcaga tagagaatat cctataagct tcagagagaa taagattatt  10740
cacattcaaa agattcaggt atcagattgg tctttttttct cagtagtcat gctggaaagt  10800
agaagacctt ggaacaggct gactgacctt ggtggctcac gcctgtaatc ccagcatttt  10860
gggaggctga ggcaggtgga tcacctgagg tcaggagttt gggaccagcc tggccaacat  10920
ggtgaaaccc cgtctctact aaaaatacaa agattagttg gacgtggtgg tgtgtgcctg  10980
tagtaccagc tacttgggag gctgaggcag gagaattgct tgaacctggg aagcagaggt  11040
tgcagtgagc cgagatcacg ccactgcaca ccagcctggg caaaagagcg aagactctgt  11100
ctcaaaaaaa aaaaaaaaaa ctttggagta atgccttcaa aattctgagg gaaaataaat  11160
tctaatttag aattccatag ctaggcaaac tatcaattag tgaaatagaa gaaatatttt  11220
catacatcca aggcatttct tacacccttt caggaatcca ctagaagata ggctctacca  11280
gtaggagata gtaaaccaag aaagtggaga tacgaaatat aggaaatagg cagtataaca  11340
cagaagaaaa atgaagcatg tagtatgcat acattggtgt tagttttcct gttttcagta  11400
cgggtccctc actttcacct ttacgtcgtg ttcactagac tgtaagacct ttgatttata  11460
ctctccagag agtaaatctg tcttttgaca gaatggagag gggtagttgc cttggttaga  11520
aggaatagag aaaaggatct aggaatccat ctctgtagta aacagatgct gaactaattc  11580
tccttatttt cacttcattc accctaccct gcatacccag agttacctgg actcaccagc  11640
ttctgagact ttggggaatt ccatagcgta aattgagttg gttttctgct ttttcccttg  11700
tcagtttagg atttagttct tgtcgatctc ccaaggcaat agtccatttt atctctagtt  11760
tcaaaaaaat tattgctctt cttctcttat tctttccatc cttgtggttt tatgtcttgt  11820
gtaaaaattt ttgcttttaa aaattttttt cctgtgtgtg agtgaagaga gaagagagta  11880
gaaatagata gatacattta attcactatc cttactcaga agttgcatag tttaaaattt  11940
tagaagtaac tacctttttcg ttgtgccatc ctcatttagg cctttatcac cttgtttttt  12000
ttattaatct tgtcttccta cttctattac ttcaaacttt aaatctgtca gattaatttt  12060
aatttatatt ttcatcttgt tactcagact taaagttata tgtttgtctt tgttgaatct  12120
gatccaggtg tttcatcgtg gcattcaaag ctttctcttg gttagcactt gacatcttac  12180
cttttatagg tctttttctt tctttttttt tttttttttg atttaaagaa aaccattttg  12240
ttttcttcag gggcaatttt ttttttacat tccaccacat attatttata tgtttatcat  12300
atttctttta tttatttatt tatttattta tttatttttt attatacttt aagttttagg  12360
gtacatgtgc acattgtgca ggttagttac atatgtatac atgtgccatg ctggtgcgct  12420
gcacccacta actggtcatc tagcattagg tatatctccc aatgctatcc ctcccccctc  12480
cccccacccc accacagtcc ccagagtgtg atattcccct tcctgtgtcc atgtgatctc  12540
attgttcagt tcccacctat gagtgagaat atgcggtgtt tggttttttg atcttgcgat  12600
```

-continued

```
agtttactga gaatgatgat ttccaatttc gtccatgtcc ctacaaagga catgaactca  12660
tcatttttta tggctgcata gtattccatg gtgtatatgt gccacatttt cttaatccag  12720
tctatcattg ttggacattt gggttggttc caataggtct ttttctttac agctcttcac  12780
agttgctgtt atgtgtcacc taatgacact ttggtcatca aaggactgca tgtatgatgg  12840
tggtcccata agattataat ggagatgaaa aattcctatt gcccagtgac atcatagttg  12900
tcataaggtc ttagcacaac acattacttt ttctatgttt agatacataa atagttacca  12960
ctgagttata gttgcctaca gtattcagta tagtaacatg ttgtacaggt tgggagtaat  13020
aggctgttac tgggagtaat aggctacata taggtatgta ggctatacac ctacatacct  13080
aggtgtgtag tggctgtacc atctagattt gtgtaagtat actcaatgat attcacacaa  13140
tgttgaaatc tcctaatgac acatttctca gaacatatcc ctgttgttaa gtgatacata  13200
actgtatttt catatctccc tttagacttg ctcatgtact tttatctatg tggaatgcct  13260
ttttcttctt ctttactttt tttttttgag acggagtttt gctcttgttg cccaggctgg  13320
agttcagtgg ctcgattggc tcactgcaac ctctgcctcc tgggttcaag caattctcct  13380
atctcagcct cctgagtagc tgggattaca ggcgcctggt aatttttat atttttagta  13440
gagacggggt ttcaccatgt tggtcaggct ggtctcgaac tcctgacctt aggtgatcca  13500
cccacctcgg cctcccaaag tgttgggatt acaggcgtga gccactgtgc ctggtctcct  13560
ttactttttt taaggcccag tttgatttac ctttttgaaa cttccccatg ggctggttgc  13620
ctgccttctt tatttccttt agtttcctct tcatattgag catcttctct gcaagtacta  13680
tgccaggcct taatttaaac caggattatc ttctctgaat ttacctggca ctcttttttt  13740
ttttttgag acagagtctc attctgttgc ccaggctgga gtgcagtggc atgatctcgg  13800
ctcactgcag cctttgcctc ccaggcgatt ctcatgcctc agtctcccaa gtagctggga  13860
ttatagacgt gtaccaccac acctgactaa tttttgtatt tttagtagag acgggatttt  13920
gccgtgttgg tcaggctggt ctcaaacttg accttaagtg atctacccac ctcagcctcc  13980
taaagtgctg gggttacagg catcagccac cgtgcctggc ctccatggta atcttttttt  14040
tttttttttt ttgagacgga atcttgctct gtcacccagg ctagagtgca gtggcacgat  14100
cttggctcat tgcaacctcc gccttttgtg ttcaagcgat tcttctgcct cagcctcccg  14160
agtagctggg actacaggtg tgcgccacca tgcctggcta atttttgtat ttttagtaga  14220
cacggagttt caccatattg gccaggctgg tctcgaactc ctgatgtcgt gatctgcctg  14280
cctcggcctc tcaaagtgct aggattacag gtttgactcc atggtactct tatatcctat  14340
ataaacgtat tactaaaagt atgaactttt tttttttttt tttttttttt acagaggcag  14400
gatctcacta tgttgctcag gctagttttg aactcctgag ctcaagcaat cctcatgcct  14460
tgacctccca aagtgctggg attataggca tgagccactg cacttggccc tgaacttttt  14520
tttttaatgg aaaaagtgtt ttttcttagg aaagtaacat atgcttacta tttcaaattt  14580
ataggctgaa atagaaaaat tagcagtaac ataaaaatat actcagcctt aatgtatgtt  14640
aaactaacag tggtaattgt tttttaccaa gaaaatgacc acaaatttga aggattccca  14700
aaacacagtg ctgttggagg tatggctaaa ttgatgcagt ggatgaggct ttaaattggt  14760
ataacctcct tggcaggtaa tgggcaatca gagttttaaa tgtgtctacc cttaggccca  14820
gggagtcatt ttcagaaata atatggaagt actggcacct gtgcatgaag atacacaatg  14880
atgttccttg aaacattatt tataatagtg aaggtttgaa tgtcataact atacatttat  14940
```

-continued

```
agtacagagt actatgtaac tgttaaaaag aatgatctac gtgtgtattt attgccatag  15000
caatatattg ttacgtggaa gggaaaaagt tcagaataag tacatctgta cttatggtgg  15060
ggttatggct tgataaaccc attgtaaatt gaaaacatcc taagtcaaaa atacatttaa  15120
tacacttaac ctattcttag cctagactac cttaaatgtg tgtggaatac ttacattagc  15180
ctgcagtggg caaaataatc taacttaaat tctactttat aataaagtac tggatattat  15240
gtaatttaca gaacactgta cattacactg aaattgtaat ggtttcccac tatcataaag  15300
gtgaaaagcc ctacatggaa ccattataag tcaggactgt ttgtatagta tgaccctttt  15360
ttttgggtaa aaattaccga aaccctggct gggcgtggtg actcatgcct gtaatcaggc  15420
acataccaca tgtatggcca attttgttca tttttttag agatagggtc tcactgtgtt  15480
gcccagggtg gtcttgaact tctggactca aatgatcctc ctccctcggc cttttaaagt  15540
gctagcctta caggtgtaag ccaccatgtt cagccccaca gtttctttat ccgttaacct  15600
gtagatagac acttgggttg ccctcaccct tgactactgt tgaatagtac ttctgtgaac  15660
gtgggtatac aaatgtttct ttgagaccct gctttcaatt ctttcaggta tatacccaga  15720
ggtggaattg ctggatcatg tggtaattct atttttaatt taattttttt tttgcgatgt  15780
tgtcttgctg tgtttcccag cctgatcttg gactcaagat tctcctgcct cagaccccga  15840
gtagctggga ctacaggtgc gcaccactgc acccagtttt atttttaatt tttggaggca  15900
tctccatact gttttctatt gctgttacgc cattttacat ttccactagc agtgcataag  15960
ggttttaatt tctccacatc cttgccaacc ctttatttat ttatatattt ttggataata  16020
gtcatcttaa tgagtagcaa atgctttctc attgtggttt tgatttgcat ttccctagcg  16080
attggttatg ttgagcactt tacatgtatt tattggccat tagtatatct tctttgtaga  16140
aatgcttgtt caagttcttt gcccatttta aaattgggtt tgctttttgt tgagttgtag  16200
gagctcttta tatattttgt tttatttttt atttgtttat ttttttgagg cagagtcttt  16260
ctctgtcgct caggctggag tgcagtggtg cgatcttggt tcactgcagt ctccgcctcc  16320
tgggttcaat taattctccc tgcctcagct tcccgagtag ctgggattac aggtgcccac  16380
caccattcct ggctaattgt tgtattttta gtagagatgg gatttcacca tgttgatcag  16440
gctggtctcg aactgctgac ctcaggtgat atgcccgcct tggcctccca aagtgctggg  16500
attacaggtg tgagccaccg tgcctggcca ctctttatat attttggata ttctgtgttg  16560
catatatgat tcgaaaattt ttttttctgc tgggcacggt ggctcatgcc tgtaatccta  16620
gcattttggg aggctgaggt gggcggatca cttgaggtca ggagttaaag accagcctgg  16680
ccaacatggt gaaaccccat ctctaataaa aatacaaaaa ttagccaggc gtggtggtgc  16740
gtgcctgtaa tcccagctat ttgggaggct gaggctcgag aatcacttga acccgagagt  16800
tggaggttgc agggagccaa gattgcgcca ctgcactcca gcctgggcga cagagtgaga  16860
ctctaactca aaaaaaaaaa aaaagaattt ttttttttct attccatggg ttgccttttc  16920
actctgttgg tagtgttatt tgatgcacaa aatattgtac actatacagt atgaactaac  16980
aaaaaacaat gagatgtgtg tagatagata ttcatgatgt atattgaaat gacgagcaag  17040
ttgaagatca ggcctccatt ttttactaag agaaaaatgc accctttttt ttttttttaga  17100
caggatcttg ctctgttgcc cagggtggag tgcagtggtg caatcacgac tcactgcagc  17160
ctcgacttcc caggctcaag tgatcctccc acatcaacct cttgagtagc tgggactaca  17220
ggcatgggcc accatgctgg ctaacttgta ttttttgtac agatgaggtt tcactgtgtt  17280
gcaaaggcta gtctcgaact cctgggctca agtgatctgc ccaccttggt ctcccaaagc  17340
```

-continued

```
tctaggattc caggcatccg ccactgtgcc cagcctgcac ctctttttga ttacagagtt  17400
aggtatatat aaactgagat tgaaaaataa gagaaaatat actcagggct gggctcagtg  17460
gctcaaacct gtaattccag tgctctggga agctgaggtg ggagtattgc ttgagctcag  17520
gagtttgaga ccagcctggg gaacacagtg agaccctatc tctacaaaga aaaaaaaaga  17580
aaaaaaaaat caccgaggtg tggtggtacc catctgtagt cccagctact taggaagctg  17640
agacaggagg atcactggag cccgggaggt tgaggctgca gtaagccatg atcatgccac  17700
tgtactccag cctgggctgg acaaagtgag accctgtctt aaaaaaaaaa aaaaaaaagt  17760
actcagctgt tactaatggt tactgctggg ggatgagatt gaattggaag gagagaggag  17820
aggtacgggg ggcaggaaag ggagacaata atgagggact ttcagtttta ctttacataa  17880
ttttctttta agtattggaa tttaggtgat ttttcctttg gggttttctg tattttccaa  17940
tcacaataaa taaaataagt tataaatatt tgttgcatga atgaaatgta taaacccatt  18000
tatgtatgta ttttttttaaa attagtatat tattaagtct atacaatatt agtatattgt  18060
tatgtatgta taagcttttt aacatgaagt ttgcagaata tagtacttct tccaaactct  18120
atgacatggg gggaactgaa gtatggggat atcttgtacc agtgtaagaa ttcaagaaga  18180
gaccgtgtgt ggtggctcat gcctataatc ccagcacttt gggatgccaa agcaggatga  18240
tctcttggag ctaggcgttc aagaccagcc tgggcaacat atcaagaccc catctctaaa  18300
aaaaaaaaaa aaaattaact gggtgtggta gtgcgggcct atagtcctag ctattccaga  18360
agctgaggtg ggaggattgc ttgagcccag gagtttgagg ctgtagtgac ctataccagt  18420
gattatacca gtgcactcta gcccaggcaa cagagtgaga cctggtctca aaaaaaaaaa  18480
aaaaaatcaa gaagagcaat ctggatatga gcatttggga tttttagcaa actgctgaga  18540
ttttgtctat agcttgaacc tttcttttag ctaacttgat gatactgatg ataagcaagg  18600
actgtctttt taaaaatgtt tacttcatta ttttcctgac agaaatgaca tcagatgtac  18660
catcactggg tccagccatt gcctctggaa actctggacc tggaattcaa ggtggaggag  18720
ccattgtcca gagggctatt aagcggcgac cagggtgagt ttgagtgtag tgtgttatga  18780
atatctctcc tataaaccaa ctttagttgc tgaatttatt tagttgctga actcacttcg  18840
ctattcctga ccatctcact tcaacttgat tacttactac actactgtca tataagtctc  18900
cttagtccct gtatttttgt ttatgaagaa tttgttttta tccaagtttc ccgtaagcag  18960
ttcttttttt aaaccaaaat ttccgtaaga taaaggactg tagctaagcc cagagatttt  19020
actatgcctg agaaaactgt ttgctgcttt cattaagctt tgtttctgtt ttcccaaaat  19080
cattttggta ggctgctttt ctgaatttag agaatgctga gctctagaat agctgtcttc  19140
taagttattg atatgttgct tggtttggaa tgcagagtcc attcagctcc aaaagtattt  19200
attaaattcc taattagtgt tatggcattg tgctgattcc aagtaggata caaagatgaa  19260
taagacacag tccttgtttc taagttggtt gtgttctgat agaaataatt attatacaca  19320
tgaatatatg atagaatatg cctagttttg ttaggaacaa atttgatact atgtttttct  19380
gtgtatggaa atatgcattt gttggtaaag actgagaaaa gcttcagaaa ggaggttgcc  19440
ttagaggggc ctggaagaat gggcactatt ttatttactt tttggtatta aattttcctt  19500
tttccttctt tttcttttta aaaattgtgc agctaattat aaccagtctt taagttttgt  19560
cccaccaata gtaatggaag agtgatgctt gggttcagtg gtaacatgag taacatatta  19620
agacttgtta tatgttcagt agctttacag attttaacca tttgctgaag cataagctga  19680
```

-continued

```
ataagtaact ttctaagatt gtaaagctag taagtgtcag atataggata tgaaccttag  19740
gggtttagct ttgtagctta ctctttaaac actgtgttat gtttatgtac agtaacaaac  19800
aaaagtatta taaatatcaa aattagggca tcacttgaga aagtcatagt atatttaaaa  19860
tggaatgcta tgtagttata agcgacaaat atgtttcagt gtagaaagat gttcacaatc  19920
tattaagaaa ggttacagta ttatagtatt tcactgtcaa aagatatgta taacatgtac  19980
ataggaaaaa actgaaagaa tatataccac atttctgggt aatagtatta tgggtgactt  20040
acggtttctt ttgtttttga tttttcagat ttttgaaatg aacatgtatg attggtaatc  20100
agaaaaatat attaaaggaa gtctttaaaa attttctttt tggttttttt agagacaggg  20160
tcttgtaccc tggctggagt gcagaggcac aatcatggcc cactgcagcc tcaaactcct  20220
gctcaagcag tcctcctgcc ttggcctccc aaagtactgg gattacaggc gtgagccact  20280
tcacctgtcc taaaagaagt cttttaatat ttcttttatt tttatttact tatttatttt  20340
cgaggcagag tcttgctctt ttgccaggct ggagtgcagt ggtgtgatct tggctcactg  20400
caatctccac ctctctggtt caagggattc tcctgcctca gcctcccaag cagctgggac  20460
tacaggcgtg cgccaccacg cccagctaat ttttgtattt ttagtagaga tgggatttca  20520
ccacgttggc caggctggtc tcgaactcct gacctcaggt gatatgccca ccttggcctc  20580
ccaaagtgct gggattacag gcatgagcca ccatgcccgg cctaatattt cttttattta  20640
tttattttat tttttatttt tttgagatgg agtctcgctc tgtcgcccag gctggagtgc  20700
agtagtgtga tctcagctca ctgtaacctc cacctcccag gttcacgcca ttctcctgtc  20760
tcagcctccc gagtagctgg gactacaggc gcccgccatg atgcccgact aatttttttg  20820
tattttcagt agagacgggg tttcaccgtg ttagccagga tggtctcgat ctcctgacct  20880
cgtgatccac ccgccttggc ctcccgaagt gcgggattac aggcacgagc cactgcaccc  20940
ggcccatatt tcttttaaag aaagattgga aaatacagaa agttagaaag aacaataaaa  21000
aggccaaaat ctactaccat gtttttagt gcatgtcctt cagtctttat atgtaaattg  21060
tttttaatag ttatgtaatt atatagtttt acatggccta gtcttttcac cttatataaa  21120
taataagcaa tacacacgca cacacacatt ttggcacctt atataaataa taagcaatac  21180
acacacacac acatttcgga gacagagtct tgctctgttg cccaggctgg agtgcagtgg  21240
catgatcatg gctcattgta gcctcaactt cttgggccca ggaagcaatc ctcctacttc  21300
agttctccga gtagctggga ccacaggcac atggcaccat acctggctat ttttttttt  21360
ttttttaaag acatggtctc actacgttga ccaggctggt ctaaaactcc taggctcaag  21420
cagccctccc atctcgacgt cctaaagtgt tgggattaca gacatgacct actgtacctg  21480
gccctttaaa aaaatattgt tacatattct atataaacat aatttttatt tattttttt  21540
tgagacggag tctcgctttg ttgtccaggc tggagtgcgg tgatgcgatc ttggctcact  21600
gcaagctccg cctcctgggt tcatgctatt ctcctgcctc agcctcccga gtagctggga  21660
ctacaggcgt ccaccaccac gtctggctaa ttttttttt ttttgtattt ttagtagaga  21720
cggggtttta ccatattagc caggatggtc tccatctcct gacttcgtga tccgcctgcc  21780
ttggcttctc aaagtgctgg gattacaggc atgagccact gcgcacagcc ataaacataa  21840
tttttaatgg ttgcgtgaaa ggatgtactt aacttcctat tttgggacat ctaaattgtt  21900
ttgaagattt tgctgttaca tatgatgcta aaaagaactt ctttgtacct aaacttttt  21960
ttcctatttc atattatttc tttagattct tagaaataga gttattgggc tgagcacgga  22020
ggctcatacc tgtagtgcca gcactttggg aggctgaggt aggaggatta cttgagccca  22080
```

-continued

```
ggaattcaag accagcctgg ggaaaatggc gagacttttt tttctttgac ttagcaatta  22140
tctttctttt ccttccttcc ttcatttttt tcctttgact tagcaattac ctttccctcc  22200
ctccttccct ctctttcccc ttccctttt ttttttttt tttttgagat gtagtttcgc  22260
tcttgttgcc taggctggag tgcagtggcg caattttggc tcactgcaac ctctgcctcc  22320
cgggttcagg caattctcat gcctcagcct cccgagtagc tgggattaca ggtgcccgcc  22380
accacaccca gctaattttt gtatttttag tagagacgag gtttcaccat gttgactggg  22440
ctggtcttga actcctgacc tcaagtgatc cgcctgcctc agcttcccaa agtgctggga  22500
ttgcagatgt gagccacagt ggctggcccc ttttcttttt tgagacaggg tcttgccatg  22560
tcactgaggt tggagtgcag tggcccaatc tcagctcact gcagccttga cctcccaggc  22620
tcaaggcctg cagcccctcc cgccccccca acccaagtag ctaggactac acatgcgcca  22680
ccatgcctgg ttagttttg tatgttttgt agagacggga tttcaccgtg ttgcccaggc  22740
tggtcttaaa ctcctgagtt caagtagtct gctcgccttg gcctcccaaa gtgcgtggac  22800
tacaggtgtg agcaaccatg cctggctgag atttttaaa ataaaaaaat ttagttgagt  22860
gcagtggtgg gctcctatag ttccagctaa ttgggaggcc aagatgggag gatcccttga  22920
gcccaggagc tcaaggtggc agtgagctat gatcatgcca ctgtactcca gcctgagtaa  22980
cagagtgaga gcttgtctct taaaaagaaa gaaaggaaga gatagagaga aagaaagaat  23040
ttgagttact gggtagatag ataggatttt acaggtgacc agattagggg attcaggaag  23100
gaggaagagg agcaaacact ttcaggattg atgctgtatg tgtacttcaa atgcgaccca  23160
tctagaggcc cataatatca aggtatccca atagtagaag taaaaagagt gatcactagg  23220
ttaaggtggt aacatgagca atattttagt tcaatagtgt acagagatta taaggggatt  23280
ggtctatttt attgtttata atctttccta atctccttta aagaaattca cttcttcttt  23340
ccctgaatgt ctgtagcatg ttgattgtac cccttatgtg acactttcct attctcactt  23400
gttttatatt tgtatttctc taggtgaaga gccccttgag ggcaaggttc ttgtttttac  23460
ctcacctagc acagtgtctt gaatgaagta tatattacat gtttattaga tcaatgaagg  23520
aaagaaacat tatctaacaa tcttcgtagg tattaagtca ctcctttatg taagatcact  23580
gctttgaaag atgtttcaga aatttggtaa cacggcttag agcagactct agaaatgaaa  23640
catggacctg aattatttac gttaattttt tcttattttt tctgagtgga ttcctgctcc  23700
ctttacagag gttgtagtct gattgaaaac tctggcaaag attgactgct actctaggaa  23760
agtgttaagg tagcagaagg tacttttgtt tctattgccc agttttgtac tttttttttt  23820
tgagatggag tcttgcagtt gtcgcccagg cttgagtgca atggtgcgat cttggctcac  23880
tgaaacctcc acctcccggg ttccagcaat tctcctgcct cagcctcctg agtagctgag  23940
attacaggca cccgccacca tgcccagcta atttttgtat ttttagtaga gatggggttt  24000
cagcatgttg gccaggctga tctcgaactc ctgacctcag gtgatccacc cacctcagcc  24060
ttccaaagtg ctgggattac aggcgtgagc caccactcct ggccccagtt ttgtacttct  24120
ttgcctagtt tgggactatg aacaagagga aatgtagctt tgtttgactt ctgccacttc  24180
ctctttccat tcttccattt gggtgggtgt tccggtagct tgtgttgaga aattttaact  24240
tcttaatgtt ttgtattatc agcaggctta aagtatttat tgttggcttt cctcaggctg  24300
gattttgatg atgatggaga agggaacagt aaatttttga ggtaagagac tgaaaaactt  24360
tccttagatg tctgatatta aaaattagtt tatgatcttt atacttctga cttgtaaatt  24420
```

-continued

```
tttgtcctta ggtctaagga gagtacttca tcctaaaact ataaatattc atatatctca  24480
gaaaattttt aagcattccg ttaatatctc tagagaaagg acctcagtga ggagaggacg  24540
gcatttacaa accctctgta tcagttctct gctacttcat agcctaaaaa gaacaacagt  24600
tcgttatttc tcaattctgt ggattgactg catgtttatt ctgcttatct cacctagact  24660
cactcataag actgcattct cagctggtca gctgagaact ggactcagct gggatggctg  24720
ggtatttctg tctatgtgtt tttttatcct caaggaggcc agactgaatt ttttcatgtg  24780
gtgatggcta caatctacag cacaaatccc agtgtgcaag tgcttatcaa gcctctgctt  24840
atatgacatt tgcttatgtc ccattggcca aagcaagtca tatgttccag gtgtgagtgt  24900
gtgagggggt tacacaagga agtacatact gagaggtgta attcattggt tgaggtgtca  24960
ttaatctgtg actctgtcat accctctgac acctgttgac acctcttata ggtagcagga  25020
attggaattt gtattttttg tttttgtttt tttttttttt gagacggagt cttgctctgt  25080
cgccaggagt gcagtggtgc aatctcggct cactgcaacc tccgcctcct gggttctagc  25140
gattctcctg cctcagcctc ccaagtagcc gggactacag gtgcgtgcca ccatgcccag  25200
ctaatttttg tatttttatt tttttatttt ttattaattt tctttttttat tgatcattct  25260
tgggtgtttc tcgcagaggg ggatttggca gggtcatagg acaatagtgg agggaaggtc  25320
agcagataaa caagtgaaca aaggtctctg gttttcctag gcagaggacc ctgcggcctt  25380
ccacagtgtt tgtgtccctg ggtacttgag attagggagt ggtgatgact cttaatgcgc  25440
atgctgcctt caagcatctg tttaacaaag cacatcttgc accgccctta atccatttaa  25500
ccctgagtgg acacagcaca tgtttcagag agcactgggt tgggggtaag gtcatagatc  25560
aacagcatcc caaggcagaa gaatttttct tagtacagaa caaaatagag tctcctatgt  25620
ctacttcttt ctacacagac acagcaacaa tctgatttct ctatcttttc cccacatttc  25680
cccctttctt attcgacaaa accgccatcg tcatcatggc ccgttctcaa tgagctgttg  25740
ggtacacctc ccagacgggg tggcggccgg gcagaggggc tcctcacttc ccagaagggg  25800
tggccgggca gaggcgcccc ccacctcccg gacggggcgg cggctgggcg gaggcgcccc  25860
caccaccctc ccggatgggg cggctggccg ggcgggggct ggccccccgcc tctctcctgg  25920
acggggtggc tggccaggcg ggggctgccc cccacctccc ggacggggcg gctgccgggc  25980
ggagatgctc ctcacttccc ggacggggcg gctgcggggc ggaggggctc ctcacttctc  26040
agacggggcg gctgccgggc ggaggggctc ctcacttctc agacggggtg gctgccgggc  26100
agaggggctc ctcaattctc agacggggcg gctgccgggc ggaggggctc ctcacctccc  26160
agacggggtc gtggccgggc agaggcgctc ctcacctccc agacggggtg gcggggcaga  26220
ggcgctcccc acatctcaga ggatgggctg cggggcagag accctcctca cttcctagac  26280
gggatggcgg ccgggaagag gcgctcctca gttcccagac tgggcagccg ggcagagggg  26340
ctcctcacat cccagacgat gggcggccag gcagagatgc tcctcacttc ccagacgggg  26400
tggcggccag gcagaggctg caatcctggc actttgggaa gccaaggcag gcggctggga  26460
ggtggaggtt gtagcgagcc gagatcacgc cactgcactc cagcctgggc aacattgagc  26520
actgagtgaa cgagactcag tctgcaatcc cggcacctcg ggaggccgag gctggcggat  26580
cactcacggt taggagctgg agaccagccc ggccaaccca gcgaaacccc gtctccacca  26640
aaaaaatacg aaaaccagtc aggcgtggcg gcgcgcgact gcaatcgcag gcactcggca  26700
ggctgaggca ggagaatcag gcagggaggt tgcagtgagc ggagatggca gcagtacagt  26760
ccagcttcgg ctcggcatca gagggagacc gtggaaagag agggagaggg agaccgtggg  26820
```

-continued

```
gagagggaga ccgtggggag agggagatgg agagggagag ggctaatttt tgtattttta  26880
gtagaaacag ggtttcacca tgttgggcag gatggtctcg atctcttgac ctcgtgatcc  26940
gccctcctcg gcctcccaaa gtgctgggat tacaggtgtg aggaatttgt atttttgagt  27000
tgttaatatt ctggagcttt taaaatggac tatttatttg tttgtttttt tgagacagag  27060
tcttcctctg ttgcccaggc tggagtgcag tgctgcagtc ttggctcact acaacttctg  27120
ccttccaggt tcaagcgatt ctagtgcctc agcctcctga gtagctggga ctaccacacc  27180
tggctaattt ttgtattttt agtagagacg gggtttcacc atgttagcca gactggtctt  27240
gaactcttgg ccttaagtgg tccacctgcc tcagcttccc aaagggctgg ggttataggc  27300
ataagccacc atgtccagcc tattttcttc ttattttttt gagacagggt cttactctgt  27360
cacccagact ggagtgcagt ggcacagtct cggctcacta cagcctcgaa ctccagggct  27420
caagcgatcc tcccacctca gtctcccaag tagctgggtc tacaggtgtg agccataata  27480
cctggctaat tttaaaatga tgttgcccag gctggtctta aactcctgtg ctcaagcaat  27540
cctcccacct tggccttcca aagtgttggg attacaggca tgagccactg tacccggcct  27600
gaaaatggac cttttaatat attgatgaag gagttctttc agaaaagggg gatattcttg  27660
ctgaagacca attgcttgtc ttcttttcaa gtaagaaaaa cagtaagact caaaaggaag  27720
agaactttga ccgcaatctg cttttttttct ttccagagtt gaaaatatta cccaggtagt  27780
ctgtacgttg ctgagtaaca gacaatttga taaaggagcc caatgaaaaa aaaatgattt  27840
gattgtgtgg gtgcccagat ttaatatcat ttatttattt tctttctttc tttttttttg  27900
agactgattt tcactcttgt tgcccaggct ggagtgcaat ggtatgatct cggctcaccg  27960
caacctctgc ctcccaggtt caagcgattc tcctgcctca gcctcccgag tagctgggat  28020
tacaggcatg cactaccatg cccggctaat tttgtatttt tagtagagat ggggtttctc  28080
catgttggtc aggctggtct tgaactgccg acctcaggtg atccgcccac ctcggcctcc  28140
caaagtgctg ggattatagg catgagccac cacacccggc ccatttcttt ttcttatttg  28200
tttgttttgt taactaagtt ttttctttaa ttgggaaagt aatataagtg tattttatta  28260
cagaaatttc aggctgggcc tggtggctta cacctgtaat cccagcactt taggaggctg  28320
aggtgggtgg atcgcttaag ctctggaatt caggaccagt ctgggcaaca tggcaaaact  28380
ccatctgtac aaaaaatgtt acaaaaatta gctggaagtg ctggtgtgtg cctgtagtct  28440
cagctactcg ggaagctgag gtgggagggt ggtttgagtc ctggaagcag agattgcagt  28500
gagccgaggt tgcgccactg ctctccaacc tgggcgacct tgcctcaaaa aagaaaaaca  28560
acaaaatttc aaacagtgca gagttatata tagtgaaagc acatcttcgt tttactttgg  28620
accttcagaa ctcctttttt tttttttgag aggagtctcg ctcttgttgc ccacgttgga  28680
gtgcagtggt tcgatctctg ctcattgcgt cctccgcctc ctgagttcaa gctattctcc  28740
tgcctcagcc tcctgagtag ctgggattac aggcgcctgc caccatgccc ggctaatttt  28800
tgtactttta gtagcgacaa ggtttcgcca tgttggccag gctggtctca aactcctgat  28860
ccactcggct cggcctccca aagtgctggg attacaagtg tgggccactg cccccagcct  28920
ggaccttcaa aactctttag acaactacag tttccagttt gttgagtatc cttccaaaaa  28980
tagtatatat agaattgtat ataaatgtgt atgtgtgagc atacacacac ttatctcctc  29040
agtttttttt acacaaagga tgtccatatt gtaaattgct tgccattttt tagttttata  29100
ttgcttcata cagttaatag catctatctt cttttttttat agtaacattt aaagttaagg  29160
```

-continued

```
ctcatatttc tggctactca ctagatgaac tttgccaaat actcttgaaa acaacaaccg  29220
tgacttggcc atcataaaga aatagttgca agtggaagta taattctcta agaggtctct  29280
tgagacttaa tgagtctcag taaatgtgaa gaagggaaga gatttcaatt tctggagaag  29340
atagactttt tcaaacagct ttattgagaa ttcctcctat tgagaatcct gaattataat  29400
gatacatgct attagtggaa cttcactgtg tgtatgaaag atatgagggt aaccactagt  29460
ctttttttat acccgtgaat tagctctaac cctgagtcat tgcttccata aaatccagta  29520
gtcacaacta catgcagatc caaagagagg ttcgtttgtc cttttcctaa ccataaaaaa  29580
agactatcgt agtttatctt accaagtcgg gttgttgtgc ctgagaaaag cactgccgaa  29640
ttccctttcc cccttctttt tttttttttt tttttttgag acggagtctc gctctgttgc  29700
cacaaatgca gtggtgtgat ctcagctcac tgcaacctcc gcctcccagg ttcaagtggt  29760
tctgctgcct cagcctccga agtagctggg actataagca cgtgccacca cacccagcta  29820
atttttgtat ttttagtaga gacggggttt caccatgttg gccagagtgg tctggatctc  29880
ttgacttcgt gatccgccca gtgttggcct cccaaagtgc tgggattaca ggcgtgagcc  29940
actgcgccca gcctccccct tctttttctg ggtatatata tacaaaataa tcgaaggcag  30000
aatcttgaag agatatttgc acactcatgt ttattggccc attttgcgca atagataaga  30060
ggtcgaagta accgaaatgt ccactgacag atgaatggtt acagaaaatg tagtatgtac  30120
atacaaggga atattattca gccttaaaaa gaaagaacct gtcatatgct gcaagatgga  30180
tgaatcttaa ggacattata ctgaaagaat aagccaataa caaaaagaca attactgtat  30240
gattccactt acatgaggta tctacaagta gtcaaattca tagacacaga aagtaaaatg  30300
gtggttgcta ggggttgggg tgaaggagaa atgagaaaat ggtgtttgat gagtatagag  30360
tttcagtttt gcaagatgaa aaagttctag atatctgttg cacaacaatg tgaatatggt  30420
tagcactact caactgtaca cttaaaaatg gtatacagta aattttatgt gtttttttacc  30480
agaattaaaa aaaaacccaa aactaacccc ttactttaga attgtgctga caggccagtc  30540
agctgtgttg tcattagatc atcatctttt tttggtgtgt ctggtaaggg taatggaaat  30600
accagaaacc tgacaaataa tagttgtggg tcttttaagt tctatggggt gctgctgtta  30660
tttctatcac tttgtgatgc ttttccattg gcttttttttc tattgaatat tttcacccct  30720
ttctagttta cttttcagag tgaaatagat ataacaagtg taatgctttg aaacaatcct  30780
ttttctctcc ttcaggtgtg atgatgatca gatgtctaac gataaggagc ggtttgccag  30840
gtaatattgt agtaggtaat atattgtaat atataatatg atccatgttg tagaaccaga  30900
cagtcctagc atattgactt aatttttttct ggatgagacg gaatttctct gtttaatatc  30960
tttcctattt ggaagtatgt gaaacttagt attataacta tcatttatgt tcaggtgaca  31020
tggcttcaaa ctggcggtat attttataca gtgtttttct gtgtatgtga taactaaagc  31080
aatgtgcttg caaggtttcc ataggagcac aaattatgga ttttgtgctt gcatttatta  31140
ttaaatggat ctacaaaaat aggaatacag ataatggttc tgtaattaat ttatttattt  31200
tgagacagag tcttgctctg ttgcccaggc tggagtgcaa tggcgccatc tcggctcact  31260
gcaaccttca cctcctgggt tcaagcgatt ctcctgcctc agcctcctga gtagctggga  31320
ttataggccc ctgccaccac gcccagctaa tttttgtatt tttagtagag atggggtttc  31380
accatgttgg tcagggtgat cttgaactcc tgaccttgtg atccgcccgc ctcggcctcc  31440
caaagtgctg ggattatagg tgtgagccac cgcacccggc ctattttatt tttttgagac  31500
agagtctcac tccatcaccc atgctgtagt acagtggtgt aatctcggct cactgtaacc  31560
```

-continued

```
tctgcctcct gggttcaagc tgttcttcca cctcagcctc cctagtagct gggaatatgg  31620
gcatttgcca ccatgcctag ctaatttttg taataatttt ttttagcaga gatggggttt  31680
caccatgttg gccaggcttg tctcgaactc ctcacctcaa gcgattcacc cacctcagcc  31740
tcccaaagtg ctgggattac aggtgtgagc cattgtgcct ggcctattat tttattttaa  31800
gatatgtata ttttttagag acattgtttt cattgtgttt cccaggctgg agtacagtgg  31860
catgatcata gctcactgca gcctcaaact ctggggtttc agtgatcctc ctacctcagc  31920
ttcccaaata ttgggattat atgcatagcc accatgcctg gttggtcctg tttttttaaa  31980
aatgacagta agaggcgggg agtggtggca tatgcctgta attccagcac tttgggaggc  32040
agatgcaggt ggatcacttg aggtcaggag ttcaaaacca gcctggccaa catggtgaaa  32100
ccccatctct actaaaaata taaaaattag ccgggcatca tggtgggcac tcataatccc  32160
agctactcta gaggctgagg catgagaatt gcatgagccc gggaggtgga ggttgcagtg  32220
agcagagatg gcaccattgc actccagcct gggtgacagc aagattttgt gtcagaaaaa  32280
aaaaaaaaag acagtaagga aacagttttt gtgacaagta gagttttgat tgaaaaaaac  32340
ttaaatttgt ttaaattacc tatcaagatg atgaaatata cttttttttta ttaaattctt  32400
aaatgtcagt tttcttttta gaaagttttt attaaatatt aggcaataaa ttatttcttt  32460
tttgaaaatt aagtttgtag ctacctcaga aagatgaata attcgttatt tcaaaatcca  32520
gtgattaact gagcacttag cacttagtat ttgttcgttg ctgatgctcc tggtctcggg  32580
aacatacttt aagaaccgtt gatgtagaga gattagaaat atcaggggaa gtagttaaaa  32640
actattctgg agtggtgaga tgcaatctca ggctttgaat tagagggtat tacataaaat  32700
gcattgtagg gatatttctc tggtagcagt tatagaattg attaaaggga tggactgtta  32760
gactgtaggg aggtagatag gaagctgttg aaataataag acagctataa aatcatgagg  32820
gcctgggtta cagtggcagt ggtaacagga aaggagtgaa gttaagaggt ttttgaagaa  32880
taatttgttt atcgaaacta attgaaataa atatttgtaa agtctttagg atgtgaacca  32940
tctctaaaat gagaagttaa tcatagatat ttggaggata gtttttcaag cttcattgaa  33000
aagtcaggcc atcagttatt attggcagta tcttgatgaa atttcaaaaa gccatgaaaa  33060
catcgcatga atgattttgg ttttcatttg tcctgcttaa tgtgcatata tttcattcag  33120
aaatactgag gtggattagg gattgtggat ctgtagtagt agtagtagta gaaataggaa  33180
ttttagatgc ttaacttttt tttaaataac agaattcatt catatgatgt gttaaggtag  33240
tgcccctcac atatcctcct tgggatatag agggtcttaa aagctgaaaa cttcttgaaa  33300
aacttttggg attatatgca tagccaccat gcctggttag tcctgttctt ttaaaaatga  33360
cagtaagagg ccgggagtgg tggcttatgc ctgtaattcc agcactttgg gaggcagagg  33420
caaaagttgc tcaacttttt gaaaaaaaag aagtttgtag tttgttaagg aactatctag  33480
aagaaataac ccaaggaatg taaaactcta aactgctgaa tatcactcag ttctccttct  33540
cttgtcatca gaatatatgc gtaaattttt acattcttct tcattgttac tgtgttattt  33600
tctgcctatt gaccatttta taaaaacatt cccatatatt gataaggtta ttgtatttgt  33660
catttttaat agctaaataa tcttttagct tgttaacctg tcatacttag acattttatt  33720
cagggcctct ttatctatat aaatatattt aaaatggaat tgacacattc ctgacacaat  33780
ggcctgccaa caccttgcta tttcctcagt tgccacccat cattacagta tctcagtttt  33840
ctagaaaaat ttagtgatgg ttctttgtat ccttctccag tggagaggga attgttactt  33900
```

-continued

```
ttgatccatt cctgtgtggc tatactgcag agaaatggca aaaggaccga atcaaagtta  33960
ataattattt taggaacaaa tcaataatag aagatatgcc agaaacctac ctcttagagt  34020
tatttatata atttctccag tgaaatctgg ttggttattt tgtcattgtg tggcacgtgc  34080
atgtgttgtt tgtgtgagag ggagagagat tatatttgtc atcacttgtt tgatagtatc  34140
atctttaatg tactctgtct ttaatttctt cattatagaa tagcacatgt ggatatcatt  34200
ttctttccag attgggagca gtgcatgaaa atggtattcc tgaattccct tggttggttc  34260
ttgttcagac tctgtatatc tttggtccct acagagatcg attggcaaaa tgctttctgt  34320
gtttagatca tgttaattta ctatatattg gctttgcttt tatgttgacc tttatcttgt  34380
aagttacttt ttctttatcc taacagatgg ctttgtagag ttacaggcaa ggttcctgcc  34440
tataattcca tttccctcct ctcttctctg catctgttta gttctatatc cttttctctc  34500
ttctttctcc ttttcttttt ttttctccct ccatttcctc tccctccctc cttccttttt  34560
tcccttcctc cctcccccct tccttccttc tttttattt taattttagc ttagttcatt  34620
aattctattt ttaggtcgga tgatgagcag agctctgcgg ataaagagag acttgccagg  34680
taggagaaca gtgtctttta gcatgatgaa gcagatgatg ctgcttttc tatccttttt  34740
cttactcttt cttttcttcc cctttctctt tgtattttc cttatctgtg gcaagagagg  34800
acaagatttt ttagaagttt gagtgtaaca ggaactttgg cttcccccat cagaaagtgg  34860
gtgagttgag ggaactttgc ttagggattt aagaaattgc tattagtttt aagtttttt  34920
ttctttttct ctttatgtca gtactaagtt tcacagaaca aaaagctctt agaaggaatg  34980
caaccgtgcc agttggtgct ttaacaggga aatactcttt ttatcagaaa accaataaat  35040
atatctgtat ttgtgattag ttcccagtat ttaggcctca gcatttactc cacacctcta  35100
ggaaactcac acctattttc ctatgaagac tcacagccta gattattctc acaacagaac  35160
tagtgttgct ttggtgaccg aatcctttct tgcggtagtt ttctagaaaa gttttagttt  35220
ccttgatgtg gctatttaaa agaccaggtt tctgtactta cgtgtcagaa atctgtcaga  35280
tactaggaag atgagtgctt tatgtttgag aatagaattt tatgtcttag gcaaagtgta  35340
actaaatatg ggcctatgtg gtgagaccct ttttgccatt tagaaaggag actctagaat  35400
tctcttggga gactgttgtt tgtaatgtag aaatgctgca gaagaaatat gcatagactt  35460
ttctgttttc tagtatctgt gatttggggg tgacttagga aatagatcat tgatgccaat  35520
acccattttt actatattcc cccttttttc tactatttcc tctttaatct gggtcacaaa  35580
ctcattttgc tgccagttta actcgagctt cttactaacc ctttcactgt tcagaaaatg  35640
gatttggcat gatgtggtgg agaaaacatt gtattgggaa gagagcagcc tggggaaagt  35700
cacttaccta cttgacctcc ctttgctctt ctcagaaaaa agagatttat gttagatttt  35760
taattttctt actttctttt ttttttggac aaagaacttt tgttcaagta gaattcttaa  35820
gtggtaacag aaataaataa aagagataaa gcaggccggg cgcagtggct catgcttgta  35880
accctagcac tttgggaggc cgaggcaggc agatcacgag gtcaagagat ggagaatatc  35940
ctggccaact tggtgaaacc gcgtctctac taaaaataaa aaaaaaaaaa actgggcgtg  36000
gtggtgtgcg cctgtagtcc cagctacctg ggaggctgag atagcagaat tgcttgaacc  36060
cagaaggcgg aggttgcagt gagccgagat cccgccactg tactccagcc tgggtgacag  36120
agcaagactc catctcaaaa aaaaaaaaaa aaaaaaagaa gaagagagat aaggcaaata  36180
tttgagtaga agcagaaatg cagcatgttg catgattatc tccttgaggc atccccatgg  36240
aggacactga gaaacttaat gggcttttaa aaattcctgt tggaaaactg ctggattatt  36300
```

-continued

```
cctgttaaca gtgatatctt tctgtcttaa ttttgaggaa gtcagtgttg gagctgtggt  36360
ctatttacct gggtgagatt caaattgtct tgtcagacct ttaatcatcc tcctctccat  36420
tccactcctc cagttaactt cgtcccagac tggggaccca tatgggactt ttagtagatg  36480
gtgtatctta agtcttgtaa gaagtttagt gcactggcag cacacccaga taaagaaggt  36540
aggactttgt gcattaatgg gccaaataaa acttcaaaat cttcaaattc tgccttttaa  36600
tgttgcaaat aagagagagg cttaccatat tttatagacc aaggaaatct gtactatcaa  36660
ttcttgtatc agctatggag ccacatactt gagttggcaa aaattggtcc ttttattttc  36720
tggcctttaa atagttgaat tagtaagcat gggagttaac caagctgagg ttatatgttc  36780
cataggaact taagtgagta aaatcagcat ttaaaaatac tatctttttt tttctcttgt  36840
tttttgtttt ttgttttttt ttgaaatgga gtcttgctct gccacccagg ctgaagtgca  36900
gtggtgtgat ctcagctcac tgcaacctcc acctcccaga ttcaagtgat tctcctgtct  36960
cagcctccca agtagctggg attacagatg catgccactg tgccctgcta atttttgtat  37020
ttttagtaga gacaggattt caccatgttg gccaggccgg tctcaaactc ctggcctcaa  37080
gtaatccacc tgcctccatc tcccaaagtg ctgggattac aggcatgagc caccatgcct  37140
gacctgtcgt ttcttaaaac agcttttgtt ctgagggagt ggtaatttac aaaggatgtg  37200
aagtttccag gaaatagggg gaagggaatt acattatctt cttgttctct gtctgcctta  37260
ttagttctgt ttcatgcttg ctttgcatga gaaggttggc aaaccttatt ttaactgctg  37320
agacttaagc atcactaaat ctgaatacca cattcttcag cagcacactt ggtatccata  37380
tcactctccc tgctaccaaa tgaccagatg tgaccacctg gatggggctt ctctttcttt  37440
ccatgcaggg aaaatcacag tgaaattgaa cggcggcgac ggaacaagat gacagcctac  37500
atcacagaac tgtcagatat ggtacccacc tgtagtgccc tggctcgaaa accagacaag  37560
ctaaccatct tacgcatggc agtttctcac atgaagtcct tgcggggaac tggcaacaca  37620
tccactgatg gctcctataa gccgtctttc ctcactgatc aggtctctgg gacttatagt  37680
tctgagagag tctggaatct gggtgaatct cttgaaagtt ttcgtttttt ggacaagaat  37740
tcagcttttc aggaagaagt cagacaatgg gaaaacgaat ttcaatcctt ggctataaca  37800
ttaattagca ttgggacaat gagaagtaga gaagagttgt gaaaactatt taataagcta  37860
ataagtatta atatttgaga acttgactca tgaatatagc atataggatg gaagaagaac  37920
agtggaatca cagaggaaat gactatgtcc atggaaccaa ttttctttct tgcctttagg  37980
gttatagaag atggaagaaa tctatttctt atccctgaag cagcttctag ttttagtaat  38040
agaatgaatc tgtcccacct ttggtgatag aagaactgag agtctaattg ttgcttaggg  38100
atgtgctctg ttacatgtga tcactatgaa aaaaagaagg cgtaaacatt ttctgccttt  38160
caggaacttc atctgaatat aagtatgtga gtggcaggat atcacagaaa ataacaggaa  38220
aatgcataaa gagaggaatt gtattttttta attagtaatt ttatgtggga ctagatagac  38280
atactgaagg gatggctaaa gtgaatagaa tggctagact tgagtgagga tggttaggga  38340
agacttctga gggtaaggaa gccatgttct gttttggtta ttaaaataac atgatcattg  38400
cagaaaaatt tggaaaatgt aggaggtata aggaagaaaa aaatttactt cagtatcaat  38460
caagtattcc cttaatgcca ccaatttaat caaatgatta gaaagaagga gagaatatag  38520
tttgagaaaa tggaataaga attttccaaa taggatggtc tacttaaaac tacatacttt  38580
gtagctatat acattgaaat agttaatatg ttctaacagt acatgtgcaa gtattcaaca  38640
```

-continued

```
gactccagtt atgcaccttt tgtgggcaaa ccaggtgtgt tgtgctgtga gaaatagaaa  38700
gaatggtgag acaaatggtt ttctggtgga aacagacatg taaataaata aattaaacat  38760
agaactagtt ctataataga agtgctgtaa tgaatcctgt aaaatgcaga tatggaaaat  38820
gagttgggga gtagtgttgt ggattttggg aagcacttga gcaaaaacct agaagtgtgg  38880
aataattggg ttatgcaaag aaagtcaagt ggtttagcat gtttttggta gataatagga  38940
aggtaggctg ggatctaatg atggaatgtt taggtgttaa agaatttaga ttttaatttt  39000
tatgcagtgg ggagacataa aaaatgtatt agatctggta gcattttaag gattgattga  39060
aagcagggcg actacttaat tagttttggt aaaagatgac taggacagtg acaaagcatt  39120
ggaaagtaga atcgataaaa ctgaattatc actggaatgt gagagaatag ttagattttg  39180
aggcttctag cttaggagga tgctgttaag aatattggaa gagcacggca ggtttttttt  39240
tttaagaggg aaataatgat tcaggttttg ggatgttgat gttgagttgc tggtagaata  39300
tttataaata ttttacagat acttgaaatt caagtctgct gaaagctcag gaaaaaacgt  39360
tagtcatgtc tagggctata gacttggtta ttatttcgta gtggggaaga gtgaatatgg  39420
tttcccagga agaaagtatg gtattaataa agagggctta agatgaactt tggaaatgtc  39480
tacatttaag acttgaacaa aggaaaggaa gtctgaaaca gaagaggaag caaaaattgg  39540
agtacagtct catagaagaa ggtagggaaa aataaaattt aaaggataag atggacgaca  39600
ttgtcacatt ctgcagagag gttgaataaa gtgatgaaga cccaggaaaa gggacttgaa  39660
ttggtaatta ggaggacatt agtaacctca ttaaaaatat atgtatgctg ttcctggcag  39720
aacaaaaacc aaaccaaaca ggaaaacagt agtttagagt gagagtgaag tgggattgag  39780
aaataattga aaggtaagag gataaagcca gtgaatataa cattattctt agtataagct  39840
tgctgctgaa aaagagagat gaggtgggtc aaactgaggg aagatttatc tagaattgag  39900
aaaacttgat catttttata ggcctgaagg gaaagagaga aagtgggaat atttgtcaag  39960
caagatccta aaaagagacc agagaggatg gaattaagaa gtcaattatt gttcatggta  40020
agcctttttt tttttgagac agggtctctt gctctgtcgc tcaggctgga gtgtggtggt  40080
atgatctcgg ctcactgcaa cctctgcttc ccaggctcag gtgatcctcc cacctcagcc  40140
tccggagtag ctgggactac aggcgtgtgc caccacacct ggctagtttt gtttttgttt  40200
ttgttttgtt ttgttttgtt tgtttgtaaa gatggagttt cgccccattg cctaggctgg  40260
tcttgaactc ctggactcag tgaccctccc actttgacct cccaaagtgc tgggattacc  40320
ggcgggagcc gctgtgccta gcccaagcct ttttattctt cttgaatcct gagatagaga  40380
ggaagaggtg gatagtgaca tagagaaagt gaggaaacat gtattagaaa aaactttctt  40440
atcgatgaac tacatttagg gtggaaacct gtggctgtgg atcaggtgtg aaccagcagt  40500
tgcttacgga gagatgcatg tggcctgaag tgtcttactt cttcctgtga atagaaatac  40560
ttgtttttc agagtaaaat attaacttct atttcttttt cttgcgcagg aactgaaaca  40620
tttgatcttg gaggcagcag atggctttct gtttattgtc tcatgtgaga caggcagggt  40680
ggtgtatgtg tctgactccg tgactcctgt tttgaaccag ccacagtctg aatggtttgg  40740
cagcacactc tatgatcagg tgcacccaga tgatgtggat aaacttcgtg agcagctttc  40800
cacttcagaa aatgccctga caggtgagag ttatgtgtat gggaaatgaa tgagaagtcc  40860
tttcttgttt ttttcctgag acttaagaga tgttttagct gttaaattgg tttgttgact  40920
ctggcaaggc ttcaagaatt ttctacttta atgaatatag tcagttcttt ttatccatat  40980
gagattatct actttgtggc tcagccttag aaaatatttc attggtgata atattttaca  41040
```

-continued

```
tttatcttaa tattggtata aatagaacag taaaagccaa acctacaata cttttttttt  41100
tccgttctaa aagaattatc catgttttta tctcatttgt atggataatt atctggtatt  41160
ttttctacct cctggtgctt ggctttgtgc taggttcaat gataacagct ttttattcta  41220
tagatatggt tattggtcaa tgtataaggt gttttctgtt gttgttgttg ttgttgtttg  41280
tatctgtact gttgttcttt ttttctcccc tattttatta tgttcagtct tttggccaga  41340
gtttggctag aggaaacaag tcatatctat tcttgagcaa ctctagaaaa aaatttaaag  41400
tggaagcaga taaaaaaact ggtagttaaa atgcaagaaa tttcaatata ctcatattag  41460
tgttgttgat ctttagtttt cctccttttt tcccacccaa aaaagagaca gggtctctct  41520
cttgcctagg ctggagtacg gtggcacatc atagcttact gtaatcttga actcttctgg  41580
gctcagtaat ctgcctgctt acagcttctt gagtagctag gagtagttca tgtcaccaca  41640
cttgaccaat ttttaaattt tttgtagaga caggttctgt ctgttgccca gactggtctc  41700
aaactcctgg ccttcagcat tcctcctccc atcttggctt ctcaaagggc tgggattatc  41760
ggcatgagcc accacacttg accagttttc ccctccttta tgtttttatg atttcatttt  41820
tctagttctt ccttttcccc aaaagttgtt cttcgtttct gtataataaa gaagacaaac  41880
agatctatat gtttctataa catataaaat tacttggttt ttttcttttt aaaatttttt  41940
ctttttattc tttttttttt ttttgagaca aggtcttgct ttattgctga ggctagagta  42000
cagtgactct tcacaggcac agtcatagca cactacagcc tcaaactcct gccctcaagc  42060
agtcctcctg cctcagcctc ctgattagct gggactacag aaaagtactt gtttttcaac  42120
caatgacatt tactctgtat gtatgtctgt atgtgtatac agataatcag ctatgagaat  42180
atagccttgc ctcttgtttt ctactactac tttccactcc tacttttcct tgcacaatgt  42240
tattttcaat gctgcctttg aacttaagag tgagattcat tgatgataat tgaagtattt  42300
taggcttgaa aaaaaattca tctcctgctt ggtcagttct gttataagca aggagattaa  42360
gggcatgaat aggatgctta cttatctttg ccttcagtat ctctcccccct cttccccaca  42420
cacaaaaatg cactccagac tgctcttcac atcttccttc agggcgtatc ctggatctaa  42480
agactggaac agtgaaaaag gaaggtcagc agtcttccat gagaatgtgt atgggctcaa  42540
ggagatcgtt tatttgccga atgaggtgag tgtcaagctg aggattgtga tttggtatag  42600
gaaggatcaa gagctgagag ttttatttct gtcagagtta agttggatta gctccagtgg  42660
attaaattta actctccata cccagatgga ttgtaacaca gaataaagta tttggaaagg  42720
gaactaacgt ttctgaactt gccagacact atgataggtg ctttatatct gtcatcttat  42780
tttatcctca caattgcctt gtagtgtaag attgatggtt accattttgc agatggaaaa  42840
acagatataa agaaatgaac ttggccaggt gcagtggctc aaggctgtaa tcccagcact  42900
ttaggaggct gaggcgagtg gatcacctga ggtcaggagt ttgagaccag cctggccaac  42960
atggtgaaac cccatctcta ctaaaaaaaa acaacaacaa aattagacgg gcgtggtggc  43020
gtgcgcccat aatcccagcc acttggaggc tgaggcagga caattgcttg aacccaggag  43080
gtggaggttg cagtgagccg agattgtgcc attacactcc agcctaggca aaaagagtga  43140
aactctgtct caaaaaaaaa aaaaagaaaa agaaaaagaa atgaatttcc cactgttaca  43200
tactgtttga tacaggattt tgttttaatt catagtagtc tgactacaaa acctctactt  43260
tttccctgtt acaacacaag gcaatatcca tttactcaga ccatttcttc tttttttttt  43320
tggttagaaa tttgagactt cctatgtctt tcagtaggtg tttagtgttt ataaattata  43380
```

-continued

```
tactgtacgt tttaggattc tgtagaaaat atggtggtcc tttctataca ggtacaaaag  43440
gcatctcagg gtcacaaagt tcaggctata taatggaaat tgactacatt gtactgagag  43500
gatagttgct agaaattatg ggtaggatat taaaggtttg cttggagagg cacaaaattg  43560
aacattatgt ggtttagtga tttattttta tttttattta tttatttttt tgagacagag  43620
tcttgctctg ttgcccaggc tggagtgcag tggcatgatc ttgggtcatt acaacctcta  43680
cctcctgggt tcaagcgatt ctcatgcctc agtttcctga gtagctggat tgccaccaca  43740
gctggctaat tttgtatttt ttagtaaaac agtgtttcac catgttggcc aggctggcct  43800
caaactcttg acctcaagtg attcgcctgc gtcagcctcc caaagtgctg agattacagg  43860
cctgaaccac tgcacccagc gtgtaattta gagtagcttc tagacccaga ctgctggatt  43920
ttgttttaat ccatattcta tggatttgaa ttctagcttt gatgctatct tctgaaacct  43980
tggatgatta catgactaca ttgtgctttg atttcatcat ctcacattgg cgataatgtt  44040
aatactgact ttataaagtt gttatgaaga ttagatgaat taatatatgt aaagatattt  44100
agaacagagc atgacacata ttaaccctat gtaagtttta tttttgtttt aaaggatagg  44160
gagagggaaa gtagcattgg caggagtatc ccaatatgtg gacatggcta atgcaaagac  44220
ataggcaaga gcaagataat aatgaactgt agcaattaca ttaagttgtg gttaatgtag  44280
agcaggagta agcaaaccac agccctttat ttgtaaataa agttttattg gaacatagcc  44340
atgcccatat ttttacatat tatctatggc tattttcatg ctataatgct agagttgact  44400
agttgcaaca gactttctgg cccgcaaagc tgaaaatatg tactatctgg tcctttacag  44460
aaaaagcttg ccaactcttg atgttgagaa tgtttgcata tgaagaacat atggaacatt  44520
ttgacttcaa attctaaaag ttttagaaat actaaacttg acctatcttt atccttcatt  44580
attagtagca ttaccaattt tctatgtctg gttgtatcca gagcatgtta ttctgctatt  44640
actgtggaaa gttctttgat agggcagtct gattgctttt aatctcttta ttccttgaaa  44700
caggtgtggc agtagctctg tggacccagt ttctgtgaat aggctgagct ttgtgaggaa  44760
cagatgcagg tgagatccta agtggtgaaa accaaaggga tggccaaata cctgcagaga  44820
tcatcacatt tttacctgtc ttactgtagt cgttccttca gcagctctca cttgcatccc  44880
ttacctccca cttaacatcc cttacctccc acttactttt tttctggcaa tattttccta  44940
aacttctaaa acttctcttg aaaatcctgt ttaaggaagt cgctatgcta ttttacctac  45000
tttcctccta ctgcatacct tttggttact ttactttggc aagggtaaaa atgtggcggt  45060
catttttggg tgggaaagat gattatcctg ttttctaaac tcctaagagc ataaacttaa  45120
aagtactaag gcagcattgc cctttgagtt ttacgggtag attttttttt tttttttcaa  45180
actcctgtaa ctcttctagg aatggacttg gctctgtaaa ggatggggaa cctcacttcg  45240
tggtggtcca ctgcacaggc tacatcaagg cctggccccc agcaggtaag aaagtgaaat  45300
agtaaatatt tccccttggt acagttggtt cctcacagag tccatgaaag ctaatattta  45360
ttatatacct ggtatatgaa atgtactttt gtgtaagatg aaagaaaata ggaaaagaaa  45420
atgtacaatc cttcccttcc attattgagc ttttattcca gttgaggaga tagataactc  45480
aggctggaaa atgattcagt attggctgtg tcacagaatg tggtttttat gtgaacaaat  45540
ttatactgaa catatgtatt ctaagcattt gttgcaaaga aacttagaca ttgaatgcag  45600
ttaatttgag aaagatttct aaagtaggaa caagactttg agagaaaagg ggaaaatgcc  45660
tttattgtaa taacttatca agaggatatt ctctgcaaag actttaaatc aagctttgag  45720
cagattagct ttaccagaac ttgaggtcaa acaaggaatg tgagaaaggt gattgggttg  45780
```

-continued

```
caggatcaaa gttttaagtt ggcttgtcag agtttccaaa tcttagcaac tttattactt  45840
ccctgctgcc tgggtattat tggaaagtag gggttttggg gagacagaaa ctaagagaaa  45900
agagaagcaa ggtgatgtgt tttggaaaaa ggttaaactt tggatgtgga gaaacctgga  45960
tgtgattcct gtcattgtta cttattagtg gcatcaccta gggtaagttg cttgaccttt  46020
ataaagctca gttttctcat ctgtaattca gagttagtac atcctgtata gggtttttgt  46080
gaggattaga tttaatgtaa ggaaagcatc cagcccagtg cctggcatat ggcaggtaac  46140
ccaataaaag taattaatgt aatttaaaaa aatttaactg aagtagtaat gacatttgaa  46200
ctacttagtc tatatactat ataagccaca cagttaaagt atgtgatctt tcatacctct  46260
atgtagcatc aaggaatact atttttctgg ataaaaagag tataactatg caaaaaacag  46320
gggagaaatg cagtcttctt ccctttctgt gtaaaacatt ggtttttctc ttttccaagg  46380
gacatgaata actattgatg gttggtataa cttcattttg ggttgcttgc taactttaaa  46440
agttacagat taggcaaagc ataaattttc tgcctataac atggtcatag aatggatgtc  46500
ttcatatgtg ccatatttgg ccagcatagt tttttagagt actctgggta ggacttgtat  46560
tttccagttt actataatta acatgggtaa aatgtaggaa ttaatatata tgtaaatact  46620
taaaacaatg actggcatat atggtaagtt ttatatactt gtttattctt atttatcatt  46680
ctctattgct ttatgcttag cctcttcata actagatgta ttttgttttg ttttgctttt  46740
tggttttttt tttgagaggg agtctcactc tgtctgtcgc ccaggctgga gtgcagtagt  46800
gcgatctcgg ctcactgcat cctccgcctc ctgggttcaa gtgattctct cacctcagcc  46860
tcccaagtag ctgggattac aggtgcatgc caccatgcct ggctaatttt tgtattttta  46920
gtagagatgg ggtttcactg tgtcggccag gctggtcctc aagtgatccg cccaccttgg  46980
cttcccaaag tgttgggatt acaggcgtca gccacggtgc ctggcccata aataggtcta  47040
ttttgaatct ttacttgtct gagttttgaa ggcatttgag ttggaggtcc ccgttaaacc  47100
ttttaacgtc acgtttctga aggtgtttcc ctcccagatg atgacccaga ggctggccag  47160
ggaagcaagt tttgcctagt ggccattggc agattgcagg caagtatgaa ttttccacat  47220
ctatattccc gttcaattag agcagatctt caggactcat tcctgttaat tttcttttac  47280
tttctgaata caaatgaaga attccataaa actctcaaaa tttgaaggaa tatggcattt  47340
atagtgacca ttgctattct tggatttaag taaagttgaa aagtatgaga ggagggagat  47400
ctttttcccc ttgtcttaat tttagcttta ctatgcttaa ttttctattt ccagttaatt  47460
tcctttgccc ctatacaaaa gaagaaagat ccttttcatt gtatcattac ctgactaaca  47520
atagaaaagt ggaattattt tgattttttc ataagtatag ataagtttct tggttacttg  47580
taccatatca acctgagtaa tgagttcagc atagccagta tgtggatttt agattgaata  47640
aactttattc ttactttact aacttggtaa agtgtaaatg tatgggagca gagctagacc  47700
ttatgccttg tctgattgtg attgtcattt ttttttcctt tttggataaa atgtgaaagt  47760
ttagaaagtc ctaaaactgg gaatcttatg tctatgcaaa agaccatgag gagataggaa  47820
atacatctgt aaataatggt atcattttac ctcattttta tctcttcact ctcaggtaac  47880
tagttctccc aactgtacag acatgagtaa tgtttgtcaa ccaacagagt tcatctcccg  47940
acacaacatt gagggtatct tcacttttgt ggatcaccgc tgtgtggcta ctgttggcta  48000
ccagccacag gtgaggagct ggagctccat taggcctcca ttttcctttg gctatgttga  48060
cattatgtaa tcatgtagtt cctaagacag ccaaaacata tcaacctcag ttaagaaaaa  48120
```

-continued

```
gagatcatca tattctgtta gtacctaaca ttattttcag cttcctatta ggactgtcat  48180
ctcatgtaga gaaatatggc ttgtcaaacc aggtgggagc agcaggtaca aatatgtatt  48240
tattttttgt tgttgatatt aatacagatg attcaaaggt actcatatta attagttata  48300
ccagtatagc tacatttaga taattcatgt aattacctaa atgaataatg gcccataaaa  48360
catgcagatt tagcaccagt tattataatt tactcatgca acagaccagt tagccatctc  48420
tgaattgacg catcatataa acttttaaaa ctgttgtggg tcggaaggac ttctggctgt  48480
ggctatgtga aagaggttgg tgaaaaagag gtcttgaaaa caaagaacaa agagaattta  48540
cactacctga ttcaacacta actataaagc tattaccaag acactgtggt gttggtgtaa  48600
ggatagatat atagatcaat agaccagaat aaggtctatt cttatacttg tcaactaatt  48660
ttcagcaaag gtgacaagac aattcaatgg ataaaataaa tatttctaac aaatggaaca  48720
attggatatc tgtatgcaaa aaaaaaaaaa aacaaaaaaa aaaccacacc caaaaatgaa  48780
aacacataga tcttacctca tacaatttac aaaaatcagc ttagaggcct aaatgtgtaa  48840
gagctaaagt tacaaataaa ctcctaggag aaaatctttg tgattttgag ttaggcaaaa  48900
gatttcttac actaaaagca tgattcacag aagaaaaaaa attataaatt ggatttaatt  48960
gtaattaaaa tttgccctct ttaaaggata ttattaagaa aatgaaaaga ccagacataa  49020
atggagagaa aatagttaca agtcatatac ctgaaagagg atttgtacca ggaatatata  49080
aacaactcat taagacaaac agctggtaaa aaagagcata agacttgaca tttgactgaa  49140
gaataaatat gcatttatgc acatgaaaag atgctcaaca tctttttacc attaggaaag  49200
tgcaaattaa aatcacaatg agataccact atatacccac tagaatggct gtaatcaaaa  49260
agtattggtg aaaatgtgta gaagctggaa ggaaccctca tacattgctg atagacatgt  49320
aaaatggtat agctactagc tttgcaaaag cattttggca gtttcctaca aagttaaaca  49380
tactcttagc ctataaccta gcaattttat tcctgagtat ctacctaaga gaaatgaaaa  49440
catgttcacc catagatttg tacacagttc atatctgtat tattcataat agccaaaaaa  49500
atgaaaacta tttaaacgtc cattaacatt ttgtaaatga atacacaact gtgttgtatc  49560
catgtgagaa tactactgag cataaaaagg aataaactac tgataatgca gccatgtaga  49620
tgaacttcaa aaataccatg ctcaatgaaa gaagccagac ccaaaagacc acatattatg  49680
ttgttttatt tatatgaaat ttgtagaaat agcagaacta gagaggcaga aagcagattt  49740
gtggttggct ggggagttgg agtgggagca gagattgact gcagatggca caagggaaca  49800
tcttggggca gtgaatgtgt tctgaaactg gattgtggta atcattgcac aactataaat  49860
ttagtagaca tcatcaaatc atacacttag aatggctgaa ttatgaatgt aaattttatc  49920
taaaatttat aatctcatta aaataaatgt ataatattct gagaaagaaa aatgttttag  49980
aagccagctc cttaacagat tctgcctttt tttagtagat ttcatctttt gtttattgtc  50040
tttttttttt ctcctcctca cttaactata atcttaggat taaaacagaa gaaataaaat  50100
ccaggtcccc agctgatgga ccaggccagt tagatgacca taaaattata tatgttggct  50160
gggcacggtg gctcacacct gtaatcccag cgctttggga ggccgaggcg ggtggatcac  50220
ttgaggtcag gagttcgaga ccagcctgac caacatggtg aaaccctgtc tctatttaaa  50280
aaaatacaaa attagccagg tgtggtagca cacccctgta atcccagcta cttgggaggt  50340
tgagacagga aaattgcttg aactcaggag gtggaggttg cagtgagcca agatcgcgcc  50400
atcgtactcc agcctgggca acaagagcga aactccatct taaaaaaaaa aaagtatata  50460
tcttactctt ctttctgtat tctaggaact cttaggaaag aatattgtag aattctgtca  50520
```

-continued

```
tcctgaagac cagcagcttc taagagacag cttccaacag gtaacttttt tcctggtttg  50580
gttctgaata aatatttgtc atattcactc cataaatatt gactactgat taactgaaca  50640
ctgtggcagg cactacagtt ttatgttctt tagtagttaa tctgcatttt taaggaatag  50700
aaaaggacta atactttgaa attatggata atgcccaagg tatttctgtt tggctttggc  50760
tatttactgt cttgtattca attaactgta tccaaggagc tgtctttaag gtatttaaac  50820
tattgcgcca ggcatggtgg ctcatgcgcc caacctctgt agatgctgtg aaaatagatg  50880
ttttcctcgt ctgggcatgg tggctcacgc ctataatccc agcactctgg gaggctgagg  50940
caggtggatc acttgaggcc aggagttcaa gcccagcctg gccaacacag tgaaacccca  51000
tgtctactaa aaatacaaaa aattagcctg gtatggtggt gcatgcctgt aatcccaggt  51060
actcgggagg ctgaggcacg agaatcactt gaacctggga ggcagaggtt gctgtgaact  51120
gagatcatgc cactgtactc tagcctggat gacagagcta gactctgtct caaaaaaaaa  51180
aagataaaaa agaaaattgt atacttcact aagcttgtag tagaaaaatt catttttatat  51240
agtttttttt ttttttaga aggagtctag ctctgtcgcc agggtggagt gtagtgtgca  51300
atctcagctc attgtaacct ctgcctctta ggttcaagcg attctcctgt ttcagccccc  51360
cgagtagctg ggattatagg cacatgctgc cacgcccagc taatttttgt atttttagta  51420
gaggcggggt ttcaccacgt tggccaggat ggtctcgatc tcctgacctc gtgatccacc  51480
cacctcagcc tcccaaggtg ctaggattac aggcatgagc cattgcgccc agcctagact  51540
gttcttttat ggatgagtga gagtcgtaat gaattatata agctgactgt taattgtcat  51600
tctcaggctc cagctcctga aaatatctgg tgaattttat agacatggct tttgataacg  51660
gtttttactt tgtattagac aagttaatta acctctttaa gtctcagtag tgtcgttatt  51720
gatacaatga atatattaat agtacctaaa ttcagacggt tgttgggaag attaaataag  51780
gtaatgaata taaaacacat cacccagtat ttgatacgta gtattacaaa ataagtggtt  51840
agcttctaat actgtttatt tttatttttt taatttttag gaatatagag ttaaaagatt  51900
attttctatt ccatgagact agtatctaaa ataacctaaa attggctggg catggtcgct  51960
catgcctgta atcccagcac tttgggaggc tgaggcaggt gatcacttga agccaggagt  52020
ttgaaccagc ctggccaaca tcttgaaacc ctgtctctac taaaaataca aaaattagcc  52080
gggtatggtg gctcatgcct gtagtcccag ctacttggga ggctgaggca tgagaattgc  52140
ttgaacccag gaggcagagg ttgcagtgac ccaagattgc cccactgcac tccagcctgg  52200
gcgatagagc aagactgtct aaaaataaaa taaaataaaa aataaaataa ctaaaattac  52260
ttttaaaaaa taaaagcaaa acaagactaa agccaactta attttattta tggaaacctc  52320
tgtagatgct gtgaaaacag atgctctcat ctgggtgcag tggctcacac ctataatccc  52380
agcactttgg gaggccaagg caggcggatc atttgaggtc aggagtttga gaccagccta  52440
gccaacatgg tgaaaacccg tctctactaa aaatacaaaa attagctggg cgtgatggtg  52500
cacgcctcta gtccccagct actcaggagg ctgaggcagg agaatcactt gaaccctgga  52560
ggcgaggttg cagtgagcca agattgcacc actgcactcc agcctggcga cagagcgaga  52620
ctccatctca aaaaaaaaaa aaaagaaaaa gaaaagaaaa cagatgttct caggtttcgg  52680
ggaaaaaata ggattgaaga gcaatatata agctatattc tgtgtcctta aacttaccaa  52740
atttctggta tagacttgta aagctaggtc agagtatctt taatggattt cccaagggaa  52800
gtagggaaac agtcttttcc ttcctggaaa taagttatta ttcctatttg actagaatag  52860
```

-continued

```
tattaggttg gtgcaaaaga aattgtgatt ttttgccatt tttttaaatg gcaaaaaaatg  52920
caattacttt tgcaccaacc taataagaaa gcttgagtct ctggccgggc tcagtggctc  52980
acgcctgtaa tcctagcact ttgggaggcc gaggcaggcg gatcccgagg tcgggaaatc  53040
gagaccatcc tggccaacat ggtgaaaccc cgtctatact aaaaatacaa aaattagctg  53100
ggcgtggtgg cacgtgccta taatctcagc tacttgggag gctgaggcag gagaatcgct  53160
tgaaccaggg agtcggaggt tgtagtgagc cgagattgcg ccactgcact ctagcctggt  53220
gacagagcga gactccgtct caaaaaaaaa aaagtctggg cacggtggct cacacttgta  53280
atcccagcac tttgggaggc cgaggcgggc ggatcacaag gtcaggagat caagaccatc  53340
ctggctaaca tggtgaaacc ccgtctctac taaaaataca aaaaattagc tgggcgtggt  53400
ggcacgcgcc tgtagtccca gccactcggg aggctgaggc aagaaaatcg cttgaacccg  53460
aggggtggtg gttgcagtga gcagagatcg tgccactgca ctccagcctg ggcgacagag  53520
ggagactccg tctcaaaaaa aaaaaaaaaa gcttaagtct ctgaaaggaa gcatgagaaa  53580
tatgcttcca tgtttaatca cttagttttt actctcattt tgttttaata ttgaaaaata  53640
ttggtgcctc aaggacaatg acaagagttt tagggttata gaaattggaa aatttttatt  53700
tatttttgta atgaaaattt tctatgagtt ccactgatgg catgaaaact ttttcaggta  53760
gtgaaattaa aaggccaagt gctgtctgtc atgttccggt tccggtctaa gaaccaagaa  53820
tggctctgga tgagaaccag ctcctttact ttccagaacc cttactcaga tgaaattgag  53880
tacatcatct gtaccaacac caatgtgaag tatgtattat acaggagtgt gaaaaaactg  53940
tttttcctct gttctcacaa cagaaaacac ttctgatgcc ctatgtgggg ggtaaacaat  54000
caagcaacaa cacaaaaatt tagccgggcg tggtggcatg tgcctgtagt cccagctact  54060
ctggaggctg agacaggaga atcacttgaa cctgagaggt ggaggttgca gtgagctggg  54120
atcatgccac tgcactccag cctgggctac agagcgagac tccatttcaa aaaaagaaaa  54180
agaaaaaaga aatcaagcaa tcagtagtgg acaccagctg ggtgtccttc cattcaattc  54240
agttcactat ctacttggag atagcatcag atccccccaat ttgtgtatgc agtaccacaa  54300
gactgctccc acttctgatg ccagttgcaa gccccaggtt gttttacctg tgcatctgac  54360
tgaccagctg tctcccatga ccccctactt gggttcagtc aatttgcttg aatggctcag  54420
ggaacattta cctatgttta ccagtttatt ataaaggata ttacaaagga tactttgtac  54480
atcagatgaa gagatagata gggcaaggta aggaggaagg agtgcagagc tttcagaccc  54540
tttctgggtg ggctaccctc cggggatctc catgtgttta cctatcaaga agctcctcaa  54600
acccagtcct tttgggtttt aatggaaatt tcattatgta gccatgagtg attaaatcat  54660
tggccattgg taatcaactt aaccttaggt accggctccc ctccatgagg ttgagggtta  54720
gggctaaaag tcccagccct ctaattttac cttgatcttt ccagagatga gcccccatct  54780
tgaagctacc taggggttgc cagccctcag tcaactcatt agcagacaaa aagacactta  54840
tcacactgaa gattccaaag attttaattg gtaaaaatcc aggtccactt atacatggat  54900
ttttttcagt aaatatatta gaaaattctt ttgatatttg tgacaatttg aaaaacccaa  54960
aaataagcta catagcctgg atatattgaa aaaattagaa aaagttagcc atgtcataca  55020
tgaatgtatt aaatatatat aaattctagt ctattttatc atttactacc atacaacata  55080
tacaaatcta ttataaaaag taaaaatgct ggacaggtgc agtggctcac acctgtaatc  55140
ccatcacttt atcactttgg gataccaagt tgggatacca agttgagcag atcacttgag  55200
gtcaggagtt cgagaccagc ctggccaaca tggtgaaacc ctgtctctac tgaaaaaaaa  55260
```

-continued

```
aaaaaaaaaa aaaagaaaat acaaaaatta gctgggcatg gtggcacacg cctatagtcc  55320
cagctacttg ggaggttaag gtatgagaat cacttgaacc tgggaggtgg aggttgcagt  55380
gagctgagat cgcaccactg cactccagcc tgggtgacag agggagactc catctcaaaa  55440
aaaataaaaa taaaaatgta tcacaacgta tacatacaca ccgtttgtac aatggcacca  55500
tttgtagttg agagaaatgt aaacaaatgt aaagatgcag ttttaaatca taaccgcgta  55560
aagttaacta tagtatatac tgtactgttg taataatttg gtagccacct attgctcaat  55620
tgttgccagt ttgcttaaaa tgctgtgtga tgctaatcat ctcttcatga gcaattcact  55680
ccagtaaatt gcatattgca gtaaacagtg aaatctcatg gttcttgcat atttttcatc  55740
gtgttgagtg caatactgaa accttgaata acatttggga acagtatgaa gtgccactag  55800
tgatgctgga agtcttccca agaagcaggg aaaagtcatg acattataag aaaaaggtga  55860
attgcttgat atgtactata gaatgaagtc tgcagctgtg gttgcttgcc acttcatata  55920
gatgactcat cttgtaagtc atcttgtaag atgatataag cttatgataa cgataaatac  55980
agtacagtgc tgtaaatgca ttttctcttc cttatgattt tcttaataac attttctctt  56040
tagctttatt gtaagaatac agtacataat acgtacaaca tacaaaacgt gttcaactgc  56100
ttatgttatt ggtaaggctt ctggccaaca gtaggctatt agtagtaacg ttttgggaga  56160
gtcagaagtt tacagtcgaa ttttcgatgg cacaggggtc agtgccccta gcctccatgt  56220
tgagcaatca gttgtatttc ataatatcac ataggcattt tccaatgttg ggatttctaa  56280
tgtaccaact cttcttagtc ttatcaagct atccctttct cctctacttt tctagtatta  56340
aacaccatta gtttgaagtt cttcattttc cagcttatag gatttgggat agttgatcag  56400
agtagagtaa ggtttttttg ttttgttttg ttttgttttg ttttttcaga cagggtctcg  56460
ctctggcacc caggctggaa tgcagtggtg tgatcatggc tcactgcagc ttgaacctcc  56520
caggctcaag tgatcctccc acctcagtcc cctgagtagc tgggactaca gacatctacc  56580
aagacgcctg gctaattttt gtattttttg tagagatggg atttttccat gttgcagagt  56640
ctggtcttaa actcctgggc acaagcagtc catcgtcctc ccaaagtgct aggatcacag  56700
gcgtaagcca ctgcacctgg ccagagtaag attttacaaa caataattca gagactaggt  56760
cctgagatgg aagggtttag tttcaattct atgtatcaac tctttctgga aaggactatg  56820
ttttgtacac cagtttattg ctctagtctg gcaggatttt cctctggagc aggggtaggc  56880
aagctctttc tataagtggg gctagatagt aaatatttta ggctttgtgg gccatgtggt  56940
ctttattcca cctactcaac tctgctgtag catgaaaaca gtcatagaca aatgaaagaa  57000
tggggctgtg ttccagtaaa tctttattta gaaaaacagg cagtgggcct gatttggtca  57060
gttttcttta gagcatagct acatcctcct ctttcattag ttactgttcc tctcttttgc  57120
acttttctat ttgagtttc tttctcagtt tcttttttaa aaagttttat gagatatatt  57180
tcacatacca tatacctcac tcatttaaag tatacagtgt tttttagtat atcacatagt  57240
tatgtaactc ttactgcagt ctaatttcag aatattttca ttccccccaaa agaaattcta  57300
gatcagttaa cagtcattcc ctgttctttc ccccggctct gaaattctgt ataactatga  57360
atctgttgtc tttataaatt tgtctattct agacttttcg tataaatgga atcatagact  57420
ttgtaattcc tttgtaactg gcctatttta cttagtataa tgtttacaga ggttatctgt  57480
actgatacat gttgtagcat gtatcagtac ttcatttctt tttattgcca aataagattt  57540
cattgtatgg atataccaca tactgtctgt atgttcgtta atggacattt ggttgtttct  57600
```

-continued

```
acttcttggt tatcaaaaat gcttccatat gtaaaatagg gataaggaac tgaaaaaatg  57660
ctttcatgaa tatttgttta ctagttttta tgtggatata tgtttttatt ctcttgaatt  57720
ccacccagga gtggaattgc tggccacata gtaactctgt tttacctttt gaggaactgc  57780
caaactgttt tccaaagctg ccccatcatt ttgcattccc aggagctctg attcctccac  57840
atccttgtta acacttgtta ttgccttttt ttttttattg tagccatcta gtaggtatca  57900
attgtcaggt taccaccttg ccatttaatc ttttctttct gtagaattgg ccttgaatcc  57960
acctcttgaa gatcagatta tgactactta gcaaatatga ataataccta gtgacaagtt  58020
ttgtccaatt cagtctttag aacttgtaaa gtttaattct ttgctaacta acttagtata  58080
acagagtgga ttgagttaga aatttttatt aacttaggac tcaagtggat ggtcatggtc  58140
attgtagttc tttattttg tctctttgca tctttatatt acacaacagc cttcattttt  58200
gtgtttccat tttgtttaaa tttttaaaaa tttaagttgt ttgaaggact cgagtttctg  58260
gaaataattg ctttctccat gtttatgtat catttccct accatgatta attttaatta  58320
gcttttaggg atttgtttgt ttgtttgttt cattgagaca gtgtctcact ctgtcaccca  58380
ggctggagtg cggtggcgct atctcagctc actgcaacct ccgcctccca ggctcaagca  58440
atcctcccat ctgtctcctg agtatctggg actacaggag cccgccacca cgcctgctaa  58500
tttttgtatt ttttgtagag acggagcttc accatgttgc ccaggctggt ctcaaactcc  58560
tgagctcaag caatccaccc tgcctcagcc tcccaaagtg ccaggattac aggtgtaagc  58620
caccgtgcct ggccagtatt ttatttttaa ataaatattc tttatagaaa atgtggaaag  58680
tattgaaaaa tacaaagaga aggaataaaa ttctcacact ccagatagtc tttgttgatg  58740
tacagtgtat gtactttcat ttttttacct atgcttttaa aaaatacctt atatgaatat  58800
atacacacat tcacaataac caggttttga atacctagaa ggagttagaa cccaacaaga  58860
tgacccctgt gtcatagaac atggtttctg tttgctgaaa ctgacaccct agattaacta  58920
taggatagga ctttaatgaa ggatttattg attgttccac ctacagatga atctatagag  58980
ctttacatac agaatcttat tcttctcttt ctctctctct ccccccttcc tccctctcca  59040
ccccctcttt actgtctact ctggtttcct aggaactcta gccaagaacc acggcctaca  59100
ctctccaaca caatccagag gccacaacta ggtcccacag ctaatttacc cctggagatg  59160
ggctcaggac agctggcacc caggtaaaaa agggtgaaat aatcatctgt tgagcagtca  59220
cccagggggt ggtcatttgc aatcccatat attttttgtt cggttggtta attttttttt  59280
ttttttttg agaaggagtt ttgctctcat tgctcaggct ggatggaata caatggcacg  59340
atctaggctc actgtgacct ctgtctcctg ggttcaagtg attcacctgc ctcagcctcc  59400
caaatagctg ggattacagg tgcctgccac cacccccggc taattttttg tatttttagt  59460
agagacgggg ttttgccatg ttggccaggc tggtgtcgaa ctcctgacct caggtgatcc  59520
acctgcttcg gcctcccaaa gtgttgggat tacaggcatg agccaccatg cccggcctgt  59580
ttaatttgtt ttaaggttct ttctccagat tcttttttaa aaaaaatttt tttttctatt  59640
tgtcttgtca actggccttt gacatatagg cagcagcaac agcaaacaga attggacatg  59700
gtaccaggaa gagatggact ggccagctac aatcattccc aggtgagttg tgtcctcttc  59760
gttgaagagg gtagggagta tttacttagg aagtgttctc cggtactagt tagaatgtac  59820
atatgttgta tatgaatttt agggttattg aattgtcatg ttaaatcttt aatggttatt  59880
tttatcattg tattccacag gtggttcagc ctgtgacaac cacaggacca gaacacagca  59940
agccccttga gaagtcagat ggtttatttg cccaggatag agatccaaga ttttcagaaa  60000
```

-continued

```
tctatcacaa catcaatgcg ggtatgtttc tttctcatta tccttttaaa ttctcattta  60060
gatcacttac tgatgggcat gccactgccc agtcagtaat cttccagtgt ttttccactt  60120
aatcataata ccacctgagt aaataggaac ttgctgaact aatatactac agccccttga  60180
ctggcccttc cccaactcct tttggtccac agatcagagt aaaggcatct cctccagcac  60240
tgtccctgcc acccaacagc tattctccca gggcaacaca ttccctccta ccccccggcc  60300
ggcagagaat ttcaggtgag ccccgtatat atgtgctgct ttacagggcc ctgagggatt  60360
cagctgctga atccaaattt tattcttccc ttgctttctc tggttacttc agaaaaagca  60420
gtgaagcttg tagggcctag cgtgaggcaa acaagctgct tttcttcctc ctatttcttt  60480
gcacctgtcc tattgccatg ttctaggctc catctctgtg tgtcctggtc agtgtgtgac  60540
tgtcagtctt tcttgtcttt tccaaattgt tatcaaattt tccttaacct gcaggaagtc  60600
aaggggatct agggatagca ctagattgtc ctttgattcc tagcttctgt gataaatcta  60660
tccttttaat cttttacctc atttattcac tcctaggaat agtggcctag cccctcctgt  60720
aaccattgtc cagccatcag cttctgcagg acagatgttg gcccagattt cccgccactc  60780
caaccccacc caaggagcaa ccccaacttg gacccctact acccgctcag gcttttctgc  60840
ccaggtaaaa cttatcatct gtgtgttccc tgtgtattat tttttgtttg tttgggcttt  60900
tttccgtatg taaaatcagt gttttctatt ttaaatacct tctccccaac ccctgttctc  60960
cggtttccaa tttccatctt tgttgagagt agctaattaa aaatcacaga taataaaaaa  61020
aaatctcagt agagtctgtg gttttcacct taaatcagaa ttgctcactt ggaacgtttt  61080
gagcacgtct gattttcaga tttgttttgg agtaaattct aagatgtttc ctctttgttt  61140
aggactccat aaggcaggag caaaggagaa aattaatgac taacttacag tgatgtctgt  61200
ttacaaaaaa gttgaaaaat tctttttttt tttttttttg agacagagtc ttgctctgtc  61260
gcccaggcta gagtgcagtg gtgcgatctt ggctcactgc aagctctgcc tcccgggttc  61320
acgccattct cctgcctcag ccttccaagt agctgggact tgtacaggcg cccgccactg  61380
cgcctaattt tttttttttg tatttttagt agagatgggg tttcaccatg ttagccagga  61440
tggtctcaac ctcctgacct tgtgatccgc ccacctcagc ctcccaaagt gctgggatta  61500
caggcgtgag ccaccgcgcc tggctgaaaa attctttttt tttttttttc ttgagacaga  61560
ctgtcacttt gttgcccagg ctctggagtg cagtggcgcg atctcggctc actgcaagct  61620
ccgcttcctg ggttcatgcc attctcctgc ctcagcctcc cgagtagctg ggactacagg  61680
gtgctcgcca ccacgcctgg ctaatttttt gtatttttag tagagacggc atttcaccgt  61740
gttagccaag atggtcttga tctcttgacc tcgtgatccg ccctcctcgg cctcccaaag  61800
tgctgggatt acaggcatga gccaccgcat ccagccgaaa aattctttta taatattcat  61860
atatataata taacgcacaa taaatacact gtctaaagaa agattcttta atattactat  61920
atatttatgt tatacaagta atagttttaa aaagtcaaaa ccaaaagcag gttccagaat  61980
gttatatgca atacgatctc aattgtgtac aaaatgcatg agaaaataga aactggaaga  62040
aattatccaa acatgttaac catggaatta tgaatgattc ttattttctt tatattttcc  62100
ttcactttct gaatattcta taatgcatat acagaactct catgagaaaa tagtttttat  62160
aaaaaataca tcattaggaa caaatgaatg cagaacagac agaataatgg tgcagagtag  62220
tttttctctg catatggtac ttttttttgtt gtttgttttt ttgagacaga gtctcgctgt  62280
tgcccaggct agagtgcagt ggcgcgatct tggctcactg caacctctgt ctcccgggtt  62340
```

-continued

```
caagtgattc tcctgcctca gcctcctggg ttgctgggat tacaggcacg tgccaccatg  62400
cccagctaat ttttgtattt ttagtagaga cggggatttc accatgttgg cccggctggt  62460
ctggaactcc tcacctcagg tggtctgcct gccttggcct cccaaagtgc tgggattata  62520
ggcatgagcc atgagccacc ccgcctggcc tgcatataat actttactgt tatgaatgcc  62580
tctagtttta tataacttca cagtttataa gatgctttca tttaattctt acaattttta  62640
ttaatcccat agttcattgc ttttttgtaa ttttatctca gctgcctaaa aaatagtgtc  62700
aagagagatt gagagttaat tggaagaaat atacaatagg aaataagtga tgagcttggt  62760
tcagaaggat gcagtgattg acagtgttga ctctcatagg catggtatgt gcaatgatgt  62820
taatgctgta tttgttctat atcccctctc catctctctt tagcaggtgg ctacccaggc  62880
tactgctaag actcgtactt cccagtttgg tgtgggcagc tttcagactc catcctcctt  62940
cagctccatg tccctccctg gtgccccaac tgcatcgcct ggtgctgctg cctaccctag  63000
tctcaccaat cgtggatcta actttggtga gtccagacca taaggagagt aacaggaaaa  63060
tcgcaccact aaagagaaag gatttggtag ttaaagttgt ttgcctgtgt tgtgggtaca  63120
ctgacctgat tgtagggaaa tgcaaggtga caatctattt agaatttaaa acctaccagc  63180
tgggtgcggt ggctcacgcc tgtaatacca gcactttggg aggctgaggc aggcggatca  63240
cttgaggttg ggagttcaac cccagcctga ccaacatgga gaaaccctgt ctctaccggg  63300
tgtggtaccg catgcctgta attccagcta ctcgggcggc tgaggcagga gaatcgcttg  63360
aacccaggag gcagaggttg cggtgagctg agatcgcgcc tttgcactcc agcctgggca  63420
acaagagtga aactccgtct caaaaaaata aaaaataaaa aaaaaaaact acccacatga  63480
aaaatacttt agcacatata acaaaaatca tgtgaatttt tatacattta atagtatgca  63540
catttaacct aaatgagtaa agaactctat ggaaaggctg cctggagaag aagaattaat  63600
ttagggctga gttttgagat agaaaaggca ttgattggca gagagaagga cagagttatc  63660
ctaggtaaaa ttaatggctt acctatagtt gtttacttgt ggcattagta cacaatggaa  63720
ttgtgtagat tggagttgtt tattcttcct tgctgtattt ctagctcctg agactggaca  63780
gactgcagga caattccaga cacggacagc agagggtgtg ggtgtctggc cacagtggca  63840
gggccagcag cctcatcatc gttcaagttc tagtgagcaa catgttcaac aaccgccagc  63900
acagcaacct ggccagcctg aggtcttcca ggtaagagag tgaaaagact ttcaaaaatt  63960
agaagctggg agagaaaggg tccaggagga ggagagacag tgaaggaagc atgcctggat  64020
tgaggtgttt ggttgggggt atatgtgaga agacagagag ggataaatgt agggatcact  64080
gtcagttatt gaaaagattg cagaagctag atgcagtggt gcttgtgtat atgatgtcag  64140
ccccttagaa ggctgaagca ggggatcact tgaggccatg agttcaaagc caggctgagc  64200
aactagcctg atcctgtccc tgtcaaacaa acaaaaaagg agtatgaatt gagtgtgata  64260
cataccattt aaccagaaca gacaaattta gcaccatagg aagatgccaa agaaagttac  64320
tttagctcat tcaaatagct ccatataccc aagtcacagt agctttgggt ttaaaagaga  64380
cagaatgatt aaaaataaaa agtagtgctc gcttcagcag catatatact aaaattggaa  64440
tgaatataga gaagattagc atggcccctg cgtaaggatg acacacaaat tcatgaagtg  64500
ttccatttaa aaaattataa aaagtaaatg aaatagaaca taatgattat agccataatg  64560
gtctatttac acaagtcctg agggactgca agagtgaatg gagtaatctt aggcaggaca  64620
aaggaagagc tggtttaaag caaagattga aagaaagcaa aacaggtctt ggtggaaaac  64680
aaataggata agagactcca tatatgtcta tagggggtta tatgaaatac agcaagcaga  64740
```

-continued

```
tttttctccc tttgaaaata ttgagaacta ggaaaaggaa aaaggtggaa ctgtaggagg  64800
aagacagaag ggattaggaa aaaaggctgc gatctaaagg agtcaaagtt gttggaagta  64860
aggaaggcta agagctcagc acagcaaaga ctcggggtca gggatggtag tgcaggggaa  64920
tggtggagta gaacttggta agtgtaagag atcaaggtgt gtgacccaaa cttaatcttt  64980
ttcttttatc aggagatgct gtccatgctg ggagatcaga gcaacagcta caacaatgaa  65040
gaattccctg atctaactat gtttcccccc ttttcagaat agaactattg gggtgaggat  65100
aaggggtggg ggagaaaaaa tcactgtttg tttttaaaaa gcaaatcttt ctgtaaacag  65160
aataaaagtt cctctccctt cccttccctc accccctgaca tgtacccccct ttcccttctg  65220
gctgttcccc tgctctgttg cctctctaag gtaacattta tagaagaaat ggaatgaatc  65280
tccaaggctt ttaggactgt ctgaaaattt gaggctgggt gaagttaaaa cacctttcct  65340
tatgtctcct gacctgaaat tgtatagtgt tgatttgtgc tgagatcaag aggcaggtta  65400
gaagaacctg acatccactg tttgccttgg atagtatggc ttgtttttgg aaagaaattc  65460
tgaagagagt ggaggagagg agaaatgtcc tcatatttga ggaccatgaa acattgtagg  65520
tatatatggg gctttagcaa gtttgagcat aggctctttt tgctgcctgt gagcagtccc  65580
tctggaaaga aacatgtgag taagtgagag agagtgtgtg tgtatgtgtg tgtgtgtgtg  65640
tgtgcgcaca catgcttctg tatttcactc tttctcccta ttagggagtt atgcaaaatt  65700
tgtccccgat tttacctttg tctttctgtg tacttttcaa agagtcctaa ggagttaaat  65760
cttccaggta ttttccactt agtattgcag ccaaagaata tttaaataaa cgtctttgct  65820
gcgcttgcat ccatgcccag ccaatataca actgtaaagc aaatatagaa agtcggctgt  65880
tgatacgatt gtctgttatc gaacacattc agtgataaag ctgggttact gctgcttttg  65940
gtgctctcac cttatctgga agatctgcaa acattaccta aataggctgg caagataaac  66000
actttctgga acccgagact tggccataaa gataatgctg catttttctg tcagaatcac  66060
atatgatgtg tgttctgtag aggttatttc tgcatggaaa ctcaacttct tggattagcc  66120
gtcccagtga aaatcctcat tgttggagtg taaaccaaat acgaagccct cttgcaaagt  66180
agcctctttc atcccatact caaaataccc agtttagcaa gcaactgaga tttaagtctc  66240
tctggcccta agaggttttt cctctttgct ccctccaatc ttgagattgg gttttgcttt  66300
agagtgcaag tatcataatt ccgtatgata gatggggcct ggacacccat ctcaacaggg  66360
tcacttggta attaacaata gccatataaa tgcggataca ggttactacc ctcacccttt  66420
accttcctca ggtaacagtc gtagatacca gcttttttttt tttttttttt aaattggctt  66480
tggccagtag ctaaagtgca agactgaatt aatgagaaga tatattaaat gtagtcatag  66540
gggactgagg agcaagggtg gccttgaaga ggccaaagga atgtccattt gctgagtttc  66600
ccttccttat gtctccagtc tggtgccagg tagtggagta aaaaaggaga cagtttattt  66660
ttttattcta tgtgcacact tacagtatac atatatattt atatcacaat ttacgaaacc  66720
aaaaagttga gtttccaatg gaacccttgt tttttaataa tcgacttttt aaatgtgatc  66780
aggactataa tattgtacag ttattatagg gcttttgggg aaggggagga tagcgagaag  66840
atgctctggg ggttttgttt ttgcttttcc ttcagggttt tatttttgac tgttttgttt  66900
tcttgttggc catttctgta ttgctggcat ctgtgctaag ctttacagtg gcaaaaaataa  66960
tgacatgtag caaagatttt caaacaaaat attttttcct tttgtaaaat ttcttgtgtt  67020
gtgtgatctt gattgcggct ttatcattcc tttccagttc ataaacaaca ggcacccaca  67080
```

-continued

```
accagaggaa tctatagttt aagctccaga catacaaaca taaggcacat tgtgtcttta  67140

atttcaggaa tcagaaatca tagggttctg atcacattgc acgcctcccc cctcacttgt  67200

cctcctgatc ctgacacatt ctgagtaaca tcagcaggaa tgctctgacc atgaggtggg  67260

ggttttgggg tgggcgttgc ctgggttctt gggagagagg ggaagagtcg ggacttgaaa  67320

accactaggg cacatctgga tgccttcccc cagtatgtcc ttttctggat taaaatgagt  67380

gaaatttaaa ctgttcaagt ctggacctgg tttccctcta ggagactatg ttggttcatt  67440

agcaactttt tttttttttt ttttttttgt gtgtgtgtgt gtgtgtgtgt gtgagagatg  67500

gagtctcgct ctgttaccca ggctggagtg cagtggcacg atcttggctc actgcaacct  67560

ctgccccttg ggttcaagca attctcctgc ctcagcttcc caagtagctg gcactacagg  67620

tgtgtgccac catgcccagc taatttttgt gttttttttt tttagtagag atggggtttc  67680

actatatgtt ggccaggcta gtctcgaact cctgacctta ggtgatccac atgctttggc  67740

ctcccaaagg cctgggatta caggcgtgaa ccactgcgcc tagcctg                67787
```

<210> SEQ ID NO 19
<211> LENGTH: 501
<212> TYPE: DNA
<213> ORGANISM: H. sapien
<220> FEATURE:
<221> NAME/KEY: misc_feature
<222> LOCATION: 217, 441, 498
<223> OTHER INFORMATION: n = A,T,C or G
<220> FEATURE:
<221> NAME/KEY: misc_feature
<222> LOCATION: 217, 441, 498
<223> OTHER INFORMATION: n = A,T,C or G

<400> SEQUENCE: 19

```
ggagggagtg gtaatttaca aaggatgtga agtttccagg aaataggggg aagggaatta     60

cattatcttc ttgttctctg tctgccttat tagttctgtt tcatgcttgc tttgcatgag    120

aaggttggca aaccttattt taactgctga gacttaagca tcactaaatc tgaataccac    180

attcttcagc agcacacttg gtatccatat cactctncct gctaccaaat gaccagatgt    240

gaccacctgg atgggggctt ctctttcttt ccatgcaggg aaaatcacag tgaaaattga    300

acggcggcga cggaacaaag atgacagcct acatcacaga actgtcagat atggtaccca    360

cctgtagttg ccctgggctc ggaaaaccag accaagctaa ccatcttacg catggcaagt    420

ttctcacatg aagtccttgc nggggaactt ggcaacacat ccactgatgg gtcctataag    480

ccggctttcc tcactganta a                                              501
```

<210> SEQ ID NO 20
<211> LENGTH: 2908
<212> TYPE: DNA
<213> ORGANISM: H. sapiens
<220> FEATURE:

<400> SEQUENCE: 20

```
cttggattcc gcggtagcgg aggcggcggt caggcgccgc ttctggggag tggcctttct     60

tttcccctcc ctcccggttc ggtggcggcg gctcctccca ctgggggggg ggtggcgcgg    120

cggcggtggc atctgcggcc atggcggcga ctactgccaa ccccgcctga tcttggactc    180

aagattctcc tgcctcagac cccgagtagc tgggactaca gaaatgacat cagatgtacc    240

atcactgggt ccagccattg cctctggaaa ctctggacct ggaattcaag gtggaggagc    300

cattgtccag agggctatta agcggcgacc agggctggat tttgatgatg atggagaagg    360
```

-continued

```
gaacagtaaa tttttgaggt gtgatgatga tcagatgtct aacgataagg agcggtttgc    420
caggtcggat gatgagcaga gctctgcgga taaagagaga cttgccaggg aaaatcacag    480
tgaaattgaa cggcggcgac ggaacaagat gacagcctac atcacagaac tgtcagatat    540
ggtacccacc tgtagtgccc tggctcgaaa accagacaag ctaaccatct tacgcatggc    600
agtttctcac atgaagtcct tgcggggaac tggcaacaca tccactgatg gctcctataa    660
gccgtctttc ctcactgatc aggaactgaa acatttgatc ttggaggcag cagatggctt    720
tctgtttatt gtctcatgtg agacaggcag ggtggtgtat gtctctgact ccgtgactcc    780
tgttttgaac cagccacagt ctgaatggtt tggcagcaca ctctatgatc aggtgcaccc    840
agatgatgtg gataaacttc gtgagcagct ttccacttca gaaaatgccc tgacagggcg    900
tatcctggat ctaaagactg gaacagtgaa aaaggaaggt cagcagtctt ccatgagaat    960
gtgtatgggc tcaaggagat cgtttatttg ccgaatgagg tgtggcagta gctctgtgga   1020
cccagtttct gtgaataggc tgagctttgt gaggaacaga tgcaggaatg gacttggctc   1080
tgtaaaggat ggggaacctc acttcgtggt ggtccactgc acaggctaca tcaaggcctg   1140
gcccccagca gatgatgacc cagaggctgg ccagggaagc aagttttgcc tagtggccat   1200
tggcagattg caggtaacta gttctcccaa ctgtacagac atgagtaatg tttgtcaacc   1260
aacagagttc atctcccgac acaacattga gggtatcttc acttttgtgg atcaccgctg   1320
tgtggctact gttggctacc agccacagga actcttagga aagaatattg tagaattctg   1380
tcatcctgaa gaccagcagc ttctaagaga cagcttccaa caggtagtga aattaaaagg   1440
ccaagtgctg tctgtcatgt tccggttccg gtctaagaac caagaatggc tctggatgag   1500
aaccagctcc tttactttcc agaaccctta ctcagatgaa attgagtaca tcatctgtac   1560
caacaccaat gtgaagaact ctagccaaga accacggcct acactctcca acacaatcca   1620
gaggccacaa ctaggtccca cagctaattt accccctggag atgggctcag gacagctggc   1680
acccaggcag cagcaacagc aaacagaatt ggacatggta ccaggaagag atggactggc   1740
cagctacaat cattcccagg tggttcagcc tgtgacaacc acaggaccag aacacagcaa   1800
gccccttgag aagtcagatg gtttatttgc ccaggataga gatccaagat tttcagaaat   1860
ctatcacaac atcaatgcgg atcagagtaa aggcatctcc tccagcactg tccctgccac   1920
ccaacagcta ttctcccagg gcaacacatt ccctcctacc ccccggccgg cagagaattt   1980
caggaatagt ggcctagccc ctcctgtaac cattgtccag ccatcagctt ctgcaggaca   2040
gatgttggcc cagatttccc gccactccaa ccccacccaa ggagcaaccc caacttggac   2100
ccctactacc cgctcaggct tttctgccca gcaggtggct acccaggcta ctgctaagac   2160
tcgtacttcc cagtttggtg tgggcagctt tcagactcca tcctccttca gctccatgtc   2220
cctccctggt gccccaactg catcgcctgg tgctgctgcc taccctagtc tcaccaatcg   2280
tggatctaac tttgctcctg agactggaca gactgcagga caattccaga cacggacagc   2340
agagggtgtg ggtgtctggc cacagtggca gggccagcag cctcatcatc gttcaagttc   2400
tagtgagcaa catgttcaac aaccgccagc acagcaacct ggccagcctg aggtcttcca   2460
ggagatgctg tccatgctgg gagatcagag caacagctac aacaatgaag aattccctga   2520
tctaactatg tttccccccct tttcagaata gaactattgg ggtgaggata aggggtgggg   2580
gagaaaaaat cactgtttgt ttttaaaaag caaatctttc tgtaaacaga ataaaagttc   2640
ctctcccttc ccttccctca cccctgacat gtaccccctt tcccttctgg ctgttcccct   2700
gctctgttgc ctctctaagg taacatttat agaagaaatg gaatgaatct ccaaggcttt   2760
```

-continued

```
taggactgtc tgaaaatttg aggctgggtg aagttaaaac acctttcctt atgtctcctg   2820

acctgaaatt gtatagtgtt gatttgtgct gagatcaaga ggcaggttag aagaacctga   2880

catccactgt taaaaaaaaa aaaaaaaa                                      2908


<210> SEQ ID NO 21
<211> LENGTH: 20
<212> TYPE: DNA
<213> ORGANISM: Artificial Sequence
<220> FEATURE:
<223> OTHER INFORMATION: Antisense Compound

<400> SEQUENCE: 21

acacacatat ctcaaggccc                                                  20


<210> SEQ ID NO 22
<211> LENGTH: 20
<212> TYPE: DNA
<213> ORGANISM: Artificial Sequence
<220> FEATURE:
<223> OTHER INFORMATION: Antisense Compound

<400> SEQUENCE: 22

aagggagcag aggactccct                                                  20


<210> SEQ ID NO 23
<211> LENGTH: 20
<212> TYPE: DNA
<213> ORGANISM: Artificial Sequence
<220> FEATURE:
<223> OTHER INFORMATION: Antisense Compound

<400> SEQUENCE: 23

caagatcagg ctgggaaaca                                                  20


<210> SEQ ID NO 24
<211> LENGTH: 20
<212> TYPE: DNA
<213> ORGANISM: Artificial Sequence
<220> FEATURE:
<223> OTHER INFORMATION: Antisense Compound

<400> SEQUENCE: 24

cccctaatct ggtcacctgt                                                  20


<210> SEQ ID NO 25
<211> LENGTH: 20
<212> TYPE: DNA
<213> ORGANISM: Artificial Sequence
<220> FEATURE:
<223> OTHER INFORMATION: Antisense Compound

<400> SEQUENCE: 25

actgccacac ctgtttcaag                                                  20


<210> SEQ ID NO 26
<211> LENGTH: 20
<212> TYPE: DNA
<213> ORGANISM: Artificial Sequence
<220> FEATURE:
<223> OTHER INFORMATION: Antisense Compound

<400> SEQUENCE: 26

taggaataat aacttatttc                                                  20
```

-continued

<210> SEQ ID NO 27
<211> LENGTH: 20
<212> TYPE: DNA
<213> ORGANISM: Artificial Sequence
<220> FEATURE:
<223> OTHER INFORMATION: Antisense Compound

<400> SEQUENCE: 27
actctcttac ctggaagacc 20

<210> SEQ ID NO 28
<211> LENGTH: 20
<212> TYPE: DNA
<213> ORGANISM: Artificial Sequence
<220> FEATURE:
<223> OTHER INFORMATION: Antisense Compound

<400> SEQUENCE: 28
caagatggcg gcttcagcag 20

<210> SEQ ID NO 29
<211> LENGTH: 20
<212> TYPE: DNA
<213> ORGANISM: Artificial Sequence
<220> FEATURE:
<223> OTHER INFORMATION: Antisense Compound

<400> SEQUENCE: 29
ggaaaagaaa ggccactccc 20

<210> SEQ ID NO 30
<211> LENGTH: 20
<212> TYPE: DNA
<213> ORGANISM: Artificial Sequence
<220> FEATURE:
<223> OTHER INFORMATION: Antisense Compound

<400> SEQUENCE: 30
gccgccatgg ccgcagatgc 20

<210> SEQ ID NO 31
<211> LENGTH: 20
<212> TYPE: DNA
<213> ORGANISM: Artificial Sequence
<220> FEATURE:
<223> OTHER INFORMATION: Antisense Compound

<400> SEQUENCE: 31
ggtacatctg atgtcatttc 20

<210> SEQ ID NO 32
<211> LENGTH: 20
<212> TYPE: DNA
<213> ORGANISM: Artificial Sequence
<220> FEATURE:
<223> OTHER INFORMATION: Antisense Compound

<400> SEQUENCE: 32
cttaatagcc ctctggacaa 20

<210> SEQ ID NO 33
<211> LENGTH: 20
<212> TYPE: DNA
<213> ORGANISM: Artificial Sequence
<220> FEATURE:
<223> OTHER INFORMATION: Antisense Compound -continued

<400> SEQUENCE: 33
atcatcaaaa tccagccctg 20

<210> SEQ ID NO 34
<211> LENGTH: 20
<212> TYPE: DNA
<213> ORGANISM: Artificial Sequence
<220> FEATURE:
<223> OTHER INFORMATION: Antisense Compound

<400> SEQUENCE: 34
tccgacctgg caaaccgctc 20

<210> SEQ ID NO 35
<211> LENGTH: 20
<212> TYPE: DNA
<213> ORGANISM: Artificial Sequence
<220> FEATURE:
<223> OTHER INFORMATION: Antisense Compound

<400> SEQUENCE: 35
catcatccga cctggcaaac 20

<210> SEQ ID NO 36
<211> LENGTH: 20
<212> TYPE: DNA
<213> ORGANISM: Artificial Sequence
<220> FEATURE:
<223> OTHER INFORMATION: Antisense Compound

<400> SEQUENCE: 36
attttccctg gcaagtctct 20

<210> SEQ ID NO 37
<211> LENGTH: 20
<212> TYPE: DNA
<213> ORGANISM: Artificial Sequence
<220> FEATURE:
<223> OTHER INFORMATION: Antisense Compound

<400> SEQUENCE: 37
ctgtcatctt gttccgtcgc 20

<210> SEQ ID NO 38
<211> LENGTH: 20
<212> TYPE: DNA
<213> ORGANISM: Artificial Sequence
<220> FEATURE:
<223> OTHER INFORMATION: Antisense Compound

<400> SEQUENCE: 38
tctgacagtt ctgtgatgta 20

<210> SEQ ID NO 39
<211> LENGTH: 20
<212> TYPE: DNA
<213> ORGANISM: Artificial Sequence
<220> FEATURE:
<223> OTHER INFORMATION: Antisense Compound

<400> SEQUENCE: 39
tttcgagcca gggcactaca 20

<210> SEQ ID NO 40

-continued

<211> LENGTH: 20
<212> TYPE: DNA
<213> ORGANISM: Artificial Sequence
<220> FEATURE:
<223> OTHER INFORMATION: Antisense Compound

<400> SEQUENCE: 40
ctggttttcg agccagggca 20

<210> SEQ ID NO 41
<211> LENGTH: 20
<212> TYPE: DNA
<213> ORGANISM: Artificial Sequence
<220> FEATURE:
<223> OTHER INFORMATION: Antisense Compound

<400> SEQUENCE: 41
aatgtttcag ttcctgatca 20

<210> SEQ ID NO 42
<211> LENGTH: 20
<212> TYPE: DNA
<213> ORGANISM: Artificial Sequence
<220> FEATURE:
<223> OTHER INFORMATION: Antisense Compound

<400> SEQUENCE: 42
agatcaaatg tttcagttcc 20

<210> SEQ ID NO 43
<211> LENGTH: 20
<212> TYPE: DNA
<213> ORGANISM: Artificial Sequence
<220> FEATURE:
<223> OTHER INFORMATION: Antisense Compound

<400> SEQUENCE: 43
ctccaagatc aaatgtttca 20

<210> SEQ ID NO 44
<211> LENGTH: 20
<212> TYPE: DNA
<213> ORGANISM: Artificial Sequence
<220> FEATURE:
<223> OTHER INFORMATION: Antisense Compound

<400> SEQUENCE: 44
gctgcctcca agatcaaatg 20

<210> SEQ ID NO 45
<211> LENGTH: 20
<212> TYPE: DNA
<213> ORGANISM: Artificial Sequence
<220> FEATURE:
<223> OTHER INFORMATION: Antisense Compound

<400> SEQUENCE: 45
catctgctgc ctccaagatc 20

<210> SEQ ID NO 46
<211> LENGTH: 20
<212> TYPE: DNA
<213> ORGANISM: Artificial Sequence
<220> FEATURE:
<223> OTHER INFORMATION: Antisense Compound

<400> SEQUENCE: 46

-continued aaagccatct gctgcctcca 20

<210> SEQ ID NO 47
<211> LENGTH: 20
<212> TYPE: DNA
<213> ORGANISM: Artificial Sequence
<220> FEATURE:
<223> OTHER INFORMATION: Antisense Compound

<400> SEQUENCE: 47
atcatctggg tgcacctgat 20

<210> SEQ ID NO 48
<211> LENGTH: 20
<212> TYPE: DNA
<213> ORGANISM: Artificial Sequence
<220> FEATURE:
<223> OTHER INFORMATION: Antisense Compound

<400> SEQUENCE: 48
atccacatca tctgggtgca 20

<210> SEQ ID NO 49
<211> LENGTH: 20
<212> TYPE: DNA
<213> ORGANISM: Artificial Sequence
<220> FEATURE:
<223> OTHER INFORMATION: Antisense Compound

<400> SEQUENCE: 49
agtttatcca catcatctgg 20

<210> SEQ ID NO 50
<211> LENGTH: 20
<212> TYPE: DNA
<213> ORGANISM: Artificial Sequence
<220> FEATURE:
<223> OTHER INFORMATION: Antisense Compound

<400> SEQUENCE: 50
cctttttcac tgttccagtc 20

<210> SEQ ID NO 51
<211> LENGTH: 20
<212> TYPE: DNA
<213> ORGANISM: Artificial Sequence
<220> FEATURE:
<223> OTHER INFORMATION: Antisense Compound

<400> SEQUENCE: 51
ctgaccttcc tttttcactg 20

<210> SEQ ID NO 52
<211> LENGTH: 20
<212> TYPE: DNA
<213> ORGANISM: Artificial Sequence
<220> FEATURE:
<223> OTHER INFORMATION: Antisense Compound

<400> SEQUENCE: 52
agactgctga ccttcctttt 20

<210> SEQ ID NO 53
<211> LENGTH: 20
<212> TYPE: DNA

-continued

<213> ORGANISM: Artificial Sequence
<220> FEATURE:
<223> OTHER INFORMATION: Antisense Compound

<400> SEQUENCE: 53
tccattcctg catctgttcc 20

<210> SEQ ID NO 54
<211> LENGTH: 20
<212> TYPE: DNA
<213> ORGANISM: Artificial Sequence
<220> FEATURE:
<223> OTHER INFORMATION: Antisense Compound

<400> SEQUENCE: 54
agccaagtcc attcctgcat 20

<210> SEQ ID NO 55
<211> LENGTH: 20
<212> TYPE: DNA
<213> ORGANISM: Artificial Sequence
<220> FEATURE:
<223> OTHER INFORMATION: Antisense Compound

<400> SEQUENCE: 55
gcctctgggt catcatctgg 20

<210> SEQ ID NO 56
<211> LENGTH: 20
<212> TYPE: DNA
<213> ORGANISM: Artificial Sequence
<220> FEATURE:
<223> OTHER INFORMATION: Antisense Compound

<400> SEQUENCE: 56
gggagaacta gttacctgca 20

<210> SEQ ID NO 57
<211> LENGTH: 20
<212> TYPE: DNA
<213> ORGANISM: Artificial Sequence
<220> FEATURE:
<223> OTHER INFORMATION: Antisense Compound

<400> SEQUENCE: 57
cagttgggag aactagttac 20

<210> SEQ ID NO 58
<211> LENGTH: 20
<212> TYPE: DNA
<213> ORGANISM: Artificial Sequence
<220> FEATURE:
<223> OTHER INFORMATION: Antisense Compound

<400> SEQUENCE: 58
ctgtacagtt gggagaacta 20

<210> SEQ ID NO 59
<211> LENGTH: 20
<212> TYPE: DNA
<213> ORGANISM: Artificial Sequence
<220> FEATURE:
<223> OTHER INFORMATION: Antisense Compound

<400> SEQUENCE: 59
catgtctgta cagttgggag 20

<210> SEQ ID NO 60
<211> LENGTH: 20
<212> TYPE: DNA
<213> ORGANISM: Artificial Sequence
<220> FEATURE:
<223> OTHER INFORMATION: Antisense Compound

<400> SEQUENCE: 60
ttactcatgt ctgtacagtt 20

<210> SEQ ID NO 61
<211> LENGTH: 20
<212> TYPE: DNA
<213> ORGANISM: Artificial Sequence
<220> FEATURE:
<223> OTHER INFORMATION: Antisense Compound

<400> SEQUENCE: 61
tcgggagatg aactctgttg 20

<210> SEQ ID NO 62
<211> LENGTH: 20
<212> TYPE: DNA
<213> ORGANISM: Artificial Sequence
<220> FEATURE:
<223> OTHER INFORMATION: Antisense Compound

<400> SEQUENCE: 62
ttgtgtcggg agatgaactc 20

<210> SEQ ID NO 63
<211> LENGTH: 20
<212> TYPE: DNA
<213> ORGANISM: Artificial Sequence
<220> FEATURE:
<223> OTHER INFORMATION: Antisense Compound

<400> SEQUENCE: 63
caatgttgtg tcgggagatg 20

<210> SEQ ID NO 64
<211> LENGTH: 20
<212> TYPE: DNA
<213> ORGANISM: Artificial Sequence
<220> FEATURE:
<223> OTHER INFORMATION: Antisense Compound

<400> SEQUENCE: 64
tagccaacag tagccacaca 20

<210> SEQ ID NO 65
<211> LENGTH: 20
<212> TYPE: DNA
<213> ORGANISM: Artificial Sequence
<220> FEATURE:
<223> OTHER INFORMATION: Antisense Compound

<400> SEQUENCE: 65
gctggtagcc aacagtagcc 20

<210> SEQ ID NO 66
<211> LENGTH: 20
<212> TYPE: DNA
<213> ORGANISM: Artificial Sequence
<220> FEATURE:

-continued

<223> OTHER INFORMATION: Antisense Compound

<400> SEQUENCE: 66
ctgtggctgg tagccaacag 20

<210> SEQ ID NO 67
<211> LENGTH: 20
<212> TYPE: DNA
<213> ORGANISM: Artificial Sequence
<220> FEATURE:
<223> OTHER INFORMATION: Antisense Compound

<400> SEQUENCE: 67
acaatattct ttcctaagag 20

<210> SEQ ID NO 68
<211> LENGTH: 20
<212> TYPE: DNA
<213> ORGANISM: Artificial Sequence
<220> FEATURE:
<223> OTHER INFORMATION: Antisense Compound

<400> SEQUENCE: 68
atttcactac ctgttggaag 20

<210> SEQ ID NO 69
<211> LENGTH: 20
<212> TYPE: DNA
<213> ORGANISM: Artificial Sequence
<220> FEATURE:
<223> OTHER INFORMATION: Antisense Compound

<400> SEQUENCE: 69
acttggcctt ttaatttcac 20

<210> SEQ ID NO 70
<211> LENGTH: 20
<212> TYPE: DNA
<213> ORGANISM: Artificial Sequence
<220> FEATURE:
<223> OTHER INFORMATION: Antisense Compound

<400> SEQUENCE: 70
acagcacttg gccttttaat 20

<210> SEQ ID NO 71
<211> LENGTH: 20
<212> TYPE: DNA
<213> ORGANISM: Artificial Sequence
<220> FEATURE:
<223> OTHER INFORMATION: Antisense Compound

<400> SEQUENCE: 71
gaacatgaca gacagcactt 20

<210> SEQ ID NO 72
<211> LENGTH: 20
<212> TYPE: DNA
<213> ORGANISM: Artificial Sequence
<220> FEATURE:
<223> OTHER INFORMATION: Antisense Compound

<400> SEQUENCE: 72
gttcttcaca ttggtgttgg 20

-continued

<210> SEQ ID NO 73
<211> LENGTH: 20
<212> TYPE: DNA
<213> ORGANISM: Artificial Sequence
<220> FEATURE:
<223> OTHER INFORMATION: Antisense Compound

<400> SEQUENCE: 73
ctagagttct tcacattggt 20

<210> SEQ ID NO 74
<211> LENGTH: 20
<212> TYPE: DNA
<213> ORGANISM: Artificial Sequence
<220> FEATURE:
<223> OTHER INFORMATION: Antisense Compound

<400> SEQUENCE: 74
ccatctcttc ctggtaccat 20

<210> SEQ ID NO 75
<211> LENGTH: 20
<212> TYPE: DNA
<213> ORGANISM: Artificial Sequence
<220> FEATURE:
<223> OTHER INFORMATION: Antisense Compound

<400> SEQUENCE: 75
ttactctgat ccgcattgat 20

<210> SEQ ID NO 76
<211> LENGTH: 20
<212> TYPE: DNA
<213> ORGANISM: Artificial Sequence
<220> FEATURE:
<223> OTHER INFORMATION: Antisense Compound

<400> SEQUENCE: 76
gagatgcctt tactctgatc 20

<210> SEQ ID NO 77
<211> LENGTH: 20
<212> TYPE: DNA
<213> ORGANISM: Artificial Sequence
<220> FEATURE:
<223> OTHER INFORMATION: Antisense Compound

<400> SEQUENCE: 77
tggaggagat gcctttactc 20

<210> SEQ ID NO 78
<211> LENGTH: 20
<212> TYPE: DNA
<213> ORGANISM: Artificial Sequence
<220> FEATURE:
<223> OTHER INFORMATION: Antisense Compound

<400> SEQUENCE: 78
agtgctggag gagatgcctt 20

<210> SEQ ID NO 79
<211> LENGTH: 20
<212> TYPE: DNA
<213> ORGANISM: Artificial Sequence
<220> FEATURE:
<223> OTHER INFORMATION: Antisense Compound -continued

<400> SEQUENCE: 79
gaaattctct gccggccggg 20

<210> SEQ ID NO 80
<211> LENGTH: 20
<212> TYPE: DNA
<213> ORGANISM: Artificial Sequence
<220> FEATURE:
<223> OTHER INFORMATION: Antisense Compound

<400> SEQUENCE: 80
ttcctgaaat tctctgccgg 20

<210> SEQ ID NO 81
<211> LENGTH: 20
<212> TYPE: DNA
<213> ORGANISM: Artificial Sequence
<220> FEATURE:
<223> OTHER INFORMATION: Antisense Compound

<400> SEQUENCE: 81
agaccactat tcctgaaatt 20

<210> SEQ ID NO 82
<211> LENGTH: 20
<212> TYPE: DNA
<213> ORGANISM: Artificial Sequence
<220> FEATURE:
<223> OTHER INFORMATION: Antisense Compound

<400> SEQUENCE: 82
ggacaatggt tacaggaggg 20

<210> SEQ ID NO 83
<211> LENGTH: 20
<212> TYPE: DNA
<213> ORGANISM: Artificial Sequence
<220> FEATURE:
<223> OTHER INFORMATION: Antisense Compound

<400> SEQUENCE: 83
tggctggaca atggttacag 20

<210> SEQ ID NO 84
<211> LENGTH: 20
<212> TYPE: DNA
<213> ORGANISM: Artificial Sequence
<220> FEATURE:
<223> OTHER INFORMATION: Antisense Compound

<400> SEQUENCE: 84
gtctcaggag caaagttaga 20

<210> SEQ ID NO 85
<211> LENGTH: 20
<212> TYPE: DNA
<213> ORGANISM: Artificial Sequence
<220> FEATURE:
<223> OTHER INFORMATION: Antisense Compound

<400> SEQUENCE: 85
cactgtggcc agacacccac 20

<210> SEQ ID NO 86
<211> LENGTH: 20

-continued

<212> TYPE: DNA
<213> ORGANISM: Artificial Sequence
<220> FEATURE:
<223> OTHER INFORMATION: Antisense Compound

<400> SEQUENCE: 86
ctggccctgc cactgtggcc 20

<210> SEQ ID NO 87
<211> LENGTH: 20
<212> TYPE: DNA
<213> ORGANISM: Artificial Sequence
<220> FEATURE:
<223> OTHER INFORMATION: Antisense Compound

<400> SEQUENCE: 87
ggctgctggc cctgccactg 20

<210> SEQ ID NO 88
<211> LENGTH: 20
<212> TYPE: DNA
<213> ORGANISM: Artificial Sequence
<220> FEATURE:
<223> OTHER INFORMATION: Antisense Compound

<400> SEQUENCE: 88
ggaaacatag ttagatcagg 20

<210> SEQ ID NO 89
<211> LENGTH: 20
<212> TYPE: DNA
<213> ORGANISM: Artificial Sequence
<220> FEATURE:
<223> OTHER INFORMATION: Antisense Compound

<400> SEQUENCE: 89
caatagttct attctgaaaa 20

<210> SEQ ID NO 90
<211> LENGTH: 20
<212> TYPE: DNA
<213> ORGANISM: Artificial Sequence
<220> FEATURE:
<223> OTHER INFORMATION: Antisense Compound

<400> SEQUENCE: 90
tcaccccaat agttctattc 20

<210> SEQ ID NO 91
<211> LENGTH: 20
<212> TYPE: DNA
<213> ORGANISM: Artificial Sequence
<220> FEATURE:
<223> OTHER INFORMATION: Antisense Compound

<400> SEQUENCE: 91
tatcctcacc ccaatagttc 20

<210> SEQ ID NO 92
<211> LENGTH: 20
<212> TYPE: DNA
<213> ORGANISM: Artificial Sequence
<220> FEATURE:
<223> OTHER INFORMATION: Antisense Compound

<400> SEQUENCE: 92

-continued agaggaactt ttattctgtt 20

<210> SEQ ID NO 93
<211> LENGTH: 20
<212> TYPE: DNA
<213> ORGANISM: Artificial Sequence
<220> FEATURE:
<223> OTHER INFORMATION: Antisense Compound

<400> SEQUENCE: 93
aagggagagg aacttttatt 20

<210> SEQ ID NO 94
<211> LENGTH: 20
<212> TYPE: DNA
<213> ORGANISM: Artificial Sequence
<220> FEATURE:
<223> OTHER INFORMATION: Antisense Compound

<400> SEQUENCE: 94
atccaaggca aacagtggat 20

<210> SEQ ID NO 95
<211> LENGTH: 20
<212> TYPE: DNA
<213> ORGANISM: Artificial Sequence
<220> FEATURE:
<223> OTHER INFORMATION: Antisense Compound

<400> SEQUENCE: 95
gtccaggccc catctatcat 20

<210> SEQ ID NO 96
<211> LENGTH: 20
<212> TYPE: DNA
<213> ORGANISM: Artificial Sequence
<220> FEATURE:
<223> OTHER INFORMATION: Antisense Compound

<400> SEQUENCE: 96
tgaaaatctt tgctacatgt 20

<210> SEQ ID NO 97
<211> LENGTH: 20
<212> TYPE: DNA
<213> ORGANISM: Artificial Sequence
<220> FEATURE:
<223> OTHER INFORMATION: Antisense Compound

<400> SEQUENCE: 97
ccaggtggtc acatctggtc 20

<210> SEQ ID NO 98
<211> LENGTH: 20
<212> TYPE: DNA
<213> ORGANISM: Artificial Sequence
<220> FEATURE:
<223> OTHER INFORMATION: Antisense Compound

<400> SEQUENCE: 98
tgagtccaag atcaggcggg 20

<210> SEQ ID NO 99
<211> LENGTH: 65001
<212> TYPE: DNA
<213> ORGANISM: M. musculus -continued
<220> FEATURE:
<221> NAME/KEY: misc_feature
<222> LOCATION: 14965, 14966, 14967, 14968, 14969, 14970, 14971, 14972,
14973, 14974, 14975, 14976, 14977, 14978, 14979, 14980, 14981,
14982, 14983, 14984, 14985, 14986, 14987, 14988, 14989,
14990, 14991, 14992, 14993, 14994, 14995, 14996, 14997
<223> OTHER INFORMATION: n = A,T,C or G
<220> FEATURE:
<221> NAME/KEY: misc_feature
<222> LOCATION: 14998, 14999, 15000, 15001, 15002, 15003, 15004, 15005,
15006, 15007, 15008, 15009, 15010, 15011, 15012, 15013, 15014,
15015, 15016, 15017, 15018, 15019, 15020, 15021, 15022,
15023, 15024, 15025, 15026, 15027, 15028, 15029, 15030
<223> OTHER INFORMATION: n = A,T,C or G
<220> FEATURE:
<221> NAME/KEY: misc_feature
<222> LOCATION: 15031, 15032, 15033, 15034, 15035, 15036, 15037, 15038,
15039, 15040, 15041, 15042, 15043, 15044, 15045, 15046, 15047,
15048, 15049, 15050, 15051, 15052, 15053, 15054, 15055,
15056, 15057, 15058, 15059, 15060, 15061, 15062, 15063
<223> OTHER INFORMATION: n = A,T,C or G
<220> FEATURE:
<221> NAME/KEY: misc_feature
<222> LOCATION: 15064
<223> OTHER INFORMATION: n = A,T,C or G
<220> FEATURE:
<221> NAME/KEY: misc_feature
<222> LOCATION: 14965, 14966, 14967, 14968, 14969, 14970, 14971, 14972,
14973, 14974, 14975, 14976, 14977, 14978, 14979, 14980, 14981,
14982, 14983, 14984, 14985, 14986, 14987, 14988, 14989,
14990, 14991, 14992, 14993, 14994, 14995, 14996, 14997
<223> OTHER INFORMATION: n = A,T,C or G
<220> FEATURE:
<221> NAME/KEY: misc_feature
<222> LOCATION: 14998, 14999, 15000, 15001, 15002, 15003, 15004, 15005,
15006, 15007, 15008, 15009, 15010, 15011, 15012, 15013, 15014,
15015, 15016, 15017, 15018, 15019, 15020, 15021, 15022,
15023, 15024, 15025, 15026, 15027, 15028, 15029, 15030
<223> OTHER INFORMATION: n = A,T,C or G

<400> SEQUENCE: 99
agataagggt cactggtgag ccttccaatt ccggattgta gttcattcca aatattgtca 60
agttgacaac caggaatagc cactacacat ggcttttttt actacatgat tataggtgta 120
atcaacatgt ctattatata ctaaaaaaaa aaagttttta accatgactt tttgtttggt 180
ttttcaacac atagtttctt tgtgttaatc atcctggctg ctttagatct taatttgtag 240
acctggctgg catccaactc aaagagatcc attggcctct acctcccaag tactgggatt 300
aaaagcatgt aatgccagtg aactacaatt tcttatatta aagtgtgcca tatagatgtc 360
atgttttgtt ttgttttgtt ttgtttttgt aaatttgaca caagctaaga tcatctgaga 420
ggaggaaaag ccattaaggc aatgcctcca tcttggcata gtggtgcccc cctttaatgc 480
cagcaaatga aagtgtgaaa gcaggtggat ttctatctgt tcacaactgt ttgaaactcc 540
aggttaatgg gatctttctt gtctgtctaa ttgtgttcca atactcaggt gtactgactt 600
aaatgcagac acattcacat aattaaaaat aaaactattc aaaaccccaa gaaaatgtct 660
aaacaaacca accaaaccaa ccaaataacc taaagcaagc aagcaaccaa caaacgagaa 720
gccagcatga tgtcactgcg cctctcactg cacctctttt tagtgaatgg gagttagttc 780
tctcctcgaa ccattgtgtg gcttttggag aatccaactt caagtacctt tagctcttga 840
gccatcttgt cagttctact tctaaatgtt tttaaaattt ttgtgtatgt gtgagtgcac 900
atgttttggt gtgaggaaag ttgaagataa tttgcaggag tcctctcctt gtgtaagttc 960
agagcattgg atcttgggat gttaggtgta gctgtgtagt ggagtcgtct ttatggctaa 1020
ttaaaaaaat ttttttggt gaatcagact gacaacaagc caaagagtag tgccatatgc 1080
ttatagttct aacattggaa ggagagggtg aattcaagac cattttcatc ctcatagtga 1140

-continued

```
atttggggtc agtctaggct acatgagacc ttgtttcaaa gaacaaaatt accctcctcc   1200
ccccagtcca catatacatg gtgatgaata taatagactt tgggtgttag tttcattcac   1260
tttgcttctc actactggat taatttgcaa ggtggccttt gtttcatgtc tttggttttt   1320
gtttgttttt gagatagtgt ctttctatat atagctcctg ctgtcttaga actcactatg   1380
tagaccaggc tggcattgaa ctcagagaaa ttggccagtc tctgcctcct gagtactagg   1440
attaaaggca tgcatcacta tgcctggatc tgtttgtagt tctttttttt ttttaaatat   1500
atatttttaa gatttattta tttattttat gtatatgagt acactgtagc tgtacagatg   1560
gctgtgagcc ttcatgtggt tattgggtat tgactttagg acctctgctt gctccaatca   1620
acctcgccca ctccagttgg tcggctcact cagttcctgc tttctctggc ccaaagattt   1680
atttattatt ctaaataagt acactgtaat tgtcttcaaa cacaccagac gagggcgtta   1740
gatctcatta ggggtggttg tgggccacca tgtggttgct gggatttgaa cgcaggacct   1800
ctgaaagagc agtcagtgct cttacccgct gagccatctc tccagcccct gcttgtagtt   1860
cttgatttgt aaaattatag aatttatctc acagtgtttt gagtcgacat tgtctgttct   1920
gaattgctca gttcttataa ttagacatta cgtctgtgtg tttactacct tgtcatttta   1980
aaaaaacttg tgacatagga cacctcactt ttggagggca gagaaaggga ctagtttcat   2040
tttgtagtac agactggtct ttgcattctg agttctggaa tacttgttta ataaaaattc   2100
tttgttcgtt gtctccattt caaatgttgg catctttggt accacgtaat cacccagctt   2160
tttcctacca gcttcagagc caactcttaa gaattagtta tcggactttt actagtgaca   2220
aaagttcata aagaaaaaac aacctagaat ggattagtga tccctgtgtt agaacctata   2280
aagagggttt gcataacaaa tcgtctgtag gaagcatatg ctgatgagcc cactaagaaa   2340
gaaaacattt tagtaaaatg ctcgttttct ttgcatttca ctgacgtcaa tttggttatg   2400
aatctctgac gccgagaagg ccggattagg gaaacagctg gttggcttcc tagctcaggc   2460
ttcctagcac tcctcgggtc accggactca ctggccgagt cactagcccg gcctctatgg   2520
cgacttactg tttctattgg ccagttctcc cagggaggct gtctggagac tgaccgcgcc   2580
catagtttgg ggcgtgtctt ctgcccagga tggggagggg ggtgggcgtc cgccatcttg   2640
gattccgcgg tagcggtggc ggcggtaagg tgcctaatct gcggagtggc tcttccctcc   2700
cctcccccag ctcggtggcg gctgcccctc ccaccgaggg tggcgcaggg acggtgccat   2760
ctcgaccatg gcggcgacta cagctaaccc aggtgaggcg gcagaaagga ctgacaagtg   2820
cggagagcca gagcagagca gcagggccgt ggcgttcggg tgttggggga ggggtgtcga   2880
ggaggcgccc tgcccggagg acctggggaa cgggtgacgg gtgtttgggg gctccgtgcc   2940
ccaacttctg gagtagtggt ggcgcttggc cagcgtctcc actctgcctg cggtgttagg   3000
gagtgttgtg gtcttttaac cctctgccag ctgatgttcc cctgatgcct agtaagtaac   3060
tgggcaaact gacttggtgt aactgcgagc gtaaactggg ctatagacgg ggccacgttg   3120
acgttttgca aagtcttgct tgattctaca cttggtttac atttaaatgg aaaacttagt   3180
tctttgagaa tctgctcaga ttcttgtaac tcctatactt tgaaatttag ggttttagcg   3240
tagttattag tgtcttgctg ctgaaggcag aggtttgggt aatggtaata gttcaggaca   3300
ggtctttagt ccagaaccca ggtttaaatc ttgttaggtc gaggtggagc aactcctgtt   3360
ctttcagaaa aatgtcccgc gccatttgtc tgtggacgtc ctcttgcttg tttgtctgtc   3420
tgtctctgtc tctcgttcat cttattttga gtcttgtctc attccagccc ccggttgact   3480
```

-continued

```
ttggatcact gcagtctccc tctcagtcct ttctactgta ttcagttaca tcttaggaag   3540
tatttcattt tagttgggct aatttacctt gttattttcc aacaaagtaa atccatcatt   3600
tcccagaagt ctgtatcatc gaagagtttg gagggagggt tgtgtaatat tggtctctgc   3660
tatttcacat tgaactttta aattttatct tgttaatgta ctatattaca gtaacagggt   3720
acacacacgt atgtatatac atacacacaa tagctgaaac actgggaaat gtattgtttt   3780
cccattattt ttggaaacag cctttttttt taagagagag agagagagag agagagagag   3840
agtcctagaa cttatatgta gcccaggttg gcttcaaatt catgtgtcaa tatcaacttt   3900
aaaaaaaata tttttaagct ttagaaatta tgtatatgat aatgtctact tgtgagtgca   3960
ggaatgggag gagtccagaa tagggtgttg gatcccctgc agcaagagtt tcaggcagtt   4020
gaaagccccg tgatgtggat gctaggaact gacattaggt cctagaagag taacacatac   4080
tcacaactac tgaaccttcc tttcagcccc tgaatatcag ttttttaaat cctaaattat   4140
tatttttttt acatgaagat gaagtaaatt gtcaggaaac tattggaata tttgatgaat   4200
tatagaataa aactatacaa ctgaaaaatg ttagagaaaa tcagaccttg tagcaaaata   4260
gcccatgtct gattagagta aacaagattt caaactgatc ccatgttgca aaatccttat   4320
ataactcttc agactgcaaa gtgtctctct tgttaaggcc gtagagacac gttagtaagt   4380
cagaagcttt tctagctgcc ctgttctgat tttaaaccaa ttactaaaac aacactttct   4440
tgaccaaata gtcatttcct tatcaatatt agcttaagtc tgtaagcagg aaatagtaat   4500
tttttctat ttttttttct gagtggggaa ttttgagagg ctggcctgca gtgttctgtg   4560
aagatcaggc tggccttgaa cttgcagtgg tcttcttgct tctatcttca agtgctggaa   4620
tcactcgcat gtgccatcct atataaacta tcaaaacttt ttaaaaagta cgatttaaga   4680
atcttttta atgaaacagt tgtttgtttg tttgtttgtt tgttttgact ttggtttttc   4740
aaggcagggc ttctatatgt atccctggct gtcatgaaac tcactctgta gaccaggatg   4800
gcctccaact caagatctgc ttgctcctgc ctcctgagtg ctggattaaa gctgtgagtg   4860
tcatcaccag tagaaataat tgattttatt tattgttatt tgattgcttg cttcttcaat   4920
tttgaggtgg gcagagtcat cataggtact taccaaacag agggagaata ggctggaatt   4980
cctttaatct ttgcagaagc agggggatat cttagttcat ggccatcttg gtctacaaag   5040
tcagttccat gctacatagt gagaccttgt ttcaaaatca aaagccagac caaaccaagc   5100
aaaaacctca aaaggtgagg tgtaggttct tagcaaacct ttgaaaatta acctgagaat   5160
gtaagagttt tcttaaattc tagtctgctg ttagttatgg catagcaccc agtggttcct   5220
gctgtagctg acatccctgc gtagcctcag cctcttatga gatgggatgg taggtctgag   5280
cggagaacag agaacgacag acccagtgag actaaccccc tgctctcttt accatctgcc   5340
ttaacttcct tttccggggg ctacattcct agctcaagat ttcttttttc catgtggaga   5400
attcttccat gtcttctaat ttattgatcc catgttcagt acatgcatga tacttaagtc   5460
ataaaataga gccttttgtt gttgcttttt cctccttcct ttttgtgtca aacaggatat   5520
gttttggcct gttgaatttt ggaaaattag attcaccact ggaggtatat acagtgggaa   5580
attactatgt tcagtgtgca cttgtacaca ggccagaaga caccggatat ccacctctgt   5640
aactttctgt cttattcctt tgaggcagaa tttcttctta actgtgggca tcttactgtg   5700
tcactctgcc ttatttcttc caggtcaggt gtctccctta acctgaggct tgtgtgtttt   5760
gctcggctga cagtcagcaa ggcctagcag tcttcctgcc ttggatcctc agagtgcatg   5820
gattcctggt ggatgcagga tgatgccaga cttgttatgt gggttctggg atccaaactc   5880
```

-continued

```
aggtctccag attgtgtagc aagtgctctt aaccactgga tcatgtcttc attccacatc   5940
ccacctccgc tttttgagac aggatctgtt actggcctgg agtgggccaa agaggataaa   6000
cttctggtta gagagcccca agctcactgg gtttcggctt taccaatgct ggaaatacaa   6060
gtaaacgcta ccatgccttg tcttttcatg tgggttctgg agattaactc aggaccttat   6120
tgcttgattg gcaattcttt tttgattgag ctaccaagcc ctttattatt aattagtcag   6180
tgttcttaat tgctggtcat atctccagcc ccactttccc cccaccccc cccaaaaaaa   6240
gattttaatt aaattatgca cattggtgta gtagttactt ttctgtggcc atgaagagac   6300
accatgacca tgggaactta gagaagcatc gctttattag acttgagttt tccagaggtg   6360
agtccatgat cactgtgact ggaagcatgg cagcagctgt attacttcca acaaagccat   6420
acctcttaat tcttcccaag acactaacac caactgtgga ccaagaatta aaatatagga   6480
gcctgtgggg accattctca ttcaaaagac cgtaattact gcatgtatgt ttgttcatgt   6540
gagtgcaggt gcagaagagt gtgttgattc tcttgtagtg caattacagg tggttgtgag   6600
ccatctaatg tgggttctca gaactgagct catgtgttat gcaggaatgc caagttgtct   6660
taacaactga gccatctctc cagcccccca aatcaatcaa tttatctctt tttttttct   6720
ttctttttaa aggaattgaa ccattttact aactcagcag ttaaaataca ataaactttt   6780
tgtttttgag gcaagtctca tttagactag gctaggttga aactcactat gtctctgagg   6840
gtgaccttga atttcttttt ttcatttttt aagatttctt tcttttttg tttttttgtt   6900
tttcgagaca gggtttctct gtatagctct ggctgtcctg gaactcactc tgtagaccag   6960
gctggcctcg aacttagaaa tccgcttgcc tcttatttct tgatattgag tacactgtag   7020
ctgttttcag agacaccaga agagggcatc agatcccatt acagatggtt gtgagccacc   7080
atgtggttgg tgggaattaa acccaggacc tctagaagag cagtcaatac tcttaaccgc   7140
tgaactatca tctctccagc cctgatctta aatttctgat ccaagtgcta tgatcttata   7200
gttacaacca tgcctgtctt accatgtgct atggatggag ccagggcttg gtgcatgcct   7260
ggcaagcatt ctaccaactg aactgcatac tcagtggata acagttttgg aacgaaactt   7320
cagttggtgt acttttatgc agtagacttg tggtaccaag tttgactcta ttttcctaga   7380
atttaagaag taaagactta cgttgagaat ggtagccgtg tatcagtaaa caaaaatggc   7440
tggagagtgg ttctgccatt agaagcaagc actggctgct cttggagttg actgaggttt   7500
ggttccagca catactggtg ctactaccca cagctataat tccagtagat ctattgccac   7560
cttctggcct ccatggacaa caagcctgca tgtgttgcat atatacacac aggcaaaaca   7620
tacacataaa gtcgtttaaa atacaaaata gagaaaagtt ctctgatgtt acaatattat   7680
aaagaatctt gaaaaatgtt tccattattt gtccagtgtt ttgtcagcta tataactgat   7740
ttcatccaga tgttgtaata ataaaagaat gtctttaaca cccctttgaa aatgtaggct   7800
tgaactcagc agagtctgag ccaactcccc aaccctcagg tagtaggcac tgcttgtata   7860
acctggttga attgcttgac ttgctgtttt gacagggtct gggtgtgtgg ttcaggctgg   7920
acttaggctc tccatctctc ctgagtgttt aagagatgga catgagaacc tcagctgggt   7980
agtgagttca aggccacttc tgggctacat gagactgcct cagcttcccc agtactagga   8040
ttataggcat gacctaccat gccttgctaa atccatctat ttttaggatt gctgtcctat   8100
tttccatgat gacttcagta ggtaaatatc agggagtgag tccattgtaa ataaaacagc   8160
actgtcctaa agggcttcag tgccagcaaa gatctgtgaa ttctgagggc agacaaaact   8220
```

-continued

```
atacagcaag agagaccatg tctcaaacaa ataaaaacaa aggatgataa ctctttgatt   8280
ttatagcaag gaaacaaacc tagagaaaga aatgaacata tttattaagt atttattatt   8340
tttctctgtg tccaggctat actttagtat tttgttggtt actcattata ttatttattt   8400
ttaaaatatt tatttgcttt atgtgtatat gcgtgcctga gtgtatgtct gtaccacatg   8460
ggtttagaag acttcagagg tcaaaagagg aggacttttt aagtcccctg gaactggagt   8520
tacagatgtt tgtgagccac catgtgggtg ctgggaattg aacctgggtc tctgcaagaa   8580
cagtcagttt cttaacccct gagatatctc tgtagttctt attctctgta tcataaagtc   8640
tcttctattt actccctcca caatttttaa aactttatac cttccttcta agcatggcgg   8700
tgcacaccat taatccgagc acttgggagg caaaggcggg tggatcagtg cgagttcaag   8760
gctagcctgg tctacaaatc cagtctagga cagccagggc tgttacacag agaaaccctg   8820
actccaaaaa caaaattata ctttaacttt tatatttctc cttttcattt ttacagtagt   8880
tgggtgacca cagtaagttt ttcctgagac aggctctcaa ataccatgct ggccttaatc   8940
ttactatcct aagctagggc ttgaacttcc agaccctact gcttatacct ctgtagtggt   9000
gggattagag ttaggtgcca tcactccagg gctattgggc tcaagatagg ggcttcatgc   9060
ctgccaggca aatacctagc tgagctacat gggttccagg tcagtcagaa ctagggtgag   9120
gtcctgtctt aaaaaaaaat aataataata aaattgggcc agggatgcag cttagttaga   9180
agaacccttg tgtgtcagat acaagatcct aagtctcatt cctagtacat tgcaaacccc   9240
acctccctcc aaacaccaaa gggtttctaa gctggataag gtggtggcct atatctgttt   9300
tttctttgtt ttttcctttg agaacgagtg taatttagct ggcctaaaat ttcatgtgaa   9360
cttcctgtga ttctcctacc gtctcctcag tgctggaatt acaggctaca ctactgacaa   9420
agcaagtccg ttctgtcaga agattccttc agttgactgc ttttttcata tatatttagt   9480
ttttcatttc ccatgaaggg ggagtcagta ttttccattt ttttccatgt gagttgatat   9540
cagtaaacct taagttcaga tatgtaaatg catatatatg tgtgtagaca aacaactcca   9600
tcaactttgg tgtctgtttt tgagacaggg tcttaccatg tagctttagc tatcctcgat   9660
cttgctatgt ggaccaggct ggtctagaac ttaaattaac ctgcttttgc ctcccatgtg   9720
ctgatattaa aggtatccac caccctatct agtaattttg ttttttagac ttattttttta   9780
attgtatata tgtatatgtg agttcaggtg cccttgaagg tcagaagagg tgttgggtcc   9840
tctggtgctg gagttccaga ttgagcttcc aggtgtaggg aacagaggaa gtcctgagta   9900
actgcattgt tgacatgcac gtggccatat tgaggtctcc aaggccacag acccatggga   9960
gattgacaaa gccattaccc atatggccag gctaaagaga gtgacaaagc tcttctgaat  10020
tctagtatga gtgtgttagt gtgtgcttac atgtgtataa atgtatgtgt gtgtatgtgc  10080
gcatatgtgc gcgtgtggag tctggctttc cctcatccgt ctacctctct tacccaagtc  10140
tggggtttta tatgtgtgcc actatacctg ccttgtagat gactaactcc tatttggtaa  10200
tcttttgtaa agtattttag tatcagtttt cagaaagaat attggtttat aattggcata  10260
tttttttactg tttgttttgt tgtgatatca gattaatact agaatcatca gtaaaatgag  10320
gccaggagag gatatcacat ccaaatattt tcttgaagag actatgtaga actcatagta  10380
aagtaatttg aacctggata tttctttttg gagtacagtt gtagaactat tattattatt  10440
attattatta ttgagacagg gtttctcttt gtagccctgg ctgtcctaga aattactctg  10500
tagaccaggc tggtcttgaa ttcaagagat ccacctatct ctgcctctgg gcttaaagtc  10560
gtgcaccact gctgcatggc tattacattt gtttatttat ttttatattt agtcagttat  10620
```

-continued

```
aattgtatgg gcttttccta gtgttgttgg tcttgaagta aaagcttaat gattgatttt  10680
gttttgtttt ttaagatgta tgtgtgtgtg tgtgtctgtg tgtgtctgtg ttattatata  10740
tatgtgccct tggaggccag aagagaaact ctggaactag agtttcaggt gactggatta  10800
tctgccgtgg tgctagggat agaactttgg gcttttggaa gggagccatc ttgctaaccc  10860
tttgctttgt tgctttttgt tttctgtgat acagcagtgt tgtaaattgc ttaccaggta  10920
gagttttaat tgtctcccgt aattttaatt ttgctatatt gtatttaaat tttttgttta  10980
ttgttgttat tattcctcct cctctccctc ctcttcttct tctctctctc tctctctctc  11040
tctctcttgc tctctcgctc tctcgctctc tctgtatgcg tgtgacacat ttttctaagt  11100
cagttttctc ctactgtggg ttcaagggca gaactttgat cagatttgca tggctggtac  11160
tttttctctc tgagtcacac tgtcagctct ctagtatatt tttgttttat gcacttgtgc  11220
atatctgtgt atgtgcttgg agtgcagtgc ccttagagac caaacaagga tgtaggatcc  11280
tctagagcaa gaggtacctg tgtttgtgag cagcccaaca tggtgccttg aagaactctg  11340
caagagcaga gcttgtgcct cacttacatt tagttaagct tgtgacagtt ttcttttgag  11400
actttgactc attcattaat tgtattgtat ttttttcatg tttgtagaga ttttcctatc  11460
tttttccttc cttctttcct tccttccttc cttccttcct tccttccttc cttcctttct  11520
ttctttcttt cttttttttga gacagggttt ctctgtgtag ccctggctgt tctgaaactc  11580
actctgtaga ccaggctggc ctcaaactca gaaattcacc tgcctctgcc tcccaagtgc  11640
taggattaaa ggcgtgcgcc accatgcccg gctttttttt tttttttttt aagatttatt  11700
tatttatttt atgtatttga gtcagatgat cgtgatccat catgtggttg ctgggaattg  11760
aactcagacc tctgctcgct ctaacccaaa gatttattta ttgttatatg taagtacact  11820
gtagctgact tcagacactc cagaagaggg caccagattc cattacggat ggtggtgaga  11880
caccatgtgg ttgctgggaa ttgaactcag gacctctgga agagcagtta tatctccaga  11940
tataatgttt ttcttttagt tgtgtcagat tttacaacac attttgccct gtcttgttta  12000
gtatatgtgc attgctgtgt tactggtggt ggattctcac tctgtaattt cttcaggtaa  12060
attttatttg ctgttttttt ggttttttttg ttttttttgg tttttcgaaa cagggtttct  12120
ctgtatagcc ctggctgtcc tggagctcac tctgtacacc aggcaggcct cgaactcaga  12180
aatctgcctg cctctgcctc ctgagtgctg ggattaaagg cgtgcgccac cacgcccagc  12240
ttatttgctg ttttatcggg tttatttgta tatataacaa ttcctataac cacagcttta  12300
ggaaaaaaag cttggtctct ctgtgtcccc tggctaggct cagtcaccta acccaattaa  12360
ttgacaacta atgatgaaat acagagattt actcattgtg gtcacattgt cctaggaaca  12420
gatagaaggg tccagtgacc cctaagtccc tttaactata ttgacttcag ctttaggttt  12480
aagtagaaca gttagggcag caggccggag gtttagccag tcctgaacac agtgtctcat  12540
tgtctcgggt cctgctaggt ggatgaatta aattgttgct gacaggacca ctgtggctcc  12600
tacaagatag tgcattctgg gtgtagcctc ttcatcacag gtaattgttc tcactgtctc  12660
agccgaggca tagcttcagt tctttatctt gtttctgctg gaatccaagg tgacaagaag  12720
acagattaaa gacagtgacc tagctctgtg tctccagaag taaaggagac agacagacaa  12780
aacggaggcg gagatgccag cctttcatct tactttagta aagcaaaggc tcacattggt  12840
ctttgcaaga gtaacttctg tcttagttag gttttctggt gctttgatga aaactttata  12900
tgtgaccaaa acatgttggg gaggaaggat ttatttcagc ttatacttcc acatacacat  12960
```

-continued

```
cacagtccat cacttaagag agtccaggca ggaactcagc agggcaggat ttggggacag  13020
gaactcaagc agaaatgact tggtttactg gcttcgtctc ccatggcttg ctcaacctgc  13080
cttcttatag cacccaggac caccagccca gggatggcat tacctacagt gaactgggcc  13140
ctcccatatc aatcactaat taagaaaact ttccacaggc ttgcctgcat accaatctag  13200
tggggcattt tctcagttga tgtccctgtt ttcagtgact cctttgtcca gttgacatga  13260
agcatagcct ctaaggctgt tgcagtccca cttaactttg gttaatgtgt gcatgatgtt  13320
cctttccttt cccctttctt tctttttttt ttttttaaag atttatttat taatatatgt  13380
aagtacactg tagctgtctt tagacactcc agaagaggga gtcagatctt gttgcggatg  13440
gttgtgagcc accatgtggt tgccgggatt tgaactctgg accttcggaa gagcattcgg  13500
gtgctcttac ccactgagcc atctcaccag ccctcctttc ccctttcctt tcccctcctt  13560
tcctttcctt tcctgaggtg gagcaccgag gatgactttg accccccagc cccgagtgct  13620
ggagttatac acccagagcc tctagcatgc taggcccata ttctactggc tgagccatac  13680
tccaagcccc atgctgtgac acagggtggg tccctttagc aagttcttga tctcatggat  13740
aaaagattga agaggctaga gagatggctc agtggttaag agcctgcatg actcgtccag  13800
aggatctgag cttggtttca agtgcccatt atcagggcaa ctcccagctg actgtgcagt  13860
gccctctttg gcatccgtag gcagcagcac tcacatgtgc acacatcctc ctcactactc  13920
cccaccacaa taaaaataaa tccttttaaa aaaatgtgct ttgaagggta tattttacta  13980
gagtcagtaa gaaaaggcag ggcaggcaag ctagagatct cagcattgtc atgaggaagg  14040
aaatgtaaag aagacaaaaa ggaaaaagtc acatccttaa atagaacagg aggaaaacga  14100
cctcttgggg gacaggtgac tcacggaaga actggggtat tcagagccca tcaccaaact  14160
gccctccttg gtagacgtac tttatggggc ggtctcactg cagcccaggt ggcctgggat  14220
tagcagccat cctgaacgct gcttttatag accagaagct ctacacttgg atggaaatag  14280
taatactact tggtttaggt ttgtaatcag tcaagagttg ctctatgtgg cctaggactc  14340
agatgtgttt aagattagaa agaataataa ctgtatgtag tgttgttagc ttagtgtcta  14400
gttttattag ctttggatca ggaagggatg aataacagtt ttgaactatg tcaatttacc  14460
tttaaaatgg tttacaaatt tgtttatggg agttcttaca tgtgtgtgca cacatacatc  14520
agaggacaac ctcaaatatt gttccttaga gtagttcacc ttgttatttg agacagtctc  14580
tcattggcct tgaacgtata acaagatggc cagcttgtct acttgttttt acctcccagc  14640
ttctacatca gtgctgggca tctgacctca ggtccttatg ctattatggt aaacactttg  14700
ctgtctgaga catgtctctc taatcccagt ttacctgttg gcaaaggcta gttttggact  14760
aatttgaagc tcctgtcatt ggctcatttt aaattttcct tagtttttgt tttgttttgt  14820
tttgagagtg tgtatgtgcc catcttgatg aaggtacaga ggtcagagga cagcttgcct  14880
gagttaggtg atcagggtcc tgctcagtct tggcaggaag ctcccgcatc tgttaagcca  14940
ttttcctagc cctcaaaacc tgagnnnnnn nnnnnnnnnn nnnnnnnnnn nnnnnnnnnn  15000
nnnnnnnnnn nnnnnnnnnn nnnnnnnnnn nnnnnnnnnn nnnnnnnnnn nnnnnnnnnn  15060
nnnntcttgc ttctctggtg ctctggttca ttctcattga tgcccatgat ctattgataa  15120
gatcatatga catttttatt tgaattatac atatttctat acaatacagt ccctactttc  15180
ttccctccca tccacacttg ttttccccat cctgttaaga tggtcttgct atgctggcct  15240
taaactaggt agctagcata ggttgacctc aaacatgcag gcccctttgcc agtctcccga  15300
gtgtcaacat tatagggatg caccgttatg cctggttcac ttacagcttt tattcccaaa  15360
```

-continued

```
gttcccattt ttcccccata ttctatgttt ttatttgcta agactgttta acatttgttt  15420
caaatgttct tctaaatact tgctgaagaa tttttatcag ggctacttgc aaaacttttg  15480
ttagataatt ctaacatctg tattgtctta gtgttggcat ctattagctg atgctccccc  15540
acccccgccc acagctctct tgagacctgc ctgattcttt gtatgaccag tgattttctt  15600
ttaaattaaa aaccttgata attttgtatt ttaaatgacc tgttctgaat atgtaattct  15660
tctaatacat acatgattaa gccatagctt aaacatttct ttctttcttt ttctttcttc  15720
aagacagggt ttctctgtat agtccctctg gctgtcctgg aacttgatct aaagaccagg  15780
ctagcctgga actcagggat ctgcctctct ttgtccccaa gtactaaaag gcgtgcagta  15840
ccactcttgg ctttttgtgg gggttttgag tcaatttcat gtggcctgga tagtgtggct  15900
ccaaatccac tttgtataat aagatgactt tgaactttgt tttgttttgt attttttgag  15960
acaggatatc tctgtgaaat tctgactgtc ttggaactct atctgtagac cagactggcc  16020
ttgaactcag agatctgcct gcctttgact cctgaatgct gctgggatta aaggcataaa  16080
ccaccattcc tgattttcct ctttccagtc tttcaagtgg tggaatcaca gatgtttgcc  16140
accaggcttg gcttgagcca gactgccttc ctgcctgcct tatttccttt cttccttcct  16200
tcttttcata tttaaattgt atgtatttac ttgtgagcaa gtgcatgtct ggaggtatat  16260
gcctacctat gagtcagttc tctctttcca ccatgtgggt gtgaaggatt gaattaaggt  16320
catcagaatt ggcagcaagg ggttttgatg acccctggtg tgagtatttc ttttagccag  16380
catcatgaca ttgattgctg agaatatgga cgatattctt ttacgacaga aatgacatca  16440
gatgtaccat cgctgggtcc caccattgct tctggaaacc ctggacctgg gattcaaggt  16500
ggaggagctg ttgtacagag ggctattaag cgacggtcag ggtaagtttg aatgtttatc  16560
atccgtgtgt ttctcttgta ccatcaactt ttgagttagt tgctgttggc tcttgtttat  16620
tcctgaccac acatctaatt gattacttac tatactgctg tcacataact aaaactaact  16680
cttagtccct ggattattcc ttatccaggc tctctatttt aagtaaattt ctttaatttt  16740
ttttgtataa tttgaatata aatatagctg taaagaaaaa aatgaggact ggagagatgg  16800
ctcagtggtt aagagcactg aggtcctgag ttcaattccc agcacccaca tggtggctca  16860
caaccatctg taatagaatc ggatgccctc gtctggtatg tttgaagaca gctacagtgt  16920
gctcatacat aaataaatgt atcttaaagg aaagaaaagg atgaaacggt cacacctatt  16980
acttatcatc cgacctcact cacagtgcct gtatgtcacg tagggttttg gcttttatta  17040
cttacatcgt tttcacataa aaatttctat acaggttaaa aattgttttc tagtatcttt  17100
attgataagc ctgtttaaaa aaaaaaaaaa cgaagccaaa ccaaaccaaa attttctgaa  17160
aggtaaaggg actgtggcaa agaagagttt cactgttggt aaaaacaaac aaacaaaacc  17220
aaaccaaaaa aaaccccaaa aatctgttgg ctttccttaa gctctggtct gcattctcaa  17280
aatcattttg ttaagcttat ttctttttta atttattaat actttctttg acttggagtg  17340
cacagttcat ttagtttcaa aagtctttat tgaagtacca gatttgaatg tgccattgaa  17400
gtatgattgc tgtcttagtc aggatttcta ttcctgcaca aacatcatga ccaagaagca  17460
agttagggag gaaagggttt attcggctta cacttccatg ctgctgttca tcaccaaagg  17520
aagtcaggac tggaactcaa acaggccatg gagggatgtt ctttactggc ttgtttcccc  17580
tggcttgctc agcctgctct tctatagaac ccaagactac cagccctgag atggtcccac  17640
ccacaagggg cctttccccc ttggtcacta attgagaaaa tgccttacag ctggatctca  17700
```

-continued

```
tggaggcatt tctccaactg aagctccttt ctctgtgata actccagctg tgtcaagttg  17760
acacaaaact agccagtaca attgctaata ggctctaaag atagatagga aaagttccta  17820
aagttctgat ggtcgttata tttatgtata aatatacaag acacagtatg acaaaagtct  17880
gcaatacctg aagttctagc agtcagtagg gctgagtcag gatggagact gagtccatcc  17940
tgagttacat agtgatactc ttatctcaaa acaaagcgaa aaacaaatta attttaaaat  18000
attatttttt aaatatatag aaacactgct tttggacggt aaagattgag aaaagttttt  18060
aaaagaagtt tgctttaggg cagtggttct caactttctt aatcctgtga ccttttaata  18120
tagttcctca tgttgtggtg actacaacca taaagttatt attattttta tttttatttt  18180
tttggttttt cgagacaggg tttctatgta tagtcctggc tatcctggaa ctcattttgt  18240
agaccaggct ggtctcgagc tcagaaatcc gcctgcctct gcctcccaag tgccgggatt  18300
aaaggtgtgt gccaccacgc ccggcttcat aaaattattt tagttctact taataactgt  18360
aatcttgcta ctgttaataa ctgtaatgta ggatatcaga tatgcaactt ccaaaggggt  18420
cgttgtgact cacaggttga gaacagctgc tttagggcct gtgaggtagc ttgttaaaag  18480
cctagttagt tacctttaat tgattcccag aacccacaca caagtagaag gagaaaacta  18540
actctaccaa attgccctct gacctctaca tgagtgtggt acctatatgc acacactact  18600
aaagcacaca aaaatattaa acttaaaaat gaatgaatga gcagcaacca catggtggct  18660
cccagccatt tgtaatgtga tatggtgccc tcttctggcc tgctgacata tttgcaagca  18720
gaacacttaa agcagtcaac actctcaatc tctgactttt ctccagccca aagagtgcac  18780
gctactcttc cagagaatct gaattcaggt cctagaaccc atgtcagtga ctcacatctg  18840
tgatctagtt ttggggttct gccacccctt ttctgggtac ctgtattcac atgggcatat  18900
atccctatac agacacatca taaaataaaa tcattttaaa aatcataaaa gatgctctct  18960
tcagtattaa aaacacattt caaatagtgt ttgctttttt tgttttttaa caaagtctgt  19020
ttaatttgat tttattattt tgacatagct ttcttgtaga ctcagctggc ctgcgttctt  19080
cctggttcca cttcccaagt gcttggaaac aaaaacatgt gaccaccaca cctagtttca  19140
gacagtcctg ctgtgtagcc atgttggtct ggaattcagt atgtacacaa agctggcctc  19200
ccactcatga ttctcctgcc ttagcttcct atgtcgcagg actacagtca agtgccacta  19260
catctgggtt ttgtggcacg tctttaaggc cagcccttga gagacaaagg cagtgtgggt  19320
gggagggcag cttggtgtac atggaggttt ctgggacagt cagagctatg tagagagatc  19380
ttgtctccaa acccaaaccc aacctcattc tcacttatta tatatattaa catgcattta  19440
tatgtttatt tactcactct gtgtttgtgt aggttagaaa acaagttgtg ggaaatcttt  19500
ctttaccatt tgggtcccag ggatccaatt tatgcctgta ggcttggtgg caggtttttt  19560
aatttgctga gctgtctatc tctctggcct cttgctttat agttgctgtt gtctgggctg  19620
aaaagctccc tgagggtatt ttttttcttt taccacgggt cccacactat tttgtgtggc  19680
gtgtgatctt gctttcttgc tttcttcttt gacaggatct ggctatgtag cttaagctgg  19740
ccttggattt atcatccttt tgcttctact tgatgaatac tttgagctaa aggtacgtgc  19800
caccaaggct ggccacttag cacagtgatt tgaatatggt atatatttta tttttagact  19860
aacaactttt tgtgtcttct ttcctctatg taatattgct ttgaaagatg tttcagaaaa  19920
ctgacaaggc ttagattaga tcataaaaat gaaaactaga tctcagggat tttctgtttt  19980
tcaggcaggg tctcacgtag ctcaccctaa ccttgaactc agtggtatag ccaaggttga  20040
ccttgagctc ccgatcatcc tgctgccacg tcccttgtgg cagaattcca ggtgtgtagg  20100
```

-continued

```
tgtgtgccac catgtccagt tttacgctgt actggaattg aaccggggct tcctgactcc  20160
tcagctgagc tgcattctta gactctgggc gctatttata ctcgtatctc ttcctggtta  20220
tggtactggc ctcctgtatg gaatccctgg tggaggggga gggggtcggt gctgctgctg  20280
ctgctccctc acttcttcat tttgcttttt gaaacagggt ctgattatgt agccaaggct  20340
agcttagaat tcattatgtg tctgaggata gccttgaact cccagaaccc accacaggct  20400
ctggacggtg ggttctatat aggcaccgct acggctgcct tttactgcct aacttctgcc  20460
cagttgtaat actatgaaaa gcatgtatta tagacatgtt tttgttttgc ttctgtccac  20520
ttttccttcc attaaggtga gtacataggc atcttttgtt aatatgtttt gctttcttat  20580
ggtgttatct ttactgtatt atcatcaata aacttagaat attgtttgtt gcctttcccc  20640
aggctggatt ttgatgatga agtagaagtg aacactaaat ttttgaggta agatttaaaa  20700
atatttttag agacttctta gtggggtgga gggctggtgg ctggctcagc aggtaacagc  20760
actcctgcca agcaggatgg tctgagtttg atacccaaag ttactgctga aggagagagc  20820
tgactgctgt aaacagccct ctgatctcca catgctggct gaggcgtgag cacccatcac  20880
cctcacagat aactaaatgt catcagatta ttttcagatc accagctggg aatgtagctt  20940
ggtgggatgc ttgcctccta tgcttcaggt tcaatccata gtaccaagaa ggttatttaa  21000
gtatgtttat actttgggca ttgtcctaaa gaatatgctt catcctaaaa ctatgttttc  21060
ctacatcata ggatagtttc aggcatttta ttatttttag agagaatact tcagggagga  21120
gggcacagaa aatataagcc agtcatgttg attcatggct taagagaagt aacacactag  21180
ggagattgct cagtggttaa gaccttggcg ttgcaaatct aaggctaata gttcagatca  21240
ccaaatctca cataaattct gagtgggcat agcagcctgc ttcctgtctt ggaaggtaga  21300
gacaggagag caagctggca ttgagaataa ttctatctgc aacctgtgaa tttgattgag  21360
aaattttgtc taattgaata aagtagtaga gtgatagagg aggattcctg acattaacct  21420
tggacctcta cctgtatgtc cactcacgtg taatgcaccc acacgtgtga gtgctgagtt  21480
tgttattatt ttgttcccat ctgtcccatg agccctgggt gagattaaat gaggctgcct  21540
catcaagtaa ggtagaagag agatgaaggg ttatatcaac tttgggcttc ttcatacttg  21600
ttcacccaca cacatgagca cccacacaga cctgtgccta tacccataca aacatgcgta  21660
tacatacaaa tggaaaataa aaaaaaaaag ttgattcgtt ttcacaggtc tataattgac  21720
taaatcttgc ttgggttcat ggtaagattg tgctcagcca cctggtctat taaaagttat  21780
actcaactgg cacagttgca cctctgtctg tctgtctgtc tgtctgtcta tctgtctctg  21840
tctgtctctc tctctcttgc tctctctctc tcatgttctc tctctctcac acacacactt  21900
gcactctcac ttaaactctt tctccatctc tccctcctta tttctcctat ccccattgtc  21960
ttgtcttcaa acagaggagt gtggtgatgg ttgtaacaca aagggcaagt ctccgtgtgc  22020
ttaacaagcc cctgcttctg tgcttttgtc cttcactgat gtctcctagg ccagagcgct  22080
tgtgtatccg tgtcctgagt cactgctgta gagggctaca gaaggacgta gatgttagag  22140
ggaataattt gataatgctc tactctgtca tgctgcagta cctgttggcc cctttttttag  22200
gtagcaggaa ttagaggttc tgtatgtata aatggtgatg gttgggcagg gtctcatgta  22260
atccaggcct gcctcaaact ttatatagcc tgagatggga tggcggcttg aatgagaatg  22320
ctcacggtaa ggttgtgtgt ttgagtgctt gctccccagt tggtagacct tttttgaag  22380
ggttaggtgt ggccttggtt ggttgtgtgg cccaagtgga tgtctctagg actacctgcg  22440
```

-continued

```
caggggaggt agtgagatag actttcctca tcaatcaata atcaaaataa tattacactg  22500
gcttgcccac aggccactct gatagagaca ttgtctcagt tgggattccc tcttctcaga  22560
tgtctaggtt tgtgtcaaat tgatagaaac gaaccagcac agcaattaaa cgtaattctt  22620
ctgatactta gtggatccta ataaatgtga agaagaaaaa agatttcact ttttgcccta  22680
ggcaagcttt cattgttact gctggattta tctattttta tcttaagtgt tttacctgta  22740
agtgtgtata tcgtgctggc agaggccaga agagggagtt gggtcctcta gtactaggag  22800
ttatagatga ttgtgagctg ccatatgggt gttggtgtta tggagtatcc accagaggat  22860
gcttggatat ggatttaatc caatagaaag ttactattag cctgccagca actacactgg  22920
tgtttgggat tccaatgcag cactcagcct ttctcagggt gagcttttaa acacgacagt  22980
atgttctgtg ttgttggcat acttcagtta acaagaacag ttagccagaa gcagaactgc  23040
agaagccaaa gagactttcc cagaactgca gactttgatg gattaggcct ttgttttagt  23100
tttggtaggt agtgctgtat acatactgaa tttcacaacc tgaatggttc ttctatcaag  23160
ggatcaattg tgttaaggtc tggagctatg ttagtactgt gaactgaacc caggtcctct  23220
gcaaaagcag caactgttct taataactga gccatttttc caccccctaag atagcatttt  23280
cacacaggac tattgggaat gtcttcatta gagaattctt aattacagtc acatgatgtt  23340
actggaccta tgttgtatga atgctacagg ggtaactaga gtatttgtca ctgtcaaata  23400
gttttgacct tgagttattc cacaaaatca agtagtcata agttttgtaa catttttggtt  23460
cttatcagac tactatatga ccgtgggttc aaacaattat aatgggagtt ataaaagtct  23520
aattacatag gacatagcta ttataacttc agagtgcaaa gaattcatca ttcatgtttg  23580
tgatgatatt cacataataa tgttgacatg atggtgttgc tggttgtatt taaatgtagc  23640
acatatgtgt acagttaata acacttgagt ataaaaaaat cccttgggta tgtatttact  23700
atgttacaat gttcattcat gtttgcactg ttagtaatca ggcacaggga ttactgaatg  23760
ctggggaagc actgtgccac tgagtcagcc ctggccccta ttgttgttat tttagagctg  23820
cccctttctt actgaatgac aaagtttact ttaacacatt gtatcatgta attgccagtt  23880
tgtgaaactt acttaagtcc taatagttct ttttgcttgt cctgaagaag taaaatgtag  23940
aattgggaaa aaatacttgc aaatcatgga tcttagcagc agtcggtatc tagaatatgt  24000
aataaactac aattctgata caacctttga aaagtgattt aatatttaag atgaagaact  24060
gtgggaattg gagagatggc tcagctatta agagtgcttg ctgctctttg agagtactag  24120
agttttgtac ctggaaccca ctttaggcaa cttacaactg cctataacta cagcgccaaa  24180
ggatctagtg ccctcttctg gcttccacag tctcccaaac acatggcaaa gcacacactc  24240
acaaatagaa atagaaataa atgtttattt attttaagta gaatttggta caacttaatt  24300
cagtgcttgt ctagagtgca tgaagctctg ggttcccttc ccagcactgc ataagccagg  24360
catggtggga tacacagcct tggggagact taatcaggac gattataggt tcaagtttga  24420
ggtcaccctg cactgtatag ccagacctta tctatacaag attaaaaaaa ccaaacaaaa  24480
caataatacc cccagccaag tatggtacct gtaattccag cactggggta atggcagcag  24540
cttagtgagt tctaccttaa tcaagttaca taggaaacag tttcaaaaag ataagacaga  24600
aatgacagca gctgtgctct tgatgctgca cagtggttaa aatagggcta cagtgtagct  24660
cagtggtgaa gcgtgtgctt agcgtgtgca cggcctgggc ttcattccca gcactactct  24720
gcgtgtgtgt actaagaagg aaattctgaa ttttattcat ccagttcagt tagtgtccat  24780
ggatagacag cgatagtaac tgtataggca tgcctttgtt gctagtgtag gggaagaaag  24840
```

-continued

```
accttccttt tcttctaagc attttgatga ccaagttgat aagacaaact gactggaggc  24900
aggtaaacag aagaggtaga tagactaata tgtggtctaa gagtagccta gctgcccaaa  24960
gggaaaacag taagtgtgca gtcagtgaaa ttggagaatt tatatggtct cataggaatg  25020
gcaacatagg caactcagta gaagattcac agatacgatg aatgggcatt tgagtaatgg  25080
gtgatagttg tggcacagtt tgccttgatc tatagttgtc tcttgacctc ctgtcctttg  25140
gttgagtact ctttccaggt tgataaatct tcctagaggg tatttgtggc tataagagaa  25200
cttaatgaat gtgtgtgtgt gtcattgtgt gttttaaaca ttttgcgtgt gtgtgtgtgt  25260
gtatcttgac acatgtgcta cacatgtatg aaggtcagag aaaacttgga ggaataggta  25320
tccgcgccct ccccccttcac cgcccccccc ccctcccatg taggttctgg gaactcagat  25380
cagcaggctt ggcagcaaat gttttatcta ttgaaacatc tcaccactta cctccatttt  25440
gtttgacaga atcccacttg gtaatccaat caagccttgt atagcccagg ctttacacaa  25500
atgtacggag agcctctttt ctcagaggct actgtaggct caagccacta caccctgctt  25560
agcacttgtt tttgttttgt tgtaaatagg tctgactctg tagctttggc tggcctgaaa  25620
cttccagagg tctgcctgtc tctgccttct aattctggga ataaagttgt gacccctaac  25680
acagtattgt tttttcacat tctttctaat ctgaataatc agtagactag agcattgagg  25740
tattttctga ctcctttgag ttaaagtcta tctcttcatg tgctgcgcct cttgtgggga  25800
ggacagtaat cagctagaca gatgagagca cttcaatagg acaggggtat tcacactact  25860
gctgtgtaac tgaggcccat attagactga agacctcaag actttggggg aggacacatt  25920
tcatctttag gctgacgtgg tgaaaaggaa gtgaaatggg atgttagcta gagaggcttc  25980
ctagaaaagg aaagggaagt acaaagaccg gaagcaagac gggaagaatg tagctgctgt  26040
tgggaacaca gagtccttgc ttgtaggcca cagttaggag ggaagtagga atccccagaa  26100
ggcagtagcc aggagcttta ccatcttgga gaacctttct cagaggaaga gttagggagt  26160
agtcttgttt caatttaatg cttttgtttg tttgttttac accaaacata gattactttc  26220
aaagttggta aaagcaaatt taaaaatgaa agggggaaaa atgccaaaag acatggagag  26280
gcatttctcc aaagaaaaga tacaaatggc caagaagcat gtgaaaggtt gacattagta  26340
atcattcaga gatatttagg aggtatacaa gtcaaagata acatttatat ccaatccaga  26400
gaccactatc aaaaccaaaa caaaatcgga gctaagtctg gagactgata cccaccagcc  26460
tcccatgggt agagggaacc cagggctgca cagggagctc ctgtctcaaa aagacacaag  26520
taacccccca gaaaataaca aaattgctag agaagtggag gaatcggaac agttatacac  26580
tgtgatattg taaaatggta cagtcacaat ggaagagaat atggtgccac tttacaagtt  26640
acagctcagg gtcacttgcc tcacaagctt aaaagattcg attgctcata ctaaaacttt  26700
gtatattagc ttttttctga agactttaga aatttttatt tttatatgtg tgttttgcct  26760
acatatgtat cttgcacagt atgtgtgcct ggttcctaga cctggagtta cagacaattg  26820
taagctgcca ggtgggttct gagaactgaa catgggctct ctgcatgaac aacaagtgct  26880
tgtaatcatt gagctctctc tctagcccct aaatgaatta gttttgagct aggtatgatg  26940
gcacatacat ataatcccaa cacttgaggc ttatgtaaaa ggatcgctgt gaattcaagt  27000
ctgagctgct ctcaataatt acacacagag acctaacgca tagagtgctt ttgaggtgac  27060
tgatctcgga acccacactg tgaaaggata gagttgttct tgaaagttgt tctccacctc  27120
catatctgcc ctgtggctgc aaacacaagt ttggttttga tggcctgaaa cttgctgtct  27180
```

-continued

```
agaccatgcc gacctccaac ttgaactgat cctctttgaa cttgcattct gcatgcaggg  27240
gttcagttgt gcacaattta tattttcata catatatata aggcattgta taccccaccc  27300
ctcaccctgg gacatcctct tctcgatagt ccccttcctt ttcccaacta gttcctcttc  27360
tactttcgtg accttttttt ttttttcttt ttcttttgga gtgggatgtt tcattagggt  27420
tgcttaccag tagtatgtgt gagtgattac actttcctcg gggctacaac aatgaagaaa  27480
agctctccca gcaactaact gcttatagat cctcaagggg gtttgtggct ttgtgaactc  27540
ctccccccttt ctatgctagg atgttgtgta gtttttgtag tcacagctgt tgtgaattca  27600
agtatgcatt gctcatgtca tttcagaagg cagtgttcca caacagtctg ccctttctct  27660
taactcagag tgttaactct tatgcaatgg tccctgaccc ttggaggctt tggctatctc  27720
tttcccatcc cccattcctt gtggagtgtt gctgtgttgc tcagaccagc ctcctacacc  27780
tggctcaaat gttcttttct ctcagctgcc taagtaggcc taaagaactg caggcacatg  27840
ctaccacacc cagcttaaag cagggtcaaa atatgggtat tagatgaata cccatattta  27900
tgatcctgtt tttcacagaa gaatgaaaac atgaaaaata tacccacacg ctgttctatt  27960
ggtttttgga tttttgtttt tgtttttgtt tttttaaagc tacaattaaa aaacaaacaa  28020
actgagtcag gcttagtgat tgacacctgt aataagcaat tgggaggcag aggcaaaggg  28080
tctgtaagtt gagagtgaat gccagactag ccagtgctac atagctgtcc ccatctcaaa  28140
aaaacacccc ccccccggaa aaaaaccaaa caaaaacccc aaatatattc ccaactttag  28200
agaaatcaca agacatttca tgttttcatc ataccatctt tctgtgtgtg gtcactgaga  28260
catgatagtc atcggctctc agtgttctct cagatgctat tagtgtctgc tgctttgtgg  28320
tgctggtcca ttatctttcc ctgttgagta gttttattta tttctagttt ttatttcaga  28380
gcggagtaga tataagtaca agggtttgaa ttaatccctg ccctttcttt tcagatgcga  28440
tgatgaccag atgtgtaatg acaaagagcg gtttgccagg taatgtacta gaattcttgt  28500
cctggttatg ggatcaagca gtctaaatgt tggatttaaa ttttatctag gtgagagtga  28560
atttctctgg ttagtctcct cctcttctga agtttgaaac agcctggaat tttatgcatgc  28620
tcattgactt gaagctaggt atatttaaca taatgtttct ctcatgcatg caagttttag  28680
taatgtgtat attgcatcta caggatcaca aactgtagac ttcttgggca tattatattt  28740
gtacaaatac agaagaatct tttatagaaa atggtttatt catttaaatg agtttttatt  28800
ctggatacca aacttaaatt tgtttaagta actgtcagaa gattatgaaa tatactgatt  28860
ttactttttt tttctcctcc cacccctgat tttacttttt attaaagagt aatcattctc  28920
aactcatata ctggttttac ttttagaaaa ttcttgctgt aagttactct tttaaaaaga  28980
ggggagggtg tcatggggct ggagagatgg ctctatgggt aaaagtgctt gttgctctga  29040
cagaggacct gaatttggtt tctagcatgc acaaccaggg agtctgacat cctcttttgg  29100
cttctgttga cgtctacatg tacatgatca tacatatata tagatgtaca cgtatacaca  29160
tacatacatg catgcataca tacatacata catacataca tgctttattt attatcatta  29220
agtgttcatg cttacttggg gagccaagat gttgggttcc aagtataagc ctgtgtccct  29280
gaccactctc cccagtatct tcaccccagc tgagtatctc tggagagaga cccagaaggc  29340
acaagtagaa ggtttgggca taagggtgaa gctcagcggg agtacttgct tcagtacagt  29400
ggccccaaac accaaatgca caataaagac cctgccttga ttcattgaac ttattcagga  29460
tcaacaaatg tttaatctaa tttcagaacc actcccaaga atttactcat tttttaggag  29520
ctctgctggt atttgggccc ctcatcttct ggtattatgt tttcaaaaca gataggggaca  29580
```

-continued gaaaatatag gaaaattgaa ctgaacattt aacctctcat ttaatttggc aagggacttt 29640
tattgctata taaatagatc tactaattta aacactggaa ataaataagt aaataaatca 29700
atactttaag ctcaaatcct gaaagttttt cccttacaca cacacacaca cacacacaca 29760
cacacacaca cacacacaca cacatataca cagtggtact catgtgcctg tacttatata 29820
tatacattgt atagacacac ttaatgataa taaataatta aaaatttaga agatactgaa 29880
tttttggctg gggagatgac tcaggattta aagtgcttaa ccccagaacc cacataaaat 29940
cttgatacag agtatcccaa gtctatgatc ctagtgagtc tttattgggc gatagaagac 30000
agagatggga atagccacaa actcatggct cagctaactt ggtgtgtgca gcagtgaaca 30060
ataagagtga ctctgggctg gagagatggc gcagtggtga agactgctct tctagaggtc 30120
ctgagttcaa ttaccagcga ccacatggtg gctcacaacc atctgaaatg ggatctgatg 30180
ccctcttctg gtgtgtctga agacagctat agtacagttg tatacataaa ataaatattt 30240
tttaaaaaac ttaaaaaaaa agagtgtctg tctcagacta agtggaaggc atcgaacaac 30300
atctgaggct gccttttaac tttcccttgc atttcatgca cacgcatgca cgtgcacgca 30360
cacacataaa attgagtttg tgatcctctc aaaaattagt aactttattt ttaaatttgt 30420
atgtaattga ttactttaaa aatgatctat ttcattttta attatgtgtt tgtatagatt 30480
atacagtttt tatagataaa tggttatata catatgaatt tggataccaa aagaagacat 30540
caggctccta gaaacgcagc aagcccattt acccaccaag ctgatcctat agcccaatga 30600
atacttactt aaggtttgat tacattgatt gattgattga gaaagtatgt gtgtttgtga 30660
catgccaaca tgctaagctc agaggacaac ttctaggagc agattcttgc ctttcacccg 30720
tgagtcccag tgttgaaact cagatttagc agcaagcacc tttacctatt aagcctgtct 30780
gctatgtctt ctgtgagtac tgatcaacag tgtttactca ttgctcagct gtctgaatgg 30840
gatctacttt gaggaccact gatcgagaga accaagaaat atcaggaaga atagttaact 30900
cttagacaca gtgttggcag tatatagagt tgactgaaaa gagcaggtag gtaggtaggt 30960
agtaggtaag taataggtag aaagagggag ggtagataga atctgctgaa gtattaggat 31020
agctatgaaa tcatgagtac ttgggcccag aaatgttgcc gtgacactag tgaaagaatg 31080
aatataggtt gttttccaag agcagtgtat caaaacttct tgaaataaat gaaatctaaa 31140
ggatacagta atctttaaag tgaaagttaa ttattgattt tgggtaataa tctttcacat 31200
tctattaaaa agtctagcta taaaactgga ggtgatcctg taacacttgt aatggaggtg 31260
gaggtaagag attagaaatt ctaggttagg gactagagag atggctcagt agttaagagc 31320
actggctact ccctgtagtg gacctgagtt tgattcccag cacttactgg tggcgcacaa 31380
ccatgtatga ttcagttctt gggggagggt ggggagtcca atgccgcctt catacatata 31440
tacatacata catacataca tacatacaca catacataca tacgagtaaa atacttacac 31500
acctaaaaat aaaaataggt aaatctttat ttttttaggt tactgggcag cagggcagtg 31560
gtggcacatg actttaatcc cagcacttag gaggcagagg caggcaggat agccagcctg 31620
ttctatagag tgaattccag gacagccagg actagagaga gaaactgttt tgaaaaacag 31680
aacaaaagaa aagttatttg gctatgtagt tcaagaccag cgttggcttc atgtgatcct 31740
aaaaaccaaa ggtcagatca tcattagggc agctaataca ggtccagtcc tcagtctttg 31800
atcgacactc tggaaagcca taaaacacaa cctggagtat ctaatctgcc tatgtcctat 31860
tctgtttaga aatattggag tagagagggg gttgtgtgac tctactatta attttaaagg 31920

-continued

```
aattaattaa aggaatttta aatgattaac ctcaaacaaa aatgcatttc ttagagttac  31980
agtttgttat gatagtttac ctcatacacc accagaaatt cagtaggtga aaagctaaaa  32040
ataggtgaat ttacttatct tttgaaaatg aatgttttgt tgcttgttaa aaactatcta  32100
ggataaggaa caggcaggtg tgactactct gttatctgtc ttctcttcag catgtgtgca  32160
tacattttat agtattcatg actatctgca gttctaactt tttttatttc ttatttttaa  32220
cattcaacaa ttttattcca gtttaaaaga agaacagaac aggtaagctg taaaatgtca  32280
gccagtggct ggaggaagag agtggaggaa agaggaagca aggccacgcc attttaagct  32340
ggcgtggaga tgagacattt gaggggcgct ttagggaaag agtagggaag cccaaaacgc  32400
tggtgagacg catgcttgga aaagacacag agagttgttt tgggtgatca aatgaccctc  32460
tcacaggggt ctcatatcag acatcctgca tatcagatgt ttatattaca aaaataattt  32520
atgattgggg tcaccacagc atgagggctg ataaagggtt gcagcattag gaaggctgag  32580
aagaaccact gtgctagaga aaggagaaag gagaaggtga cagataatga tccttacatg  32640
gctgaggcct gttcaggttc tgctattaga cattagctga ttgtgtttat gtatgtgagt  32700
atgtgcatat gaaggcatat aggattttcc agttgaattt acaggcagct gtaagctatc  32760
cagcatggat gctggggatc agactccgat cctgtgccag aacagtgtgt gcttttaact  32820
cctgagccat ctttccttct cctttttttg agttaagatc tcaccaggcc aggctttcct  32880
ggaacctgca gaaaataatt ttacctttgt ttctgactgt tggtattaaa taaagttgag  32940
caccaccaca gccagttgtt ctttttctac tgatcatttg tgtatatatg tgcatggaga  33000
ggacagagga caactccagg tgtcatttct cagccccacc cccacccccg ccgagatgga  33060
gcccttctct gtcttggatt gcactaggtc gactaggatg ctgttcagtg agcccatagg  33120
atcctcctat ctctgccttt cctgtgccaa gattgtaagg attgtagttt ccactttatt  33180
tttacatata ttgataaaat tattattatt aagctcaagt tttactctgt tgcaaatccc  33240
taggctcaag cagttcttcc atttcatcat caccagtagc taggactaca aggtccctgc  33300
ttcctgctgt atccatttta aggcagagtc ttaggaagtt attttatttg cgtgtctggc  33360
tttattattt tggtttatgt gagacagtct tggcctgtca cccatgctca tgctctcagg  33420
ggatgattga gattatgctc catggaggac aggagagggc gtcaggtctt ctagagttag  33480
agctagagac tgtcatgaat tgctggacat tgaacccagt ttctctggag gagtagccag  33540
tgttccttat ctactcacct catctctcca gccccatcat ctttaatagt gaagtctttt  33600
tggactatta atataccta ctagataatt tatttgaggc ttatctctct taaaatgagc  33660
acttataata ctgagttagc tagtaccttg ttttggtttg tttgcgtttt tgtgtagcct  33720
ggctgtcctg gaactcactt tgtagaccag gctggcctca agctcagaaa tccacctgcc  33780
tctgcctccc aagtgctggg attaaaggcg tgcgccacca cacccagccc ttgttttttt  33840
tcagttgctt ctctctcccc tttttgtgcg gtgggtattg agccagtcct tccacattgc  33900
cctggttatc ctggaactct ctatctctgt gtgtaccaat ctggacttga actcctcaag  33960
tgctaggatc ggaggcacca ccaccatgcc tagcccctgc cacccattct taaagtgttt  34020
tgtttttctg gaagagttta atgaaaacct ttgtctttct tcgagggagg agggattgac  34080
atactggtta aaccatagaa gaaatgctaa ggtgcctaaa ccagagttca ttaaattagg  34140
agtgtgtcag tgatagagaa tatgcaggaa acctagctct tgatttttat catgtgatca  34200
tgtcaagcta cacggctcgg tgtatggctt tcactccaag cctgagaact caggttcttc  34260
ctcacagggt agaaggagag agccaactcc cgcagtcgcc ttctgacctg tggcacacag  34320
```

-continued

```
acacactaag tactacaatg ggaaaaataa atcttgtcat aatttgtgtg tgtgaatgtg  34380
tgtgtgtgag gaaattatat ttctaatccg ttgtttgaag ctgtgtaatc tagtcactag  34440
tagacaatag cgaatgtgaa taagtgtttc ttcccagatt ggcagcagtt tataagaatg  34500
ataattctga taattctgaa tttcctggtt ggttcttgtt cacactctgt atctttggtt  34560
tctgtagaga ttgtttgaca aagtgttttt tgtgttgaga ttatgttagt ttctaattgt  34620
ccttgacttt cgacttataa tttacttgtt acaaaaatac agttctatag gttctcaagg  34680
ttcttccttg tatggccttt cctcactttt tctgtatcca tttcatttct tcctttcttt  34740
ccttttcatt ttgcatttca ttttccctcc ctcgctttca tctgcctttt cttctttcct  34800
ttcttccttt ttattttaat tttcgcttag ttcatcaatt ctgtttttag gtcggatgat  34860
gagcagagct ctgcggataa agagagactt gccaggtagg agctgtgctg tttagcatga  34920
agcacatact gccttcttac cctttgtcta acccatcttt ttttcccttt ctgtattttt  34980
ctcttacctg tggcaaagga ggacatgagg ttttacaagt tggggtacaa taagaacttt  35040
ggcttcccca acaggaagtg ggtgaattaa gccaggtatg gtggctcact cttttgatcc  35100
ctgcatttgg gaagcagagt ggagttctgt aagattgagg ccagcctggt ttacaaagaa  35160
attctaagac agagaaaccc tacctgaggg tgatggaaga ataaattata aattactgtt  35220
catctttaag atttttattt tttctttact tcatcactaa gttccacaga taatgattta  35280
gaagtaatgt ggctgtgtcc acagatgctt taacaggcgc atactctctc agaataccga  35340
taattaccat agttctatca gaataccgat aattaccata gctcccagaa tttaggccat  35400
agcacatact ctgacttccc tatgccgatt cacagtctag attactatga tggtagaact  35460
gattgaatcc ttataatttc tgaggaaagt tttagctact ttggtatgac tatttaaagg  35520
atggattttc tagggtggag agatagtctg taaaatactt gctctgcagg tatgattacc  35580
agagtttgat cctcagaacc cattgaatag aagggtgcgg gtttataact gcacatgttt  35640
atgattctag tacaataggg aagcaggggc agacctctca ctgggcagct gcactggctt  35700
aggagaagag ccctgggtcc ccatgagaga tgctgtctca gaaaacaacg tgggaagtgg  35760
atatcttaaa aatgacattt taaattgacc tttggatttg acatacatgc acatgcatgc  35820
tcacacagtg tgtatttgca cacatagttt tctggacttc agtctcagaa atttgtcaga  35880
tactaagaag atgggtactt caaaattaag agtagatttt tttaaatgtc tgagagtagc  35940
taaatattaa cctataaagt aggttctttt ttctttcgga aagagaccac ttttcctttc  36000
cttcaggaca gggtctcatg tactttatgc aggccctaac gtcctgatcc tcctgccggg  36060
gtgctggatt gcaagggtgt gccgtcatgt ccagataaac atctccatag gcagatttcc  36120
ttctgaggga ctcccagctt tgtgtgttgt gggtgacact gtgacactca ctgagctaca  36180
ttcagggacc tgttttagtt ctctttagag tgttgtccat gatacagaaa tagtgctttc  36240
ctgctctggc ctttgagttg gtgtacctgg atcattataa aaatactttt accactgtcc  36300
ccttgtgtta cttcttcaag ctaggccaca cattcattct gtgactgtta acccagggtt  36360
gctactgcga tgcttccagc cttcagagaa ctggaaggcc ttacactggg gaggagggca  36420
gctctgagaa agccagctaa ctcttgcttc atttggctca ttaaacacaa ggatgtcagt  36480
gttagggttt gtggttttgt ttttctcttc agaagagatc cataagtggc gagagagata  36540
cataaagaca gtaaagccaa gctgttcctt cgaggcgtcc tcgtgggaga ccccaaagag  36600
tccatttgta aactcttagg ttattccttt tgacagttgt attgcaatcc tgcctcacgt  36660
```

-continued

```
ttgcggtctt tgttaccctg gtgagatgcg ggttctcttt cagtgctttt gatgttcatt  36720
tccccagcta ctcctcttcc cacaatacct tttgcccagg ctgggaaacc acatgataac  36780
cagcactctt ttaagttcag cgcactgcca aacccagaga agaattttgt gcattagtat  36840
aacaaataaa attccaacat accccaattc tgtatcttaa tgccataagc aactttgaca  36900
aggcagcatt taatatacta aaagaattta cactatcatg tcttcttttt ctttcctttt  36960
ttccttttgg gataagatct cactatgtag cgctggctgt tctagaactc agagattccc  37020
ctgcctccac ctctgagtac tgcaattaaa ggtgggcgcc accaccctgg cgcgcgctcg  37080
ctctctctct ctctctctct ctctctctct ctctctctct ctctctctct cacacacaca  37140
cacacacaca cacacacaca cacgctctcc attttaaagg cagtcttatg tattccagga  37200
ggtgagaagg aattatccac tcaagtgctg gactcacagg ttctcctgac tgctagcgat  37260
cagacccaga gccttggcct tgctagacaa gcactccaac acctgagcta aattaccagg  37320
ccaaggtggc tgctgctttt cttcttcctt aaaaaggagg cattgggtag ttttgagatc  37380
catcttgctt catagcccag gctggcttca aactcacctt gaagttgatg gtgattctct  37440
tgcctcagcc tcccagtagc agggattata gacaggcatg tgccagcatg cctggcctca  37500
tttggatatt tggaacaggg tatcactatg tagtccatgc tgccctgtat agcccaggct  37560
ggcctcaaac ccaaaactct tgtgctttat agtcttcgga gtgctgaatt gtagtatttg  37620
ctaccagctc tggcctttat actattattt ctttcataag ctactggttc atttacttaa  37680
cttttcaaaa gttggtcatt ttattttata gccttcaaat gttttaacta gaaaacatgt  37740
ggtcagtgaa gctgagattt atccccttag gaacttaaat gagtgaaatc aacatttaaa  37800
aaaacactca ctctcaacct taccccctgag acaggatttc tgtgtgttgc ccttgctgtt  37860
actttgtaga ccaggctggc ttagaactca gtgatccatc tgcctgcctc tgcctcatga  37920
gtgctgggat taaaggcatg caccaccaac accttgtttt aattatttct taaactattc  37980
actctgaagt ggtgatttaa tggaagtggt tgactggaga ggcgatatgt acttgttctt  38040
tgtctagact ttgttagttt gtttcattct tactctgcat gaggttggcc tgcttggctt  38100
ctgagatttg aacatcatca gacctaagtt actgcatcct tcagcagctg accaggtatc  38160
catatcactc tcctgatacc aaaggaacag atgtgaccac ctagaatgga gcctctttct  38220
ctttttttat gcagggaaaa tcatagtgaa atagaacggc ggcgacggaa caagatgaca  38280
gcttacatca cagaactgtc agacatggta cctacatgta gtgccctggc tcgaaaacca  38340
gacaagctaa ccatcttacg catggccgtt tctcacatga agtccttgag gggaactggc  38400
aacacatcta ctgatggctc ctacaagcca tctttcctca ctgatcaggt ctctggatct  38460
taaaactgac tctgggtata tctgttgaaa gttttggact aatttaatgg ttttgtttgg  38520
ttgcttgctt ggtttttttt gggagggtct catgtagccc aggctgacat ccaactcagt  38580
atattgccaa catgtgccac catgtccagc ttcaggagag tgattcttca ggagacatca  38640
gatgtagaaa agtgaattca gcccttagct ataagtgatc aagtattggg ggagtgagaa  38700
tagataaatt tagttgtgag aacttattta gcaaggtgtc aggtatttta gaacttggct  38760
catacaaatg acctgtgaag tgaaagaagg gtgtgtcccc agagaggttg ccacactcat  38820
ggatcagtgt tccttgggtt atatttctag agcatggaag aaatctgcct caccccttgaa  38880
gcaactttta gtcttaacga tgagagacgt gtagtaaaca acccctgttg ctccatgata  38940
tgttttgtta cacttgatat atcatgagga aaacagaaag ggcagaaata cttgccatca  39000
ttcaggagcc ccatctaaga gttatctcac tattgccagg agagagaact aaatgtgagt  39060
```

-continued agagtaaacg ggtgagtagt aagatgccta agtgaaaaac gatgggaaga ggcatgcgga 39120
aaagagccgg tgtctttgtt aatagtttgt gtgtgataga tatacaatgg tggcatgtct 39180
aactttattt agtctctcta gacttgactg agaatgacta ggaaagacaa gttacatttc 39240
acttaaaaat ccacgattgg gtagggcata gtggtgaatg cctttaatcc cagtactcag 39300
gaagctaagg ccagcttgtt ctacagaggt ccaggccagc cagagctaca tagcaagacc 39360
ctgtttcaaa aataaaaaga catatgattg ttcataccta gcctatgcaa agccctgaat 39420
ttggtcccaa cactatatgc agttgtgtat ggtaactgga tatggctgct cataacccgt 39480
ctttcagcac tgaggcacaa gtaggaggtt gagggttaga gttattctca aggccagcct 39540
gttaacatag gagactgtct aaaatagata catacacaca taagatggtc atataggaga 39600
ctgtctaaaa tagatacata cacacataag atggtcatat aggagactgt ctaaaataga 39660
tacatacaca cataagatgg taatatagga gactgtctaa aatagataca cacataagat 39720
ggtaatatag gagactgtct aaaatagata aatacacaca taagatggta acataggaga 39780
ctgtctaaaa tagatacata cacacataag atggtaacat aggagactgt ctaaaataga 39840
tacatacaca cataagatgg taatatagga gactgtctaa aatagataca tacacacata 39900
agatggtaat ataggagact gtctaaaata gatacacaca taagatggta atataggaga 39960
ctgtctaaaa tagatacata cacacataag atggtcatat aggagactgt ctaaaataga 40020
tacatacaca cataagatgg tcatatagga gactgtctaa aatagataca tacacacata 40080
agatggtcat ataggagact gtctaaaata gatacataca cacataagat ggtaatatag 40140
gagactgtct aaaatagata catacacaca taagatggtc atataggaga ctgtctaaaa 40200
tagatacata cacacataag atggtaatat aggagactgt ctaaaataga tacacacata 40260
agatggtaat ataggagact gtctaaaata gataaataca cacataagat ggtaacatag 40320
gagactgtct aaaatagata catacacaca taagatggta acataggaga ctgtctaaaa 40380
tagatacata cacacataag atggtaatat aggagactgt ctaaaataga tacatacaca 40440
cataagatgg taatatagga gactgtctaa aatagataca cacataagat ggtaatatag 40500
gagactgtct aaaatagata catacacaca taagatggta atataggaga ctgtctaaaa 40560
tagatacata cacacataag atggtcatat aggagactgt ctaaaataga tacatacaca 40620
cataagatgg tcatatagga gactgtctaa aatagataca tacacacata agatggtaat 40680
ataggagact gtctaaaata gatacataca cacataagat ggtaatatag gagactgtct 40740
aaaatagata catacacaca taagatggta acataggaga ctgtctaaaa tagatacata 40800
cacacataag atggtaacat aggagactgt ctaaaataga tacatacaca tataagatgg 40860
taatatagga gactgtctaa aatagataca tacacatata agatggtaat ataggagact 40920
gtctaaagta agtgtcaaca tataaaatgt gtgagtagtg tgggaagttt tagaaaatac 40980
aggaaatgac acttaatgta atgtcaccat tgctgtctga gaattatagg aatacttctt 41040
gagagaaagg gataaatttt ccaaataggg cagtctgttt gctagccatg gagtacattt 41100
aatagctatg tacatagaaa tagtcaattc atgtcctcag aatacgtcag gtatttatta 41160
aactccagtc atgctccttt tgtggcaaac caggtacttg cgctatgaga aatccaaaga 41220
atttaaaaag gaaataaagg tcactggtgg aatcagataa tataaattga taactaataa 41280
tacgaaacta gagttgtaac aggaacagta acaaggctaa tagagtatag gtatagaaga 41340
ggaactaggt gctggccatg gtgacccact actgtagtcc cagcagtcaa ggtatctgag 41400

-continued

```
ttacattgca attcagtgat acgtggaagt gggggaggag tgtggtggta tggagggtaa  41460
gtacagggta tacttggatt ttattttatg atgtggaagc atgtgtatgg tttctaagaa  41520
gagaggatga ataggatcta ggaagtgttt acatgtaaca tacgaacaaa gggaagagta  41580
tctgggcaga aaataaagca gaaatgaatg gaatttcaga agatactaag caaaaatgaa  41640
atttctaggg ttccatgggc agtattaaca ggttgtgtag agagattgaa tttaaaaaat  41700
gatgagaatc caggagaagg gacttgaatc atcaattagg aggatgtaat tgaatcctca  41760
attacagaag tagtgggtta cagtgaagat ggagggataa ttgaaaagca agagagtgta  41820
aaatatggtc tcacccatct taccatcttt tatctaccct caaaatgaca gtgatctaat  41880
taggtttttg tagtgctgac ttagttaaac ctttggctcc tggtgagcat ccgctcaaga  41940
gctctctgga tttgtggatg aaagacgtgt gccagcttaa ttttgatatg ccttgactag  42000
ttcaatggct gggcagttct aaaactccca aagccagcaa acactcccct tgggtattcc  42060
tgggttaata tcttttaaaa tctgtatttt ctttgcttcc ctggctcctt tggggcagcc  42120
ctttcttttt ccccctttgt tttcccccag ggaacctaga agtcccgcct ctttcatcct  42180
gcccatcctg gctctttatt gatcaatcaa aaaccagttt gggtgaccaa aattagcatt  42240
ataacacaag cagcattaga ccaaacccac ttcatgtttt tatggttact tcctaagcat  42300
taaaacctag atcctttaat aacatattct gaacaagttg agggaggcta tgtttgtgtt  42360
tataagttgg agtggaaagg gggaaagtga gaggctccta accctaaccc ctgccccctc  42420
cagaagtctt atcatttaat gtaagccttt ttattttcct ttgagtgcta agaggcaaat  42480
agcaacttag agaaattgca ggaatactta ctgtaaaaag tttgccagtg gatatttagg  42540
gtaggaaccc atggcttata tcgtggtata agcctgtgat tcctagtgga gcagtgcata  42600
tgtacccaag gatcttgctg cttcccatga tcagttgtgt atgtttttttc agagttcact  42660
attaactttg gtttattttc ttgaccagga actgaaacat ttgatcttgg aggcagcaga  42720
tggctttctg tttattgtct cctgtgagac tggacgggtg gtgtatgtct ctgactcagt  42780
gactcccgtt ttgaaccagc cacagtctga atggttcggg agcacactgt atgatcaggt  42840
gcacccagat gatgtggata aacttcgaga gcagctctct acatcagaaa atgccctaac  42900
aggtgagagc tggctggaca gcagatatgt gggggaaaag tctttatttc actcaagtag  42960
ttaagatatt taagcccgaa aaaccaaaaa aaaaaaaaaa aaaaaaaaga tatttaagcc  43020
tgtacattgg ttggttgaat ctagcaaagc ttctaaaatt tttttcctta atgactataa  43080
ttgtttttaa ttcacgtgca aaatatccac tctgtagctt attcttagaa aatatttcat  43140
cagtgcttgt gttcttataa aagctcattt ctatcttaat aatatcttaa aataggatgg  43200
agaggctgtt ggttagtgta taagggactt gtttgttgtc actgtatctc tattaggtca  43260
tttcccctcc accagtaggt gagactcagt cctttaccat cgtttggaga ataagtgcca  43320
cctgttctca gcaactgtac aggaagtaac aaaatggaaa caaataacta ggagttaaaa  43380
taggagaaac tagggctgga gaggtggctt agtggttaag agcactgact gctttttcag  43440
aggtcttgag ttcaattctc agcatggtga gatggtggct cacaaccatc tgtaatgaga  43500
tctgatgcct tcctctggtg tgtctgaaga tactacaatg tactcataaa catgaaataa  43560
ataaataagt ctaaaaaatt taaaagaaaa agaaactcca atatctttgc agtgggaatg  43620
ttcatattaa tgttgtttgt ttgtttgttt gtttgttttc cccctctttt gtgattttgt  43680
acatttcatt tctataattt tccttttccc caaatgttac ttacattttt aaaaaaataa  43740
ataaaggaga gagactgttt tgtttttgga cacatgcatg tttcttagca tgtaaaatta  43800
```

-continued

```
cttgttttta aaccagacac tgtccctacc cgaagcgtga cgatagttag tgactggcct  43860
aatggctcgg tggtgaagga gcatgccacg taagcccagc agtctacgct cagtctgcag  43920
actgcataac agtggaagca gtgacagctc cacatagttg tcttctgacc tccacataca  43980
ggagtgggct cacatgcaca atagttctag tagtttccac tcctgcttta ctcagttctt  44040
gtgccgtttt ggagctaata gtgagattcc tagatgagga cgcaagtagt ttaggcttca  44100
agaataaagc atctctgtca taaacacgga atctggaagg cttggctgga cccaagcttt  44160
gccgcggtgt ctccttcctt tcccatccac aagaagtaac ttgagattgc tctctacctc  44220
cttgaccagg gcgggtcctg gatctgaaga ctggaacagt gaaaaaggaa ggccagcagt  44280
cttccatgag gatgtgcatg ggctcacgaa ggtcgttcat ctgccgcatg aggtgtggtg  44340
cttgggattg tgttgggtgg gaataagagc agctaaggct tccatttctg tcagaggcat  44400
tagttagtat ctagtatcta gagctacgtt ccttgccaca gttggattac atttaacttt  44460
caagaaccag ttgttttacc atacttataa tatgtaagag aataacagtg aattacagtt  44520
aaggcacagt tggtaggtcc tttgtgttga cttcttactt ctgtcttagc ttcactactg  44580
ttcatagggt aagagtcaac gttcattatt ttgttcaggg gctagagaga tggctcagca  44640
gttaagagca ccttttgctc ttccagacga cctcagtttg aattccaaca ccacatggca  44700
gctcacaaca tctgtaactc cagttccagg ggaatctgat ttctctcttc tcgattctgt  44760
gggcatcagg catgcatgtg gtgcacagtc atgcaggcaa aaacccatac gcattaaaaa  44820
tgttttaact ggatttaaga tgtgggagag ttgtcttact agttaagagc acttgttttg  44880
ttcgtctaaa ggacttaggt ttcttttgta gtacccatgt ggtggctcac agccacttgt  44940
ggctccagtt ctaaggggtc tgatatcctc ttgggccagc aggccatata catggtgcat  45000
atatttgcat gcaggcaaaa cattcataca cataaaataa aaataaatct tttttccctt  45060
tttaaagtga atgcagaaat tggagagata gcccagtact aagtgtgtga tgcacaaaca  45120
tgaagaacct gagctcaatc cccagcacct atggaaagtt agatagtccc atttctggag  45180
aggcctagcc aaattaatga gcctcaggtc ctagtgagag accctgtctc aaaattcagg  45240
gtaggagggg ctggagagat ggctcagcag ttaagaataa tagctgctct tccagaggac  45300
tggctcaatt cccagcatct gcatggttgc tcacagccat ctatgacccc agttccaggg  45360
catcggatac ctttttctgg ttcctgtgta tccaggcgtg cacgtaatgc acttagagac  45420
aggtagagca ttaatacaca tttcaaaaga attacgatgg agagctcttg aggaactaca  45480
tgtgaggctt gtctctggcc tccgcatgcc tgtgcgtgta cagcatgaac atatacatac  45540
atatacatgg atcaagaaac cggctgcaga gatggctatg cagggataag agattatatt  45600
gctcttgcag aggactagct ggggttagtt tcccagcatt cttatcagat agcttgtaac  45660
catctgtgct tctagctgca aggagattca aagcctccag cctccacagg tagctcaaca  45720
tgcacatact cccctccttt tccatgcata cagctaaata aaataaatct tacaaaacag  45780
aacagatgtg ctagaaagat ggctcatcag ttaagggccc taactgctct tctagaagtc  45840
ctgggttcaa atcccatcac ctaatggcag ctcgaaactg taactacaag atctgacgct  45900
ttgacactga catacatgca ggcaaaacac caatgcatat aaagtaaaaa caatagacaa  45960
accgagtgtg acattgcttg tcttaaatca tagtgctcag gaggcagagg ccggcatatg  46020
tgagtgaagc attaggttct cgagatcacg agactgatag agaatcttgt tttagttcat  46080
agcagcagaa ctccaccatt gatgtgtatt cagacttaaa actcaagact gacctgcttc  46140
```

-continued atcatccaag tgctgagatt ataggcggtt tttgtttgtt ttgtttttca gattaaaaaa 46200
aattatgtgt gcatgatata tgtggatgtg gactcgtgtg tggtgtttgg ggtgcaagtt 46260
gttggttctt tcctacaaca ctgtgggttg aggtaatcaa atttaggtca tgaggcttgt 46320
cacaagcacc tttacctgat ggccaatctc cctggctacg ttaaaaaaaa aaaaaaaaaa 46380
aaagagtttc tggcagaggt acaaaattga ctattccata gtttaatagt ttagaggagc 46440
cgctggaatc aggctactct ggtttatttt gaggggggtgg ggtcttatta tgttgtccag 46500
gctcatttaa agatcctcgg ctcaagttat cctccatttg agtttcctaa gtagcttggg 46560
tctacagaag gtatatcact gtagttgact gaatgttggt atttgtttag ggatggggtc 46620
tcactgtgta cccctggctg ttctagaatt ggctatgtag gacaggctga ccttgaaatc 46680
acagagacct gtctgactgc ctcccaagta agttgtttga atccatagta ttccctggat 46740
ttgaattcta atttgatact ataagacttg tgttgctttg atgtcatcat ccactattgg 46800
aggtgagact gtcaaacgta aaacattgtt atcaggatta gctcgattga tagtatgaaa 46860
atactttaaa aagaacgttg aggcaggagg attcctacaa ggccagtatg gcctatatag 46920
caagttctgg atctcctggg ctatatagtg aaaccttgtc tcaaacaatc aatctagatt 46980
tggtggtgca tgcctgtaat cccagaacct tggaggctaa ggtaggaaga tcatgaattc 47040
caggctagaa tgaactacat agtaagacct tatctctaaa aaaaaaaaaa aaatagagaa 47100
agaatagaag taggattgga gggcgtatct tgtggacatg gtaagcctgg agtaaggtga 47160
ataataatga aatatagcac acagagatga tatgcttaga gcagaagtca gagaacagaa 47220
gttcttattt gtgactaaag cttcattgca ccatagctct tcctgtgtga acacttgtca 47280
tctttggctg cttttatgct tgattgctca gaattgtcta gttaaaagac tgtgtgacca 47340
tcagactaaa accacttact gtctagtcat tcacagaaaa cagtaaaaca gtcaccaact 47400
cctgatgtaa aaagatggca tttgaagagt gtatgcaatt gttttagttg gagttttagg 47460
ccaattaaaa gttttaaagg agtccaaacc tttcatcttt gctcctcttg aggctaagga 47520
aagaggatct caatcaagat caaggccagt gtgggcaact tggtgagctc cagtccaaag 47580
ttagggaaat aaaacataaa aggaggactt actgctcgga ggccagaggc tcgcctggca 47640
agcacagaaa cagctcaata ctcagttttt aagtaatcta ctaactctgt tggcctggtg 47700
gtactttcta tatctcatta cttgggactt aaaggcaagc agacagtttg tgttcattct 47760
gtgttgtatg agatcctgtt tcaaaaagtg gtctgggttg gaaaccagag atagatagct 47820
tagtgtaagg aaacttggca gaaagcctga taatacacgg ttgattactg gaacctacat 47880
agggcatgca cagagacaga gacagagaga gagaccgaca gacagacaga cagacagaca 47940
gacagacaga cagacagaca gacacacaat cagccagggt cgggaatata atatggcttg 48000
gttggtagag tgcttgtcta aaatgcatgg agtcatgggt tcaataccta acaccgactg 48060
gtatgttgat acctgcctgt agtgccatca ctcaggtgct gttgatcaaa gggtcagaag 48120
ttcaaggtct tccctggcca catagaaagt ttcaaaccag cctaagcctg aaggtgctgc 48180
ctcaaattaa acaaaacaac aagcaaacaa aataatagaa ggtttttcca tctcagcctg 48240
acttttcttg ttacttacta gttttcagtg tgtagttgga tcttcttatt ctgttgttac 48300
tgtttcccat agcccagcaa tttgcatctt ctgtttgttg acaggtgtgg tactagctcc 48360
gtggaccctg tttccatgaa tagactgagc tttttgagga acagatgcag gtaagatctt 48420
aggcagtgga gatcaagaga tgggattttt accttctcta ctggctctca ccttctttta 48480
cctcacggtc acttaccgtc tcacaatgtg tttctgaact tactgaatag atcaatccat 48540

-continued

```
ccatcaattg attgactgat tggtttttct gtgacagggt ttctctgtgt agccctggct  48600
gtcctgaaac ttaatctgta gaccaggctg gtcttgaact cagagatctt gagtgctggg  48660
atcaaaggca tgcaccaccc tgcctgtatt gtttctgaac tttaaaagct tctcttgttc  48720
aaggaagttg cttactatgt tacctatttt tcttgtgtgt tttatttcaa caagggctgg  48780
tgcagcatcc acacacgtac cagtaataaa tggataaata aataaataaa taaataaata  48840
aatgctttta aaacacaggt ttcctttgta gaatttcacc ccggattcct atacctttc  48900
taggaatggg cttggctctg tgaaggaagg agaacctcac tttgtggtag tccactgcac  48960
aggctacatc aaggcctggc caccagcagg tagggaaaat atacagtaat ttctctctgg  49020
tatatttggt tacataaaca attggcaata tgttactaac agttagcaat actatgtacc  49080
cctttatgaa atgtgcttaa gaataattca aaagatagat agacaaataa aacagactcc  49140
ctctcatctg ttaccaatgt tatagtctat ttgagcatat ggattactaa aacataaaaa  49200
tgactcaata ttagctttat tacaaaatgc tgtaggtttg ttttcgaagc aggtttctct  49260
gtagccctgg ctgctttgga gctgactttg tagaccaagc ctcatttcca ctgcctctgt  49320
ctccccagag ctggattaac taaagcctac accacaactg ctcaaccttt tttttttttt  49380
tttttttttt aaatgtttta ttgggagctg gaaagagggc tcagcagcag ttaagaacac  49440
ttactgctct tgcagaaaat ctgggttcag ttctcagaac ccacatgttg gcttaaaact  49500
gcctataact ccagtttctt gtgatctgtc actctcttct ggcctctgca ggttcctgta  49560
cttatattgt gtccataaat tcacacaggc aaatacacaa aaacaaatgt attactgatg  49620
cttatcccta tatttatagt agataatatc atatgtaaag tagatacttt tcatctctgg  49680
cctggaactc ctattttcag caattttctc ttcaatacct tctctgggaa ttgcaagcat  49740
gagctgctgt agttggtgta gaattcagtt attagtgcta agaatatagc tcagtaatag  49800
agtacttgcc aggtttatgt caggaccaaa acaacagaac aaaacaagcc agtgtgtggt  49860
ttaaaataat tctcaagtat aatagtagta tacactgaat actgtgtctt taagtagctg  49920
tggcaaaaca aacaaacaaa aaaaaaacca ctggagtttt attttatttt ttgggtctta  49980
gtgtattcct ggctgccctg gagctggcct cagattcaca gagatccacc tgcctttatc  50040
gtgctaaggg ctaggataga aggtgtgtgc cactatgccc agcttgaaac attggtattt  50100
aatgcaatta atttgggcaa gctgaaatgg aagagaaact ttaagcaatg aatgcaatgg  50160
ctttcttgca gtaactttaa aagggaggtt tctcttgaaa tgttagtcgt gagtagagta  50220
gctttatttt aatttgagat taactaaggg atgtagcaaa agaggtaggc tgtggggtca  50280
gacttggttt ttagatcatg gccatgaact ccttacctca gtctaacaaa ttctgaatta  50340
cgggctggtt ctccatgccc agcaaggcca gctttttaaa ctgactgtca actttccaga  50400
tctcacccta ttactttcct actataaaag gattgctggg aaatggggat ttacagaaga  50460
cagaaatgca gagaaaagag agacaggttt ttaatactta gttgttttgt gtgtggtagt  50520
gtttcgtctg catatatgta tgtctgtgca ccacttgttt gtctggcgcc cacagaggtc  50580
agaagaggat gttgaatccc ctggaactgg aattacaggc ggttgtgagc tgccatgtgg  50640
gtaatgggat ttgagcctag tctggaagag cagccagtgc tcttaaccac tgagcctttt  50700
ctcagcttcc ttttctcagc tgatatattt taaaaggaaa ttaacattga tttgtgtctt  50760
agggtttcta ttcgtgcaca aacatatgac caagaagcaa gttggggagg aaagggttta  50820
ttcagcgtat actttccaca ttgctgttta tcacggaagt caggcctgga actcaagcag  50880
```

-continued

```
gtcaggaagc aggagctgat gtagaggcca tggagggatg ttccttactg gcttgcttcc  50940
cctggcttgc tcagcctgct ctcttataga accaagacta ccagcccaga gatggtccca  51000
cccaccaggg gcctttcccc cttgatcact aattgagaaa atgccttaca gctggatctc  51060
atggaggcat ttccccaact gaagctcctt tctctgtgat aactccagct gtgtcaagtt  51120
gacacaaaac tagccagtac gatttgggaa aaacttaata tttgctctct ggcatttgtg  51180
aatagtttaa cctatggcaa gtttcttgac ctttacatgt ttttccttat ctgcagtcca  51240
ggtcatacat cctgtatatc atcatcgtga gttagattta gtgtaaggaa agaacacccc  51300
agtgcctggc acatgctcta tagccaagaa atgggaatta ataattgagg aaatattatg  51360
tatagtggca catgaactgt tgagttaact tcctatgtaa atcatacctt tactgtatgt  51420
atgatctttg atacttctgc atagctgtcc tagataagaa tgagagataa agacattgtg  51480
agggatgaac tcttattccc tttttctgtg gaaatgaata tcttttggtg ttgggacaat  51540
ttaattttc tttactttaa aaatcactgg ttaggcagga atatttactt ctctgtgtat  51600
gatatagtca catagcataa gtaaagttta tatttttaga ctcctttgat tgggacttgc  51660
attttcaaat ttcttaaaat ggttaaagcc aggtgtgctc atatgcctga aatcctgcat  51720
tgaaaagatg aagagtccag gttacacaca cacacacaca cacacacgca cacactcaca  51780
cgtgtgtcac atgaaacagt aactggttat tttattaaat cttagcatct tcatagggaa  51840
atagtgagtc ttcagtgact tgcccttaaa gggatttgaa tttgtgatct ctctgagtca  51900
ttctcctttt tcttcatgaa ggtgtctccc tcccagatga tgacccagag gctggccagg  51960
ggagcaaatt ctgcctagtg gccattggca ggctgcaggc aagtatgagt cttcacatct  52020
atgtcctttc agtttaggga aaaaaaactt ttcagatttt atttgtggta attatctttt  52080
gctctgtgaa tacatagaaa aattccataa aactcaagat ctaaaataat gtgatattta  52140
taataaacat tgctattctc agacttagct aaaatcaaaa gcatgagaga gggtggtaat  52200
cttgttgttg ttgatcttgg taatgactcg tccctgttac ctaggcctcg agctccttgg  52260
ttcaagggat cctcccccta aagcctcctg catgttggga gagaggcagg cgtccgtcac  52320
catgccaggc tcccctggac attgttagtt ttagctttac agtacttact tttctatttc  52380
caattaattt cttttgttcc tatgcaaagt aagaacaatc atttttatta tgtcattaca  52440
ttctttataa tagatctaaa atatcttaaa atttttattt tatgtgtatg ggtgttttgc  52500
tttcatgtgt gtctgtgcac ttgcatgcct ggtacccgag gaggctagaa gaggttattg  52560
aatcccctgg aactggagtt ccagaaagtt gtgacttgac gtatgggttc tgggaatgga  52620
acgcgggttc tctggaaagc agtcagtgct cttaacactg agccgtctct ccagcccttg  52680
attttgatta ttttcatgaa ccctgttcag tttctcagaa acttgaatca ctctgaataa  52740
tgaatacggg ctaaccaaat aaaaagtagg tggtttaggg taacattcac tattttctta  52800
ctttaccaac ttggtaagag aacttacata ggagtagagt tagagtttat gcctgtcgtt  52860
aggattgaca tttttgcatt tctgggtaaa acttctaaga agtttctaaa tctggtagtt  52920
tcatatctac acagatactc atgaaatatt aaaagtattt atgtaagtaa tggtgttatt  52980
tgggctcatt ttatctctcc tttcttaggt aactagttct cccaactgta cagacatgag  53040
taacatttgt cagccaacag agttcatctc ccgacacaac attgaaggga tattcacttt  53100
tgtagaccat cgttgtgtgg ctactgttgg ctaccagcca caggtgagga gcgtagcttc  53160
tgcattagta acacgtaggc ctctgttttc tgttaccagt gttgaggtta catggctaat  53220
tccagagatg accaaaatat agcagtccag ttcagaaaaa gagatgctcc tattttgcga  53280
```

-continued

```
gtagcaaaat atagtctcaa cttcctttca agactatcac tccatataga gaaatgtagt  53340
tggtaaaacc atatggaaat agtaggtata aatatatagt ttttattact aatgtcaata  53400
cagatcattt aaaactcctt attttaatta ttctagtata actagaattt atataattac  53460
tatattttag taatttatat aattactagt agaataagcc tataataatt ataagtgtag  53520
cactgcttat taaaattctc atacagtagt atatcagtta actacccctg acttacatgg  53580
acatggtctc tgttatttat gagcgtggct atgagtgtgt gaagtggtca gtcaagatgt  53640
catcttgggg gctggagaga tggcttagtg gttaagagtt caaatcccag caaccacatg  53700
gtggcttata accatctgta atagatctaa tgccctcttc tggtgcgtct gaagacagct  53760
acagtgtacg tatattaaat aaataaataa ataaataaat ctttaaaaaa aaaaagaagt  53820
tgccttgaaa atgaagaagg tcgggcagtg gtggtgtatg cctttaatcc cagcacttgg  53880
gaggcagagg caagccgatt tctgagttca aggccagcct agtctataga gtgagttcca  53940
ggacagccag ggctatacag agaaaccctg tgtcaacccc cccccccaaa aaaaaaaaaa  54000
gaaaatgaag aagaaagttg gagaatttac ttacacccag atccaacact ccctgtaaag  54060
gtgctgttat taaggctgtg tggtgttaat gtactgatct attctcatga gtaagctaaa  54120
gagtcttttt tgcattggta attggatttt cagcaaagat gcttagacat ttcaagggga  54180
ttctatatag accacagcca ccacccctaa aaatcatcat accatagaca aaaatcgact  54240
caaagcccta aatgtataag tactaattgg aaacaccttt tagaagaaaa tctttatgct  54300
cataggtgag caggccgcgg cacaccttgg gagggtggga ctcaccgggt gctattcatc  54360
tttttgtttt gaggcaagat ctcccattgg actagaactt gcccagtagt atagacttgc  54420
tggccactga gctcccataa tccactgctc taagattatg agaatatcct acacttgact  54480
ttttgttttt tggaaacagt gtctcactcc attgctttgg gtactggagc tctttataga  54540
gaccaggctg gcctcaattt cagaggtctg cctgcctctg cctcctaagt gctgagatta  54600
aaaggcctgg ctatttttta tttttatttt atgtatatat gtgagtgcct aagtatatga  54660
atgtgtgcca tgtgtttact tagtaccaga aagaccagaa aaatgcgttg gttctcctga  54720
aactggattc taggtggtta taacattctt gataacaact gctctacagg aagtgttggg  54780
tcagggattg taaatttttc aacttagttc ttcattttta acgtctggtg tgtgatcttt  54840
gcaaatgcag gaagtgcttt taagggatga gccatctctt ctgctctgcc atacccctac  54900
ctttttctat ggtttttgaa aatgtattct aaggaccaca ctcagctcct ctaatgttat  54960
ctacaggctt agctctttcc atccctccgt ccctcctaac tcccatcttt ttctaggcta  55020
gcctcaaact ggaaatcttt ctgtcctagc ctgtgatgct gagattagag tatgccacta  55080
tgcctggcaa aaattttctc taaaatgata tcattaaaag agctggtaaa gtgattttgt  55140
gagaaaggcc tctttgtttc tagttgttcc attacattct tcaagcacac acgtgaccca  55200
tagagtccaa gtgtgttttg gaggacactg agcaggagtc agctccccga gttgggttcc  55260
agagatggac tcactgaacc atctactggc cctgcttctc cacacaccta tttatagtag  55320
gataaagaga agaagtaaca tccatatctc taacagatgg gaaggcgggt ttattttacg  55380
tctctccttc ccttctagga gctcttaggg aagaatattg tagaattttg tcatcctgaa  55440
gaccaacaac ttctaagaga cagctttcag caggtaacat ttttcctggt ttgatctgag  55500
tacatatttt gatcaattct tcaagtttat tctagatact tactgataag tgttcagttg  55560
agcactgtgg tggatactat ctacctatct taatttctaa aaaatataaa atgataatac  55620
```

-continued

```
tttgaaacta gacaaagtcc aaggtatttc tgctttggtt ttatccaata aattctcttc  55680
aaagcattta aaatattatc tgcttaacta ctttatttta gattatagca gaaaaattgt  55740
ctcagaattc ttttctctat aattgaaagt taactcacta gtaactcact ggtaacttgc  55800
tgtagttctc aggcacgagc tcttgaaaac actcggagac gataaatggc cttggcttta  55860
gataacaggt ctttatattt tgtaagttaa ttaagtcttg atactgtgct tcctgataca  55920
atggctatag taatacttaa ggtagaagct tgtgggagag tcaagtatgg taaagccata  55980
ggcacatata tacatatggc ccagcctttg acacatgttc attgctaata tctttattgt  56040
tagagatgga taactaagag attgtcttct gttccataag acagaaacta aaacattaac  56100
atagtacttc tcttaggggc tttgtggaaa ccaaaattgt taagttttga gttgaagagc  56160
tgggattgct aagtaaggtg taaagtgtat ttagtgtcac ccacctgggg ttcctggtat  56220
taacctagaa agccagtttg ttgagaatgt ctgcatcaaa cttcaaggaa acatggagac  56280
actcgcttct gtgttccctc ttcactgtac agtcatacag gctgcagctc tgggaagata  56340
cctgatagat agatgccccc cttaatttcc tcttcctcgt ttgaacgttg aaaaagactg  56400
gtgcttcagg ggcaacaaca cgagtcctaa ggctgtaaac atggcaagat tattacttaa  56460
ttttcttttt ttttaagtcc actgatggat gaaacccctt tcaggtggtg aaattaaaag  56520
gtcaggtgct gtccgtcatg ttccgattcc gatctaagac ccgagaatgg ctgtggatga  56580
gaacgagctc ctttaccttc caaaaccctt attcagatga aattgagtat attatctgca  56640
ccaacaccaa tgtgaagtat gtacccttca gtctgcccct gtgttgggtt cttcatcctg  56700
tagccactcc tagggtgggg tgggggtgca gcagggcaag tcttagcttt atcatgctgt  56760
cttctcttca gcttgaactt actaaataac atcagtttga gattcctcat ttaacattta  56820
aatttaacat taattgaaat tcctttctat aggagttgat gtagttgagg tagagaacaa  56880
ggtgggtttt agttgctgtt ggtatctact ttctaatttg tgtatgttga atgggcccgt  56940
aatagcatgt gtgaacatca gagcacagct tgcagtagtg ggtccccctt tatcaagtag  57000
gtcgcaggca tggaattcaa gttgtcagct gttggctggc acttttccta ccaggccatc  57060
tcattggctc acggtggaat aagtgttaat aagcagcagt agttggtgct gtgagcagag  57120
ctttcactgc tgcccagcct tgttgcccac tgcagtgtgc tcagccaact tgttttctaa  57180
aaggctgcaa gtaaaatttc caaagattag atttttttgt tttttcttct ttttggtttt  57240
acgagacagg gtttctctgt gtagccttgg ctgtcctgga actcactttg tagaccaggc  57300
tggcctccaa ctcagagatc cccctgcctc tgcctcctga gttctgggat taaaggcatg  57360
gaccagcact gcctttcttg ttgtaaattt ttatataata tattctgatc acactttccc  57420
cttctagctc cttccagatc ctcccaccta ctaaactcca tgacctacac acacccgaga  57480
gagacagaga cacagagaga gacagacaga cagacagaga gaccaaaata tataaacaaa  57540
agacccaata agacaaaaaa aatgcctgaa cagagcaaga tgagataaaa accctgtaaa  57600
aatatcactg aatacatagg ttacctatgg gactggacta agatgttagt aattgttcac  57660
ctttagtcaa tatatggagt ttattgtatt gagtaattcc ttgtttcccc ttttgtgttc  57720
ttgtctactc tattttccta ggaactctag ccaggaacca cggcctacac tgtccaacac  57780
catcccaagg tcacagctag gtccgacagc caatttatcc ctagagatgg gtacagggca  57840
gctgccatcc aggtaagaaa tggtgaaata gttagctttt caagtaaaaa ctagctgggt  57900
gtagtgatgt gcaatcacat atttttgttg ttgctgcatg tggtttattt tttaaagtct  57960
ttttctccaa attctttgtt aaaagtctaa ttttccccta tcgctttcca cactgatgtt  58020
```

-continued

```
tgacgtatag gcagcagcag cagcagcaca cagaactgga tatggtacca ggaagagatg  58080
ggctggccag ctataatcat tcccaggtga gtgtaccttt ttcctataag gagacaatga  58140
acatttcttt aaaatgtata ttgaagctac cagaatggtt tagtggttaa gagagtactg  58200
ctcttggaga aagcccaaat tcaattccta gtaaccatag tgggtggctc acaatcacct  58260
gtagacacta tgttcatata cacagacaca gacacaacaa tttaaaacaa aaatgaatct  58320
taaaaacaat atttatcagt gccagtgaga atgttctata taaaattgaa cattattgat  58380
tgttttcact attttattcc ataggtttct gtccagcctg tggcaagtgc aggatcagaa  58440
cacagcaagc cccttgagaa gtcagaaggt ctctttgcac aggacagaga tccaaggttt  58500
ccagaaatct atcccagcat cactgcaggt atgggtttct tccgcaggct ccttttacag  58560
gctgagtttc attattactg atgggactgc ccagtcagca tacttctact tcagttacag  58620
tacttcatga ataagtagga attgattaaa ctatgtgcta cagccccttg atggccctcc  58680
cccaactcct tttggtctgc agatcagagt aaaggcatct cctccagcac tgtccctgcc  58740
acccaacagc tgttctccca gggcagctca ttccctccta acccccggcc ggcagagaat  58800
ttcaggtgag ccccatatgt gtgtgctgct tgacagggct ctgcagggtt cagttgctgg  58860
atccgtgtgt catcttccct tgctttctct ggtcacctca gacaaagcag tagaacttac  58920
tggacctagg gtgagacaac gaagctgctt ttcctcctgt ttttgcacct attctattgc  58980
cttgctctag gttccaaacg tctctgtgtg gtcagtgtgt gacagtcagt ctttcttgtg  59040
tttttaaatt tatcaggttt tccttaactc caagaaatca gaggaatcta gggatagaat  59100
gtgtcctttg attcatagct tctgtgatgg agtcaacctt ttaaccttca ctttctattt  59160
gttccttcct aggaatagtg gtcttacccc tcctgtaacc attgtccagc catcatcttc  59220
tgcagggcag atactggccc agatttcacg tcactccaac cctgcccagg gatcagcgcc  59280
gacctggacc tctagctccc gcccaggctt tgccgcccag gtagcgcctc ttacctgtct  59340
gaccctgtgt gttgttgttt gtgggatctt tttttttcc tccaggtaaa tttattattg  59400
tcagatacct ccttttcagt tcctgttctt catcttttaa ttttcatctt ttttgcgagg  59460
agctagataa ttaaaatacc agagataaca tccagaagtc tctttagaac ctatgttttc  59520
atatgctcac cttaagacag aactgctcat tcacagcagt ttgaacagct ttggtctcag  59580
gcttgtttgg agtaaattca aagagtttgt ctttgtttag gactatgtaa tatagtacca  59640
aagtagaaaa ttagtaatta tattcattta tttatgaaaa tatagtatcc atctatataa  59700
tatatagtaa atatgttaaa tttatttatt actatgtatt tctcttgtct atataataat  59760
ttagaaaagt ttaaaaaaaa atgaaaactc aaacttgact ccagaattgt tctctatagc  59820
tttttgtgt atgtgtaaaa atactcagga atgttgccca tgactcttgg tcaggatgtg  59880
ccgtgatgtt gatgacagct gctaccatgg ttttcatact ggtgacataa tcaagcatgc  59940
atatattatc tcccttggag ttacttttta aattgtggat ttaaaacggt ctctagaaat  60000
tattgtatct cacaaaaaat gttagaggca ataactagtt tcttaatcaa tatacagtaa  60060
atgggtgtga gaaaggacag ctttaatttc aacaaagaga ctgaggcagg agcatgggcc  60120
tgggccacat agtgagagat aaactgtctc ataaaagaaa gaacagaaca aaaccaaaat  60180
agcataatgg aaaataaaag aggacattgt ccactgtgcc aagtaacagt ctcttctggt  60240
ggggttaaca gtgaggtttc atttctagtt tattttttcc aattttttc tattcttttt  60300
gaggcagatt tagaatttat attaaacaac cctttgcaga tttacactta aagtcaagag  60360
```

-continued

```
caaaagagaa gcactcagaa ctgagtgtgg gtgtgaactc cctaagatgc caccaaattc  60420
ctctgtaaca catagggatt ccagtaaaaa agaaaatggt tgtgccttta ggaaaaggat  60480
ctagaaacgg gtgcagtgtg gagtgagtgg tttctctttt ataacactct accattggga  60540
cccgagagat gacgccattg ggaaagtgtt ttgtcacttg agcctgacct gatgacctga  60600
gtttaatccc caatctcctt ggggggaaga gagaaccaat tcctgcatgt tgtcctctaa  60660
catgcgtgcc agagcatgca tgtgttctca tgtgcataca tactcatgca cactaaaaat  60720
aaggtggaaa cctttaatac caccacttgg gaggccaatt caggtagatt tctgagtttg  60780
agttcagcct ggtcttcaga gtgagttcca tgacctcaga gaaatcctga ctccaaagac  60840
aatagaaaaa agaaataata ataataatgt ggaaaataat aaaggaaaac acccagtgtt  60900
attgacatct gtgtgtacat gcaaccatta tacagagaca tgcacatgaa cacacacaaa  60960
tgaagtgaag acatgttgat ctctggttcc cattaatttg tgcacaatag cctgtacatg  61020
tatgttgaac ttggacacac atggatgtta tgctttctat taattgccat aatttatgag  61080
ctgattatat ataggaatag tttttttttt taagatttat ttacttatta tatgtaagta  61140
cactgtagct gtcctcagac acaccagacg agggcgtcag atctcatttc gggtggttgt  61200
gagccaccat gtggttgctg ggatttgaac tctggacctt tcggaagagc agtcgggtgc  61260
tcttacccac tgagccatct caccagcccc aggaatgggt ttttaataat gttttcatgt  61320
atttatatag tgttgttttg ggttttttgg tctttttgaa atagagtttc tctgtataac  61380
agagtcctgg ctgtccttaa cctgacttaa tagaccaggc tgaccttgaa ctcacaagag  61440
gtctatctgc cttcatctct ccttcccgag tgctggctgg gattaaaggc atgtgccacc  61500
acactgaccc gtatacagtg tattttgatc ataacgtgtt ctactccaga ccagtgatgc  61560
ctctccctct taccaaccag tccctcttgt atgtcagtgt ctctttccca tttcatgatc  61620
cagtgagctt aattatcaca atttgtaatt ctttgttttt ttctttttca cttttatttt  61680
agtttcctaa aacatttagt tttaggaaga attgggagtt aatcagaagt atacattaga  61740
agcaggtaat gggttgggtt tggaagaagg tagtggttga tgagtatcga cttacaggaa  61800
tgcagtacac gattaacaat cctttgttct gtacccccctt cctttagcag gtgcccaccc  61860
aggctacagc caagactcgt tcttcccaat ttggtgtgaa caactttcag acttcttcct  61920
ccttcagtgc tatgtctctt ccgggtgctc ccactgcctc atctggtact gctgcctacc  61980
ctgctctccc caaccgtggc tccaactttc gtaagtgcag acaagggaga taacaggaaa  62040
atcaaactac taaagaagga ggacttggca gttatgattg ttttccctgc gtcctgcatg  62100
tgctgaccga attataagga aatgcatggt ccaggtctgt ttgattttaa acagccttgc  62160
atagggcctg ttgaaatggc tcattgtgca aagtgctcga cacacaaacc gggtaacctg  62220
agttcatatc caggagagag ctgacgccac catgagctca catgcaccat acacaagaca  62280
gtaagaatct taagaatcat tataaaaaca tggtatagga aaaccattta actcctgtag  62340
ttaaagacca tgtgaatcat tttaatatgt ataacaatct tacttaatag actgcatatg  62400
taaatgaaca aggaattctt cagaaatgct atctaggaaa tgaaacttac tgtgagactg  62460
agttttgaaa atagaagcag ccctgaccag cagagagaag agcagaaggt agcatatgga  62520
gactactgac ttacacgtag ttgtgtgctg gtttctcctc tccattacaa ctataaatgc  62580
ttattcttat ttctagctcc tgagactgga cagaccacag gacagttcca ggcccggaca  62640
gcagagggcg tgggtgtctg gccacagtgg cagggccagc agccccatca tcggtctagt  62700
tccagtgagc agcatgttca gcagacacaa gcacaagcac ctagccagcc tgaggtcttt  62760
```

-continued

```
caagtgagtg ggtaaagact tcagagagag atcggtcagg gaagagagga agaaagaagc  62820
acatggtatt ggttagggct gaacggaatg agacagagga tgcatgtcag cagttgaagc  62880
aattataaac atagcctgta accagaccag gcagaggtac tgatgggaag caacatgcaa  62940
agatgctaaa gaaaggtatt ttaattttat acagagattt acatctcaaa gtagtagtta  63000
tggatttaaa tagaagaata cgaaaatata tggagtagaa catactgatc atagctataa  63060
gtatctgttt cctttgaggg gcctgcaaga ttgaatgtgg tcatctcaga gaagccagtc  63120
agaaagacca aaggaaggca acataggggtt tgattgagaa cagatgtgat taggcacatt  63180
tcagatgtgc ctgtaggagt taaatgaaat gttggcatgc atatttcttc agttaaaaat  63240
attgagtaca agaaaagagg aaaataaatg atctcagagg aagatagaac agagaatgag  63300
gaaagagttc tcagaagagg gaggttgaga gaactcgcca tgcagacttg tgcggctcag  63360
gaatggtggt ggtgtgggtg ggggaagggg gtcctggaag ggaactcact aaaataaggg  63420
tatgtgaccc aagtctaccc tttttctcat taggaaatgc tgtccatgct gggagaccaa  63480
agcaacacct acaacaatga agaatttcct gatctaacta tgtttccccc cttttccgaa  63540
tagaactatt ggggtgagga taagggtggg gggaaatcac tgtttgtttt taaaagcaaa  63600
tcttttgtaa acagaataaa agttcctctc ccttcccttc cctcacccct gatatgtacc  63660
ctttccaccc cttgacttgc tgaagaaacg ttatagaaga aattaaatga atttcccagg  63720
cttttaggat cctctgaaat tttgaggata ggtgaggcct gaattcctgt ccttatttct  63780
tctgaccaga agttgcacag acatgatttg tgctggagtc aaggggcaga acagaagaat  63840
ctgacaggca ctaattggat actgtggctt gtttggatag aaattctgaa tggagtggag  63900
gaaaggagaa atgccctcat cactgaggat catgaaacac agtaggggtg tgtggagcct  63960
tgggacgtga gcagtctcca gaaagaggcc tgagagagag catgaacact tatctttgtg  64020
agtgagtgag tgagtgagtg agtgagtgtg tgtgtgtgtg tgtgtgtgtg tgagagagag  64080
agagagagag taagagacag agacagatgg ggtgaggggg gcatttgagc tcctatgttt  64140
tgttccctat tatagagtat atgcaaaatt tgtcccagat cttctttgac tttgtgcttg  64200
ctctttaaag tgtcctaaga aaattaattt tttcaggtat ttttctattt agtgttgcag  64260
ccaaagagta tttaaattaa gtctttgctg cacttaaatt catacccagc caaaatggaa  64320
ctttaggcca acccccagcc ttctgttgct agggttggtc tcctacagac acagtgatca  64380
agctggatga ctcctgctct ttggtgcttt caactcattg ggaagagctg cagatattac  64440
caaaataggc tggctacatg aacactgtca gaaatcccag acttgcccac aaggataatg  64500
ctgcattttt ctgtcagagt cacacatgtt tttctggaga ggttatttct gcatggaaac  64560
tcaacttctt ggattagcta tcttgagtga aagtcctcac tgacgagtat gcaaaccaaa  64620
tagcctcctg cacagtagcc tctccttcct gtcaccaaaa cagttttagg tctgctgaag  64680
tctggtgttc tttgctcctt ctgcaatctt gaaattgggg tttgctttag agcacaaaca  64740
taagtctgtg ttaggtggac ttaaatccca acagggtcac ttgataatta tagccataga  64800
aatgcagatg caggtaactg cttttaccct ttaccgtcct caggtgagtc tcctagatca  64860
acagcctttt tttttttttt tttccttaaa ctggctcctg tcaaagatta agttaatatg  64920
gaaaagacct cttatgtgta ttgatggggc atgaggagcc caggcaagga gaggctcgtg  64980
gagaggctga gggaatgtta c                                            65001
```

<210> SEQ ID NO 100

-continued

<211> LENGTH: 2557
<212> TYPE: DNA
<213> ORGANISM: M. musculus
<220> FEATURE:
<220> FEATURE:
<221> NAME/KEY: CDS
<222> LOCATION: (150)...(2174)

<400> SEQUENCE: 100

```
ggggggggcg tccgccatct tggattccgc ggtagcggtg gcggcggtaa ggtgcctaat      60

ctgcggagtg gctcttccct cccctccccc agctcggtgg cggctgcccc tcccaccgag     120

ggtggcgcag ggacggtgcc atctcgacc atg gcg gcg act aca gct aac cca      173
                                Met Ala Ala Thr Thr Ala Asn Pro
                                 1               5

gaa atg aca tca gat gta cca tcg ctg ggt ccc acc att gct tct gga      221
Glu Met Thr Ser Asp Val Pro Ser Leu Gly Pro Thr Ile Ala Ser Gly
     10                  15                  20

aac cct gga cct ggg att caa ggt gga gga gct gtt gta cag agg gct      269
Asn Pro Gly Pro Gly Ile Gln Gly Gly Gly Ala Val Val Gln Arg Ala
 25                  30                  35                  40

att aag cga cgg tca ggg ctg gat ttt gat gat gaa gta gaa gtg aac      317
Ile Lys Arg Arg Ser Gly Leu Asp Phe Asp Asp Glu Val Glu Val Asn
                 45                  50                  55

act aaa ttt ttg aga tgc gat gat gac cag atg tgt aat gac aaa gag      365
Thr Lys Phe Leu Arg Cys Asp Asp Asp Gln Met Cys Asn Asp Lys Glu
             60                  65                  70

cgg ttt gcc agg tcg gat gat gag cag agc tct gcg gat aaa gag aga      413
Arg Phe Ala Arg Ser Asp Asp Glu Gln Ser Ser Ala Asp Lys Glu Arg
         75                  80                  85

ctt gcc agg gaa aat cat agt gaa ata gaa cgg cgg cga cgg aac aag      461
Leu Ala Arg Glu Asn His Ser Glu Ile Glu Arg Arg Arg Arg Asn Lys
     90                  95                 100

atg aca gct tac atc aca gaa ctg tca gac atg gta cct aca tgt agt      509
Met Thr Ala Tyr Ile Thr Glu Leu Ser Asp Met Val Pro Thr Cys Ser
105                 110                 115                 120

gcc ctg gct cga aaa cca gac aag cta acc atc tta cgc atg gcc gtt      557
Ala Leu Ala Arg Lys Pro Asp Lys Leu Thr Ile Leu Arg Met Ala Val
                125                 130                 135

tct cac atg aag tcc ttg agg gga act ggc aac aca tct act gat ggc      605
Ser His Met Lys Ser Leu Arg Gly Thr Gly Asn Thr Ser Thr Asp Gly
            140                 145                 150

tcc tac aag cca tct ttc ctc act gat cag gaa ctg aaa cat ttg atc      653
Ser Tyr Lys Pro Ser Phe Leu Thr Asp Gln Glu Leu Lys His Leu Ile
        155                 160                 165

ttg gag gca gca gat ggc ttt ctg ttt att gtc tcc tgt gag act gga      701
Leu Glu Ala Ala Asp Gly Phe Leu Phe Ile Val Ser Cys Glu Thr Gly
    170                 175                 180

cgg gtg gtg tat gtc tct gac tca gtg act ccc gtt ttg aac cag cca      749
Arg Val Val Tyr Val Ser Asp Ser Val Thr Pro Val Leu Asn Gln Pro
185                 190                 195                 200

cag tct gaa tgg ttc ggg agc aca ctg tat gat cag gtg cac cca gat      797
Gln Ser Glu Trp Phe Gly Ser Thr Leu Tyr Asp Gln Val His Pro Asp
                205                 210                 215

gat gtg gat aaa ctt cga gag cag ctc tct aca tca gaa aat gcc cta      845
Asp Val Asp Lys Leu Arg Glu Gln Leu Ser Thr Ser Glu Asn Ala Leu
            220                 225                 230

aca ggg cgg gtc ctg gat ctg aag act gga aca gtg aaa aag gaa ggc      893
Thr Gly Arg Val Leu Asp Leu Lys Thr Gly Thr Val Lys Lys Glu Gly
        235                 240                 245

cag cag tct tcc atg agg atg tgc atg ggc tca cga agg tcg ttc atc      941
```

-continued

```
Gln Gln Ser Ser Met Arg Met Cys Met Gly Ser Arg Arg Ser Phe Ile
    250                 255                 260

tgc cgc atg agg tgt ggt act agc tcc gtg gac cct gtt tcc atg aat      989
Cys Arg Met Arg Cys Gly Thr Ser Ser Val Asp Pro Val Ser Met Asn
265                 270                 275                 280

aga ctg agc ttt ttg agg aac aga tgc agg aat ggg ctt ggc tct gtg     1037
Arg Leu Ser Phe Leu Arg Asn Arg Cys Arg Asn Gly Leu Gly Ser Val
                285                 290                 295

aag gaa gga gaa cct cac ttt gtg gta gtc cac tgc aca ggc tac atc     1085
Lys Glu Gly Glu Pro His Phe Val Val Val His Cys Thr Gly Tyr Ile
            300                 305                 310

aag gcc tgg cca cca gca ggt gtc tcc ctc cca gat gat gac cca gag     1133
Lys Ala Trp Pro Pro Ala Gly Val Ser Leu Pro Asp Asp Asp Pro Glu
        315                 320                 325

gct ggc cag ggg agc aaa ttc tgc cta gtg gcc att ggc agg ctg cag     1181
Ala Gly Gln Gly Ser Lys Phe Cys Leu Val Ala Ile Gly Arg Leu Gln
    330                 335                 340

gta act agt tct ccc aac tgt aca gac atg agt aac att tgt cag cca     1229
Val Thr Ser Ser Pro Asn Cys Thr Asp Met Ser Asn Ile Cys Gln Pro
345                 350                 355                 360

aca gag ttc atc tcc cga cac aac att gaa ggg ata ttc act ttt gta     1277
Thr Glu Phe Ile Ser Arg His Asn Ile Glu Gly Ile Phe Thr Phe Val
                365                 370                 375

gac cat cgt tgt gtg gct act gtt ggc tac cag cca cag gag ctc tta     1325
Asp His Arg Cys Val Ala Thr Val Gly Tyr Gln Pro Gln Glu Leu Leu
            380                 385                 390

ggg aag aat att gta gaa ttt tgt cat cct gaa gac caa caa ctt cta     1373
Gly Lys Asn Ile Val Glu Phe Cys His Pro Glu Asp Gln Gln Leu Leu
        395                 400                 405

aga gac agc ttt cag cag gtg gtg aaa tta aaa ggt cag gtg ctg tcc     1421
Arg Asp Ser Phe Gln Gln Val Val Lys Leu Lys Gly Gln Val Leu Ser
    410                 415                 420

gtc atg ttc cga ttc cga tct aag acc cga gaa tgg ctg tgg atg aga     1469
Val Met Phe Arg Phe Arg Ser Lys Thr Arg Glu Trp Leu Trp Met Arg
425                 430                 435                 440

acg agc tcc ttt acc ttc caa aac cct tat tca gat gaa att gag tat     1517
Thr Ser Ser Phe Thr Phe Gln Asn Pro Tyr Ser Asp Glu Ile Glu Tyr
                445                 450                 455

att atc tgc acc aac acc aat gtg aag aac tct agc cag gaa cca cgg     1565
Ile Ile Cys Thr Asn Thr Asn Val Lys Asn Ser Ser Gln Glu Pro Arg
            460                 465                 470

cct aca ctg tcc aac acc atc cca agg tca cag cta ggt ccg aca gcc     1613
Pro Thr Leu Ser Asn Thr Ile Pro Arg Ser Gln Leu Gly Pro Thr Ala
        475                 480                 485

aat tta tcc cta gag atg ggt aca ggg cag ctg cca tcc agg cag cag     1661
Asn Leu Ser Leu Glu Met Gly Thr Gly Gln Leu Pro Ser Arg Gln Gln
    490                 495                 500

cag cag cag cac aca gaa ctg gat atg gta cca gga aga gat ggg ctg     1709
Gln Gln Gln His Thr Glu Leu Asp Met Val Pro Gly Arg Asp Gly Leu
505                 510                 515                 520

gcc agc tat aat cat tcc cag gtt tct gtc cag cct gtg gca agt gca     1757
Ala Ser Tyr Asn His Ser Gln Val Ser Val Gln Pro Val Ala Ser Ala
                525                 530                 535

gga tca gaa cac agc aag ccc ctt gag aag tca gaa ggt ctc ttt gca     1805
Gly Ser Glu His Ser Lys Pro Leu Glu Lys Ser Glu Gly Leu Phe Ala
            540                 545                 550

cag gac aga gat cca agg ttt cca gaa atc tat ccc agc atc act gca     1853
Gln Asp Arg Asp Pro Arg Phe Pro Glu Ile Tyr Pro Ser Ile Thr Ala
        555                 560                 565
```

-continued

```
gat cag agt aaa ggc atc tcc tcc agc act gtc cct gcc acc caa cag     1901
Asp Gln Ser Lys Gly Ile Ser Ser Ser Thr Val Pro Ala Thr Gln Gln
    570                 575                 580

ctg ttc tcc cag ggc agc tca ttc cct cct aac ccc cgg ccg gca gag     1949
Leu Phe Ser Gln Gly Ser Ser Phe Pro Pro Asn Pro Arg Pro Ala Glu
585                 590                 595                 600

aat ttc agg aat agt ggt ctt acc cct cct gta acc att gtc cag cca     1997
Asn Phe Arg Asn Ser Gly Leu Thr Pro Pro Val Thr Ile Val Gln Pro
                605                 610                 615

tca tct tct gca ggg cag ata ctg gcc cag att tca cgt cac tcc aac     2045
Ser Ser Ser Ala Gly Gln Ile Leu Ala Gln Ile Ser Arg His Ser Asn
            620                 625                 630

cct gcc cag gga tca gcg ccg acc tgg acc tct agc tcc cgc cca ggc     2093
Pro Ala Gln Gly Ser Ala Pro Thr Trp Thr Ser Ser Ser Arg Pro Gly
        635                 640                 645

ttt gcc gcc cag gta gcg cct ctt acc tgt ctg acc ctg tgt gtt gtt     2141
Phe Ala Ala Gln Val Ala Pro Leu Thr Cys Leu Thr Leu Cys Val Val
    650                 655                 660

gtt tgt ggg atc ttt ttt ttt tcc tcc agg taa atttattatt gtcagatacc   2194
Val Cys Gly Ile Phe Phe Phe Ser Ser Arg
665                 670

tccttttcag ttcctgttct tcatctttta attttcatct tttttgcgag gagctagata   2254

attaaaatac cagagataac atccagaagt ctctttagaa cctatgtttt catatgctca   2314

ccttaagaca gaactgctca ttcacagcag tttgaacagc tttggtctca ggcttgtttg   2374

gagtaaattc aaagagtttg tctttgttta ggactatgta atatagtacc aaagtagaaa   2434

attagtaatt atattcattt atttatgaaa atatagtatc catctatata atatatagta   2494

aatatgttaa atttatttat tactatgtat ttctcttgtc tatataataa tttagaaaag   2554

ttt                                                                 2557


<210> SEQ ID NO 101
<211> LENGTH: 4259
<212> TYPE: DNA
<213> ORGANISM: M. musculus
<220> FEATURE:
<220> FEATURE:
<221> NAME/KEY: CDS
<222> LOCATION: (135)...(2417)

<400> SEQUENCE: 101

gatcttggat tccgcggtag cggtggcggc ggtaaggtgc ctaatctgcg gagtggctct     60

tccctcccct cccccagctc ggtggcggct gcccctccca ccgagggtgg cgcagggacg    120

gtgccatctc gacc atg gcg gcg act aca gct aac cca gaa atg aca tca      170
                Met Ala Ala Thr Thr Ala Asn Pro Glu Met Thr Ser
                  1               5                  10

gat gta cca tcg ctg ggt ccc acc att gct tct gga aac cct gga cct      218
Asp Val Pro Ser Leu Gly Pro Thr Ile Ala Ser Gly Asn Pro Gly Pro
         15                  20                  25

ggg att caa ggt gga gga gct gtt gta cag agg gct att aag cga cgg      266
Gly Ile Gln Gly Gly Gly Ala Val Val Gln Arg Ala Ile Lys Arg Arg
     30                  35                  40

tca ggg ctg gat ttt gat gat gaa gta gaa gtg aac act aaa ttt ttg      314
Ser Gly Leu Asp Phe Asp Asp Glu Val Glu Val Asn Thr Lys Phe Leu
 45                  50                  55                  60

aga tgc gat gat gac cag atg tgt aat gac aaa gag cgg ttt gcc agg      362
Arg Cys Asp Asp Asp Gln Met Cys Asn Asp Lys Glu Arg Phe Ala Arg
                65                  70                  75

gaa aat cat agt gaa ata gaa cgg cgg cga cgg aac aag atg aca gct      410
```

-continued

```
Glu Asn His Ser Glu Ile Glu Arg Arg Arg Arg Asn Lys Met Thr Ala
            80                  85                  90

tac atc aca gaa ctg tca gac atg gta cct aca tgt agt gcc ctg gct      458
Tyr Ile Thr Glu Leu Ser Asp Met Val Pro Thr Cys Ser Ala Leu Ala
        95                  100                 105

cga aaa cca gac aag cta acc atc tta cgc atg gcc gtt tct cac atg      506
Arg Lys Pro Asp Lys Leu Thr Ile Leu Arg Met Ala Val Ser His Met
    110                 115                 120

aag tcc ttg agg gga act ggc aac aca tct act gat ggc tcc tac aag      554
Lys Ser Leu Arg Gly Thr Gly Asn Thr Ser Thr Asp Gly Ser Tyr Lys
125                 130                 135                 140

cca tct ttc ctc act gat cag gaa ctg aaa cat ttg atc ttg gag gca      602
Pro Ser Phe Leu Thr Asp Gln Glu Leu Lys His Leu Ile Leu Glu Ala
                145                 150                 155

gca gat ggc ttt ctg ttt att gtc tcc tgt gag act gga cgg gtg gtg      650
Ala Asp Gly Phe Leu Phe Ile Val Ser Cys Glu Thr Gly Arg Val Val
            160                 165                 170

tat gtc tct gac tca gtg act ccc gtt ttg aac cag cca cag tct gaa      698
Tyr Val Ser Asp Ser Val Thr Pro Val Leu Asn Gln Pro Gln Ser Glu
        175                 180                 185

tgg ttc ggg agc aca ctg tat gat cag gtg cac cca gat gat gtg gat      746
Trp Phe Gly Ser Thr Leu Tyr Asp Gln Val His Pro Asp Asp Val Asp
    190                 195                 200

aaa ctt cga gag cag ctc tct aca tca gaa aat gcc cta aca ggg cgg      794
Lys Leu Arg Glu Gln Leu Ser Thr Ser Glu Asn Ala Leu Thr Gly Arg
205                 210                 215                 220

gtc ctg gat ctg aag act gga aca gtg aaa aag gaa ggc cag cag tct      842
Val Leu Asp Leu Lys Thr Gly Thr Val Lys Lys Glu Gly Gln Gln Ser
                225                 230                 235

tcc atg agg atg tgc atg ggc tca cga agg tcg ttc atc tgc cgc atg      890
Ser Met Arg Met Cys Met Gly Ser Arg Arg Ser Phe Ile Cys Arg Met
            240                 245                 250

agg tgt ggt act agc tcc gtg gac cct gtt tcc atg aat aga ctg agc      938
Arg Cys Gly Thr Ser Ser Val Asp Pro Val Ser Met Asn Arg Leu Ser
        255                 260                 265

ttt ttg agg aac aga tgc agg aat ggg ctt ggc tct gtg aag gaa gga      986
Phe Leu Arg Asn Arg Cys Arg Asn Gly Leu Gly Ser Val Lys Glu Gly
    270                 275                 280

gaa cct cac ttt gtg gta gtc cac tgc aca ggc tac atc aag gcc tgg     1034
Glu Pro His Phe Val Val Val His Cys Thr Gly Tyr Ile Lys Ala Trp
285                 290                 295                 300

cca cca gca ggt gtc tcc ctc cca gat gat gac cca gag gct ggc cag     1082
Pro Pro Ala Gly Val Ser Leu Pro Asp Asp Asp Pro Glu Ala Gly Gln
                305                 310                 315

ggg agc aaa ttc tgc cta gtg gcc att ggc agg ctg cag gta act agt     1130
Gly Ser Lys Phe Cys Leu Val Ala Ile Gly Arg Leu Gln Val Thr Ser
            320                 325                 330

tct ccc aac tgt aca gac atg agt aac att tgt cag cca aca gag ttc     1178
Ser Pro Asn Cys Thr Asp Met Ser Asn Ile Cys Gln Pro Thr Glu Phe
        335                 340                 345

atc tcc cga cac aac att gaa ggg ata ttc act ttt gta gac cat cgt     1226
Ile Ser Arg His Asn Ile Glu Gly Ile Phe Thr Phe Val Asp His Arg
    350                 355                 360

tgt gtg gct act gtt ggc tac cag cca cag gag ctc tta ggg aag aat     1274
Cys Val Ala Thr Val Gly Tyr Gln Pro Gln Glu Leu Leu Gly Lys Asn
365                 370                 375                 380

att gta gaa ttt tgt cat cct gaa gac caa caa ctt cta aga gac agc     1322
Ile Val Glu Phe Cys His Pro Glu Asp Gln Gln Leu Leu Arg Asp Ser
                385                 390                 395
```

-continued

```
ttt cag cag gtg gtg aaa tta aaa ggt cag gtg ctg tcc gtc atg ttc      1370
Phe Gln Gln Val Val Lys Leu Lys Gly Gln Val Leu Ser Val Met Phe
            400                 405                 410

cga ttc cga tct aag acc cga gaa tgg ctg tgg atg aga acg agc tcc      1418
Arg Phe Arg Ser Lys Thr Arg Glu Trp Leu Trp Met Arg Thr Ser Ser
        415                 420                 425

ttt acc ttc caa aac cct tat tca gat gaa att gag tat att atc tgc      1466
Phe Thr Phe Gln Asn Pro Tyr Ser Asp Glu Ile Glu Tyr Ile Ile Cys
    430                 435                 440

acc aac acc aat gtg aag aac tct agc cag gaa cca cgg cct aca ctg      1514
Thr Asn Thr Asn Val Lys Asn Ser Ser Gln Glu Pro Arg Pro Thr Leu
445                 450                 455                 460

tcc aac acc atc cca agg tca cag cta ggt ccg aca gcc aat tta tcc      1562
Ser Asn Thr Ile Pro Arg Ser Gln Leu Gly Pro Thr Ala Asn Leu Ser
                465                 470                 475

cta gag atg ggt aca ggg cag ctg cca tcc agg cag cag cag cag cag      1610
Leu Glu Met Gly Thr Gly Gln Leu Pro Ser Arg Gln Gln Gln Gln Gln
            480                 485                 490

cac aca gaa ctg gat atg gta cca gga aga gat ggg ctg gcc agc tat      1658
His Thr Glu Leu Asp Met Val Pro Gly Arg Asp Gly Leu Ala Ser Tyr
        495                 500                 505

aat cat tcc cag gtt tct gtc cag cct gtg gca agt gca gga tca gaa      1706
Asn His Ser Gln Val Ser Val Gln Pro Val Ala Ser Ala Gly Ser Glu
    510                 515                 520

cac agc aag ccc ctt gag aag tca gaa ggt ctc ttt gca cag gac aga      1754
His Ser Lys Pro Leu Glu Lys Ser Glu Gly Leu Phe Ala Gln Asp Arg
525                 530                 535                 540

gat cca agg ttt cca gaa atc tat ccc agc atc act gca gat cag agt      1802
Asp Pro Arg Phe Pro Glu Ile Tyr Pro Ser Ile Thr Ala Asp Gln Ser
                545                 550                 555

aaa ggc atc tcc tcc agc act gtc cct gcc acc caa cag ctg ttc tcc      1850
Lys Gly Ile Ser Ser Ser Thr Val Pro Ala Thr Gln Gln Leu Phe Ser
            560                 565                 570

cag ggc agc tca ttc cct cct aac ccc cgg ccg gca gag aat ttc agg      1898
Gln Gly Ser Ser Phe Pro Pro Asn Pro Arg Pro Ala Glu Asn Phe Arg
        575                 580                 585

aat agt ggt ctt acc cct cct gta acc att gtc cag cca tca tct tct      1946
Asn Ser Gly Leu Thr Pro Pro Val Thr Ile Val Gln Pro Ser Ser Ser
    590                 595                 600

gca ggg cag ata ctg gcc cag att tca cgt cac tcc aac cct gcc cag      1994
Ala Gly Gln Ile Leu Ala Gln Ile Ser Arg His Ser Asn Pro Ala Gln
605                 610                 615                 620

gga tca gcg ccg acc tgg acc tct agc tcc cgc cca ggc ttt gcc gcc      2042
Gly Ser Ala Pro Thr Trp Thr Ser Ser Ser Arg Pro Gly Phe Ala Ala
                625                 630                 635

cag gtg ccc acc cag gct aca gcc aag act cgt tct tcc caa ttt ggt      2090
Gln Val Pro Thr Gln Ala Thr Ala Lys Thr Arg Ser Ser Gln Phe Gly
            640                 645                 650

gtg aac aac ttt cag act tct tcc tcc ttc agt gct atg tct ctt ccg      2138
Val Asn Asn Phe Gln Thr Ser Ser Ser Phe Ser Ala Met Ser Leu Pro
        655                 660                 665

ggt gct ccc act gcc tca tct gct cct gag act gga cag acc aca gga      2186
Gly Ala Pro Thr Ala Ser Ser Ala Pro Glu Thr Gly Gln Thr Thr Gly
    670                 675                 680

cag ttc cag gcc cgg aca gca gag ggc gtg ggt gtc tgg cca cag tgg      2234
Gln Phe Gln Ala Arg Thr Ala Glu Gly Val Gly Val Trp Pro Gln Trp
685                 690                 695                 700

cag ggc cag cag ccc cat cat cgg tct agt tcc agt gag cag cat gtt      2282
Gln Gly Gln Gln Pro His His Arg Ser Ser Ser Ser Glu Gln His Val
                705                 710                 715
```

-continued

```
cag cag aca caa gca caa gca cct agc cag cct gag gtc ttt caa gaa     2330
Gln Gln Thr Gln Ala Gln Ala Pro Ser Gln Pro Glu Val Phe Gln Glu
            720                 725                 730

atg ctg tcc atg ctg gga gac caa agc aac acc tac aac aat gaa gaa     2378
Met Leu Ser Met Leu Gly Asp Gln Ser Asn Thr Tyr Asn Asn Glu Glu
        735                 740                 745

ttt cct gat cta act atg ttt ccc ccc ttt tcc gaa tag aactattggg      2427
Phe Pro Asp Leu Thr Met Phe Pro Pro Phe Ser Glu
    750                 755                 760

gtgagaataa gggtgggggg aaatcactgt ttgtttttaa aagcaaatct tttgtaaaca   2487

gaataaaagt tcctctccct tcccttccct cacccctgat atgtaccctt tccacccctt   2547

gacttgctga agaaacgtta tagaagaaat taaatgaatt tcccaggctt ttaggatcct   2607

ctgaaatttt gaggataggt gaggcctgaa ttcctgtcct tatttcttct gaccagaagt   2667

tgcacagaca tgatttgtgc tggagtcaag gggcagaaca gaagaatctg acaggcacta   2727

attggatact gtggcttgtt tggatagaaa ttctgaatgg agtggaggaa aggagaaatg   2787

ccctcatcac tgaggatcat gaaacacagt aggggtgtgt ggagccttgg gacgtgagca   2847

gtctccagaa agaggcctga gagagagcat gaacacttat ctttgtgagt gagtgagtga   2907

gtgagtgagt gagtgtgtgt gtgtgtgtgt gtgtgtgaga gagagagaga gagagtaaga   2967

gacagagaca gatggggtga ggggggcatt tgagctccta tgttttgttc cctattatag   3027

agtatatgca aaatttgtcc cagatcttct ttgactttgt gcttgctctt taaagtgtcc   3087

taagaaaatt aatttttttca ggtatttttc tatttagtgt tgcagccaaa gagtatttaa   3147

attaagtctt tgctgcactt aaattcatac ccagccaaaa tggaacttta ggccaacccc   3207

cagccttctg ttgctagggt tggtctccta cagacacagt gatcaagctg gatgactcct   3267

gctctttggt gctttcaact cattgggaag agctgcagat attaccaaaa taggctggct   3327

acatgaacac tgtcagaaat cccagacttg cccacaagga taatgctgca tttttctgtc   3387

agagtcacac atgtttttct ggagaggtta tttctgcatg gaaactcaac ttcttggatt   3447

agctatcttg agtgaaagtc ctcactgacg agtatgcaaa ccaaatagcc tcctgcacag   3507

tagcctctcc ttcctgtcac caaaacagtt ttaggtctgc tgaagtctgg tgttctttgc   3567

tccttctgca atcttgaaat tggggtttgc tttagagcac aaacataagt ctgtgttagg   3627

tggacttaaa tcccaacagg gtcacttgat aattatagcc atagaaatgc agatgcaggt   3687

aactgctttt accctttacc gtcctcaggt gagtctccta gatcaacagc cttttttttt   3747

ttttttttcct taaactggct cctgtcaaag attaagttaa tatggaaaag acctcttatg   3807

tgtattgatg gggcatgagg agcccaggca aggagaggct cgtggagagg ctgagggaat   3867

gttactaagt ttccctccgt ttgtctccag tctggtgcca ggcagtagag tggaaaagga   3927

ggctattttt ttattctatg tgcacacata cagtatacat atatatttat atcacatttt   3987

actgaaccaa aaagttgggt tttccaataa aatacttgtt ttttaataac cgacttgttt   4047

ttaactgtga tctgaactat aacgtacagt tattacaggg cttctgaaga aggggggggcg   4107

gggagaagct tctctgaggg gctcgctctg cttttccttc acggttttat ttttgattgt   4167

tttttcttgt tgcccatctg tgctaagcct taactgtggc aaaaataatg acatgtagca   4227

aagattttaa aacaaagtat tttttctttt at                                 4259
```

<210> SEQ ID NO 102
<211> LENGTH: 701
<212> TYPE: DNA

-continued

```
<213> ORGANISM: M. musculus
<220> FEATURE:
<221> NAME/KEY: unsure
<222> LOCATION: 670
<223> OTHER INFORMATION: unknown

<400> SEQUENCE: 102

ggaaaccctg gacctgggat tcaaggtgga ggagctgttg tacagagggc tattaagcga     60

cggtcagggc tggattttga tgatgaagta gaagtgaaca ctaaattttt gagatgcgat    120

gatgaccaga tgttttatga caaagagcgg tttgccaggg aaaatcatag tgaaatagaa    180

cggcggcgac ggaacaagat gacagcttac atcacagaac tgtcagacat ggtacctaca    240

tgtagtgccc tggctcgaaa accagacaag ctaaccatct tacgcatggc cgtttctcac    300

atgaagtcct tgaggggaac tggcaacaca tctactgatg gctcctacaa gccatctttc    360

ctcactgatc aggaactgaa acatttgatc ttggaggcag cagatggctt tctgtttatt    420

gtctcctgtg agactggacg ggtggtgtat gtctctgact cagtgactcc cgttttgaac    480

cagccacagt ctgaatggtt cgggagcaca ctgtatgatc aggtgcaccc agatgatgtg    540

gataaacttc gagagcagct ctctacatca gaaaatgccc taacaggtga gagctggctg    600

gacagcagat atgtggggga aaagtcttta tttcactcaa gtagttaaga tattttaagc    660

ccgaaaccan aaaaaaaaaa aaaaaaaaaa agggcggccg c                        701


<210> SEQ ID NO 103
<211> LENGTH: 2412
<212> TYPE: DNA
<213> ORGANISM: M. musculus
<220> FEATURE:
<220> FEATURE:
<221> NAME/KEY: CDS
<222> LOCATION: (120)...(551)

<400> SEQUENCE: 103

aaaaaaaatg cctgaacaga gcaagatgag ataaaaaccc tgtaaaaata tcactgaata     60

cataggttac ctatgggact ggactaagat gttagtaatt gttcaccttt agtcaatat     119

atg gag ttt att gta ttg agt aat tcc ttg ttt ccc ctt ttg tgt tct      167
Met Glu Phe Ile Val Leu Ser Asn Ser Leu Phe Pro Leu Leu Cys Ser
  1               5                  10                  15

tgt cta ctc tat ttt cct agg aac tct agc cag gaa cca cgg cct aca      215
Cys Leu Leu Tyr Phe Pro Arg Asn Ser Ser Gln Glu Pro Arg Pro Thr
             20                  25                  30

ctg tcc aac acc atc cca agg tca cag cta ggt ccg aca gcc aat tta      263
Leu Ser Asn Thr Ile Pro Arg Ser Gln Leu Gly Pro Thr Ala Asn Leu
         35                  40                  45

tcc cta gag atg ggt aca ggg cag ctg cca tcc agg cag cag cag cag      311
Ser Leu Glu Met Gly Thr Gly Gln Leu Pro Ser Arg Gln Gln Gln Gln
     50                  55                  60

cag cac aca gaa ctg gat atg gta cca aga aga gat ggg ctg gcc agc      359
Gln His Thr Glu Leu Asp Met Val Pro Arg Arg Asp Gly Leu Ala Ser
 65                  70                  75                  80

tat aat cat tcc cag gtt tct gtc cag cct gtg gca agt gca gga tca      407
Tyr Asn His Ser Gln Val Ser Val Gln Pro Val Ala Ser Ala Gly Ser
                 85                  90                  95

gaa cac agc aag ccc ctt gag aag tca gaa ggt ctc ttt gca cag gac      455
Glu His Ser Lys Pro Leu Glu Lys Ser Glu Gly Leu Phe Ala Gln Asp
            100                 105                 110

aga gat cca agg ttt cca gaa atc tat ccc agc atc act gca ggt atg      503
Arg Asp Pro Arg Phe Pro Glu Ile Tyr Pro Ser Ile Thr Ala Gly Met
        115                 120                 125
```

-continued

```
ggt ttc ttc cgc agg ctc ctt tta cag gct gag ttt cat tat tac tga      551
Gly Phe Phe Arg Arg Leu Leu Leu Gln Ala Glu Phe His Tyr Tyr
    130                 135                 140

tgggactgcc cagtcagcat acttctactt cagttacagt acttcatgaa taagtaggaa    611

ttgattaaac tatgtgctac agccccttga tggccctccc ccaactcctt ttggtctgca    671

gatcagagta aaggcatctc ctccagcact gtccctgcca cccaacagct gttctcccag    731

ggcagctcat tccctcctaa cccccggccg gcagagaatt tcaggtgagc cccatatgtg    791

tgtgctgctt gacagggctc tgcagggttc agttgctgga tccgtgtgtc atcttccctt    851

gctttctctg gtcacctcag acaaagcagt agaacttact ggacctaggg tgagacaacg    911

aagctgcttt tcctcctgtt tttgcaccta ttctattgcc ttgctctagg ttccaaacgt    971

ctctgtgtgg tcagtgtgtg acagtcagtc tttcttgtgt ttttaaattt atcaggtttt   1031

ccttaactcc aagaaatcag aggaatctag ggatagaatg tgtcctttga ttcatagctt   1091

ctgtgatgga gtcaaccttt taaccttcac tttctatttg ttccttccta ggaatagtgg   1151

tcttacccct cctgtaacca ttgtccagcc atcatcttct gcagggcaga tactggccca   1211

gatttcacgt cactccaacc ctgcccaggg atcagcgccg acctggacct ctagctcccg   1271

cccaggcttt gccgcccagg tagcgcctct tacctgtctg accctgtgtg ttgttgtttg   1331

tgggatcttt tttttttcct ccaggtaaat ttattattgt cagatacctc cttttcagtt   1391

cctgttcttc atcttttaat tttcatcttt tttgcgagga gctagataat taaaatacca   1451

gagataacat ccagaagtct ctttagaacc tatgttttca tatgctcacc ttaagacaga   1511

actgctcatt cacagcagtt tgaacagctt tggtctcagg cttgtttgga gtaaattcaa   1571

agagtttgtc tttgtttagg actatgtaat atagtaccaa agtagaaaat tagtaattat   1631

attcatttat ttatgaaaat atagtatcca tctatataat atatagtaaa tatgttaaat   1691

ttatttatta ctatgtattt ctcttgtcta tataataatt tagaaaagtt taaaaaaaaa   1751

tgaaaactca aacttgactc cagaattgtt ctctatagct tttttgtgta tgtgtaaaaa   1811

tactcaggaa tgttgcccat gactcttggt caggatgtgc cgtgatgttg atgacagctg   1871

ctaccatggt tttcatactg gtgacataat caagcatgca tatattatct cccttggagt   1931

tactttttaa attgtggatt taaaacggtc tctagaaatt attgtatctc acaaaaaatg   1991

ttagaggcaa taactagttt cttaatcaat atacagtaaa tgggtgtgag aaaggacagc   2051

tttaatttca acaaagagac tgaggcagga gcatgggcct gggccacata gtgagagata   2111

aactgtctca taaaagaaag aacagaacaa aaccaaaata gcataatgga aaataaaaga   2171

ggacattgtc cactgtgcca agtaacagtc tcttctggtg gggttaacag tgaggtttca   2231

tttctagttt attttttcca atttttttct attctttttg aggcagattt agaatttata   2291

ttaaacaacc ctttgcagat ttacacttaa agtcaagagc aaaagagaag cactcagaac   2351

tgagtgtggg tgtgaactcc ctaagatgcc accaaattcc tctgtaacac atagggattc   2411

c                                                                   2412
```

```
<210> SEQ ID NO 104
<211> LENGTH: 20
<212> TYPE: DNA
<213> ORGANISM: Artificial Sequence
<220> FEATURE:
<223> OTHER INFORMATION: Antisense Compound

<400> SEQUENCE: 104
```

-continued gattccagca gaaacaagat 20

<210> SEQ ID NO 105
<211> LENGTH: 20
<212> TYPE: DNA
<213> ORGANISM: Artificial Sequence
<220> FEATURE:
<223> OTHER INFORMATION: Antisense Compound

<400> SEQUENCE: 105
agtaccataa ccaggaagag 20

<210> SEQ ID NO 106
<211> LENGTH: 20
<212> TYPE: DNA
<213> ORGANISM: Artificial Sequence
<220> FEATURE:
<223> OTHER INFORMATION: Antisense Compound

<400> SEQUENCE: 106
atcatcgcat ctgaaaagaa 20

<210> SEQ ID NO 107
<211> LENGTH: 20
<212> TYPE: DNA
<213> ORGANISM: Artificial Sequence
<220> FEATURE:
<223> OTHER INFORMATION: Antisense Compound

<400> SEQUENCE: 107
tcatacttgc ctgcagcctg 20

<210> SEQ ID NO 108
<211> LENGTH: 20
<212> TYPE: DNA
<213> ORGANISM: Artificial Sequence
<220> FEATURE:
<223> OTHER INFORMATION: Antisense Compound

<400> SEQUENCE: 108
agattaggca ccttaccgcc 20

<210> SEQ ID NO 109
<211> LENGTH: 20
<212> TYPE: DNA
<213> ORGANISM: Artificial Sequence
<220> FEATURE:
<223> OTHER INFORMATION: Antisense Compound

<400> SEQUENCE: 109
gccgccatgg tcgagatggc 20

<210> SEQ ID NO 110
<211> LENGTH: 20
<212> TYPE: DNA
<213> ORGANISM: Artificial Sequence
<220> FEATURE:
<223> OTHER INFORMATION: Antisense Compound

<400> SEQUENCE: 110
gttagctgta gtcgccgcca 20

<210> SEQ ID NO 111
<211> LENGTH: 20
<212> TYPE: DNA
<213> ORGANISM: Artificial Sequence -continued
<220> FEATURE:
<223> OTHER INFORMATION: Antisense Compound

<400> SEQUENCE: 111
tcatttctgg gttagctgta 20

<210> SEQ ID NO 112
<211> LENGTH: 20
<212> TYPE: DNA
<213> ORGANISM: Artificial Sequence
<220> FEATURE:
<223> OTHER INFORMATION: Antisense Compound

<400> SEQUENCE: 112
acatctgatg tcatttctgg 20

<210> SEQ ID NO 113
<211> LENGTH: 20
<212> TYPE: DNA
<213> ORGANISM: Artificial Sequence
<220> FEATURE:
<223> OTHER INFORMATION: Antisense Compound

<400> SEQUENCE: 113
ttccagaagc aatggtggga 20

<210> SEQ ID NO 114
<211> LENGTH: 20
<212> TYPE: DNA
<213> ORGANISM: Artificial Sequence
<220> FEATURE:
<223> OTHER INFORMATION: Antisense Compound

<400> SEQUENCE: 114
agctcctcca ccttgaatcc 20

<210> SEQ ID NO 115
<211> LENGTH: 20
<212> TYPE: DNA
<213> ORGANISM: Artificial Sequence
<220> FEATURE:
<223> OTHER INFORMATION: Antisense Compound

<400> SEQUENCE: 115
cgtcgcttaa tagccctctg 20

<210> SEQ ID NO 116
<211> LENGTH: 20
<212> TYPE: DNA
<213> ORGANISM: Artificial Sequence
<220> FEATURE:
<223> OTHER INFORMATION: Antisense Compound

<400> SEQUENCE: 116
cagccctgac cgtcgcttaa 20

<210> SEQ ID NO 117
<211> LENGTH: 20
<212> TYPE: DNA
<213> ORGANISM: Artificial Sequence
<220> FEATURE:
<223> OTHER INFORMATION: Antisense Compound

<400> SEQUENCE: 117
catcaaaatc cagccctgac 20

-continued

<210> SEQ ID NO 118
<211> LENGTH: 20
<212> TYPE: DNA
<213> ORGANISM: Artificial Sequence
<220> FEATURE:
<223> OTHER INFORMATION: Antisense Compound

<400> SEQUENCE: 118
ctggcaaacc gctctttgtc 20

<210> SEQ ID NO 119
<211> LENGTH: 20
<212> TYPE: DNA
<213> ORGANISM: Artificial Sequence
<220> FEATURE:
<223> OTHER INFORMATION: Antisense Compound

<400> SEQUENCE: 119
atcatccgac ctggcaaacc 20

<210> SEQ ID NO 120
<211> LENGTH: 20
<212> TYPE: DNA
<213> ORGANISM: Artificial Sequence
<220> FEATURE:
<223> OTHER INFORMATION: Antisense Compound

<400> SEQUENCE: 120
agctctgctc atcatccgac 20

<210> SEQ ID NO 121
<211> LENGTH: 20
<212> TYPE: DNA
<213> ORGANISM: Artificial Sequence
<220> FEATURE:
<223> OTHER INFORMATION: Antisense Compound

<400> SEQUENCE: 121
gtctctcttt atccgcagag 20

<210> SEQ ID NO 122
<211> LENGTH: 20
<212> TYPE: DNA
<213> ORGANISM: Artificial Sequence
<220> FEATURE:
<223> OTHER INFORMATION: Antisense Compound

<400> SEQUENCE: 122
ctggcaagtc tctctttatc 20

<210> SEQ ID NO 123
<211> LENGTH: 20
<212> TYPE: DNA
<213> ORGANISM: Artificial Sequence
<220> FEATURE:
<223> OTHER INFORMATION: Antisense Compound

<400> SEQUENCE: 123
tttccctggc aagtctctct 20

<210> SEQ ID NO 124
<211> LENGTH: 20
<212> TYPE: DNA
<213> ORGANISM: Artificial Sequence
<220> FEATURE:
<223> OTHER INFORMATION: Antisense Compound -continued

<400> SEQUENCE: 124
atgattttcc ctggcaagtc 20

<210> SEQ ID NO 125
<211> LENGTH: 20
<212> TYPE: DNA
<213> ORGANISM: Artificial Sequence
<220> FEATURE:
<223> OTHER INFORMATION: Antisense Compound

<400> SEQUENCE: 125
gtaagctgtc atcttgttcc 20

<210> SEQ ID NO 126
<211> LENGTH: 20
<212> TYPE: DNA
<213> ORGANISM: Artificial Sequence
<220> FEATURE:
<223> OTHER INFORMATION: Antisense Compound

<400> SEQUENCE: 126
gttctgtgat gtaagctgtc 20

<210> SEQ ID NO 127
<211> LENGTH: 20
<212> TYPE: DNA
<213> ORGANISM: Artificial Sequence
<220> FEATURE:
<223> OTHER INFORMATION: Antisense Compound

<400> SEQUENCE: 127
tagcttgtct ggttttcgag 20

<210> SEQ ID NO 128
<211> LENGTH: 20
<212> TYPE: DNA
<213> ORGANISM: Artificial Sequence
<220> FEATURE:
<223> OTHER INFORMATION: Antisense Compound

<400> SEQUENCE: 128
caaatgtttc agttcctgat 20

<210> SEQ ID NO 129
<211> LENGTH: 20
<212> TYPE: DNA
<213> ORGANISM: Artificial Sequence
<220> FEATURE:
<223> OTHER INFORMATION: Antisense Compound

<400> SEQUENCE: 129
taaacagaaa gccatctgct 20

<210> SEQ ID NO 130
<211> LENGTH: 20
<212> TYPE: DNA
<213> ORGANISM: Artificial Sequence
<220> FEATURE:
<223> OTHER INFORMATION: Antisense Compound

<400> SEQUENCE: 130
tggttcaaaa cgggagtcac 20

<210> SEQ ID NO 131

-continued

<211> LENGTH: 20
<212> TYPE: DNA
<213> ORGANISM: Artificial Sequence
<220> FEATURE:
<223> OTHER INFORMATION: Antisense Compound

<400> SEQUENCE: 131
gctgctctcg aagtttatcc 20

<210> SEQ ID NO 132
<211> LENGTH: 20
<212> TYPE: DNA
<213> ORGANISM: Artificial Sequence
<220> FEATURE:
<223> OTHER INFORMATION: Antisense Compound

<400> SEQUENCE: 132
gcacatcctc atggaagact 20

<210> SEQ ID NO 133
<211> LENGTH: 20
<212> TYPE: DNA
<213> ORGANISM: Artificial Sequence
<220> FEATURE:
<223> OTHER INFORMATION: Antisense Compound

<400> SEQUENCE: 133
ttcatggaaa cagggtccac 20

<210> SEQ ID NO 134
<211> LENGTH: 20
<212> TYPE: DNA
<213> ORGANISM: Artificial Sequence
<220> FEATURE:
<223> OTHER INFORMATION: Antisense Compound

<400> SEQUENCE: 134
gctcagtcta ttcatggaaa 20

<210> SEQ ID NO 135
<211> LENGTH: 20
<212> TYPE: DNA
<213> ORGANISM: Artificial Sequence
<220> FEATURE:
<223> OTHER INFORMATION: Antisense Compound

<400> SEQUENCE: 135
tcctcaaaaa gctcagtcta 20

<210> SEQ ID NO 136
<211> LENGTH: 20
<212> TYPE: DNA
<213> ORGANISM: Artificial Sequence
<220> FEATURE:
<223> OTHER INFORMATION: Antisense Compound

<400> SEQUENCE: 136
ctgcatctgt tcctcaaaaa 20

<210> SEQ ID NO 137
<211> LENGTH: 20
<212> TYPE: DNA
<213> ORGANISM: Artificial Sequence
<220> FEATURE:
<223> OTHER INFORMATION: Antisense Compound

<400> SEQUENCE: 137

-continued tgcagtggac taccacaaag 20

<210> SEQ ID NO 138
<211> LENGTH: 20
<212> TYPE: DNA
<213> ORGANISM: Artificial Sequence
<220> FEATURE:
<223> OTHER INFORMATION: Antisense Compound

<400> SEQUENCE: 138
ggccagcctc tgggtcatca 20

<210> SEQ ID NO 139
<211> LENGTH: 20
<212> TYPE: DNA
<213> ORGANISM: Artificial Sequence
<220> FEATURE:
<223> OTHER INFORMATION: Antisense Compound

<400> SEQUENCE: 139
cagaatttgc tcccctggcc 20

<210> SEQ ID NO 140
<211> LENGTH: 20
<212> TYPE: DNA
<213> ORGANISM: Artificial Sequence
<220> FEATURE:
<223> OTHER INFORMATION: Antisense Compound

<400> SEQUENCE: 140
ggccactagg cagaatttgc 20

<210> SEQ ID NO 141
<211> LENGTH: 20
<212> TYPE: DNA
<213> ORGANISM: Artificial Sequence
<220> FEATURE:
<223> OTHER INFORMATION: Antisense Compound

<400> SEQUENCE: 141
cagcctgcca atggccacta 20

<210> SEQ ID NO 142
<211> LENGTH: 20
<212> TYPE: DNA
<213> ORGANISM: Artificial Sequence
<220> FEATURE:
<223> OTHER INFORMATION: Antisense Compound

<400> SEQUENCE: 142
gtgaatatcc cttcaatgtt 20

<210> SEQ ID NO 143
<211> LENGTH: 20
<212> TYPE: DNA
<213> ORGANISM: Artificial Sequence
<220> FEATURE:
<223> OTHER INFORMATION: Antisense Compound

<400> SEQUENCE: 143
acagtagcca cacaacgatg 20

<210> SEQ ID NO 144
<211> LENGTH: 20
<212> TYPE: DNA

-continued

<213> ORGANISM: Artificial Sequence
<220> FEATURE:
<223> OTHER INFORMATION: Antisense Compound

<400> SEQUENCE: 144
gacaaaattc tacaatattc 20

<210> SEQ ID NO 145
<211> LENGTH: 20
<212> TYPE: DNA
<213> ORGANISM: Artificial Sequence
<220> FEATURE:
<223> OTHER INFORMATION: Antisense Compound

<400> SEQUENCE: 145
gtcttcagga tgacaaaatt 20

<210> SEQ ID NO 146
<211> LENGTH: 20
<212> TYPE: DNA
<213> ORGANISM: Artificial Sequence
<220> FEATURE:
<223> OTHER INFORMATION: Antisense Compound

<400> SEQUENCE: 146
gaagttgttg gtcttcagga 20

<210> SEQ ID NO 147
<211> LENGTH: 20
<212> TYPE: DNA
<213> ORGANISM: Artificial Sequence
<220> FEATURE:
<223> OTHER INFORMATION: Antisense Compound

<400> SEQUENCE: 147
gctgtctctt agaagttgtt 20

<210> SEQ ID NO 148
<211> LENGTH: 20
<212> TYPE: DNA
<213> ORGANISM: Artificial Sequence
<220> FEATURE:
<223> OTHER INFORMATION: Antisense Compound

<400> SEQUENCE: 148
cctgctgaaa gctgtctctt 20

<210> SEQ ID NO 149
<211> LENGTH: 20
<212> TYPE: DNA
<213> ORGANISM: Artificial Sequence
<220> FEATURE:
<223> OTHER INFORMATION: Antisense Compound

<400> SEQUENCE: 149
aatttcacca cctgctgaaa 20

<210> SEQ ID NO 150
<211> LENGTH: 20
<212> TYPE: DNA
<213> ORGANISM: Artificial Sequence
<220> FEATURE:
<223> OTHER INFORMATION: Antisense Compound

<400> SEQUENCE: 150
tcatccacag ccattctcgg 20

-continued

<210> SEQ ID NO 151
<211> LENGTH: 20
<212> TYPE: DNA
<213> ORGANISM: Artificial Sequence
<220> FEATURE:
<223> OTHER INFORMATION: Antisense Compound

<400> SEQUENCE: 151
gtggttcctg gctagagttc 20

<210> SEQ ID NO 152
<211> LENGTH: 20
<212> TYPE: DNA
<213> ORGANISM: Artificial Sequence
<220> FEATURE:
<223> OTHER INFORMATION: Antisense Compound

<400> SEQUENCE: 152
gtcggaccta gctgtgacct 20

<210> SEQ ID NO 153
<211> LENGTH: 20
<212> TYPE: DNA
<213> ORGANISM: Artificial Sequence
<220> FEATURE:
<223> OTHER INFORMATION: Antisense Compound

<400> SEQUENCE: 153
ctgtacccat ctctagggat 20

<210> SEQ ID NO 154
<211> LENGTH: 20
<212> TYPE: DNA
<213> ORGANISM: Artificial Sequence
<220> FEATURE:
<223> OTHER INFORMATION: Antisense Compound

<400> SEQUENCE: 154
ccagcccatc tcttcctggt 20

<210> SEQ ID NO 155
<211> LENGTH: 20
<212> TYPE: DNA
<213> ORGANISM: Artificial Sequence
<220> FEATURE:
<223> OTHER INFORMATION: Antisense Compound

<400> SEQUENCE: 155
ggacagaaac ctgggaatga 20

<210> SEQ ID NO 156
<211> LENGTH: 20
<212> TYPE: DNA
<213> ORGANISM: Artificial Sequence
<220> FEATURE:
<223> OTHER INFORMATION: Antisense Compound

<400> SEQUENCE: 156
gggcttgctg tgttctgatc 20

<210> SEQ ID NO 157
<211> LENGTH: 20
<212> TYPE: DNA
<213> ORGANISM: Artificial Sequence
<220> FEATURE:

-continued

<223> OTHER INFORMATION: Antisense Compound

<400> SEQUENCE: 157
aagagacctt ctgacttctc 20

<210> SEQ ID NO 158
<211> LENGTH: 20
<212> TYPE: DNA
<213> ORGANISM: Artificial Sequence
<220> FEATURE:
<223> OTHER INFORMATION: Antisense Compound

<400> SEQUENCE: 158
cctgggagaa cagctgttgg 20

<210> SEQ ID NO 159
<211> LENGTH: 20
<212> TYPE: DNA
<213> ORGANISM: Artificial Sequence
<220> FEATURE:
<223> OTHER INFORMATION: Antisense Compound

<400> SEQUENCE: 159
aatgagctgc cctgggagaa 20

<210> SEQ ID NO 160
<211> LENGTH: 20
<212> TYPE: DNA
<213> ORGANISM: Artificial Sequence
<220> FEATURE:
<223> OTHER INFORMATION: Antisense Compound

<400> SEQUENCE: 160
gttaggaggg aatgagctgc 20

<210> SEQ ID NO 161
<211> LENGTH: 20
<212> TYPE: DNA
<213> ORGANISM: Artificial Sequence
<220> FEATURE:
<223> OTHER INFORMATION: Antisense Compound

<400> SEQUENCE: 161
cactattcct gaaattctct 20

<210> SEQ ID NO 162
<211> LENGTH: 20
<212> TYPE: DNA
<213> ORGANISM: Artificial Sequence
<220> FEATURE:
<223> OTHER INFORMATION: Antisense Compound

<400> SEQUENCE: 162
atctgccctg cagaagatga 20

<210> SEQ ID NO 163
<211> LENGTH: 20
<212> TYPE: DNA
<213> ORGANISM: Artificial Sequence
<220> FEATURE:
<223> OTHER INFORMATION: Antisense Compound

<400> SEQUENCE: 163
aagaacgagt cttggctgta 20

-continued

<210> SEQ ID NO 164
<211> LENGTH: 20
<212> TYPE: DNA
<213> ORGANISM: Artificial Sequence
<220> FEATURE:
<223> OTHER INFORMATION: Antisense Compound

<400> SEQUENCE: 164
tctgaaagtt gttcacacca 20

<210> SEQ ID NO 165
<211> LENGTH: 20
<212> TYPE: DNA
<213> ORGANISM: Artificial Sequence
<220> FEATURE:
<223> OTHER INFORMATION: Antisense Compound

<400> SEQUENCE: 165
gtctcaggag gaaagttgga 20

<210> SEQ ID NO 166
<211> LENGTH: 20
<212> TYPE: DNA
<213> ORGANISM: Artificial Sequence
<220> FEATURE:
<223> OTHER INFORMATION: Antisense Compound

<400> SEQUENCE: 166
cctgccactg tggccagaca 20

<210> SEQ ID NO 167
<211> LENGTH: 20
<212> TYPE: DNA
<213> ORGANISM: Artificial Sequence
<220> FEATURE:
<223> OTHER INFORMATION: Antisense Compound

<400> SEQUENCE: 167
ttcttgaaag acctcaggct 20

<210> SEQ ID NO 168
<211> LENGTH: 20
<212> TYPE: DNA
<213> ORGANISM: Artificial Sequence
<220> FEATURE:
<223> OTHER INFORMATION: Antisense Compound

<400> SEQUENCE: 168
tctcccagca tggacagcat 20

<210> SEQ ID NO 169
<211> LENGTH: 20
<212> TYPE: DNA
<213> ORGANISM: Artificial Sequence
<220> FEATURE:
<223> OTHER INFORMATION: Antisense Compound

<400> SEQUENCE: 169
ccaatagttc tattcggaaa 20

<210> SEQ ID NO 170
<211> LENGTH: 20
<212> TYPE: DNA
<213> ORGANISM: Artificial Sequence
<220> FEATURE:
<223> OTHER INFORMATION: Antisense Compound -continued

<400> SEQUENCE: 170
tctgtttaca aaagatttgc 20

<210> SEQ ID NO 171
<211> LENGTH: 20
<212> TYPE: DNA
<213> ORGANISM: Artificial Sequence
<220> FEATURE:
<223> OTHER INFORMATION: Antisense Compound

<400> SEQUENCE: 171
cggaatccaa gatggcggac 20

<210> SEQ ID NO 172
<211> LENGTH: 20
<212> TYPE: DNA
<213> ORGANISM: Artificial Sequence
<220> FEATURE:
<223> OTHER INFORMATION: Antisense Compound

<400> SEQUENCE: 172
ctccaaacaa gcctgagacc 20

<210> SEQ ID NO 173
<211> LENGTH: 20
<212> TYPE: DNA
<213> ORGANISM: Artificial Sequence
<220> FEATURE:
<223> OTHER INFORMATION: Antisense Compound

<400> SEQUENCE: 173
atgattttcc ctggcaaacc 20

<210> SEQ ID NO 174
<211> LENGTH: 20
<212> TYPE: DNA
<213> ORGANISM: Artificial Sequence
<220> FEATURE:
<223> OTHER INFORMATION: Antisense Compound

<400> SEQUENCE: 174
ggcacctggg cggcaaagcc 20

<210> SEQ ID NO 175
<211> LENGTH: 20
<212> TYPE: DNA
<213> ORGANISM: Artificial Sequence
<220> FEATURE:
<223> OTHER INFORMATION: Antisense Compound

<400> SEQUENCE: 175
agacttttcc cccacatatc 20

<210> SEQ ID NO 176
<211> LENGTH: 20
<212> TYPE: DNA
<213> ORGANISM: Artificial Sequence
<220> FEATURE:
<223> OTHER INFORMATION: Antisense Compound

<400> SEQUENCE: 176
taacctatgt attcagtgat 20

<210> SEQ ID NO 177
<211> LENGTH: 20

-continued

<212> TYPE: DNA
<213> ORGANISM: Artificial Sequence
<220> FEATURE:
<223> OTHER INFORMATION: Antisense Compound

<400> SEQUENCE: 177
ttcgcggctg gacgattcag 20

<210> SEQ ID NO 178
<211> LENGTH: 21
<212> TYPE: DNA
<213> ORGANISM: Artificial Sequence
<220> FEATURE:
<223> OTHER INFORMATION: Antisense Compound

<400> SEQUENCE: 178
cctggcaaca tctggggttg g 21

<210> SEQ ID NO 179
<211> LENGTH: 25
<212> TYPE: DNA
<213> ORGANISM: Artificial Sequence
<220> FEATURE:
<223> OTHER INFORMATION: Antisense Compound

<400> SEQUENCE: 179
caacaggctg gagtgactgg gctcc 25

<210> SEQ ID NO 180
<211> LENGTH: 26
<212> TYPE: DNA
<213> ORGANISM: Artificial Sequence
<220> FEATURE:
<223> OTHER INFORMATION: Antisense Compound

<400> SEQUENCE: 180
gtggagacag gactagtgca cgaatg 26

<210> SEQ ID NO 181
<211> LENGTH: 25
<212> TYPE: DNA
<213> ORGANISM: Artificial Sequence
<220> FEATURE:
<223> OTHER INFORMATION: Antisense Compound

<400> SEQUENCE: 181
ctgtggaggc atggactgag aatgg 25

<210> SEQ ID NO 182
<211> LENGTH: 24
<212> TYPE: DNA
<213> ORGANISM: Artificial Sequence
<220> FEATURE:
<223> OTHER INFORMATION: Antisense Compound

<400> SEQUENCE: 182
ctgggaacct ccaaatcccc tggc 24

<210> SEQ ID NO 183
<211> LENGTH: 26
<212> TYPE: DNA
<213> ORGANISM: Artificial Sequence
<220> FEATURE:
<223> OTHER INFORMATION: Antisense Compound

<400> SEQUENCE: 183

-continued ctgggcaggg ttggcagctg ccttac 26

<210> SEQ ID NO 184
<211> LENGTH: 20
<212> TYPE: DNA
<213> ORGANISM: Artificial Sequence
<220> FEATURE:
<223> OTHER INFORMATION: Antisense Compound

<400> SEQUENCE: 184
tgagctgtct gtgatccagc 20

<210> SEQ ID NO 185
<211> LENGTH: 20
<212> TYPE: DNA
<213> ORGANISM: Artificial Sequence
<220> FEATURE:
<223> OTHER INFORMATION: Antisense Compound

<400> SEQUENCE: 185
gcgctgctcc caagaactct 20

<210> SEQ ID NO 186
<211> LENGTH: 20
<212> TYPE: DNA
<213> ORGANISM: Artificial Sequence
<220> FEATURE:
<223> OTHER INFORMATION: Antisense Compound

<400> SEQUENCE: 186
tcctcatggt cacatggatg 20

<210> SEQ ID NO 187
<211> LENGTH: 19
<212> TYPE: DNA
<213> ORGANISM: Artificial Sequence
<220> FEATURE:
<223> OTHER INFORMATION: Antisense Compound

<400> SEQUENCE: 187
cgagaggcgg acgggaccg 19

<210> SEQ ID NO 188
<211> LENGTH: 21
<212> TYPE: DNA
<213> ORGANISM: Artificial Sequence
<220> FEATURE:
<223> OTHER INFORMATION: Antisense Compound

<400> SEQUENCE: 188
cgagaggcgg acgggaccgt t 21

<210> SEQ ID NO 189
<211> LENGTH: 21
<212> TYPE: DNA
<213> ORGANISM: Artificial Sequence
<220> FEATURE:
<223> OTHER INFORMATION: Antisense Compound

<400> SEQUENCE: 189
ttgctctccg cctgccctgg c 21

<210> SEQ ID NO 190
<211> LENGTH: 19
<212> TYPE: DNA
<213> ORGANISM: Artificial Sequence -continued

```
<220> FEATURE:
<223> OTHER INFORMATION: Antisense Compound

<400> SEQUENCE: 190

gctctccgcc tgccctggc                                              19
```